United States Patent
Faloon et al.

(10) Patent No.: US 9,745,261 B2
(45) Date of Patent: Aug. 29, 2017

(54) INHIBITORS OF THE MITF MOLECULAR PATHWAY

(71) Applicants: THE GENERAL HOSPITAL CORPORATION, Boston, MA (US); THE BROAD INSTITUTE, INC., Cambridge, MA (US); UNIVERSITY OF KANSAS, Lawrence, KS (US)

(72) Inventors: Patrick Faloon, Cambridge, MA (US); Warren S. Weiner, Phoenix, AZ (US); Robert A. Smith, Lawrence, KS (US); Frank John Schoenen, Lawrence, KS (US); David E. Fisher, Newton, MA (US); Rizwan Haq, Boston, MA (US)

(73) Assignees: THE GENERAL HOSPITAL CORPORATION, Boston, MA (US); THE BROAD INSTITUTE, INC., Cambridge, MA (US); UNIVERSITY OF KANSAS, Lawrence, KS (US)

( * ) Notice: Subject to any disclaimer, the term of this patent is extended or adjusted under 35 U.S.C. 154(b) by 0 days.

(21) Appl. No.: 14/897,445

(22) PCT Filed: Jun. 10, 2014

(86) PCT No.: PCT/US2014/041730
§ 371 (c)(1),
(2) Date: Dec. 10, 2015

(87) PCT Pub. No.: WO2014/201016
PCT Pub. Date: Dec. 18, 2014

(65) Prior Publication Data
US 2016/0130222 A1    May 12, 2016

Related U.S. Application Data

(60) Provisional application No. 61/833,192, filed on Jun. 10, 2013.

(51) Int. Cl.
| | | |
|---|---|---|
| C07C 311/16 | (2006.01) |
| A61K 31/18 | (2006.01) |
| C07C 311/17 | (2006.01) |
| C07D 333/34 | (2006.01) |
| C07D 409/12 | (2006.01) |
| C07D 209/48 | (2006.01) |
| C07D 307/91 | (2006.01) |
| C07D 307/68 | (2006.01) |
| A61K 31/4184 | (2006.01) |

(52) U.S. Cl.
CPC ........ *C07C 311/17* (2013.01); *A61K 31/4184* (2013.01); *C07D 209/48* (2013.01); *C07D 307/68* (2013.01); *C07D 307/91* (2013.01); *C07D 333/34* (2013.01); *C07D 409/12* (2013.01)

(58) Field of Classification Search
None
See application file for complete search history.

(56) References Cited

U.S. PATENT DOCUMENTS

2011/0201609 A1    8/2011    Lawrence et al.

FOREIGN PATENT DOCUMENTS

| DE | 1010968 B | 6/1957 |
| EP | 1398031 A1 | 3/2004 |
| WO | 02/077609 A2 | 10/2002 |
| WO | 2010/005534 A2 | 1/2010 |
| WO | 2010/026592 A1 | 3/2010 |

OTHER PUBLICATIONS

Database CAPLUS in STN, Acc. No. 1944:24954, Sjogren et al., Svensk Kemisk Tidskrift (1942), 54, pp. 200-204 From: Chem. Zentr. I, 1774 (1943) (abstract).*
Fieser et al., Journal of the American Chemical Society (1934), 56, pp. 1565-1578.*
Database CAPLUS in STN, Acc. No. 1934:41939, Fieser et al., Journal of the American Chemical Society (1934), 56, pp. 1565-1578 (abstract).*
Pubchem Chemical Structure Compound Summary CID 12387474 (2007).
Du et al., "Critical role of CDK2 for melanoma growth linked to its melanocyte-specific transcriptional regulation by MITF", Cancer Cell 6:565-576 (2004).

(Continued)

*Primary Examiner* — Brian J Davis
(74) *Attorney, Agent, or Firm* — Nixon Peabody LLP; David S. Resnick

(57) ABSTRACT

Provided herein are compounds of the formula (IV) as well as pharmaceutically acceptable salts thereof, wherein the substituents are as those disclosed in the specification. These compounds, and the pharmaceutical compositions containing them, are useful as MITF inhibitors, MITF pathway inhibitors and for the treatment of cancer.

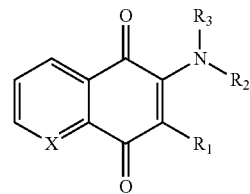

1 Claim, 24 Drawing Sheets

(56) References Cited

OTHER PUBLICATIONS

Furet et al., "Identification of cylin-dependent kinase 1 inhibitors of a new chemical type by structure-based design and database searching", Journal of Computer-Aided Molecular Design 15:489-495 (2001).

Carroll et al., "Preparation of Some Sulfonamide and Diaminodiphenyl Sulfone Analogs of 1,4-Naphthoquinone", Journal of Medicinal Chemistry 12:187-189 (1969).

Carroll et al., "Synthesis of 1H-Naphth [2,3-d] imidazole-4,9-diones by Acid Catalyzed Cyclization of 2-Acylamino-3-amino-1,4-naphthoquinones (1)", Journal of Heterocyclic Chemistry 6:909-916 (1969).

Egleton et al., "Structure—activity relationships and colorimetric properties of specific probes for the putative cancer biomarker human arylamine N-acetyltransferase 1", Bioorganic & Medicinal Chemistry 22:3030-3054 (2014).

Germanas et al., "Discovery of small-molecule inhibitors of tyrosinase", Bioorganic & Medicinal Chemistry Letters 17:6871-6875 (2007).

Hadden et al., "Synthesis and evaluation of Hsp90 inhibitors that contain the 1,4-naphthoquinone scaffold", Bioorganic & Medicinal Chemistry 17:634-640 (2009).

Loskutov et al., "Polymorphism of N-Ethoxymalonyl-2, 3-Diamino-1, 4-Naphthoquinone", Chemischer Informationsdienst 9:159-164 (1978).

Martins et al., "Photolysis of 2-Amino-and 2-Methylamino-1, 4-Naphthoquinone", Tetrahedron 44(2):591-598 (1988).

Marx et al., "Data Mining the NCI Cancer Cell Line Compound GI50 Values: Identifying Quinone Subtypes Effective Against Melanoma and Leukemia Cell Classes", Journal of Chemical Information and Computer Sciences 43(5):1652-1667 (2003).

Richter et al., "The Lead Tetraacetate Oxidation of 1- and 2-Benzenesulfonamido- and Benzamidonaphthalenes", The Journal of Organic Chemistry 27:4066-4068 (1962).

Ryu et al., "Cytotoxic Activities of 6-Arylamino-7-halo-5,8-quinolinediones against Human Tumor Cell Lines", Archives of Pharmacal Research 23(1):42-45 (2000).

Wang et al., "[1,1'-Bis(diphenylphosphino)ferrocene]dichloropalladium/1,1'-Bis(diphenylphosphino)ferrocene Catalyzed Synthesis of 2,3-Diamino-1,4-naphthoquinones", Synthesis 7:989-998 (2007).

\* cited by examiner

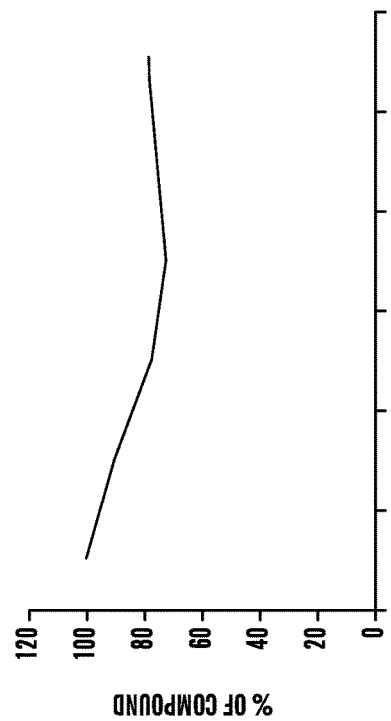
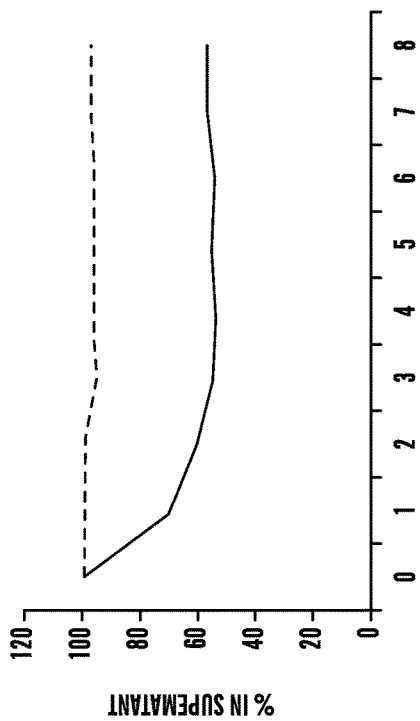
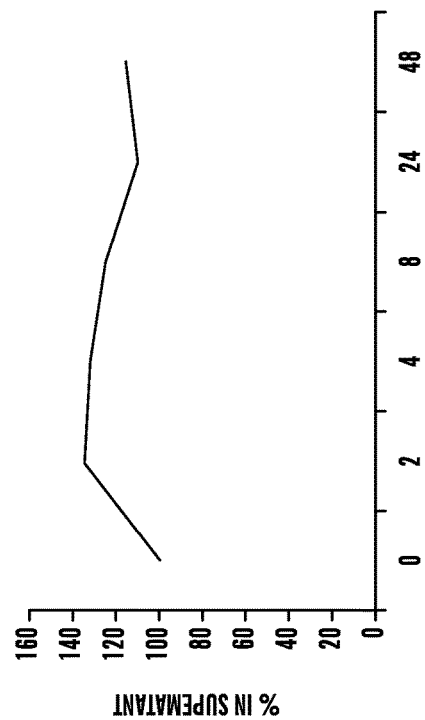
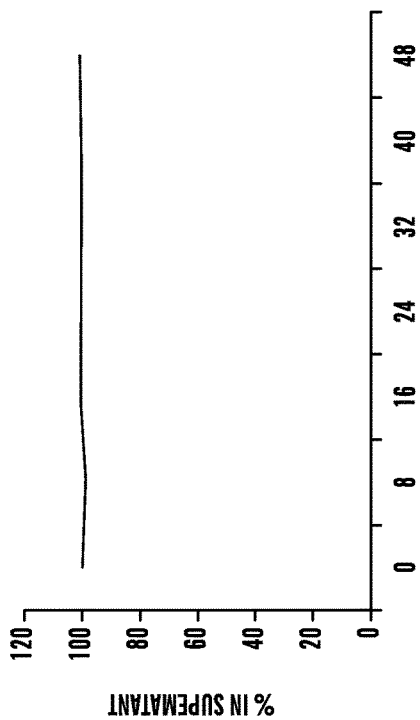
FIG. 1A
FIG. 1B
FIG. 1C
FIG. 1D

INHIBITORS OF THE MITF MOLECULAR PATHWAY

CROSS REFERENCE TO RELATED APPLICATIONS

This application is a 371 National Phase Entry of International Patent Application No. PCT/US2014/041730 filed Jun. 10, 2014 which claims benefit under 35 U.S.C. §119(e) of the U.S. Provisional Application No. 61/833,192 filed Jun. 10, 2013, the contents of which are incorporated herein by reference in their entirety.

GOVERNMENT SUPPORT

This invention was made with government support under RO3 DA031089, U54 HG005032, and U54 HG005031 awarded by the National Institutes of Health. The government has certain rights in the invention.

TECHNICAL FIELD

The present disclosure relates generally to compounds Formula (I):

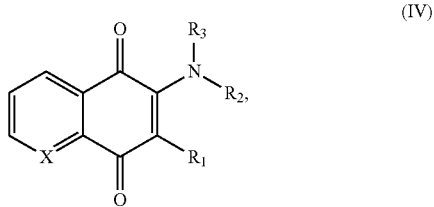

and to pharmaceutical compositions comprising the compounds. The compounds and compositions disclosed herein are inhibitors of the MITF molecular pathway and are useful for the treatment of cancer.

BACKGROUND

The microphthalmia-associated transcription factor (MITF) was identified as the product of a gene that affects murine coat color. The MITF gene encodes a basic-helix-loop-helix leucine zipper (bHLH-ZIP) transcription factor that homo- or heterodimerizes with the related transcription factors: TFEB, TFE3 and TFEC. These transcription factors, collectively termed the MiT family of transcription factors, are more ubiquitously expressed and unlike MITF are not essential for melanocytic differentiation (6). However, all members of the MiT family bind via their basic domains to identical DNA target sequences containing the canonical E-box promoter element CACGTC or the non-palindromic sequence CACATG.

When its activity is up-regulated in normal melanocytes, MITF initiates a transcriptional program leading to melanocyte differentiation, cell cycle arrest, and survival. It has also been suggested that MITF may induce cell cycle arrest during melanocytic differentiation, potentially via transcriptional targeting of the cyclic dependent kinase inhibitors p21, CDKN1A (13) and CDK4A (INK4A) (14). The anti-apoptotic protein Bcl-2 is directly activated by MITF and supports the survival of melanocytes since Bcl-2 knockout results in white coat-color due to melanocyte death (15).

A role for MITF in melanocyte survival is further supported by the consequence of MITF mutation in mice and people: melanocyte death, rather than presence of unpigmented melanocytes. Correspondingly, amplification and over-expression of MITF occurs in 15-20% of melanomas, leading to its designation as a bona fide melanoma oncogene (1). Suppression of MITF activity is lethal to melanomas, and high MITF expression is a poor prognostic factor in melanoma patients, as MITF over-expression is associated with a decrease in 5-year overall survival. Moreover, enforced MITF overexpression was shown to cooperate with the common melanoma oncogene BRAF(V600E) to transform human melanocytes (1). These results indicate that MITF can have either differentiative or tumorigenic effects depending on the cellular context. Whereas physiologic activation of Bcl-2 expression may protect melanocytes (for example, from ultraviolet light), its up-regulation in the context of melanoma may actually contribute to this cancer's notorious chemoresistance.

The above results suggest that small molecule compounds that suppress MITF would be useful not only in understanding the biology of context-specific transcriptional control, but also for developing therapeutic strategies for cancer, such as melanoma. With the exception of nuclear hormone receptors, success in directly targeting transcription factors has been very limited (16). Therefore, the identification of upstream druggable pathways that regulate MITF would be important as an alternative therapeutic strategy.

SUMMARY

In one aspect the disclosure provides a compound of Formula (IV):

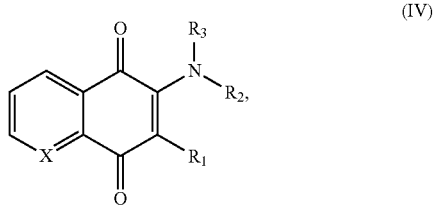

wherein:
X is CH or N;
R$_1$ is hydrogen, halogen, optionally substituted heterocycloalkyl, optionally substituted heteroaryl, optionally substituted aryl, optionally substituted alkoxy, optionally substituted lower alkyl, amino, optionally substituted alkylamino, optionally substituted dialkylamino;
R$_2$ is hydrogen, optionally substituted lower alkyl, optionally substituted aryl or heteroaryl, optionally substituted benzyl, —C(O)—R$_4$, —S(O)$_2$—R$_4$, or —CH(R$_5$)—R$_4$;
R$_3$ is hydrogen, optionally substituted lower alkyl, or acyl;
R$_4$ is optionally substituted aryl or heteroaryl;
R$_5$ is hydrogen or lower alkyl; and
pharmaceutically acceptable salts thereof.

The present invention is also directed to pharmaceutical compositions containing the above compounds and to methods of treating cancer. In some embodiments, the cancer is MITF-dependent cancer.

BRIEF DESCRIPTION OF THE DRAWINGS

FIG. 1 shows the stability of 4-((1,4-dioxo-1,4-dihydronaphthalen-2-yl)amino)benzenesulfonamide (ML329) in PBS buffer & GSH and DTT stability assays. The compound was tested over a time course in a PBS stability assay (A), GSH stability assay over 6 hours (B), DTT stability assay over 48 hours (C), and DTT stability assay for ethacrynic acid over 8 hours (D) (for C and D, no DTT (upper curve) and with 50 µM DTT (lower curve). The percent of compound remaining in the supernatant at the various time points is plotted.

DETAILED DESCRIPTION

Figure 2A:
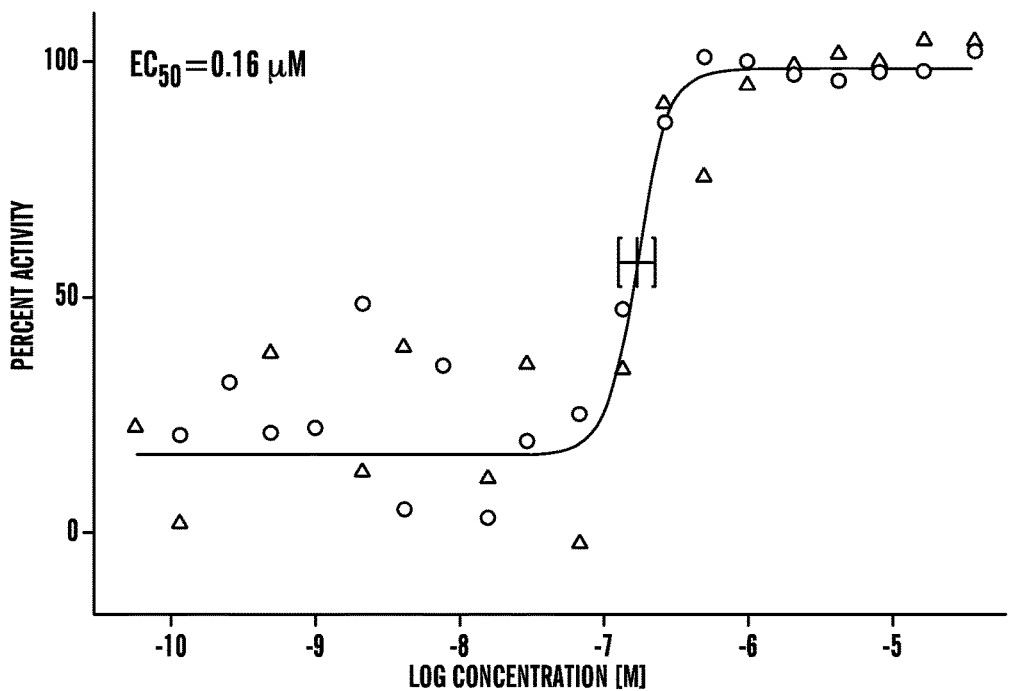
FIG. 2 shows qPCR for MITF and several target genes. 4-((1,4-dioxo-1,4-dihydronaphthalen-2-yl)amino)benzenesulfonamide was tested across a range of concentrations up to 35 µM in SK-MEL-5 melanoma cells for multiple qPCR assays. Concentration response curves were generated with Genedata Screener Condeseo and show normalized percent activity for the individual doses based upon fold change. An increase in fold change correlates with a reduction in gene expression. TRPM-1 qPCR assay (PubChem AID 651770), $EC_{50}$=0.16 µM (A); MITF qPCR assay (PubChem AID 651773), $EC_{50}$=0.16 µM (B); CDK2 qPCR assay (PubChem AID 651772), $EC_{50}$=0.5 µM (C) DCT qPCR assay (PubChem AID 651771), $EC_{50}$=0.1 µM (D) and MLANA qPCR assay (PubChem AID 651795), $EC_{50}$=0.5 µM (E). □=replicate 1, ∆=replicate 2.

Small molecule compounds were developed that inhibit the expression of numerous MITF target genes and block the proliferation of numerous cell lines that require MITF for proliferation. The compounds could directly or indirectly interact with MITF or components of the MITF regulatory network. MITF is a major molecular node in the development, proliferation and maintenance of melanocytes (2). It also has an important role in the progression and persistence of melanomas. As a transcription factor that regulates cell cycle, interference of MITF with the compounds of the invention will be useful in characterizing the specific roles of MITF in melanoma and validate blockade of MITF function as a potential treatment of melanoma. The compounds of the invention will benefit many researchers investigating melanoma and the underlying molecular changes in the early stages of oncogenesis and the subsequent changes in disease progression and metastasis. An inhibitor of MITF will also benefit the study of melanogenesis by parsing out MITF's function in this biological process away from its role in the development of other neural crest derived lineages, like the inner ear and osteoclasts (2, 3). MITF has been implicated in clear cell sarcoma and the compounds of the present invention could be used to determine if it is efficacious in that disease context (4). The compound of the invention can also be used as treatments of disease or disorders wherein MITF pathway is involved in the pathology or symptomology of the disease or disorder, such as, but not limited to, cancer.

In one aspect the disclosure provides a compound of Formula (IV):

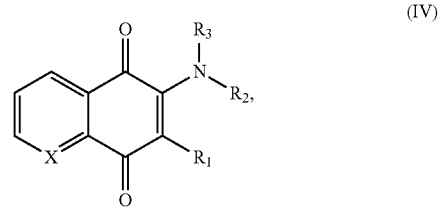

wherein:

X is CH or N;

$R_1$ is hydrogen, halogen, optionally substituted heterocycloalkyl, optionally substituted heteroaryl, optionally substituted aryl, optionally substituted alkoxy, optionally substituted lower alkyl, amino, optionally substituted alkylamino, optionally substituted dialkylamino;

$R_2$ is hydrogen, optionally substituted lower alkyl, optionally substituted aryl or heteroaryl, optionally substituted benzyl, —C(O)—$R_4$, —S(O)$_2$—$R_4$, or —CH($R_5$)—$R_4$;

$R_3$ is hydrogen, optionally substituted lower alkyl, or acyl;

$R_4$ is optionally substituted aryl or heteroaryl;

$R_5$ is hydrogen or lower alkyl; and pharmaceutically acceptable salts thereof.

In various embodiments of compounds of Formula (IV), $R_1$ can be selected from the group consisting of hydrogen; halogen; a 5- or 6-membered heterocyclyl or heteroaryl, said heterocyclyl or heteroaryl optionally substituted with lower alkyl or phenyl; alkoxy; phenyl; lower alkyl, optionally substituted with phenyl, alkylamino or dialkylamino; and amino.

In some embodiments of the various aspects disclosed herein, $R_1$ can be selected from the group consisting of hydrogen, chlorine, methyl, methoxy, phenyl, piperazinyl, methylpiperazinyl, ethylpiperzinyl, piperidinyl, morpholinyl, thiomorpholinyl, phenyl-piperazinyl, ethyl-piperazinyl, —NHCH$_2$CH=CH$_2$, —NH$_2$, tert-butyl-piperazinyl, pyrrolidinyl, —NHCH$_2$CH$_2$CH$_2$N(CH$_2$CH$_3$)$_2$ and —NHCH(CH$_3$)phenyl.

In some embodiments, X is CH and $R_1$ is selected from selected from the group consisting of hydrogen; halogen; a 5- or 6-membered heterocyclyl or heteroaryl, said heterocyclyl or heteroaryl optionally substituted with lower alkyl or phenyl; alkoxy; phenyl; lower alkyl, optionally substituted with phenyl, alkylamino or dialkylamino; and amino.

In various compounds of Formula (IV), X can be CH and $R_1$ can be hydrogen, chlorine, methyl, methoxy, phenyl, piperazinyl, methylpiperazinyl, ethylpiperzinyl, piperidinyl, morpholinyl, thiomorpholinyl, phenyl-piperazinyl, ethyl-piperazinyl, —NHCH$_2$CH=CH$_2$, —NH$_2$, tert-butyl-piperazinyl, pyrrolidinyl, —NHCH$_2$CH$_2$CH$_2$N(CH$_2$CH$_3$)$_2$ and —NHCH(CH$_3$)phenyl.

In some compounds of Formula (IV), X is CH and $R_1$ can be selected from hydrogen, chlorine, methyl, methoxy, phenyl, piperazinyl, methylpiperazinyl, piperidinyl, morpholinyl, thiomorpholinyl, phenyl-piperazinyl, ethyl-piperazinyl, —CH$_2$CH=CH$_2$, —NH$_2$, tert-butyl-piperazinyl, pyrrolidinyl, —CH$_2$CH$_2$CH$_2$N(CH$_2$CH$_3$)$_2$ or —CH(CH$_3$)phenyl.

In various embodiments, $R_2$ can be selected from hydrogen; lower alkyl; phenyl, optionally mono- or bi-substituted independently with halogen, lower alkyl, —S(O)$_2$NH$_2$ or alkoxy; optionally substituted benzyl; C(O)-phenyl, said phenyl unsubstituted or substituted with halogen; S(O)$_2$-phenyl, said phenyl unsubstituted or substituted with halogen; (O)$_2$-thiophenyl, said thiophenyl unsubstituted or substituted with halogen; and thiophenyl.

In some embodiments of the various aspects disclosed herein, $R_2$ can be selected from the group consisting of methyl, hydrogen, —CH$_2$CH=CH$_2$, phenyl, —CH$_2$-chlorophenyl, chlorophenyl, acetyl, —C(O)-phenyl, —C(O)-bromophenyl, —S(O)$_2$-phenyl, —S(O)$_2$-bromophenyl, —S(O)$_2$-thiazolyl, —S(O)$_2$-bromothiazolyl, difluorophenyl, methoxyphenyl, and -phenyl-S(O)$_2$NH$_2$.

In some embodiments, X is CH and $R_2$ can be selected from the group consisting of hydrogen; lower alkyl; phenyl, optionally mono- or bi-substituted independently with halogen, lower alkyl, —S(O)$_2$NH$_2$ or alkoxy; optionally substituted benzyl; C(O)-phenyl, said phenyl unsubstituted or substituted with halogen; S(O)$_2$-phenyl, said phenyl unsubstituted or substituted with halogen; S(O)$_2$-thiophenyl, said thiophenyl unsubstituted or substituted with halogen; and thiophenyl. In some compounds of Formula (IV), X is CH and $R_2$ is selected from methyl, hydrogen, —CH$_2$CH=CH$_2$, phenyl, —CH$_2$-chlorophenyl, chlorophenyl, acetyl, —C(O)-phenyl, —C(O)— bromophenyl, —S(O)$_2$-phenyl, —S(O)$_2$-bromophenyl, —S(O)$_2$-thiazolyl, —S(O)$_2$-bromothiazolyl, difluorophenyl, methoxyphenyl, and -phenyl-S(O)$_2$NH$_2$.

In some compounds of Formula (IV), $R_2$ is selected from methyl, hydrogen, —CH$_2$CH=CH$_2$, phenyl, —CH$_2$-chlorophenyl, chlorophenyl, acetyl, —C(O)-phenyl, —C(O)— bromophenyl, —S(O)$_2$-phenyl, —S(O)$_2$-bromophenyl, —S(O)$_2$-thiazolyl, —S(O)$_2$-bromothiazolyl, difluorophenyl, methoxyphenyl, and -phenyl-S(O)$_2$NH$_2$; and $R_1$ is selected form the group consisting of hydrogen, chlorine, methyl, methoxy, phenyl, piperazinyl, methylpiperazinyl, ethylpiperzinyl, piperidinyl, morpholinyl, thiomorpholinyl, phenyl-piperazinyl, ethyl-piperazinyl, —NHCH$_2$CH=CH$_2$, —NH$_2$, tert-butyl-piperazinyl, pyrrolidinyl, —NHCH$_2$CH$_2$CH$_2$N(CH$_2$CH$_3$)$_2$ and —NHCH(CH$_3$)phenyl.

In various embodiments of compounds of Formula (IV), $R_3$ can be selected from hydrogen, methyl, or acetyl.

In some embodiments, X is CH and $R_3$ is hydrogen, lower alkyl or acyl. In some embodiments, X is CH and $R_3$ is hydrogen, methyl or acetyl.

In some compounds, $R_3$ is hydrogen, lower alkyl or acyl and $R_1$ is a 5- or 6-membered heteroacycloalkyl (optionally substituted with lower alkyl or phenyl), lower alkyl (optionally substituted with diethylamino (—N(CH$_2$CH$_3$)$_2$)), or amino. In one embodiment, $R_3$ is acetyl and $R_1$ is a 5- or 6-membered heteroacycloalkyl (optionally substituted with lower alkyl) or lower alkyl (optionally substituted with diethylamino). In other embodiments, $R_3$ is hydrogen and $R_1$ is a 5- or 6-membered heteroacycloalkyl (optionally substituted with lower alkyl or phenyl).

In some embodiments, $R_3$ is hydrogen, lower alkyl or acyl and $R_2$ is selected from the group consisting of hydrogen; lower alkyl; phenyl, optionally mono- or bi-substituted independently with halogen, lower alkyl, —S(O)$_2$NH$_2$ or alkoxy; optionally substituted benzyl; C(O)-phenyl, said phenyl unsubstituted or substituted with halogen; S(O)$_2$-phenyl, said phenyl unsubstituted or substituted with halogen; S(O)$_2$-thiophenyl, said thiophenyl unsubstituted or substituted with halogen; and thiophenyl.

In some embodiments, $R_3$ is hydrogen, methyl or acetyl and $R_2$ is methyl, hydrogen, —CH$_2$CH=CH$_2$, phenyl, —CH$_2$-chlorophenyl, chlorophenyl, acetyl, —C(O)-phenyl, —C(O)-bromophenyl, —S(O)$_2$-phenyl, —S(O)$_2$-bromophenyl, —S(O)$_2$-thiazolyl, —S(O)$_2$-bromothiazolyl, difluorophenyl, methoxyphenyl, and -phenyl-S(O)$_2$NH$_2$; and $R_1$ is selected form the group consisting of hydrogen, chlorine, methyl, methoxy, phenyl, piperazinyl, methylpiperazinyl, ethylpiperzinyl, piperidinyl, morpholinyl, thiomorpholinyl, phenyl-piperazinyl, ethyl-piperazinyl, —NHCH$_2$CH=CH$_2$, —NH$_2$, tert-butyl-piperazinyl, pyrrolidinyl, —NHCH$_2$CH$_2$CH$_2$N(CH$_2$CH$_3$)$_2$ or —NHCH(CH$_3$) phenyl In various embodiments of compounds of Formula (IV), $R_4$ can be an optionally substituted phenyl or thiophenyl. In some embodiments, $R_4$ is a phenyl or thiophenyl, wherein the phenyl or thiophenyl is optionally substituted with halogen.

In some embodiments of compounds of Formula (IV), $R_5$ can be hydrogen or methyl.

In some embodiments, a compound of Formula (IV) is a compound of Formula (I):

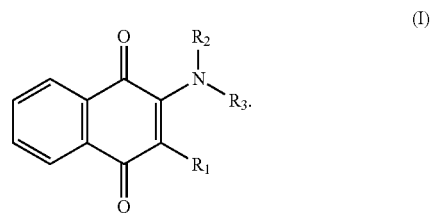

(I)

wherein $R_1$ is hydrogen, halogen, a 5- or 6-membered heterocycloalkyl or heteroaryl (optionally substituted with lower alkyl or phenyl), alkoxy, phenyl, lower alkyl (optionally substituted with phenyl or —N(CH$_2$CH$_3$)$_2$), or NH$_2$; R$_2$ is hydrogen, lower alkyl, phenyl (optionally mono- or di-substituted independently with halogen, lower alkyl, —S(O)$_2$NH$_2$ or alkoxy), —CH$_2$-phenyl (said phenyl optionally substituted with halogen, C(O)-phenyl (said phenyl optionally substituted with halogen), S(O)$_2$-phenyl (said phenyl optionally substituted with halogen), S(O)$_2$-thiophenyl (said thiophenyl optionally substituted with halogen), or thiophenyl; R$_3$ is hydrogen, lower alkyl, or acetyl; and pharmaceutically acceptable salts thereof.

In some embodiments of the various aspects disclosed herein, provided is a compound of formula (I), wherein R$_1$ is hydrogen, chlorine, methyl, methoxy, phenyl, piperazinyl, methylpiperazinyl, piperidinyl, morpholinyl, thiomorpholinyl, phenyl-piperazinyl, ethyl-piperazinyl, —NHCH$_2$CH=CH$_2$, —CH$_2$CH=CH$_2$, —NH$_2$, tert-butyl-piperazinyl, pyrrolidinyl, —CH$_2$CH$_2$CH$_2$N(CH$_2$CH$_3$)$_2$ or —CH(CH$_3$)phenyl.

In another embodiment of the invention, provided is a compound of formula (I), wherein R$_2$ is methyl, hydrogen, —CH$_2$CH=CH$_2$, phenyl, —CH$_2$-chlorophenyl, chlorophenyl, acetyl, —C(O)-phenyl, —C(O)-bromophenyl, —S(O)$_2$-phenyl, —S(O)$_2$-bromophenyl, —S(O)$_2$-thiazolyl, —S(O)$_2$-bromothiazolyl, difluorophenyl, methoxyphenyl or -phenyl-S(O)$_2$NH$_2$.

In another embodiment of the invention, provided is a compound of formula (I), wherein R$_3$ is hydrogen, methyl or acetyl.

In various compounds of Formula (IV), a compound of Formula (IV) is a compound of Formula (Ia):

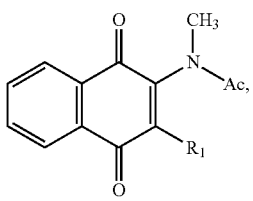

(Ia)

wherein R$_1$ is a 5- or 6-membered heterocycloalkyl (optionally substituted with lower alkyl) or a lower alkyl (optionally substituted with diethylamino); and pharmaceutically acceptable salts thereof.

In another embodiment of the present invention, a ring carbon in the benzo-ring of the naphthoquinone of the compound of Formula (I) can be replaced with a nitrogen atom.

In some other embodiments, a compound of Formula (IV) is a compound of Formula (Ib):

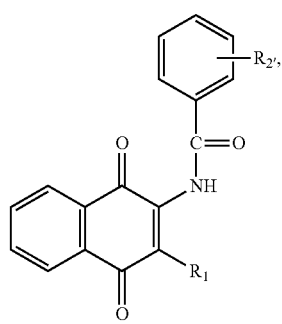

(Ib)

wherein R$_1$ is a 5- or 6-membered heterocycloalkyl (unsubstituted or substituted with lower alkyl or phenyl) or NH$_2$; R$_{2'}$ is hydrogen or halogen; and pharmaceutically acceptable salts thereof.

In yet some other embodiments, a compound of Formula (IV) is a compound of Formula (IC):

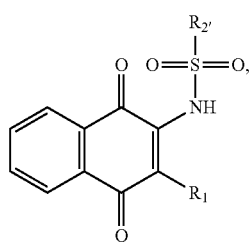

(Ic)

wherein R$_1$ is a 5- or 6-membered heterocycloalkyl (optionally substituted with lower alkyl), hydrogen, alkoxy, or NH$_2$; R$_{2'}$ is a phenyl (optionally substituted with halogen) or a thiophenyl (optionally substituted with halogen); and pharmaceutically acceptable salts thereof.

In still some other embodiments, a compound of Formula (IV) is a compound of Formula (Id):

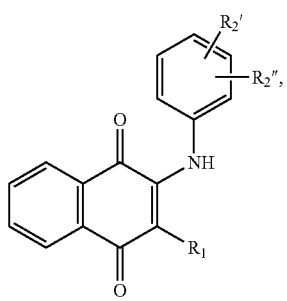

(Id)

wherein R$_1$ is a 5- or 6-membered heterocycloalkyl (optionally substituted with lower alkyl or phenyl); R$_{2'}$ and R$_{2''}$ are independently or each other hydrogen, halogen or alkoxy; and pharmaceutically acceptable salts thereof.

In some embodiments, X is N and R$_1$ is selected from selected from the group consisting of hydrogen; halogen; a 5- or 6-membered heterocyclyl or heteroaryl, said heterocyclyl or heteroaryl optionally substituted with lower alkyl or phenyl; alkoxy; phenyl; lower alkyl, optionally substituted with phenyl, alkylamino or dialkylamino; and amino.

In various compounds of Formula (IV), X can be N and R$_1$ can be hydrogen, chlorine, methyl, methoxy, phenyl, piperazinyl, methylpiperazinyl, ethylpiperzinyl, piperidinyl, morpholinyl, thiomorpholinyl, phenyl-piperazinyl, ethyl-piperazinyl, —NHCH$_2$CH=CH$_2$, —NH$_2$, tert-butyl-piperazinyl, pyrrolidinyl, —NHCH$_2$CH$_2$CH$_2$N(CH$_2$CH$_3$)$_2$ and —NHCH(CH$_3$)phenyl.

In some compounds of Formula (IV), X is N and R$_1$ can be selected from hydrogen, chlorine, methyl, methoxy, phenyl, piperazinyl, methylpiperazinyl, piperidinyl, morpholinyl, thiomorpholinyl, phenyl-piperazinyl, ethyl-piperazinyl, —CH$_2$CH=CH$_2$, —NH$_2$, tert-butyl-piperazinyl, pyrrolidinyl, —CH$_2$CH$_2$CH$_2$N(CH$_2$CH$_3$)$_2$ or —CH(CH$_3$)phenyl. In one embodiment, X is N and R$_1$ is phenyl.

In some embodiments, X is N and R$_2$ can be selected from the group consisting of hydrogen; lower alkyl; phenyl, optionally mono- or bi-substituted independently with halogen, lower alkyl, —S(O)$_2$NH$_2$ or alkoxy; optionally substituted benzyl; C(O)-phenyl, said phenyl unsubstituted or substituted with halogen; S(O)$_2$-phenyl, said phenyl unsubstituted or substituted with halogen; S(O)$_2$-thiophenyl, said thiophenyl unsubstituted or substituted with halogen; and thiophenyl. In some compounds of Formula (IV), X is N and R$_2$ is selected from methyl, hydrogen, —CH$_2$CH=CH$_2$, phenyl, —CH$_2$-chlorophenyl, chlorophenyl, acetyl, —C(O)-phenyl, —C(O)-bromophenyl, —S(O)$_2$-phenyl, —S(O)$_2$-bromophenyl, —S(O)$_2$-thiazolyl, —S(O)$_2$-bromothiazolyl, difluorophenyl, methoxyphenyl, and -phenyl-S(O)$_2$NH$_2$. In one embodiment, X is N and R$_2$ is H.

In some embodiments, X is N and R$_3$ is hydrogen, lower alkyl or acyl. In some embodiments, X is N and R$_3$ is hydrogen, methyl or acetyl. In one embodiment, X is N and R$_3$ is hydrogen.

In some embodiments, a compound of Formula (IV) is a compound of Formula (III):

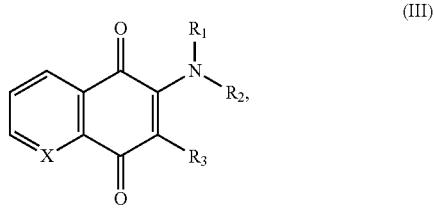

(III)

wherein X is nitrogen; R$_3$ is hydrogen, halogen, a 5- or 6-membered heterocycloalkyl or heteroaryl (optionally substituted with lower alkyl or phenyl), alkoxy, lower alkyl (optionally substituted with phenyl or —N(CH$_2$CH$_3$)$_2$), or NH$_2$; R$_2$ is hydrogen, lower alkyl, phenyl (optionally mono- or di-substituted independently with halogen, lower alkyl, —S(O)$_2$NH$_2$ or alkoxy), CH$_2$-phenyl (said phenyl optionally substituted with halogen, C(O)-phenyl (said phenyl optionally substituted with halogen), S(O)$_2$-phenyl (said phenyl optionally substituted with halogen), S(O)$_2$-thiophenyl (said thiophenyl optionally substituted with halogen), or thiophenyl; and R$_1$ is hydrogen, lower alkyl, or acetyl.

In some embodiments, a compound of Formula (IV) is a compound selected from the group of compounds shown in Tables 5-10. In one embodiment, the compound of Formula (IV) is 4-((1,4-dioxo-1,4-dihydronaphthalen-2-yl)amino) benzenesulfonamide (ML329).

It will be appreciated that the compounds of general Formula (IV) can be derivatized at functional groups to provide derivatives which are capable of conversion back to the parent compound in vivo. Physiologically acceptable and metabolically labile derivatives, which are capable of producing the parent compounds of general Formula IV in vivo are also within the scope of this invention. Thus, the disclosure also provides derivates, analogues, prodrugs, and pharmaceutically acceptable salts of the compounds of Formula (IV).

Compounds disclosed herein can be prepared beginning with commercially available starting materials and utilizing general synthetic techniques and procedures known to those skilled in the art. Chemicals may be purchased from companies such as for example Sigma-Aldrich, VWR and Alfa Aesar. Chromatography supplies and equipment may be purchased from such companies as for example Biotage AB, Charlottesville, Va.; Analytical Sales and Services, Inc., Pompton Plains, N.J.; Teledyne Isco, Lincoln, Nebr.; VWR International, Bridgeport, N.J.; Varian Inc., Palo Alto, Calif., and Mettler Toledo Instrument Newark, Del. Biotage, ISCO and Analogix columns are pre-packed silica gel columns used in standard chromatography. Exemplary synthesis of various compounds of Formula (IV) is described in the Examples section. Ordinarily skilled artisans can easily adapt the methods described in the Examples sections for preparing any one of the compounds of Formula (IV).

For example, compounds of Formula (I) can be prepared according to the following schemes:

Scheme 1. Synthesis of 4-((1,4-dioxo-1,4-dihydronaphthalen-2-yl)amino)benzenesulfonamide

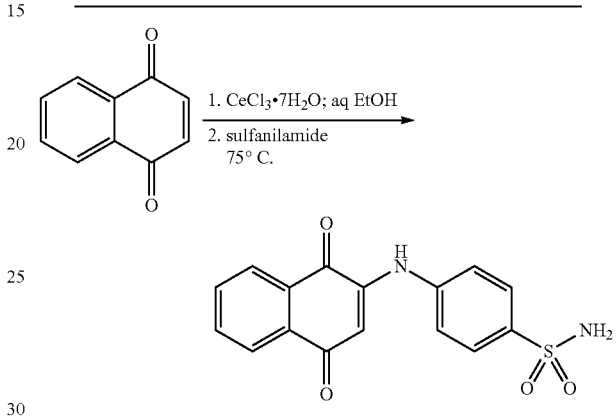

Compound 4-((1,4-dioxo-1,4-dihydronaphthalen-2-yl)amino)-benzenesulfonamide of Example 1 can be synthesized in one step from commercially available 1,4-naphthoquinone and sulfanilamide using cerium(III) chloride heptahydrate as a Lewis acid catalyst as shown in Scheme 1. The reaction was allowed to stir at 75° C. for three days (unoptimized) then dilute citric acid was added to the reaction suspension and the insoluble material was collected by filtration. The filter cake was washed with water, dried, then purified by preparative RPLC.

The compounds disclosed herein have anti-cancer activity or anti-cancer properties. Accordingly, in another aspect, the disclosure provides a method of treating cancer. The method comprising administering a therapeutically effective amount of a compound of Formula (IV) to subject in need thereof.

As used herein, the term "anti-cancer activity" or "anti-cancer properties" refers to the inhibition (in part or in whole) or prevention of unregulated cell growth and/or the inhibition (in part or in whole) or prevention of a cancer as defined herein. Anticancer activity includes, e.g., the ability to reduce, prevent, or repair genetic damage, modulate undesired cell proliferation, modulate misregulated cell death, or modulate mechanisms of metastasis (e.g., ability to migrate).

In some embodiments, the cancer is a MITF-dependent cancer. Thus, in yet another aspect, the disclosure provides a method of treating a MITF-dependent cancer. The method comprising administering a therapeutically effective amount of a compound of Formula (IV) to subject in need thereof.

As used herein, the term "cancer" refers to an uncontrolled growth of cells that may interfere with the normal functioning of the bodily organs and systems. Cancers that migrate from their original location and seed vital organs can eventually lead to the death of the subject through the functional deterioration of the affected organs. Metastasis is a cancer cell or group of cancer cells, distinct from the primary tumor location resulting from the dissemination of cancer cells from the primary tumor to other parts of the body. At the time of diagnosis of the primary tumor mass, the subject may be monitored for the presence of in transit metastases, e.g., cancer cells in the process of dissemination. As used herein, the term cancer, includes, but is not limited to the following types of cancer, breast cancer, biliary tract cancer, bladder cancer, brain cancer including glioblastomas and medulloblastomas; cervical cancer; choriocarcinoma; colon cancer; endometrial cancer; esophageal cancer, gastric cancer; hematological neoplasms including acute lymphocytic and myelogenous leukemia; T-cell acute lymphoblastic leukemia/lymphoma; hairy cell leukemia; chronic myelogenous leukemia, multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Merkel cell carcinoma, Kaposi's sarcoma, basal cell carcinoma, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma, Wilms tumor. Examples of cancer include but are not limited to, carcinoma, including adenocarcinoma, lymphoma, blastoma, melanoma, sarcoma, and leukemia. More particular examples of such cancers include squamous cell cancer, small-cell lung cancer, non-small cell lung cancer, gastrointestinal cancer, Hodgkin's and non-Hodgkin's lymphoma, pancreatic cancer, Glioblastoma, cervical cancer, ovarian cancer, liver cancer such as hepatic carcinoma and hepatoma, bladder cancer, breast cancer, colon cancer, colorectal cancer, endometrial carcinoma, salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, and various types of head and neck cancer. Other cancers will be known to the artisan.

As used herein, the term "cancer" includes, but is not limited to, solid tumors and blood born tumors. The term cancer refers to disease of skin, tissues, organs, bone, cartilage, blood and vessels. The term "cancer" further encompasses primary and metastatic cancers. Examples of cancers that can be treated with the compounds of the invention include, but are not limited to, carcinoma, including that of the bladder, breast, colon, kidney, lung, ovary, pancreas, stomach, cervix, thyroid, and skin, including squamous cell carcinoma; hematopoietic tumors of lymphoid lineage, including, but not limited to, leukemia, acute lymphocytic leukemia, acute lymphoblastic leukemia, B-cell lymphoma, T-cell lymphoma, Hodgkins lymphoma, non-Hodgkins lymphoma, hairy cell lymphoma, and Burketts lymphoma; hematopoietic tumors of myeloid lineage including, but not limited to, acute and chronic myelogenous leukemias and promyelocytic leukemia; tumors of mesenchymal origin including, but not limited to, fibrosarcoma, rhabdomyosarcoma, and osteosarcoma; other tumors including melanoma, seminoma, tetratocarcinoma, neuroblastoma, and glioma; tumors of the central and peripheral nervous system including, but not limited to, astrocytoma, neuroblastoma, glioma, and schwannomas; and other tumors including, but not limited to, xenoderma, pigmentosum, keratoactanthoma, thyroid follicular cancer, and teratocarcinoma. The compounds of the invention are useful for treating patients who have been previously treated for cancer, as well as those who have not previously been treated for cancer. Indeed, the methods and compositions of this invention can be used in first-line and second-line cancer treatments.

As used herein, the term "precancerous condition" has its ordinary meaning, i.e., an unregulated growth without metastasis, and includes various forms of hyperplasia and benign hypertrophy. Accordingly, a "precancerous condition" is a disease, syndrome, or finding that, if left untreated, can lead to cancer. It is a generalized state associated with a significantly increased risk of cancer. Premalignant lesion is a morphologically altered tissue in which cancer is more likely to occur than its apparently normal counterpart. Examples of pre-malignant conditions include, but are not limited to, oral leukoplakia, actinic keratosis (solar keratosis), Barrett's esophagus, atrophic gastritis, benign hyperplasia of the prostate, precancerous polyps of the colon or rectum, gastric epithelial dysplasia, adenomatous dysplasia, hereditary nonpolyposis colon cancer syndrome (HNPCC), Barrett's esophagus, bladder dysplasia, precancerous cervical conditions, and cervical dysplasia.

For administration to a subject, the compounds described herein can be provided in pharmaceutically acceptable compositions. These pharmaceutically acceptable compositions comprise a therapeutically-effective amount of one or more of the compounds described herein, formulated together with one or more pharmaceutically acceptable carriers (additives) and/or diluents. As described in detail below, the pharmaceutical compositions of the present invention can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 3,270,960.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

Useful pharmaceutical carriers for the preparation of the compositions hereof, can be solids, liquids or gases. Thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. For example, an amount of a compound administered to a subject that is sufficient to produce a statistically significant, measurable change in at least one symptom of cancer or metastasis.

The amount of the compound described herein that can be combined with a carrier material to produce a single dosage form will generally be that amount of the compound that produces a therapeutic effect. Generally out of one hundred percent, this amount will range from about 0.01% to 99% of the compound, preferably from about 5% to about 70%, most preferably from 10% to about 30%.

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices, are preferred.

As used herein, the term ED denotes effective dose and is used in connection with animal models. The term EC denotes effective concentration and is used in connection with in vitro models.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the IC50 (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay.

Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents. The dose of a compound of disclosed herein depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as a "therapeutically effective amount".

The dosage can be determined by a physician and adjusted, as necessary, to suit observed effects of the treatment. Generally, the dose of a compound described herein is typically in the range of about 1 to about 1000 mg per day. Preferably, the therapeutically effective amount is in an amount of from about 1 mg to about 500 mg per day. For example, the compositions are administered so that the compound described herein is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like.

In some embodiments, the compositions are administered at a dosage so that the compound or a metabolite thereof has an in vivo concentration of less than 500 nM, less than 400 nM, less than 300 nM, less than 250 nM, less than 200 nM, less than 150 nM, less than 100 nM, less than 50 nM, less than 25 nM, less than 20, nM, less than 10 nM, less than 5 nM, less than 1 nM, less than 0.5 nM, less than 0.1 nM, less than 0.05 nM, less than 0.01, nM, less than 0.005 nM, less than 0.001 nM after 15 mins, 30 mins, 1 hr, 1.5 hrs, 2 hrs, 2.5 hrs, 3 hrs, 4 hrs, 5 hrs, 6 hrs, 7 hrs, 8 hrs, 9 hrs, 10 hrs, 11 hrs, 12 hrs or more of time of administration.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the compound. The desired dose can be administered everyday or every third, fourth, fifth, or sixth day. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments of the aspects described herein, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

As used herein, the term "administer" refers to the placement of a composition into a subject by a method or route which results in at least partial localization of the composition at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered by intravenous infusion or injection.

By "treatment", "prevention" or "amelioration" of a disease or disorder is meant delaying or preventing the onset of such a disease or disorder, reversing, alleviating, ameliorating, inhibiting, slowing down or stopping the progression, aggravation or deterioration the progression or severity of a condition associated with such a disease or disorder. In one embodiment, at least one symptom of a disease or disorder is alleviated by at least 5%, at least 10%, at least 20%, at least 30%, at least 40%, or at least 50%.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used as subjects that represent animal models of disorders associated with inflammation.

In addition, the methods described herein can be used to treat domesticated animals and/or pets. A subject can be male or female. A subject can be one who has been previously diagnosed with or identified as suffering from or having a disorder a cancer or metastasis, but need not have already undergone treatment.

The compounds described herein are also useful in combination with known anti-cancer treatments, including radiation. The methods of the invention are especially useful in combination with anti-cancer treatments that involve administering a second drug that acts in a different phase of the cell cycle.

In another embodiment of the invention, provided is a pharmaceutical composition, comprising a therapeutically effective amount of a compound of formula (II):

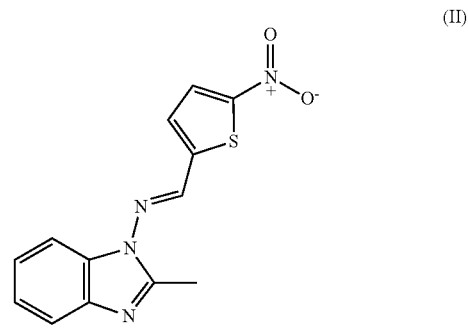

or a pharmaceutically acceptable salt thereof and a pharmaceutically acceptable carrier.

In another embodiment of the invention, provided is a method of treating cancer, comprising the step of administering a therapeutically effective amount of a compound of formula (II):

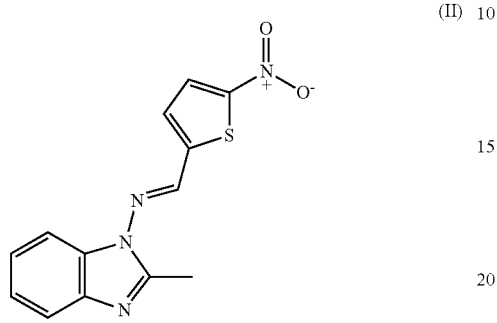

(II)

to a subject in need thereof.

In another embodiment of the invention, provided is a method of treating a MITF-dependent cancer, comprising the step of administering a therapeutically effective amount of a compound of formula (II):

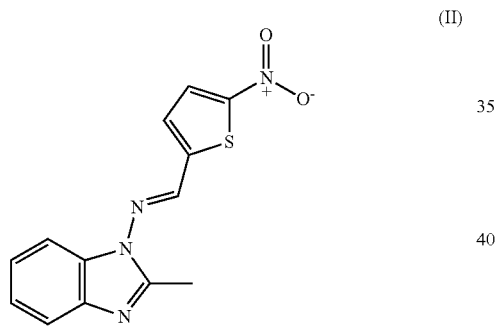

(II)

to a subject in need thereof

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered, for example, ocularly, orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Exemplary embodiments of the various aspects disclosed herein can be described by one or more of the following paragraphs:

1. A compound of Formula (IV):

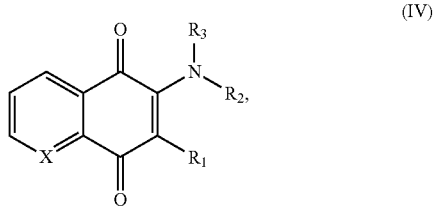

(IV)

wherein:
X is CH or N;
R₁ is hydrogen, halogen, optionally substituted heterocycloalkyl, optionally substituted heteroaryl, optionally substituted aryl, optionally substituted alkoxy, optionally substituted lower alkyl, amino, optionally substituted alkylamino, optionally substituted dialkylamino;
R₂ is hydrogen, optionally substituted lower alkyl, optionally substituted aryl or heteroaryl, optionally substituted benzyl, —C(O)—R₄, —S(O)₂—R₄, or —CH(R₅)—R₄;
R₃ is hydrogen, optionally substituted lower alkyl, or acyl;
R₄ is optionally substituted aryl or heteroaryl;
R₅ is hydrogen or lower alkyl; and
pharmaceutically acceptable salts thereof 2. The compound of paragraph 1, wherein the compound is of Formula (I):

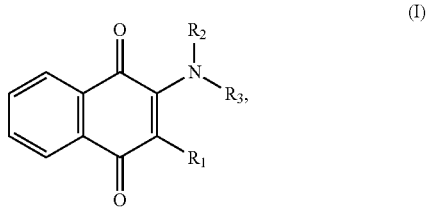

(I)

wherein:
R₁ is hydrogen, halogen, a 5- or 6-membered heterocycloalkyl or heteroaryl (optionally substituted with lower alkyl or phenyl), alkoxy, phenyl, lower alkyl (optionally substituted with phenyl or —N(CH₂CH₃)₂), or NH₂;
R₂ is hydrogen, lower alkyl, phenyl (optionally mono- or di-substituted independently with halogen, lower alkyl, —S(O)₂NH₂ or alkoxy), —CH₂-phenyl (said phenyl optionally substituted with halogen, C(O)-phenyl (said phenyl optionally substituted with halogen), S(O)₂-phenyl (said phenyl optionally substituted with halogen), S(O)₂-thiophenyl (said thiophenyl optionally substituted with halogen), or thiophenyl;
R₃ is hydrogen, lower alkyl, or acetyl; and
pharmaceutically acceptable salts thereof.

3. The compound of paragraph 1 or 2, wherein $R_1$ is hydrogen, chlorine, methyl, methoxy, phenyl, piperazinyl, methylpiperazinyl, piperidinyl, morpholinyl, thiomorpholinyl, phenyl-piperazinyl, ethyl-piperazinyl, —NHCH$_2$CH=CH$_2$, —CH$_2$CH=CH$_2$, —NH$_2$, tert-butyl-piperazinyl, pyrrolidinyl, —NCH$_2$CH$_2$CH$_2$N(CH$_2$CH$_3$)$_2$, —CH$_2$CH$_2$CH$_2$N(CH$_2$CH$_3$)$_2$, or —CH(CH$_3$)phenyl.

4. The compound of any of paragraphs 1-3, wherein $R_2$ is methyl, hydrogen, —CH$_2$CH=CH$_2$, phenyl, —CH$_2$-chlorophenyl, chlorophenyl, acetyl, —C(O)-phenyl, —C(O)-bromophenyl, —S(O)$_2$-phenyl, —S(O)$_2$-bromophenyl, —S(O)$_2$-thiazolyl, —S(O)$_2$-bromothiazolyl, difluorophenyl, methoxyphenyl or -phenyl-S(O)$_2$NH$_2$.

5. The compound of any of paragraphs 1-4, wherein $R_3$ is hydrogen, methyl or acetyl.

6. The compound of any of paragraphs 1-5, wherein the compound is of Formula (Ia):

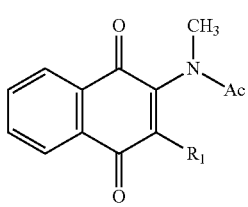

(Ia)

wherein:
$R_1$ is a 5- or 6-membered heterocycloalkyl (optionally substituted with lower alkyl), or a lower alkyl (optionally substituted with —N(CH$_2$CH$_3$)$_2$); and
Pharmaceutically acceptable salts thereof.

7. The compound of any of paragraphs 1-6, wherein the compound is of Formula (Ib):

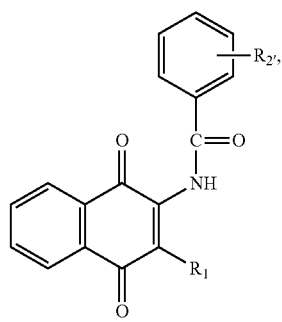

(Ib)

wherein:
$R_1$ is a 5- or 6-membered heterocycloalkyl (optionally substituted with lower alkyl or phenyl), or NH$_2$;
$R_2'$ is hydrogen or halogen; and
pharmaceutically acceptable salts thereof 8. The compound of any of paragraphs 1-7, wherein the compound is of Formula (Ic):

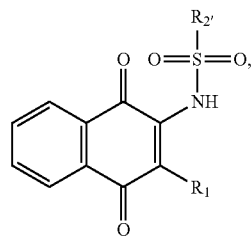

(Ic)

wherein:
$R_1$ is a hydrogen, alkoxy, NH$_2$, or a 5- or 6-membered heterocycloalkyl (optionally substituted with lower alkyl);
$R_2'$ is a phenyl or thiophenyl, each can be optionally substituted with halogen; and
pharmaceutically acceptable salts thereof 9. The compound of any of paragraphs 1-8, wherein the compound is of Formula (Id):

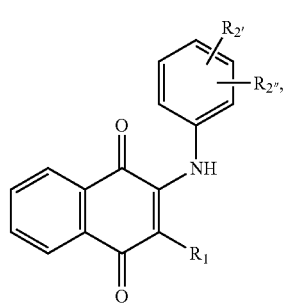

(Id)

wherein:
$R_1$ is a 5- or 6-membered heterocycloalkyl (optionally substituted with lower alkyl or phenyl);
$R_2'$ and $R_2''$ are independently or each other hydrogen, halogen, or alkoxy; and
pharmaceutically acceptable salts thereof 10. The compound of any of paragraphs 1-9, wherein the compound is of Formula (III):

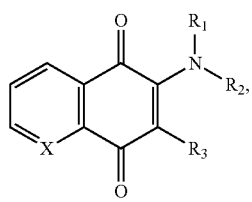

(III)

wherein:
X is nitrogen;
$R_1$ is hydrogen, lower alkyl, or acetyl;
$R_2$ is hydrogen, lower alkyl, phenyl (optionally mono- or di-substituted independently with halogen, lower alkyl, —S(O)$_2$NH$_2$ or alkoxy), CH$_2$-phenyl (said phenyl optionally substituted with halogen, C(O)-phenyl (said phenyl optionally substituted with halogen), S(O)$_2$-phenyl (said phenyl optionally substituted with halogen), S(O)$_2$-thiophenyl (said thiophenyl optionally substituted with halogen), or thiophenyl;

R₃ is hydrogen, halogen, a 5- or 6-membered heterocycloalkyl or heteroaryl (optionally substituted with lower alkyl or phenyl), alkoxy, lower alkyl (optionally substituted with phenyl or —N(CH₂CH₃)₂), or NH₂; and pharmaceutically acceptable salts thereof.

11. The compound of any of paragraphs 1-10, wherein the compound is selected from the group consisting of compounds shown in Tables 5-10.

12. The compound of any of paragraphs 1-11, wherein the compound is 4-((1,4-dioxo-1,4-dihydronaphthalen-2-yl)amino)benzenesulfonamide.

13. A pharmaceutical composition, comprising a therapeutically effective amount of a compound of any of paragraphs 1-12 and a pharmaceutically acceptable carrier.

14. A pharmaceutical composition, comprising a therapeutically effective amount of a compound of formula (II):

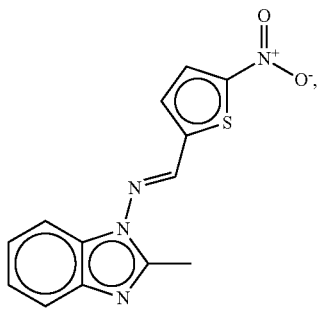

(II)

or a pharmaceutically acceptable salt thereof and a pharmaceutically acceptable carrier.

15. A method for treating cancer, comprising administering a therapeutically effective amount of a compound of any of paragraphs 1-12 to a subject in need thereof.

16. A method for treating cancer, comprising administering a therapeutically effective amount of a compound of formula (II):

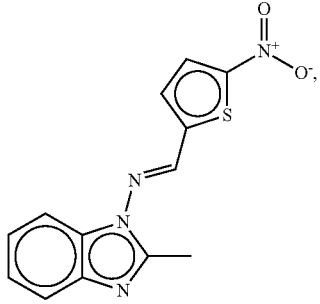

(II)

or a pharmaceutically acceptable salt thereof to a subject in need thereof.

17. The method of paragraph 15 or 16, wherein the cancer is a MITF-dependent cancer.

SOME SELECTED DEFINITIONS

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. It is to be understood that the terminology employed herein is for the purpose of describing particular embodiments, and is not intended to be limiting. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Unless defined otherwise, all technical and scientific terms used herein have the same meaning as those commonly understood to one of ordinary skill in the art to which this invention pertains. Although any known methods, devices, and materials similar or equivalent to those described herein can be used in the practice or testing of the invention, the methods, devices, and materials in this regard are described herein.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, systems, and respective components thereof as described herein, which are exclusive of any element not recited in that description of the embodiment The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean±5% of the value being referred to. For example, about 100 means from 95 to 105.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statistically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means at least two standard deviation (2SD) away from a reference level. The term refers to statistical evidence that there is a difference. It is defined as the probability of making a decision to reject the null hypothesis when the null hypothesis is actually true.

As used herein, the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

As used herein, the term "alkenyl", alone or in combination with other groups, refers to a straight-chain or branched hydrocarbon residue having an olefinic bond.

The term "cycloalkyl" refers to a monovalent mono- or polycarbocyclic radical of three to ten, preferably three to six carbon atoms. This term is further exemplified by radicals such as cyclopropyl, cyclobutyl, cyclopentyl, cyclohexyl, cycloheptyl, norbornyl, adamantyl, indanyl and the like. In a preferred embodiment, the "cycloalkyl" moieties can optionally be substituted with one, two, three or four substituents. Each substituent can independently be, alkyl, alkoxy, halogen, amino, hydroxyl or oxygen unless otherwise specifically indicated. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, optionally substituted cyclohexylene, optionally substituted cycloheptyl, and the like or those which are specifically exemplified herein.

The term "heterocycloalkyl" denotes a mono- or polycyclic alkyl ring, wherein one, two or three of the carbon ring atoms is replaced by a heteroatom such as N, O or S. Examples of heterocycloalkyl groups include, but are not limited to, morpholinyl, thiomorpholinyl, piperazinyl, piperidinyl, pyrrolidinyl, tetrahydropyranyl, tetrahydrofuranyl, 1,3-dioxanyl and the like. The heterocycloalkyl groups may be unsubstituted or substituted and attachment may be through their carbon frame or through their heteroatom(s) where appropriate. For example, the term "heterocyclyl" can refer to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). $C_x$heterocyclyl and $C_x$-$C_y$heterocyclyl are typically used where X and Y indicate the number of carbon atoms in the ring system. In some embodiments, 1, 2 or 3 hydrogen atoms of each ring can be substituted by a substituent. Exemplary heterocyclyl groups include, but are not limited to piperazinyl, pyrrolidinyl, dioxanyl, morpholinyl, tetrahydrofuranyl, piperidyl, 4-morpholyl, 4-piperazinyl, pyrrolidinyl, perhydropyrrolizinyl, 1,4-diazaperhydroepinyl, 1,3-dioxanyl, 1,4-dioxanyland the like.

The terms "bicyclic" and "tricyclic" refers to fused, bridged, or joined by a single bond polycyclic ring assemblies.

The term "lower alkyl", alone or in combination with other groups, refers to a branched or straight-chain alkyl radical of one to nine carbon atoms, preferably one to six carbon atoms, more preferably one to four carbon atoms. This term is further exemplified by radicals such as methyl, ethyl, n-propyl, isopropyl, n-butyl, s-butyl, isobutyl, tert-butyl, n-pentyl, 3-methylbutyl, n-hexyl, 2-ethylbutyl and the like.

The term "aryl" refers to monocyclic, bicyclic, or tricyclic fused aromatic ring system. $C_x$ aryl and $C_x$-$C_y$aryl are typically used where X and Y indicate the number of carbon atoms in the ring system. The term "aryl" includes aromatic mono- or polycarbocyclic radicals of 6 to 12 carbon atoms having at least one aromatic ring. Exemplary aryl groups include, but are not limited to, 1,2,3,4-tetrahydronaphthalene, 1,2-dihydronaphthalene, indanyl, 1H-indenyl, pyridinyl, pyrimidinyl, furanyl, thienyl, imidazolyl, thiazolyl, pyrazolyl, pyridazinyl, pyrazinyl, triazinyl, tetrazolyl, indolyl, benzyl, phenyl, naphthyl, anthracenyl, azulenyl, fluorenyl, indanyl, indenyl, naphthyl, phenyl, tetrahydronaphthyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl, and the like. In some embodiments, 1, 2, 3, or 4 hydrogen atoms of each ring can be substituted by a substituent.

The alkyl, lower alkyl and aryl groups can be substituted or unsubstituted. When substituted, there will generally be, for example, 1 to 4 substituents present. These substituents may optionally form a ring with the alkyl, lower alkyl or aryl group with which they are connected. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl, more preferably, for example, methoxy and ethoxy), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The term "heteroaryl," refers to an aromatic mono- or polycyclic radical of 5 to 12 atoms having at least one aromatic ring containing one, two, three, or four ring heteroatoms selected from N, O, and S, with the remaining ring atoms being C. One or two ring carbon atoms of the heteroaryl group can be replaced with a carbonyl group. For example, the term "heteroaryl" can refer to an aromatic 5-8 membered monocyclic, 8-12 membered fused bicyclic, or 11-14 membered fused tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively. $C_x$ heteroaryl and $C_x$-$C_y$ heteroaryl are typically used where X and Y indicate the number of carbon atoms in the ring system. Heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2,3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3c]pyridine, pyrrolo[3,2-c]pyridine, pyrrolo[3,2-b]pyridine, pyrrolo[2,3-d]pyrimidine, pyrrolo[3,2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo[3,2,1-hi]indole, indolizine, pyrido[1,2-a]indole, 2(1H)-pyridinone, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Some exemplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, 2-amino-4-oxo-3,4-dihydropteridin-6-yl, tetrahydroisoquinolinyl, and the like. In some embodiments, 1, 2, 3, or 4 hydrogen atoms of each ring may be substituted by a substituent.

The heterocycloalkyl and heteroaryl groups described above can be substituted independently with one, two, or three substituents. Substituents can include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl, benzothiazoyl and carbolinyl).

As used herein, the term "alkoxy" means alkyl-O—; and "alkoyl" means alkyl-CO—. Alkoxy substituent groups or alkoxy-containing substituent groups may be substituted by, for example, one or more alkyl groups.

As used herein, the term "halogen" means a fluorine, chlorine, bromine or iodine radical, preferably a fluorine, chlorine or bromine radical, and more preferably a bromine or chlorine radical. The term "cyano" means the radical —CN.

The term, "heteroatom" refers to an atom that is not a carbon atom. Particular examples of heteroatoms include, but are not limited to nitrogen, oxygen, sulfur and halogens. A "heteroatom moiety" includes a moiety where the atom by which the moiety is attached is not a carbon. Examples of heteroatom moieties include —N=, —NR$^N$—, —N$^+$(O$^-$)=, —O—, —S— or —S(O)$_2$—, —OS(O)$_2$—, and —SS—, wherein R$^N$ is H or a further substituent.

The term "hydroxy" means the radical —OH.

The term "imine derivative" means a derivative comprising the moiety —C(NR)—, wherein R comprises a hydrogen or carbon atom alpha to the nitrogen.

The term "nitro" means the radical —NO$_2$.

An "oxaaliphatic," "oxaalicyclic," or "oxaaromatic" mean an aliphatic, alicyclic, or aromatic, as defined herein, except where one or more oxygen atoms (—O—) are positioned between carbon atoms of the aliphatic, alicyclic, or aromatic respectively.

An "oxoaliphatic," "oxoalicyclic," or "oxoaromatic" means an aliphatic, alicyclic, or aromatic, as defined herein, substituted with a carbonyl group. The carbonyl group can be an aldehyde, ketone, ester, amide, acid, or acid halide As used herein, the term "amino" means —NH$_2$. The term "alkylamino" means a nitrogen moiety having at least one straight or branched unsaturated aliphatic, cyclyl, or heterocyclyl radicals attached to the nitrogen. For example, representative amino groups include —NH$_2$, —NHCH$_3$, —N(CH$_3$)$_2$, —NH(C$_1$-C$_{10}$alkyl), —N(C$_1$-C$_{10}$alkyl)$_2$, and the like. The term "alkylamino" includes "alkenylamino," "alkynylamino," "cyclylamino," and "heterocyclylamino." The term "arylamino" means a nitrogen moiety having at least one aryl radical attached to the nitrogen. For example —NHaryl, and —N(aryl)$_2$. The term "heteroarylamino" means a nitrogen moiety having at least one heteroaryl radical attached to the nitrogen. For example —NHheteroaryl, and —N(heteroaryl)$_2$. Optionally, two substituents together with the nitrogen can also form a ring. Unless indicated otherwise, the compounds described herein containing amino moieties can include protected derivatives thereof. Suitable protecting groups for amino moieties include acetyl, tert-butoxycarbonyl, benzyloxycarbonyl, and the like.

The term "aralkyl", as used herein, refers to an alkyl group substituted with an aryl group (e.g., an aromatic or heteroaromatic group).

The term "alkylthio" refers to an alkyl group, as defined above, having a sulfur radical attached thereto. In preferred embodiments, the "alkylthio" moiety is represented by one of —S-alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups.

The term "sulfinyl" means the radical —SO—. It is noted that the sulfinyl radical can be further substituted with a variety of substituents to form different sulfinyl groups including sulfinic acids, sulfinamides, sulfinyl esters, sulfoxides, and the like.

The term "sulfonyl" means the radical —SO$_2$—. It is noted that the sulfonyl radical can be further substituted with a variety of substituents to form different sulfonyl groups including sulfonic acids (—SO$_3$H), sulfonamides, sulfonate esters, sulfones, and the like.

The term "thiocarbonyl" means the radical —C(S)—. It is noted that the thiocarbonyl radical can be further substituted with a variety of substituents to form different thiocarbonyl groups including thioacids, thioamides, thioesters, thioketones, and the like.

The term "aminoalkyl" means an alkyl, alkenyl, and alkynyl as defined above, except where one or more substituted or unsubstituted nitrogen atoms (—N—) are positioned between carbon atoms of the alkyl, alkenyl, or alkynyl. For example, an (C$_2$-C$_6$) aminoalkyl refers to a chain comprising between 2 and 6 carbons and one or more nitrogen atoms positioned between the carbon atoms.

The term "alkoxyalkoxy" means —O-(alkyl)-O-(alkyl), such as —OCH$_2$CH$_2$OCH$_3$, and the like.

The term "alkoxycarbonyl" means —C(O)O-(alkyl), such as —C(=O)OCH$_3$, —C(=O)OCH$_2$CH$_3$, and the like.

The term "alkoxyalkyl" means -(alkyl)-O-(alkyl), such as —CH$_2$OCH$_3$, —CH$_2$OCH$_2$CH$_3$, and the like.

The term "aryloxy" means —O-(aryl), such as —O-phenyl, —O-pyridinyl, and the like.

The term "arylalkyl" means -(alkyl)-(aryl), such as benzyl (i.e., —CH$_2$phenyl), —CH$_2$-pyrindinyl, and the like.

The term "arylalkyloxy" means —O-(alkyl)-(aryl), such as —O-benzyl, —O—CH$_2$-pyridinyl, and the like.

The term "cycloalkyloxy" means —O-(cycloalkyl), such as —O-cyclohexyl, and the like.

The term "cycloalkylalkyloxy" means —O-(alkyl)-(cycloalkyl, such as —OCH$_2$cyclohexyl, and the like.

The term "aminoalkoxy" means —O-(alkyl)-NH$_2$, such as —OCH$_2$NH$_2$, —OCH$_2$CH$_2$NH$_2$, and the like.

The term "mono- or di-alkylamino" means —NH(alkyl) or —N(alkyl)(alkyl), respectively, such as —NHCH$_3$, —N(CH$_3$)$_2$, and the like.

The term "mono- or di-alkylaminoalkoxy" means —O-(alkyl)-NH(alkyl) or —O-(alkyl)-N(alkyl)(alkyl), respectively, such as —OCH$_2$NHCH$_3$, —OCH$_2$CH$_2$N(CH$_3$)$_2$, and the like.

The term "arylamino" means —NH(aryl), such as —NH-phenyl, —NH-pyridinyl, and the like.

The term "arylalkylamino" means —NH-(alkyl)-(aryl), such as —NH-benzyl, —NHCH$_2$-pyridinyl, and the like.

The term "cycloalkylamino" means —NH-(cycloalkyl), such as —NH-cyclohexyl, and the like.

The term "cycloalkylalkylamino" —NH-(alkyl)-(cycloalkyl), such as —NHCH$_2$-cyclohexyl, and the like.

It is noted in regard to all of the definitions provided herein that the definitions should be interpreted as being open ended in the sense that further substituents beyond those specified may be included. Hence, a C$_1$ alkyl indicates that there is one carbon atom but does not indicate what are the substituents on the carbon atom. Hence, a C$_1$ alkyl comprises methyl (i.e., —CH$_3$) as well as —CR$_a$R$_b$R$_c$ where R$_a$, R$_b$, and R$_c$ can each independently be hydrogen or any other substituent where the atom alpha to the carbon is a heteroatom or cyano. Hence, CF$_3$, CH$_2$OH and CH$_2$CN are all C$_1$ alkyls.

The term "optionally substituted" means that the specified group or moiety is unsubstituted or is substituted with one or more (typically 1, 2, 3, 4, or 5) of the hydrogen atoms on the substituted moiety with substituents independently selected from the group of substituents listed below in the definition for "substituents" or otherwise specified. In general, a non-hydrogen substituent can be any substituent that can be bound to an atom of the given moiety that is specified to be substituted.

The term "substituent" refers to a group "substituted" on the substituted entity at any atom of that entity. Examples of substituents include, but are not limited to, acyl, acylamino, acyloxy, aldehyde, alicyclic, aliphatic, alkanesulfonamido, alkanesulfonyl, alkaryl, alkenyl, alkoxy, alkoxycarbonyl, alkyl, alkylamino, alkylcarbanoyl, alkylene, alkylidene, alkylthios, alkynyl, amide, amido, amino, amino, aminoalkyl, aralkyl, aralkylsulfonamido, arenesulfonamido, arenesulfonyl, aromatic, aryl, arylamino, arylcarbanoyl, aryloxy, azido, carbamoyl, carbonyl, carbonyls (including ketones, carboxy, carboxylates, CF$_3$, cyano (CN), cycloalkyl, cycloalkylene, ester, ether, haloalkyl, halogen, halogen, heteroaryl, heterocyclyl, hydroxy, hydroxy, hydroxyalkyl, imino, iminoketone, ketone, mercapto, nitro, oxaalkyl, oxo, oxoalkyl, phosphoryl (including phosphonate and phosphinate), silyl groups, sulfonamido, sulfonyl (including sulfate, sulfamoyl and sulfonate), thiols, and ureido moieties, each of which may optionally also be substituted or unsubstituted. In some cases, two substituents, together with the carbon(s) to which they are attached to, can form a ring. In some embodiments, the substituent group is selected from alkyl, ester, amide, monocarbonyl, dicarbonyl, ketones, aldehydes, and the like. As used herein, the term, "aromatic" means a moiety wherein the constituent atoms make up an unsaturated ring system, all atoms in the ring system are sp$^2$ hybridized and the total number of pi electrons is equal to 4n+2. An aromatic ring can be such that the ring atoms are only carbon atoms (e.g., aryl) or can include carbon and non-carbon atoms (e.g., heteroaryl).

Compounds of formula I can have one or more asymmetric carbon or sulfur atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). The invention embraces all of these forms. The invention encompasses the compounds as individual isomers substantially free of other isomers and alternatively, as mixtures of various isomers, e.g., racemic mixtures of enantiomers.

Certain compounds, as described herein can have one or more double bonds that can exist as either a Z or E isomer, unless otherwise indicated. The compounds disclosed herein can also have axial chirality. As used herein, the term "axial chirality", refers to chirality in which a molecule, or a portion thereof, does not possess a stereogenic center but has an axis of chirality about which a set of substituents is held in a spatial arrangement that is not superimposable on its minor image. Axial chirality may be observed, for example, in atropisomeric biaryl compounds where the rotation about the aryl-aryl bond is restricted. It will be appreciated that a compound of the present invention may possess axial chirality whether or not other stereogenic centers are present elsewhere in the molecule.

As used here in the term "isomer" refers to compounds having the same molecular formula but differing in structure. Isomers which differ only in configuration and/or conformation are referred to as "stereoisomers." The term "isomer" is also used to refer to an enantiomer.

The term "enantiomer" is used to describe one of a pair of molecular isomers which are mirror images of each other and non-superimposable. Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate plane polarized light in different directions). Enantiomers generally have identical physical properties, such as melting points and boiling points, and also have identical spectroscopic properties. Enantiomers can differ from each other with respect to their interaction with plane-polarized light and with respect to biological activity.

The designations "R and S" are used to denote the absolute configuration of the molecule about its chiral center(s). The designations may appear as a prefix or as a suffix; they may or may not be separated from the isomer by a hyphen; they may or may not be hyphenated; and they may or may not be surrounded by parentheses.

The designations or prefixes "(+) and (−)" are employed to designate the sign of rotation of plane-polarized light by the compound, with (−) meaning that the compound is levorotatory (rotates to the left). A compound prefixed with (+) is dextrorotatory (rotates to the right).

The term "racemic mixture," "racemic compound" or "racemate" refers to a mixture of the two enantiomers of one compound. An ideal racemic mixture is one wherein there is a 50:50 mixture of both enantiomers of a compound such that the optical rotation of the (+) enantiomer cancels out the optical rotation of the (−) enantiomer.

The term "resolving" or "resolution" when used in reference to a racemic mixture refers to the separation of a racemate into its two enantiomorphic forms (i.e., (+) and (−); 65 (R) and (S) forms). The terms can also refer to enantioselective conversion of one isomer of a racemate to a product.

The term "enantiomeric excess" or "ee" refers to a reaction product wherein one enantiomer is produced in excess of the other, and is defined for a mixture of (+)- and (−)-enantiomers, with composition given as the mole or weight or volume fraction F$_{(+)}$ and F$_{(−)}$ (where the sum of F$_{(+)}$ and F$_{(−)}$=1). The enantiomeric excess is defined as *F$_{(+)}$−F$_{(−)}$* and the percent enantiomeric excess by 100×*F$_{(+)}$−F$_{(−)}$*. The "purity" of an enantiomer is described by its ee or percent ee value (% ee).

Whether expressed as a "purified enantiomer" or a "pure enantiomer" or a "resolved enantiomer" or "a compound in enantiomeric excess", the terms are meant to indicate that the amount of one enantiomer exceeds the amount of the other. Thus, when referring to an enantiomer preparation, both (or either) of the percent of the major enantiomer (e.g. by mole or by weight or by volume) and (or) the percent enantiomeric excess of the major enantiomer may be used to determine whether the preparation represents a purified enantiomer preparation.

The term "enantiomeric purity" or "enantiomer purity" of an isomer refers to a qualitative or quantitative measure of the purified enantiomer; typically, the measurement is expressed on the basis of ee or enantiomeric excess.

The terms "substantially purified enantiomer," "substantially resolved enantiomer" "substantially purified enantiomer preparation" are meant to indicate a preparation (e.g. derived from non optically active starting material, substrate, or intermediate) wherein one enantiomer has been enriched over the other, and more preferably, wherein the other enantiomer represents less than 20%, more preferably less than 10%, and more preferably less than 5%, and still more preferably, less than 2% of the enantiomer or enantiomer preparation.

The terms "purified enantiomer," "resolved enantiomer" and "purified enantiomer preparation" are meant to indicate a preparation (e.g. derived from non optically active starting material, substrates or intermediates) wherein one enantiomer (for example, the R-enantiomer) is enriched over the other, and more preferably, wherein the other enantiomer (for example the S-enantiomer) represents less than 30%, preferably less than 20%, more preferably less than 10% (e.g. in this particular instance, the R-enantiomer is substantially free of the S-enantiomer), and more preferably less than 5% and still more preferably, less than 2% of the preparation. A purified enantiomer may be synthesized substantially free of the other enantiomer, or a purified enantiomer may be synthesized in a stereopreferred procedure, followed by separation steps, or a purified enantiomer may be derived from a racemic mixture.

The term "enantioselectivity," also called the enantiomeric ratio indicated by the symbol "E," refers to the selective capacity of an enzyme to generate from a racemic substrate one enantiomer relative to the other in a product racemic mixture; in other words, it is a measure of the ability of the enzyme to distinguish between enantiomers. A non-selective reaction has an E of 1, while resolutions with E's above 20 are generally considered useful for synthesis or resolution. The enantioselectivity resides in a difference in conversion rates between the enantiomers in question. Reaction products are obtained that are enriched in one of the enantiomers; conversely, remaining substrates are enriched in the other enantiomer. For practical purposes it is generally desirable for one of the enantiomers to be obtained in large excess. This is achieved by terminating the conversion process at a certain degree of conversion.

In some embodiments, the compounds disclosed herein are pure isomers or enantiomers.

The term "analog" as used herein refers to a compound that results from substitution, replacement or deletion of various organic groups or hydrogen atoms from a parent compound. As such, some monoterpenoids can be considered to be analogs of monoterpenes, or in some cases, analogs of other monoterpenoids, including derivatives of monoterpenes. An analog is structurally similar to the parent compound, but can differ by even a single element of the same valence and group of the periodic table as the element it replaces.

The term "derivative" as used herein refers to a chemical substance related structurally to another, i.e., an "original" substance, which can be referred to as a "parent" compound. A "derivative" can be made from the structurally-related parent compound in one or more steps. The phrase "closely related derivative" means a derivative whose molecular weight does not exceed the weight of the parent compound by more than 50%. The general physical and chemical properties of a closely related derivative are also similar to the parent compound.

As used herein, a "prodrug" refers to compounds that can be converted via some chemical or physiological process (e.g., enzymatic processes and metabolic hydrolysis) to a therapeutic agent. Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* ll:345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", Arfv. *Drug Delivery Rev.* 8(1): 1-38 (1992); Fleisher et al. "Improved oral drug delivery: solubility limitations overcome by the use of prodrugs", Arfv. *Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.,* 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.,* 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Prodrug, molecular structure and percutaneous delivery", *Des. Biopharm. Prop. Prodrugs Analogs, [Symp.]* Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.,* 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.:* 39(1-3):63-80 (1999); Waller et al., "Prodrugs", *Br. J. Clin. Pharmac.* 28: 497-507 (1989), content of all of which is herein incorporated by reference in its entirety.

As used herein, the term "pharmaceutically-acceptable salts" refers to the conventional nontoxic salts or quaternary ammonium salts of therapeutic agents, e.g., from non-toxic organic or inorganic acids. These salts can be prepared in situ in the administration vehicle or the dosage form manufacturing process, or by separately reacting a therapeutic agent in its free base or acid form with a suitable organic or inorganic acid or base, and isolating the salt thus formed during subsequent purification. Conventional nontoxic salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", *J. Pharm. Sci.* 66:1-19 (1977), content of which is herein incorporated by reference in its entirety.

In some embodiments of the aspects described herein, representative salts include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

The disclosure is further illustrated by the following examples which should not be construed as limiting. The examples are illustrative only, and are not intended to limit, in any manner, any of the aspects described herein. The following examples do not in any way limit the invention.

EXAMPLES

General synthesis and analysis experimental details: All reagents were used as received from commercial suppliers. The $^1$H NMR spectra were recorded on a 400 MHz Bruker Avance spectrometer equipped with a broadband observe probe or a 500 MHz Bruker AVIII spectrometer equipped with a dual cryoprobe. The $^{13}$C NMR spectra were recorded on a 500 MHz Bruker AVIII spectrometer equipped with a dual cryoprobe (at 125 MHz). Column chromatography separations were performed using the Teledyne Isco CombiFlash $R_f$ using RediSep $R_f$ silica gel or RediSep $R_f$ C18 High Performance Gold columns. The analytical RPLC method used an Agilent 1200 RRLC system with UV detection (Agilent 1200 DAD SL) and mass detection (Agilent 6224 TOF). The analytical method conditions included a Waters Aquity BEH C18 column (2.1×50 mm, 1.7 µm) and elution with a linear gradient of 5% acetonitrile in pH 9.8 buffered aqueous ammonium formate to 100% acetonitrile at 0.4 mL/min flow rate. Compound purity was measured on the basis of peak integration (area under the curve) from UV-vis absorbance at 214 nm, and compound identity was determined on the basis of mass spectral and NMR analyses. All compounds used for biological studies have purity of >92%.

Example 1: 4-((1,4-Dioxo-1,4-dihydronaphthalen-2-yl)amino)benzenesulfonamide

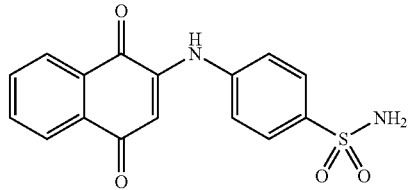 [SMILES: NS(=O)(=O)c1ccc(NC2=CC(=O)c3ccccc3C2=O)cc1]

Cerium chloride heptahydrate (36 mg; 97 µmol), followed by 4-aminobenzenesulfonamide (689 mg; 4.00 mmol), was added to a suspension of naphthalene-1,4-dione (316 mg; 2.00 mmol) in 95% ethanol (8.0 mL). The reaction vial was capped then put into a 75° C. block. After three days the reaction was cooled to room temperature, then 80 mL of 1.0 M citric acid was added with vigorous stirring. The insoluble material was collected by filtration, washed with water, and dried in vacuo at 45° C. affording crude product as a rust colored solid (370 mg). A portion of this (225 mg) was purified by pRPLC yielding 4-((1,4-dioxo-1,4-dihydronaphthalen-2-yl)amino)benzenesulfonamide as a rust-colored solid (101 mg). $^1$H NMR (400 MHz, DMSO-d$_6$) δ 9.45 (s, 1H), 8.09 (dd, J=1.0, 7.6 Hz, 1H), 7.98 (dd, J=1.1, 7.6 Hz, 1H), 7.92-7.79 (m, 4H), 7.60 (m, 2H), 7.37 (s, 2H), 6.33 (s, 1H). $^{13}$C NMR (125 MHz, DMSO-d$_6$) δ 183.0, 181.3, 145.2, 141.5, 139.6, 134.9, 132.9, 132.3, 130.4, 127.0, 126.2, 125.3, 122.7, 103.8. LC-MS (ESI+): Purity at 214 nm is 100%. HRMS: 329.0591 (calcd for C$_{16}$H$_{13}$N$_2$O$_4$S=[M+H]$^+$); 329.0594 (found/[M+H]$^+$).

Example 2: Synthesis of Exemplary Embodiments of the Compounds

General Experimental Section:
HPLC/MS analysis was carried out with gradient elution (5% CH3CN to 100% CH3CN) on an Agilent 1200 RRLC with a photodiode array UV detector and an Agilent 6224 TOF mass spectrometer (also used to produce high resolution mass spectra). Automated preparative RP HPLC purification was carried out by Mass Directed Fractionation with gradient elution (a narrow CH3CN gradient was chosen based on the retention time of the target from LCMS analysis of the crude sample) on an Agilent 1200 instrument with photodiode array detector, an Agilent 6120 quadrupole mass spectrometer, and a HTPAL LEAP autosampler. Fractions were triggered using an MS and UV threshold determined by HPLC/MS analysis of the crude sample. One of two column/mobile phase conditions were chosen for both analysis and purification to promote the targets neutral state: 0.02% formic acid with Waters Atlantis T3 5 um, 19×150 mm (Prep scale), Waters Atlantis T3 1.7 um, 2.1×50 mm (Analytical Scale); pH 9.8 NH4OH with Waters XBridge C18 Sum, 19×150 mm (Prep scale), Waters BEH C-18 1.7 um, 2.1×50 mm (Analytical Scale). Medium pressure liquid chromatography (MPLC) was preformed on a Teledyne Icso CombiFlash Rf purification system using gradient elution through standard RediSep Rf columns.

Synthetic Protocols for Intermediates

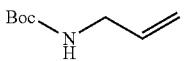

KSC-288-055-1 tert-butyl allylcarbamate (KSC-288-055-1)

Allylamine (0.75 mL, 10.02 mmol), abs. EtOH (50 mL), and Boc$_2$O (2.40 g, 11.00 mmol) were stirred at room temperature under air until the effervescence subsided. Imidazole (0.81 g, 11.90 mmol) was then added and the reaction continued at room temperature under air for 1 h. The reaction was then concentrated in vacuo. The crude residue was purified via MPLC (silica, 10-20% hexanes/EtOAc) to provide KSC-288-055-1 (1.2637 g, 8.04 mmol, 80% yield). $^1$H NMR (500 MHz, Chloroform-d) δ 5.82 (ddt, J=15.8, 10.6, 5.4 Hz, 1H), 5.15 (dq, J=17.2, 1.6 Hz, 1H), 5.08 (dq, J=10.3, 1.4 Hz, 1H), 4.73 (s, 1H), 3.79-3.60 (m, 2H), 1.43 (s, 9H); $^{13}$C NMR (126 MHz, CDCl$_3$) δ 155.77, 134.91, 115.59, 79.25, 43.02, 28.36; HRMS (ESI-TOF) m/z: [M-C$_5$H$_9$O$_2$+2H]$^+$ Calcd for C$_3$H$_8$N 58.0651; Found 58.0661.

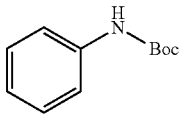

KSC-292-001-1 tert-butyl phenylcarbamate (KSC-292-001-1)

To a stirred solution of Boc$_2$O (784.8 mg, 3.60 mmol) and guanidine monohydrochloride (46.8 mg, 0.490 mmol), in abs. EtOH (4.0 mL) was added aniline (280.3 mg, 3.01 mmol). The reaction mixture was heated to 38° C. and stirred under air for 3 h then concentrated in vacuo. The residue was redissolved in dichloromethane and filtered. The filtrate was concentrated in vacuo to afford KSC-292-001-1 (579.7 mg, 3.00 mmol, 100% yield) which was used without further purification. HRMS (ESI-TOF) m/z: [M-C$_5$H$_9$O$_2$]$^+$ Calcd for C$_6$H$_6$N 92.0495. Found 92.0497.

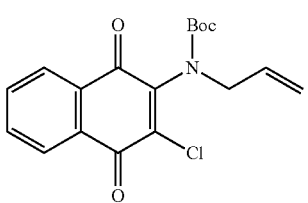

KSC-288-079-1 tert-butyl allyl(3-chloro-1,4-dioxo-1,4-dihydronaphthalen-2-yl)carbamate (KSC-288-079-1)

To a flame-dried flask was added KSC-288-055-1 (924.8 mg, 5.88 mmol) (pp. 41) and anhydrous THF (5.0 mL). The solution was cooled to −78° C. and then 2.15 M n-butyllithium (2.8 mL, 6.02 mmol) in hexanes was slowly added. The ice bath was removed and the solution was allowed to stir at room temperature under argon for 30 minutes, after which time 2,3-dichloronaphthalene-1,4-dione (1.2717 g, 5.60 mmol) was added at once. The mixture was stirred 16 h, after which time the mixture was quenched with water and extracted 3 times with EtOAc. The EtOAc layers were combined, dried (Na$_2$SO$_4$), filtered, and concentrated in vacuo. The crude residue was purified via MPLC (silica, 100% hexanes→10% EtOAc/hexanes) to provide KSC-288-079-1 (996.3 mg, 2.86 mmol, 51.1% yield) as a brown oil. $^1$H NMR (400 MHz, Chloroform-d) δ 8.18-8.07 (m, 2H), 7.82-7.71 (m, 2H), 5.93-5.76 (m, 1H), 5.13 (dq, J=17.1, 1.3 Hz, 1H), 5.08-4.99 (m, 1H), 4.49-4.21 (m, 1H), 4.14 (dd, J=14.8, 7.1 Hz, 1H), 1.36 (s, 9H); $^{13}$C NMR (101 MHz, CDCl$_3$) δ 178.15, 152.82, 134.55, 134.21, 132.72, 131.24, 131.11, 127.32, 127.24, 118.74, 82.05, 28.02, 27.80; HRMS (ESI-TOF) m/z: [M-C$_5$H$_9$O$_2$+2H]$^+$ Calcd for C$_{13}$H$_{11}$ClNO$_2$ 248.0473. Found 248.0476.

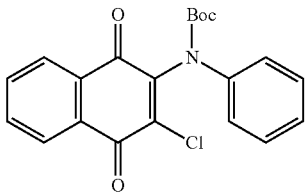

KSC-292-002-1 tert-butyl (3-chloro-1,4-dioxo-1,4-dihydronaphthalen-2-yl)(phenyl)carbamate (KSC-292-002-1)

This compound was prepared using the same protocol described for KSC-288-079-1 (pp. 42) using KSC-292-001-1 (pp. 42). Yield: 721.8 mg; 61%. $^1$H NMR (400 MHz, Chloroform-d) δ 8.27-8.17 (m, 2H), 7.88-7.79 (m, 2H), 7.41-7.22 (m, 5H), 1.47 (s, 9H); $^{13}$C NMR (101 MHz, CDCl$_3$) δ 179.71, 178.35, 152.12, 145.42, 139.83, 134.60, 134.34, 131.39, 131.18, 128.87, 127.42, 127.36, 126.72, 126.14, 82.98, 28.00; HRMS (ESI-TOF) m/z: [M+H]$^+$ Calcd for C$_{21}$H$_{19}$ClNO$_4$ 384.0997. Found 384.0998.

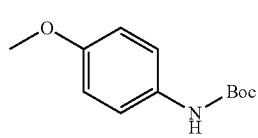

KSC-304-076-1 tert-butyl(4-methoxyphenyl)carbamate (KSC-304-076-1)

This compound was prepared using the same protocol described for KSC-292-001-1 (pp. 42) using 4-methoxyaniline. Yield: 669.6 mg; quant. $^1$H NMR (400 MHz, DMSO-$d_6$) δ 9.17 (s, 1H), 7.40 (d, J=8.7 Hz, 2H), 6.94-6.82 (m, 2H), 3.75 (s, 3H), 1.52 (s, 9H); HRMS (ESI-TOF) m/z: [M-$C_5H_9O_2$]$^+$ Calcd for $C_7H_8NO$ 122.0600. Found 122.0598.

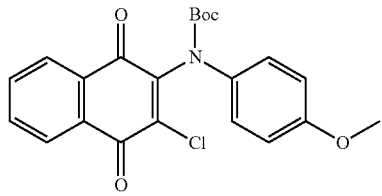

KSC-307-001-1 tert-butyl (3-chloro-1,4-dioxo-1,4-dihydronaphthalen-2-yl)(4-methoxyphenyl)carbamate (KSC-307-001-1)

This compound was prepared using the same protocol described for KSC-288-079-1 (pp. 42) using KSC-304-076-1 (pp. 43). Yield: 723.6 mg; 60%. $^1$H NMR (400 MHz, DMSO-$d_6$) δ 8.18-8.08 (m, 2H), 7.99-7.91 (m, 2H), 7.28-7.19 (m, 2H), 6.95-6.86 (m, 2H), 3.76 (s, 3H), 1.36 (s, 9H); HRMS (ESI-TOF) m/z: [M+H]$^+$ Calcd for $C_{22}H_{21}ClNO_5$ 414.1103. Found 414.1107.

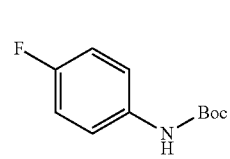

KSC-304-081-1 tert-butyl(4-fluorophenyl)carbamate (KSC-304-081-1)

This compound was prepared using the same protocol described for KSC-292-001-1 (pp. 42) using 4-fluoroaniline. Yield: 615.0 mg; 98%. $^1$H NMR (400 MHz, DMSO-$d_6$) δ 9.43 (s, 1H), 7.51 (dd, J=8.9, 5.0 Hz, 2H), 7.21-7.07 (m, 2H), 1.53 (s, 9H); HRMS (ESI-TOF) m/z: [M-$C_5H_9O_2$]$^+$ Calcd for $C_6H_5FN$ 110.0401. Found 110.0403.

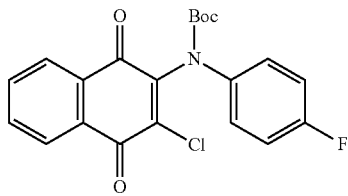

KSC-307-006-1 tert-butyl (3-chloro-1,4-dioxo-1,4-dihydronaphthalen-2-yl)(4-fluorophenyl)carbamate (KSC-307-006-1)

This compound was prepared using the same protocol described for KSC-288-079-1 (pp. 42) using KSC-304-081-1 (pp. 44). Yield: 931.3 mg; 81%. $^1$H NMR (400 MHz, DMSO-$d_6$) δ 8.19-8.07 (m, 2H), 8.01-7.90 (m, 2H), 7.43-7.32 (m, 2H), 7.27-7.14 (m, 2H), 1.37 (s, 9H); HRMS (ESI-TOF) m/z: [M-$C_5H_9O_2$]$^+$ Calcd for $C_{16}H_8ClFNO_2$ 300.0222. Found 300.0226.

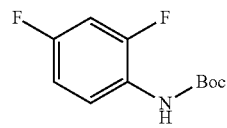

KSC-304-082-1 tert-butyl(2,4-difluorophenyl)carbamate (KSC-304-082-1)

This compound was prepared using the same protocol described for KSC-292-001-1 (pp. 42) using 2,4-difluoroaniline. Yield: 591.4 mg; 86%. $^1$H NMR (400 MHz, DMSO-$d_6$) δ 8.87 (s, 1H), 7.59-7.36 (m, 1H), 7.18 (ddd, J=11.0, 9.0, 2.9 Hz, 1H), 7.02-6.83 (m, 1H), 1.38 (s, 9H); HRMS (ESI-TOF) m/z: [M-$C_5H_9O_2$]$^+$ Calcd for $C_6H_4F_2N$ 128.0306. Found 128.0307.

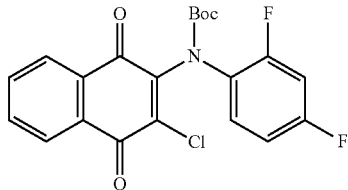

KSC-307-007-1 tert-butyl (3-chloro-1,4-dioxo-1,4-dihydronaphthalen-2-yl)(2,4-difluorophenyl)carbamate (KSC-307-007-1)

This compound was prepared using the same protocol described for KSC-288-079-1 (pp. 42) using KSC-304-082-1 (pp. 44). Yield: 652.3 mg; 62%. $^1$H NMR (400 MHz, DMSO-$d_6$) δ 8.18-8.07 (m, 2H), 8.01-7.91 (m, 2H), 7.43 (ddd, J=11.7, 9.1, 2.8 Hz, 1H), 7.29 (td, J=8.9, 6.0 Hz, 1H), 7.13-7.02 (m, 1H), 1.38 (s, 9H); HRMS (ESI-TOF) m/z: [M-$C_5H_9O_2$]$^+$ Calcd for $C_{16}H_7ClF_2NO_2$ 318.0128. Found 318.0136.

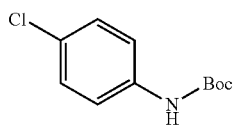

tert-butyl(4-chlorophenyl)carbamate
(KSC-304-078-1)

This compound was prepared using the same protocol described for KSC-292-001-1 (pp. 42) using 4-chloroaniline. Yield: 677.4 mg; 99%. $^1$H NMR (400 MHz, Chloroform-d) δ 9.49 (s, 1H), 7.52-7.42 (m, 2H), 7.34-7.24 (m, 2H), 1.47 (s, 9H); HRMS (ESI-TOF) m/z: [M-C$_5$H$_9$O$_2$]$^+$ Calcd for C$_6$H$_5$ClN 126.0105. Found 126.0107.

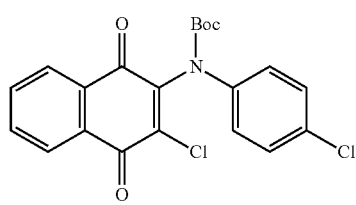

tert-butyl (3-chloro-1,4-dioxo-1,4-dihydronaphthalen-2-yl)(4-chlorophenyl)carbamate (KSC-307-003-1)

This compound was prepared using the same protocol described for KSC-288-079-1 (pp. 42) using KSC-304-078-1 (pp. 45). Yield: 877 mg; 72%. $^1$H NMR (400 MHz, DMSO-d$_6$) δ 8.18-8.11 (m, 2H), 8.00-7.93 (m, 2H), 7.46-7.35 (m, 4H), 1.37 (s, 9H); HRMS (ESI-TOF) m/z: [M-C$_5$H$_9$O$_2$+2H]$^+$ Calcd for C$_{16}$H$_{10}$Cl$_2$NO$_2$ 318.0083. Found 318.0086.

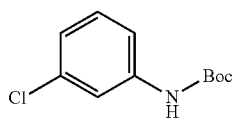

tert-butyl(3-chlorophenyl)carbamate
(KSC-304-083-1)

This compound was prepared using the same protocol described for KSC-292-001-1 (pp. 42) using 3-chloroaniline. Yield: 840.0 mg; quant. $^1$H NMR (400 MHz, DMSO-d$_6$) δ 9.51 (s, 1H), 7.55 (t, J=1.8 Hz, 1H), 7.29 (ddd, J=8.3, 1.9, 0.9 Hz, 1H), 7.20 (t, J=8.1 Hz, 1H), 6.93 (ddd, J=7.9, 2.1, 1.0 Hz, 1H), 1.41 (s, 9H); HRMS (ESI-TOF) m/z: [M-C$_5$H$_9$O$_2$]$^+$ Calcd for C$_6$H$_5$ClN 126.0105. Found 126.0105.

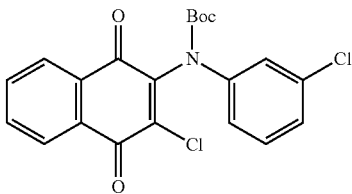

tert-butyl (3-chloro-1,4-dioxo-1,4-dihydronaphthalen-2-yl)(3-chlorophenyl)carbamate (KSC-307-008-1)

This compound was prepared using the same protocol described for KSC-288-079-1 (pp. 42) using KSC-304-083-1 (pp. 45). Yield: 1.1648 g; 79%. $^1$H NMR (400 MHz, DMSO-d$_6$) δ 8.19-8.09 (m, 2H), 8.00-7.92 (m, 2H), 7.51-7.26 (m, 4H), 1.37 (s, 9H); HRMS (ESI-TOF) m/z: [M-C$_5$H$_9$O$_2$+2H]$^+$ Calcd for C$_{16}$H$_{10}$Cl$_2$NO$_2$ 318.0083. Found 318.0086.

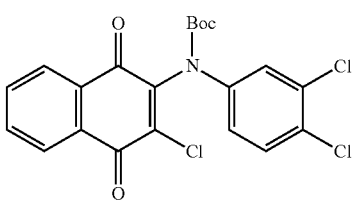

tert-butyl(3,4-dichlorophenyl)carbamate
(KSC-304-080-1)

This compound was prepared using the same protocol described for KSC-292-001-1 (pp. 42) using 3,4-dichloroaniline. Yield: 776.5 mg; quant. $^1$H NMR (400 MHz, DMSO-d$_6$) δ 9.64 (s, 1H), 7.72 (d, J=2.3 Hz, 1H), 7.43 (d, J=8.8 Hz, 1H), 7.32 (dd, J=8.9, 2.5 Hz, 1H), 1.41 (s, 9H); HRMS (ESI-TOF) m/z: [M-C$_5$H$_9$O$_2$]$^+$ Calcd for C$_6$H$_4$Cl$_2$N 159.9715. Found 159.9722.

tert-butyl (3-chloro-1,4-dioxo-1,4-dihydronaphthalen-2-yl)(3,4-dichlorophenyl)carbamate (KSC-307-005-1)

This compound was prepared using the same protocol described for KSC-288-079-1 (pp. 42) using KSC-304-080-1 (pp. 46). Yield: 700 mg; 54%. $^1$H NMR (400 MHz, DMSO-d$_6$) δ 8.23-8.12 (m, 2H), 8.06-7.96 (m, 2H), 7.76-7.62 (m, 2H), 7.46 (dd, J=8.8, 2.6 Hz, 1H), 1.41 (s, 9H); HRMS (ESI-TOF) m/z: [M-C$_5$H$_9$O$_2$+2H]$^+$ Calcd for C$_{16}$H$_9$Cl$_3$NO$_2$ 351.9694. Found 351.9694.

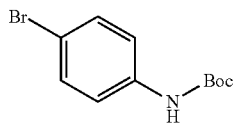

tert-butyl(4-bromophenyl)carbamate (KSC-304-079-1)

This compound was prepared using the same protocol described for KSC-292-001-1 (pp. 42) using 4-bromoaniline. Yield: 800.4 mg; 99%. $^1$H NMR (400 MHz, Chloroform-d) δ 9.50 (s, 1H), 7.42 (s, 4H), 1.47 (s, 9H); HRMS (ESI-TOF) m/z: [M-C$_5$H$_9$O$_2$]$^+$ Calcd for C$_6$H$_5$BrN 169.9600. Found 169.9601.

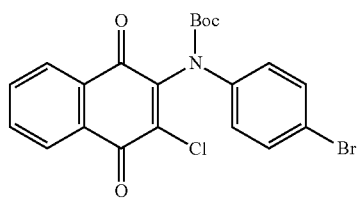

tert-butyl(4-bromophenyl)(3-chloro-1,4-dioxo-1,4-dihydronaphthalen-2-yl)carbamate (KSC-307-004-1)

This compound was prepared using the same protocol described for KSC-288-079-1 (pp. 42) using KSC-304-079-1 (pp. 47). Yield: 756.5 mg; 57%. $^1$H NMR (400 MHz, DMSO-d$_6$) δ 8.24-8.13 (m, 2H), 8.04-7.95 (m, 2H), 7.65-7.51 (m, 2H), 7.45-7.30 (m, 2H), 1.41 (s, 9H); HRMS (ESI-TOF) m/z: [M-C$_5$H$_9$O$_2$+2H]$^+$ Calcd for C$_{16}$H$_{10}$BrClNO$_2$ 361.9578. Found 361.9573.

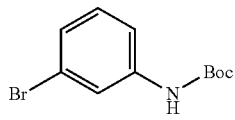

tert-butyl(3-bromophenyl)carbamate (KSC-304-084-1)

This compound was prepared using the same protocol described for KSC-292-001-1 (pp. 42) using 3-bromoaniline. Yield: 976.0 mg; quant. $^1$H NMR (400 MHz, DMSO-d$_6$) δ 9.49 (s, 1H), 7.69 (s, 1H), 7.32 (ddd, J=8.1, 1.9, 1.0 Hz, 1H), 7.14 (t, J=8.0 Hz, 1H), 7.07 (ddd, J=7.9, 1.9, 1.1 Hz, 1H), 1.40 (d, J=2.5 Hz, 9H); HRMS (ESI-TOF) m/z: [M-C$_5$H$_9$O$_2$]$^+$ Calcd for C$_6$H$_5$BrN 169.9600. Found 169.9598.

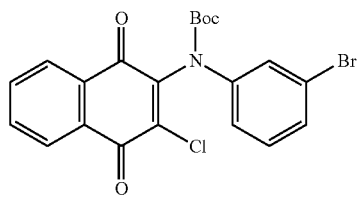

tert-butyl(3-bromophenyl)(3-chloro-1,4-dioxo-1,4-dihydronaphthalen-2-yl)carbamate (KSC-307-009-1)

This compound was prepared using the same protocol described for KSC-288-079-1 (pp. 42) using KSC-304-084-1 (pp. 47). Yield: 1.0605 g; 66%. $^1$H NMR (400 MHz, DMSO-d$_6$) δ 8.20-8.08 (m, 2H), 8.01-7.90 (m, 2H), 7.58 (s, 1H), 7.48-7.26 (m, 3H), 1.37 (s, 9H); HRMS (ESI-TOF) m/z: [M-C$_5$H$_9$O$_2$+H]$^+$ Calcd for C$_{16}$H$_{10}$BrClNO$_2$ 361.9578. Found 361.9579.

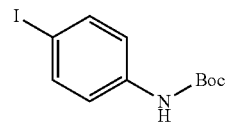

tert-butyl(4-iodophenyl)carbamate (KSC-304-077-1)

This compound was prepared using the same protocol described for KSC-292-001-1 (pp. 42) using 4-iodoaniline. Yield: 936.3 mg; 98%. $^1$H NMR (400 MHz, Chloroform-d) δ 9.47 (s, 1H), 7.64-7.49 (m, 2H), 7.36-7.22 (m, 2H), 1.46 (s, 9H).

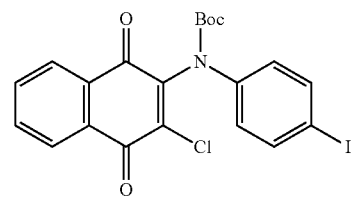

tert-butyl (3-chloro-1,4-dioxo-1,4-dihydronaphthalen-2-yl)(4-iodophenyl)carbamate (KSC-307-002-1)

This compound was prepared using the same protocol described for KSC-288-079-1 (pp. 42) using KSC-304-077-1 (pp. 48). Yield: 599.3 mg; 41%. $^1$H NMR (400 MHz, DMSO-d$_6$) δ 8.23-8.13 (m, 2H), 8.04-7.95 (m, 2H), 7.77-7.71 (m, 1H), 7.44-7.34 (m, 2H), 7.31-7.16 (m, 1H), 1.41 (s, 9H); HRMS (ESI-TOF) m/z: [M-C$_5$H$_9$O$_2$+2H]$^+$ Calcd for C$_{16}$H$_{10}$ClINO$_2$ 409.9439. Found 409.9442.

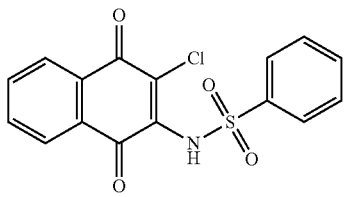

KSC-292-029-1

N-(3-chloro-1,4-dioxo-1,4-dihydronaphthalen-2-yl)benzenesulfonamide (KSC-292-029-1)

This compound was prepared using the same protocol described for KSC-279-067-1 (pp. 51) using the appropriate sulfonyl chloride. Yield: 334.8 mg; 17%. $^1$H NMR (500 MHz, DMSO-d$_6$) δ 7.95-7.90 (m, 1H), 7.90-7.85 (m, 2H), 7.85-7.81 (m, 1H), 7.75 (td, J=7.5, 1.4 Hz, 1H), 7.67 (td, J=7.5, 1.3 Hz, 1H), 7.63-7.55 (m, 1H), 7.48-7.40 (m, 2H), 7.36 (s, 1H); $^{13}$C NMR (126 MHz, DMSO) δ 179.90, 175.57, 152.44, 148.37, 133.72, 132.50, 131.88, 131.75, 131.04, 129.46, 128.90, 127.91, 126.09, 125.52, 125.29, 125.16; HRMS (ESI-TOF) m/z: [M+H]$^+$ Calcd for C$_{16}$H$_{11}$ClNO$_4$S 348.0092. Found 348.0090.

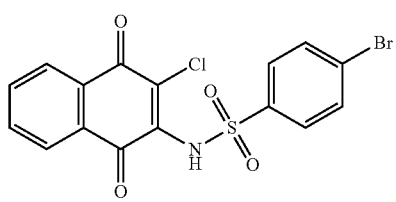

KSC-288-054-1

4-bromo-N-(3-chloro-1,4-dioxo-1,4-dihydronaphthalen-2-yl)benzenesulfonamide (KSC-288-054-1)

This compound was prepared using the same protocol described for KSC-279-067-1 (pp. 51) using the appropriate sulfonyl chloride. Yield: 436.7 mg; 21%. HRMS (ESI-TOF) m/z: [M+H]$^+$ Calcd for C$_{16}$H$_{10}$BrClNO$_4$S 425.9197. Found 425.9195.

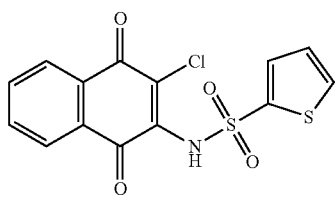

KSC-292-031-1

N-(3-chloro-1,4-dioxo-1,4-dihydronaphthalen-2-yl)thiophene-2-sulfonamide (KSC-292-031-1)

This compound was prepared using the same protocol described for KSC-279-067-1 (pp. 51) using the appropriate sulfonyl chloride. Yield: 437.9 mg; 21%. $^1$H NMR (500 MHz, DMSO-d$_6$) δ 8.10-8.04 (m, 1H), 8.03-7.95 (m, 2H), 7.93-7.86 (m, 2H), 7.74 (dd, J=3.8, 1.3 Hz, 1H), 7.18 (dd, J=5.0, 3.8 Hz, 1H); $^{13}$C NMR (126 MHz, DMSO) δ 178.72, 177.42, 134.56, 134.45, 133.28, 132.60, 131.02, 130.51, 127.42, 126.67, 126.61; HRMS (ESI-TOF) m/z: [M+H]$^+$ Calcd for C$_{14}$H$_9$ClNO$_4$S$_2$ 353.9656. Found 353.9652.

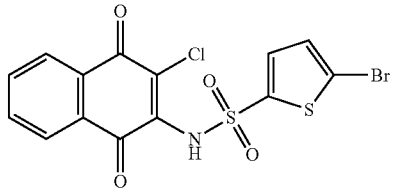

KSC-292-032-1

5-bromo-N-(3-chloro-1,4-dioxo-1,4-dihydronaphthalen-2-yl)thiophene-2-sulfonamide (KSC-292-032-1)

This compound was prepared using the same protocol described for KSC-279-067-1 (pp. 51) using the appropriate sulfonyl chloride. Yield: 783.2 mg; 31%. $^1$H NMR (500 MHz, DMSO-d$_6$) δ 7.91-7.80 (m, 2H), 7.70 (td, J=7.5, 1.4 Hz, 1H), 7.64 (td, J=7.5, 1.4 Hz, 1H), 7.16 (d, J=3.9 Hz, 1H), 7.06 (d, J=3.9 Hz, 1H); $^{13}$C NMR (126 MHz, DMSO) δ 179.37, 176.01, 152.84, 151.36, 133.91, 132.32, 132.18, 130.75, 129.83, 126.92, 126.25, 125.32, 113.85; HRMS (ESI-TOF) m/z: [M+H]$^+$ Calcd for C$_{14}$H$_8$BrClNO$_4$S$_2$ 431.8761. Found 431.8761.

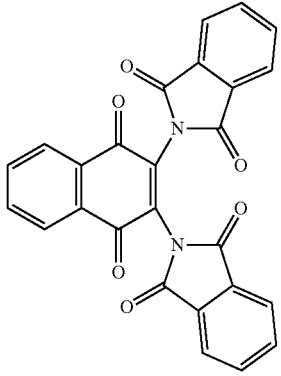

KSC-292-062-1

2,2'-(1,4-dioxo-1,4-dihydronaphthalene-2,3-diyl)bis(isoindoline-1,3-dione) (KSC-292-062-1): To a stirred solution of 2,3-dichloronaphthalene-1,4-dione (2.30 g, 10.1 mmol) in anhydrous MeCN (50 mL) under argon at room temperature was added potassium phthalimide (7.72 g, 41.7 mmol). The mixture was refluxed for 3 h, after which time the mixture was vacuum filtered while hot and the filtrand was subsequently washed with 100 mL of cold acetonitrile, 100 mL cold water, and 100 mL cold MeOH. The filtrand was then dried at 50° C. under vacuum overnight to provide KSC-292-062-1 (5.24 g, 11.7 mmol, 100%) as a yellow powder. HRMS (ESI-TOF) m/z: [M+H]$^+$ Calcd for C$_{26}$H$_{13}$N$_2$O$_6$ 449.0768. Found 449.0763.

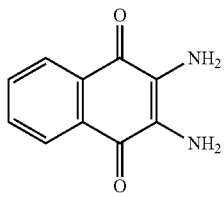

2,3-diaminonaphthalene-1,4-dione (KSC-292-065-1)

To a to a stirred mixture of KSC-292-062-1 (5.25 g, 11.71 mmol) (pp. 50) and water (240 mL) at room temperature under air was added Hydrazine monohydrate (40 mL, 825 mmol). The mixture was heated to 92° C. for 2 h. Upon cooling, the mixture was vacuum filtered the filtrand was collected and dried overnight under vacuum at 80° C. to afford KSC-292-065-1 (1.6433 g, 8.73 mmol, 74.6% yield) as a purple solid. $^1$H NMR (400 MHz, DMSO-$d_6$) δ 7.80-7.73 (m, 2H), 7.63-7.56 (m, 2H), 5.46 (s, 4H); $^{13}$C NMR (101 MHz, DMSO) δ 178.38, 132.61, 131.07, 127.60, 124.54; HRMS (ESI-TOF) m/z: [M+H]$^+$ Calcd for $C_{10}H_9N_2O_2$ 189.0659. Found 189.0660.

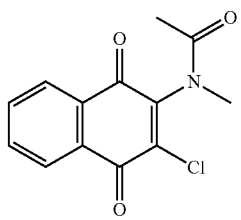

N-(3-chloro-1,4-dioxo-1,4-dihydronaphthalen-2-yl)-N-methylacetamide (KSC-292-004-1)

To a flame-dried flask containing N-methylacetamide (1.2120 g, 16.58 mmol) stirring in 50 mL anhydrous THF at −78 C was added lithium diisopropylamide (33.0 mL, 17.16 mmol). The solution was warmed to room temperature and stirred under argon for 1.5 h, after which time the solution was cannulated dropwise into another flame-dried flask containing 2,3-dichloronaphthalene-1,4-dione (3.89 g, 17.13 mmol) stirring in 100 mL anhydrous THF at room temperature. The mixture was allowed to stir under argon at room temperature overnight. reaction was quenched with water, concentrated in vacuo to remove THF, then diluted further with water and extracted 3 times with EtOAc. The combined organic extracts were combined, dried ($Na_2SO_4$), filtered, and concentrated in vacuo. The crude residue was purified via flash via MPLC (silica, 100% hexanes→100% EtOAc) to afford KSC-292-004-1 (184.9 mg, 0.701 mmol, 4.23% yield). $^1$H NMR (400 MHz, Chloroform-d) δ 8.28-8.08 (m, 2H), 7.94-7.73 (m, 2H), 3.20 (s, 3H), 1.94 (s, 3H); HRMS (ESI-TOF) m/z: [M+H]$^+$ Calcd for $C_{13}H_{11}ClNO_3$ 264.0422. Found 264.0428.

Synthetic Protocols for KSC-279-059-1 to KSC-288-018-1

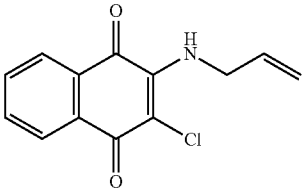

2-(allylamino)-3-chloronaphthalene-1,4-dione (KSC-279-059-1)

To a stirring solution of 2,3-dichloronaphthalene-1,4-dione (103.5 mg, 0.456 mmol) in abs. EtOH (6 mL) was added dropwise allylamine (47.1 mg, 0.825 mmol) in abs. EtOH (4 mL). The reaction was allowed to stir at room temperature under air for 2.5 days. The reaction was then concentrated in vacuo and purified via flash chromatography (silica, 100% hexanes→35% EtOAc/hexanes) to afford KSC-279-059-1 (90.5 mg, 0.365 mmol, 80% yield) as a red solid. m.p.=112-118° C.; $^1$H NMR (500 MHz, DMSO-$d_6$) δ 8.00-7.95 (m, 2H), 7.83 (td, J=7.6, 1.3 Hz, 1H), 7.74 (td, J=7.5, 1.3 Hz, 1H), 7.70-7.63 (m, 1H), 5.97 (ddt, J=17.2, 10.2, 4.9 Hz, 1H), 5.17-5.09 (m, 2H), 4.35 (ddt, J=6.7, 4.8, 1.7 Hz, 2H); $^{13}$C NMR (126 MHz, DMSO) δ 180.01, 175.48, 145.21, 135.82, 134.85, 132.66, 131.91, 129.88, 126.46, 125.77, 115.44, 45.75; HRMS (ESI-TOF) m/z: [M+H]$^+$ Calcd for $C_{13}H_{11}ClNO_2$ 248.6843. Found 248.0474.

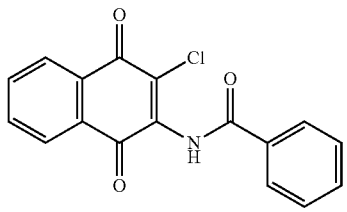

N-(3-chloro-1,4-dioxo-1,4-dihydronaphthalen-2-yl)benzamide (KSC-279-067-1)

To a solution of 2-amino-3-chloronaphthalene-1,4-dione (1.2315 g, 5.93 mmol) in anhydrous THF (50 mL) was added 60% sodium hydride suspension (680 mg, 17.00 mmol). The mixture was stirred at room temperature under argon for 45 minutes and then benzoyl chloride (0.70 mL, 6.03 mmol) was added. The mixture stirred for 2 hours at room temperature and the mixture was subsequently concentrated in vacuo, redissolved in EtOAc, and washed once with water, and once with brine solution. The organic layer was dried ($Na_2SO_4$), filtered, and concentrated in vacuo. The crude residue was purified via flash via MPLC (silica, 100% hexanes→100% EtOAc) to afford KSC-279-067-1 (1.375 g, 4.41 mmol, 74.4% yield) as a yellow solid. $^1$H NMR (500 MHz, DMSO-$d_6$) δ 10.50 (s, 1H), 8.15-8.10 (m, 1H), 8.10-8.05 (m, 1H), 8.05-8.01 (m, 2H), 7.95-7.90 (m, 2H), 7.69-7.64 (m, 1H), 7.60-7.55 (m, 2H); $^{13}$C NMR (126 MHz, DMSO) δ 178.49, 177.49, 165.25, 141.85, 136.48, 134.65, 134.64, 132.67, 132.55, 130.99, 130.78, 128.52, 128.30, 126.80, 126.72; HRMS (ESI-TOF) m/z: [M+H]⁺ Calcd for C₁₇H₁₁ClNO₃ 312.7263; Found 312.0421.

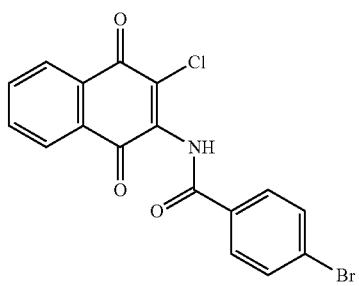

4-bromo-N-(3-chloro-1,4-dioxo-1,4-dihydronaphthalen-2-yl)benzamide (KSC-292-034-1)

This compound was prepared using the same protocol described for KSC-279-067-1 (pp. 51) using the appropriate acyl chloride. Yield: 447.8 mg; 20%. ¹H NMR (500 MHz, DMSO) δ 10.62 (s, 1H), 8.15-8.11 (m, 1H), 8.09-8.06 (m, 1H), 7.99-7.92 (m, 4H), 7.82-7.78 (m, 2H); ¹³C NMR (126 MHz, DMSO) δ 178.41, 177.46, 164.43, 141.59, 136.73, 134.68, 131.78, 131.61, 131.01, 130.77, 130.36, 126.82, 126.73, 126.47; HRMS (ESI-TOF) m/z: [M+H]⁺ Calcd for C₁₇H₁₀BrClNO₃ 389.9527. Found 389.9518.

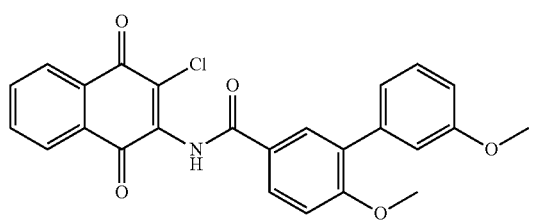

N-(3-chloro-1,4-dioxo-1,4-dihydronaphthalen-2-yl)-3',6-dimethoxy-[1,1'-biphenyl]-3-carboxamide (KSC-288-018-1)

Compound was prepared according to the procedures of Blagg et al.¹ ¹H NMR (500 MHz, DMSO-d₆) δ 10.42 (s, 1H), 8.16-8.10 (m, 1H), 8.10-8.06 (m, 1H), 8.06-8.01 (m, 2H), 7.98-7.90 (m, 2H), 7.38 (t, J=8.0 Hz, 1H), 7.31-7.26 (m, 1H), 7.15-7.09 (m, 2H), 6.96 (ddd, J=8.3, 2.6, 0.8 Hz, 1H), 3.88 (s, 3H), 3.80 (s, 3H); ¹³C NMR (126 MHz, DMSO) δ 178.59, 177.53, 164.54, 159.47, 158.92, 142.11, 138.56, 134.64, 131.00, 130.84, 130.67, 129.90, 129.34, 129.09, 126.77, 126.72, 124.80, 121.68, 115.21, 112.53, 111.60, 55.94, 55.08; HRMS (ESI-TOF) m/z: [M+H]⁺ Calcd for C₂₅H₁₉ClNO₅ 448.0946. Found 448.0937.

Synthetic Protocols for KSC-279-070-1 to KSC-279-069-1

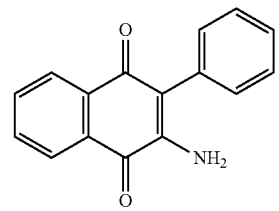

2-amino-3-phenylnaphthalene-1,4-dione (KSC-279-070-1)

Compound was prepared according to the procedures of Blagg et al.¹ ¹H NMR (500 MHz, DMSO-d₆) δ 8.04-7.94 (m, 2H), 7.83 (td, J=7.5, 1.4 Hz, 1H), 7.75 (td, J=7.5, 1.3 Hz, 1H), 7.49-7.42 (m, 2H), 7.36 (tt, J=8.7, 1.3 Hz, 1H), 7.32-7.25 (m, 2H), 6.54 (s, 2H); ¹³C NMR (126 MHz, DMSO) δ 181.69, 180.14, 146.12, 134.71, 133.19, 132.79, 132.25, 130.41, 130.12, 128.29, 127.22, 125.68, 125.43, 114.57; HRMS (ESI-TOF) m/z: [M+H]⁺ Calcd for C₁₆H₁₂NO₂ 250.2713. Found 250.0861.

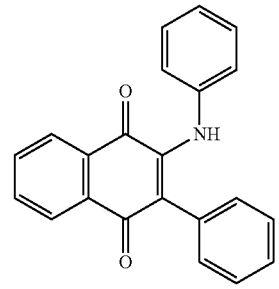

2-phenyl-3-(phenylamino)naphthalene-1,4-dione (KSC-292-086-1)

Compound was prepared according to the procedures of Blagg et al.¹ ¹H NMR (400 MHz, DMSO-d₆) δ 8.94 (s, 1H), 8.15-8.09 (m, 1H), 8.08-8.02 (m, 1H), 7.90 (td, J=7.5, 1.4 Hz, 1H), 7.83 (td, J=7.5, 1.4 Hz, 1H), 7.03-6.94 (m, 5H), 6.89-6.81 (m, 2H), 6.78-6.68 (m, 3H); ¹³C NMR (101 MHz, DMSO) δ 182.77, 181.57, 141.94, 138.26, 134.78, 133.32, 132.76, 132.72, 130.45, 130.23, 127.23, 126.66, 126.46, 125.92, 125.71, 122.99, 122.49, 117.13; HRMS (ESI-TOF) [M+H]⁺ Calcd for C₂₂H₁₆NO₂ 326.1176. Found 326.1175.

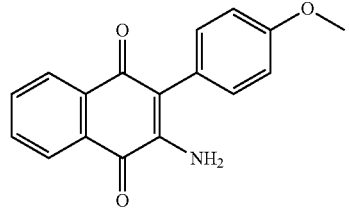

2-amino-3-(4-methoxyphenyl)naphthalene-1,4-dione (KSC-288-003-1)

Compound was prepared according to the procedures of Blagg et al.[1] $^1$H NMR (500 MHz, DMSO-$d_6$) δ 8.02-7.94 (m, 2H), 7.82 (td, J=7.5, 1.4 Hz, 1H), 7.74 (td, J=7.5, 1.3 Hz, 1H), 7.24-7.17 (m, 2H), 7.05-6.98 (m, 2H), 6.48 (s, 2H), 3.80 (s, 3H); $^{13}$C NMR (126 MHz, DMSO) δ 181.70, 180.33, 158.34, 146.16, 134.63, 132.82, 132.21, 131.58, 130.15, 125.67, 125.37, 125.10, 114.45, 113.79, 55.02; HRMS (ESI-TOF) m/z: [M+H]$^+$ Calcd for $C_{17}H_{14}NO_3$ 280.0968. Found 280.0974.

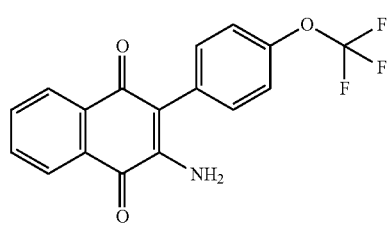

KSC-279-069-1

2-amino-3-(4-(trifluoromethoxy)phenyl)naphthalene-1,4-dione (KSC-279-069-1)

Compound was prepared according to the procedures of Blagg et al.[1] $^1$H NMR (500 MHz, DMSO-$d_6$) δ 8.03-7.99 (m, 1H), 7.99-7.95 (m, 1H), 7.83 (td, J=7.5, 1.4 Hz, 1H), 7.75 (td, J=7.5, 1.3 Hz, 1H), 7.44-7.37 (m, 4H), 6.79 (s, 2H); $^{13}$C NMR (126 MHz, DMSO) δ 181.57, 179.93, 147.36, 147.35, 146.53, 134.76, 132.77, 132.65, 132.54, 132.29, 130.12, 125.68, 125.51, 121.15, 120.79, 113.00; HRMS (ESI-TOF) m/z: [M+H]$^+$ Calcd for $C_{17}H_{11}F_3NO_3$ 334.2683; Found 334.0690.

Synthetic Protocols for KSC-279-090-1 to KSC-279-083-1

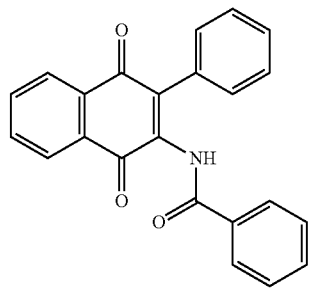

KSC-279-090-1

N-(1,4-dioxo-3-phenyl-1,4-dihydronaphthalen-2-yl)benzamide (KSC-279-090-1)

Compound was prepared according to the procedures of Blagg et al.[1] $^1$H NMR (500 MHz, DMSO-$d_6$) δ 10.00 (s, 1H), 8.13-8.06 (m, 2H), 7.97-7.91 (m, 2H), 7.83-7.78 (m, 2H), 7.58 (tt, J=8.7, 1.3 Hz, 1H), 7.51-7.45 (m, 2H), 7.43-7.33 (m, 5H); $^{13}$C NMR (126 MHz, DMSO) δ 183.45, 180.77, 165.93, 141.34, 140.49, 134.54, 134.30, 133.15, 132.03, 131.82, 131.65, 131.05, 129.51, 128.54, 128.37, 127.80, 127.57, 126.45, 126.08; HRMS (ESI-TOF) m/z: [M+H]$^+$ Calcd for $C_{23}H_{16}NO_3$ 354.1125. Found 354.1120.

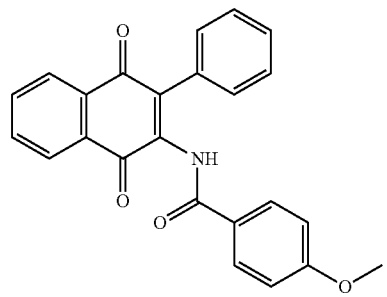

KSC-279-087-1

N-(1,4-dioxo-3-phenyl-1,4-dihydronaphthalen-2-yl)-4-methoxybenzamide (KSC-279-087-1)

Compound was prepared according to the procedures of Blagg et al.[1] $^1$H NMR (500 MHz, DMSO-$d_6$) δ 9.80 (s, 1H), 8.12-8.08 (m, 2H), 7.97-7.92 (m, 2H), 7.82-7.78 (m, 2H), 7.42-7.31 (m, 5H), 7.03-6.98 (m, 2H), 3.81 (s, 3H); $^{13}$C NMR (126 MHz, DMSO) δ 183.46, 180.88, 165.32, 162.21, 140.83, 140.79, 134.53, 134.27, 131.90, 131.64, 131.09, 129.85, 129.52, 128.46, 127.55, 126.42, 126.06, 125.26, 113.60, 55.41; HRMS (ESI-TOF) m/z: [M+H]$^+$ Calcd for $C_{24}H_{18}NO_4$ 384.1230. Found 384.1223.

KSC-279-084-1

4-bromo-N-(1,4-dioxo-3-phenyl-1,4-dihydronaphthalen-2-yl)benzamide (KSC-279-084-1)

Compound was prepared according to the procedures of Blagg et al.[1] $^1$H NMR (500 MHz, DMSO-$d_6$) δ 10.11 (s, 1H), 8.13-8.06 (m, 2H), 7.96-7.90 (m, 2H), 7.77-7.73 (m, 2H), 7.73-7.67 (m, 2H), 7.43-7.32 (m, 5H); $^{13}$C NMR (126 MHz, DMSO) δ 183.39, 180.68, 165.08, 141.44, 140.24, 134.55, 134.29, 132.22, 131.75, 131.64, 131.46, 131.01, 129.90, 129.48, 128.59, 127.59, 126.46, 126.07, 125.92; HRMS (ESI-TOF) m/z: [M+H]+ Calcd for $C_{23}H_{15}BrNO_3$ 432.0230. Found 432.0208.

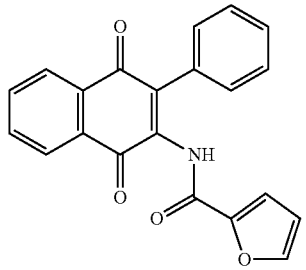

KSC-279-085-1

N-(1,4-dioxo-3-phenyl-1,4-dihydronaphthalen-2-yl) furan-2-carboxamide (KSC-279-085-1)

Compound was prepared according to the procedures of Blagg et al.[1] 1H NMR (500 MHz, DMSO-$d_6$) δ 9.85 (s, 1H), 8.14-8.04 (m, 2H), 7.99-7.87 (m, 3H), 7.45-7.31 (m, 5H), 7.25 (dd, J=3.5, 0.8 Hz, 1H), 6.65 (dd, J=3.5, 1.8 Hz, 1H); 13C NMR (126 MHz, DMSO) δ 183.40, 180.67, 156.35, 146.58, 146.12, 141.28, 139.44, 134.60, 134.31, 131.83, 131.64, 130.94, 129.51, 128.57, 127.58, 126.47, 126.08, 115.57, 112.15; HRMS (ESI-TOF) m/z: [M+H]+ Calcd for $C_{21}H_{14}NO_4$ 344.0917. Found 344.0910.

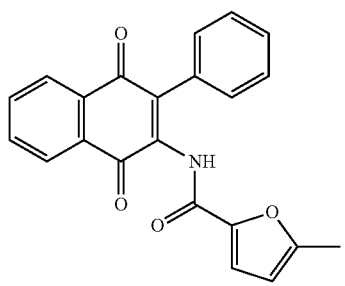

KSC-279-086-1

N-(1,4-dioxo-3-phenyl-1,4-dihydronaphthalen-2-yl)-5-methylfuran-2-carboxamide (KSC-279-086-1)

Compound was prepared according to the procedures of Blagg et al.[1] 1H NMR (500 MHz, DMSO-$d_6$) δ 9.67 (s, 1H), 8.12-8.04 (m, 2H), 7.96-7.88 (m, 2H), 7.44-7.31 (m, 5H), 7.16 (d, J=3.4 Hz, 1H), 6.28 (dd, J=3.4, 1.0 Hz, 1H), 2.33 (s, 3H); 13C NMR (126 MHz, DMSO) δ 182.26, 179.65, 155.09, 154.51, 144.00, 139.62, 138.40, 133.44, 133.13, 130.87, 130.50, 129.79, 128.38, 127.36, 126.45, 125.31, 124.92, 115.79, 107.48, 12.36; HRMS (ESI-TOF) m/z: [M+H]+ Calcd for $C_{22}H_{16}NO_4$ 358.1074. Found 358.1067.

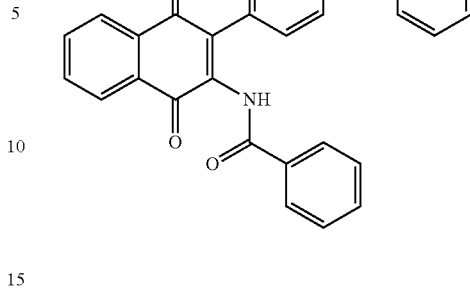

KSC-288-017-1

N-(1,4-dioxo-3-(4-phenoxyphenyl)-1,4-dihydronaphthalen-2-yl)benzamide (KSC-288-017-1)

Compound was prepared according to the procedures of Blagg et al.[1] 1H NMR (500 MHz, DMSO-$d_6$) δ 10.03 (s, 1H), 8.14-8.06 (m, 2H), 7.98-7.89 (m, 2H), 7.86-7.79 (m, 2H), 7.59 (tt, J=7.4, 1.0 Hz, 1H), 7.53-7.46 (m, 2H), 7.44-7.35 (m, 4H), 7.20-7.13 (m, 1H), 7.04-6.97 (m, 4H); 13C NMR (126 MHz, DMSO) δ 180.82, 156.09, 134.49, 131.98, 131.60, 131.57, 131.11, 130.07, 130.05, 128.36, 128.33, 127.86, 127.84, 126.42, 126.03, 123.78, 123.74, 118.94, 118.91, 117.39, 117.36; HRMS (ESI-TOF) m/z: [M+H]+ Calcd for $C_{29}H_{20}NO_4$ 446.1387. Found 446.1389.

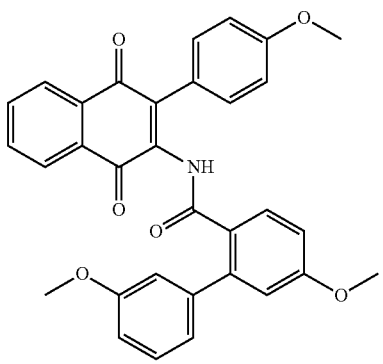

KSC-288-026-1

3',5-dimethoxy-N-(3-(4-methoxyphenyl)-1,4-dioxo-1,4-dihydronaphthalen-2-yl)-[1,1'-biphenyl]-2-carboxamide (KSC-288-026-1)

Compound was prepared according to the procedures of Blagg et al.[1] 1H NMR (500 MHz, DMSO-$d_6$) δ 9.88 (s, 1H), 8.12-8.06 (m, 2H), 7.96-7.90 (m, 2H), 7.87 (dd, J=8.6, 2.3 Hz, 1H), 7.82 (d, J=2.3 Hz, 1H), 7.37-7.31 (m, 3H), 7.21 (d, J=8.8 Hz, 1H), 7.09-7.02 (m, 2H), 6.98-6.91 (m, 3H), 3.84 (s, 3H), 3.78 (s, 3H), 3.75 (s, 3H); 13C NMR (126 MHz, DMSO) δ 183.66, 180.78, 165.42, 159.47, 159.02, 158.89, 138.62, 134.40, 134.20, 131.71, 131.24, 131.14, 130.14, 129.32, 129.20, 129.07, 126.42, 125.99, 125.45, 123.86, 121.62, 115.11, 113.11, 112.51, 111.45, 55.86, 55.06, 55.04; HRMS (ESI-TOF) m/z: [M+H]+ Calcd for $C_{32}H_{26}NO_6$ 520.1755. Found 520.1751.

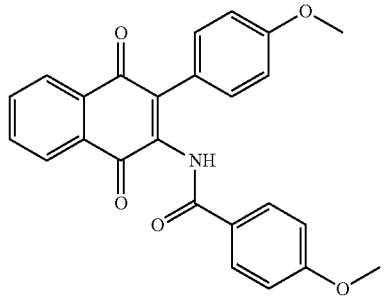

KSC-288-033-1

4-methoxy-N-(3-(4-methoxyphenyl)-1,4-dioxo-1,4-dihydronaphthalen-2-yl)benzamide (KSC-288-033-1)

Compound was prepared according to the procedures of Blagg et al.[1] $^1$H NMR (500 MHz, DMSO-$d_6$) δ 9.79 (s, 1H), 8.14-8.04 (m, 2H), 7.98-7.87 (m, 2H), 7.87-7.78 (m, 2H), 7.38-7.29 (m, 2H), 7.06-6.99 (m, 2H), 6.99-6.91 (m, 2H), 3.82 (s, 3H), 3.76 (s, 3H); $^{13}$C NMR (126 MHz, DMSO) δ 183.63, 180.83, 165.48, 162.17, 159.43, 134.39, 134.17, 131.74, 131.23, 131.14, 129.86, 126.41, 125.98, 125.44, 123.93, 113.60, 113.09, 55.41, 55.07; HRMS (ESI-TOF) m/z: [M+H]$^+$ Calcd for $C_{25}H_{20}NO_5$ 414.1336. Found 414.1321.

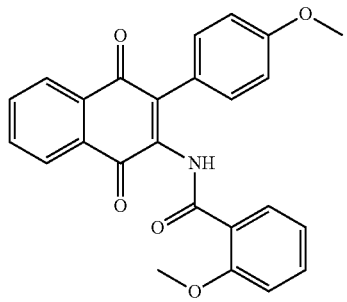

KSC-288-035-1

2-methoxy-N-(3-(4-methoxyphenyl)-1,4-dioxo-1,4-dihydronaphthalen-2-yl)benzamide (KSC-288-035-1)

Compound was prepared according to the procedures of Blagg et al.[1] $^1$H NMR (500 MHz, DMSO-$d_6$) δ 9.98 (s, 1H), 8.13-8.04 (m, 2H), 7.96-7.89 (m, 2H), 7.65 (dd, J=7.7, 1.8 Hz, 1H), 7.55 (ddd, J=8.5, 7.3, 1.8 Hz, 1H), 7.39-7.31 (m, 2H), 7.20 (d, J=7.9 Hz, 1H), 7.05 (td, J=7.7, 0.9 Hz, 1H), 7.03-6.97 (m, 2H), 3.90 (s, 3H), 3.79 (s, 3H); $^{13}$C NMR (126 MHz, DMSO) δ 183.59, 180.73, 162.47, 159.30, 157.06, 139.63, 137.16, 134.44, 134.09, 133.59, 131.67, 131.07, 130.90, 126.37, 125.95, 124.44, 121.01, 120.87, 113.19, 112.39, 56.20, 55.10; HRMS (ESI-TOF) m/z: [M+H]$^+$ Calcd for $C_{25}H_{20}NO_5$ 414.1336. Found 414.1341.

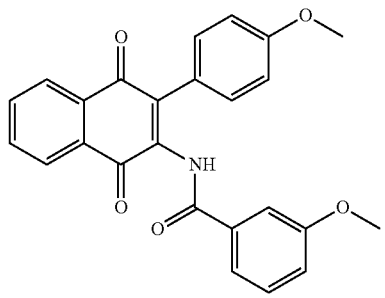

KSC-288-016-1

3-methoxy-N-(3-(4-methoxyphenyl)-1,4-dioxo-1,4-dihydronaphthalen-2-yl)benzamide (KSC-288-016-1)

Compound was prepared according to the procedures of Blagg et al.[1] $^1$H NMR (500 MHz, DMSO-$d_6$) δ 9.88 (s, 1H), 8.07-7.97 (m, 2H), 7.91-7.81 (m, 2H), 7.38-7.30 (m, 2H), 7.30-7.24 (m, 3H), 7.12-7.05 (m, 1H), 6.94-6.86 (m, 2H), 3.72 (s, 3H), 3.69 (s, 3H); $^{13}$C NMR (126 MHz, DMSO) δ 159.08, 134.41, 131.26, 129.54, 126.43, 125.98, 120.05, 113.10, 112.92, 99.49, 55.27, 55.08; HRMS (ESI-TOF) m/z: [M+H]$^+$ Calcd for $C_{25}H_{20}NO_5$ 414.1336. Found 414.1339.

KSC-288-015-1

4-chloro-N-(3-(4-methoxyphenyl)-1,4-dioxo-1,4-dihydronaphthalen-2-yl)benzamide (KSC-288-015-1)

Compound was prepared according to the procedures of Blagg et al.[1] $^1$H NMR (500 MHz, DMSO-$d_6$) δ 10.09 (s, 1H), 8.14-8.05 (m, 2H), 7.98-7.90 (m, 2H), 7.88-7.82 (m, 2H), 7.62-7.53 (m, 2H), 7.39-7.29 (m, 2H), 7.00-6.92 (m, 2H), 3.76 (s, 3H); $^{13}$C NMR (126 MHz, DMSO) δ 183.58, 180.65, 159.53, 136.83, 134.44, 134.21, 131.74, 131.22, 131.08, 129.76, 128.52, 126.46, 126.00, 113.13, 55.08; HRMS (ESI-TOF) m/z: [M+H]$^+$ Calcd for $C_{24}H_{17}ClNO_4$ 418.0841. Found 418.0843.

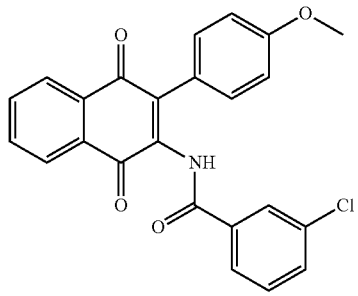

KSC-288-020-1

3-chloro-N-(3-(4-methoxyphenyl)-1,4-dioxo-1,4-dihydronaphthalen-2-yl)benzamide (KSC-288-020-1)

Compound was prepared according to the procedures of Blagg et al.[1] $^1$H NMR (500 MHz, DMSO-$d_6$) δ 10.15 (s, 1H), 8.14-8.05 (m, 2H), 8.00-7.89 (m, 2H), 7.87 (t, J=1.8 Hz, 1H), 7.84-7.76 (m, 1H), 7.67 (ddd, J=8.0, 2.1, 1.0 Hz, 1H), 7.54 (t, J=7.9 Hz, 1H), 7.37-7.30 (m, 2H), 7.01-6.93 (m, 2H), 3.76 (s, 3H); $^{13}$C NMR (126 MHz, DMSO) δ 183.57, 180.55, 164.69, 159.58, 135.21, 134.45, 134.23, 133.18, 131.83, 131.73, 131.21, 131.07, 130.48, 127.57, 126.61, 126.46, 126.01, 123.70, 113.17, 55.10; HRMS (ESI-TOF) m/z: [M+H]$^+$ Calcd for $C_{24}H_{17}ClNO_4$ 418.0841. Found 418.0843.

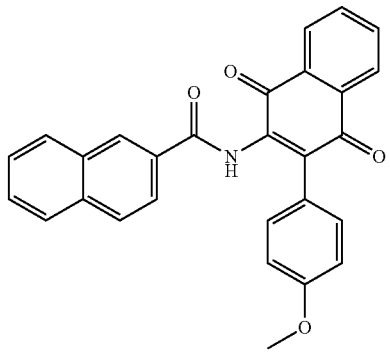

KSC-288-012-1

N-(3-(4-methoxyphenyl)-1,4-dioxo-1,4-dihydronaphthalen-2-yl)-2-naphthamide (KSC-288-012-1)

Compound was prepared according to the procedures of Blagg et al.[1] $^1$H NMR (500 MHz, DMSO-$d_6$) δ 10.14 (s, 1H), 8.50 (s, 1H), 8.16-8.07 (m, 2H), 8.07-7.98 (m, 3H), 7.98-7.92 (m, 2H), 7.90 (dd, J=8.6, 1.8 Hz, 1H), 7.69-7.58 (m, 2H), 7.42-7.35 (m, 2H), 7.01-6.92 (m, 2H), 3.74 (s, 3H); $^{13}$C NMR (126 MHz, DMSO) δ 183.65, 180.75, 166.11, 159.51, 134.45, 134.41, 134.22, 131.92, 131.76, 131.25, 131.13, 130.57, 128.95, 128.56, 128.24, 128.01, 127.65, 127.19, 126.90, 126.46, 126.02, 124.33, 123.89, 113.14, 55.06; HRMS (ESI-TOF) m/z: [M+H]$^+$ Calcd for $C_{28}H_{20}NO_4$ 434.1387. Found 434.1382.

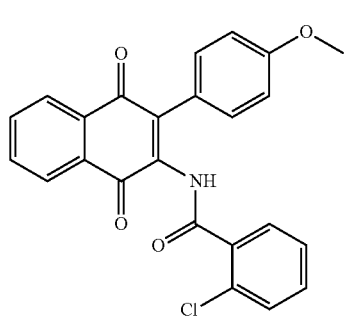

KSC-288-032-1

2-chloro-N-(3-(4-methoxyphenyl)-1,4-dioxo-1,4-dihydronaphthalen-2-yl)benzamide (KSC-288-032-1)

Compound was prepared according to the procedures of Blagg et al.[1] $^1$H NMR (500 MHz, DMSO-$d_6$) δ 10.22 (s, 1H), 8.15-8.05 (m, 2H), 7.98-7.88 (m, 2H), 7.54-7.44 (m, 2H), 7.44-7.34 (m, 4H), 7.05-6.97 (m, 2H), 3.80 (s, 3H); $^{13}$C NMR (126 MHz, DMSO) δ 180.49, 159.58, 134.38, 134.16, 131.73, 131.40, 131.25, 131.11, 130.12, 129.72, 129.15, 126.91, 126.40, 125.98, 113.09, 55.16; HRMS (ESI-TOF) m/z: [M+H]$^+$ Calcd for $C_{24}H_{17}ClNO_4$ 418.0841. Found 418.0842.

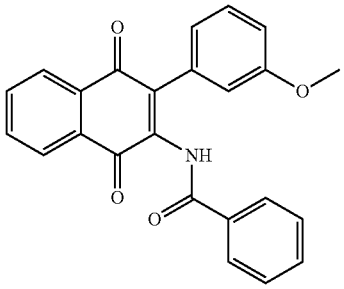

KSC-288-024-1

N-(3-(3-methoxyphenyl)-1,4-dioxo-1,4-dihydronaphthalen-2-yl)benzamide (KSC-288-024-1)

Compound was prepared according to the procedures of Blagg et al.[1] $^1$H NMR (500 MHz, DMSO-$d_6$) δ 9.99 (s, 1H), 8.13-8.06 (m, 2H), 7.98-7.90 (m, 2H), 7.85-7.78 (m, 2H), 7.61-7.54 (m, 1H), 7.52-7.45 (m, 2H), 7.30 (t, J=7.9 Hz, 1H), 6.98-6.89 (m, 3H), 3.71 (s, 3H); $^{13}$C NMR (126 MHz, DMSO) δ 180.76, 158.38, 158.37, 134.51, 131.97, 131.08, 128.63, 128.36, 128.33, 127.83, 127.81, 126.42, 126.05, 126.01, 121.86, 115.27, 114.02, 54.96; HRMS (ESI-TOF) m/z: [M+H]$^+$ Calcd for $C_{24}H_{18}NO_4$ 384.1230. Found 384.1237.

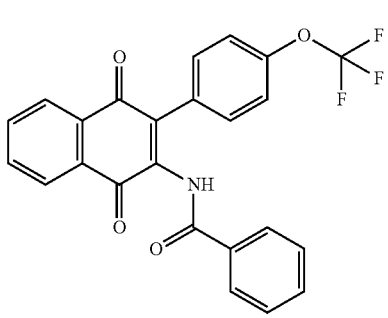

KSC-279-078-1

N-(1,4-dioxo-3-(4-(trifluoromethoxy)phenyl)-1,4-dihydronaphthalen-2-yl)benzamide (KSC-279-078-1)

Compound was prepared according to the procedures of Blagg et NMR (500 MHz, DMSO-$d_6$) δ 10.06 (s, 1H), 8.13-8.08 (m, 2H), 7.97-7.92 (m, 2H), 7.82-7.78 (m, 2H), 7.61-7.56 (m, 1H), 7.53-7.46 (m, 4H), 7.44-7.38 (m, 2H); $^{13}$C NMR (126 MHz, DMSO) δ 183.10, 180.66, 165.88, 148.23, 148.22, 140.70, 139.39, 134.60, 134.32, 133.07, 132.55, 132.14, 131.65, 131.60, 131.26, 131.04, 128.40, 127.84, 126.45, 126.12, 123.04, 121.01, 120.15, 118.97, 116.93; HRMS (ESI-TOF) m/z: [M+H]$^+$ Calcd for $C_{24}H_{15}F_3NO_4$ 438.3743; Found 438.0944.

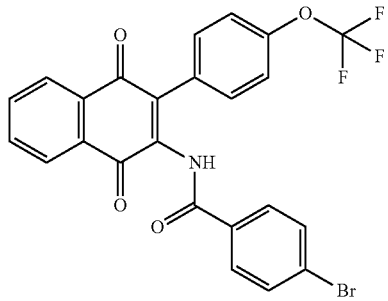

KSC-279-079-1

4-bromo-N-(1,4-dioxo-3-(4-(trifluoromethoxy)phenyl)-1,4-dihydronaphthalen-2-yl)benzamide (KSC-279-079-1)

Compound was prepared according to the procedures of Blagg et al.[1] $^1$H NMR (500 MHz, DMSO-$d_6$) δ 10.17 (s, 1H), 8.12-8.06 (m, 2H), 7.96-7.89 (m, 2H), 7.79-7.73 (m, 2H), 7.73-7.67 (m, 2H), 7.53-7.47 (m, 2H), 7.43-7.37 (m, 2H); $^{13}$C NMR (126 MHz, DMSO) δ 181.92, 179.44, 163.91, 147.15, 147.13, 139.35, 138.37, 133.47, 133.17, 131.01, 130.52, 130.47, 130.34, 130.05, 129.88, 128.82, 125.33, 124.98, 124.91, 119.88, 119.03, 117.84; HRMS (ESI-TOF) m/z: [M+H]$^+$ Calcd for $C_{24}H_{14}BrF_3NO_4$ 516.0053. Found 516.0032.

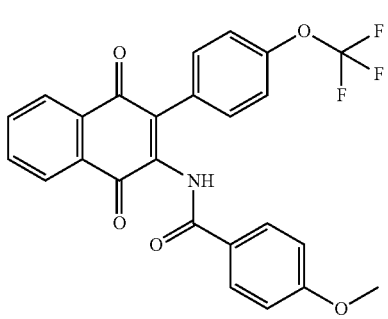

KSC-279-082-1

N-(1,4-dioxo-3-(4-(trifluoromethoxy)phenyl)-1,4-dihydronaphthalen-2-yl)-4-methoxybenzamide (KSC-279-082-1)

Compound was prepared according to the procedures of Blagg et al.[1] $^1$H NMR (500 MHz, DMSO-$d_6$) δ 9.87 (s, 1H), 8.15-8.05 (m, 2H), 7.98-7.90 (m, 2H), 7.84-7.78 (m, 2H), 7.52-7.45 (m, 2H), 7.43-7.36 (m, 2H), 7.05-6.98 (m, 2H), 3.82 (s, 3H); $^{13}$C NMR (126 MHz, DMSO) δ 183.10, 180.76, 165.22, 162.31, 148.16, 148.15, 140.98, 138.79, 134.57, 134.28, 131.65, 131.59, 131.37, 131.06, 129.93, 126.42, 126.10, 125.16, 121.01, 120.12, 118.97, 113.63, 55.42; HRMS (ESI-TOF) m/z: [M+H]$^+$ Calcd for $C_{25}H_{17}F_3NO_5$ 468.4003; Found 468.1054.

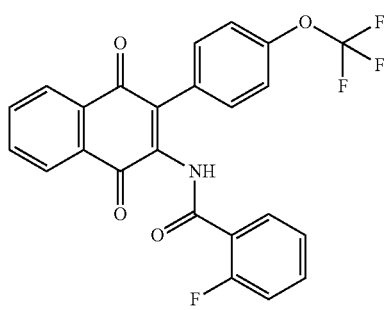

KSC-279-089-1

N-(1,4-dioxo-3-(4-(trifluoromethoxy)phenyl)-1,4-dihydronaphthalen-2-yl)-2-fluorobenzamide (KSC-279-089-1)

Compound was prepared according to the procedures of Blagg et al.[1] $^1$H NMR (500 MHz, DMSO-$d_6$) δ 10.11 (d, J=1.9 Hz, 1H), 8.16-8.06 (m, 2H), 7.98-7.90 (m, 2H), 7.60-7.53 (m, 1H), 7.53-7.48 (m, 2H), 7.48-7.40 (m, 3H), 7.34-7.24 (m, 2H); $^{13}$C NMR (126 MHz, DMSO) δ 183.08, 180.56, 162.57, 160.18, 158.18, 148.24, 148.23, 139.73, 138.77, 134.62, 134.30, 133.28, 133.21, 131.63, 131.57, 131.41, 130.92, 130.01, 129.99, 126.44, 126.09, 124.45, 124.42, 122.89, 122.78, 121.04, 120.16, 119.00, 116.30, 116.13; HRMS (ESI-TOF) m/z: [M+H]$^+$ Calcd for $C_{24}H_{14}F_4NO_4$ 456.0854. Found 456.0845.

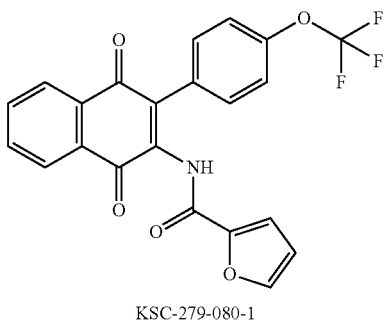 [SMILES: O=C(NC1=C(c2ccc(OC(F)(F)F)cc2)C(=O)c2ccccc2C1=O)c1ccco1]

KSC-279-080-1

N-(1,4-dioxo-3-(4-(trifluoromethoxy)phenyl)-1,4-dihydronaphthalen-2-yl)furan-2-carboxamide (KSC-279-080-1)

Compound was prepared according to the procedures of Blagg et al.[1] $^1$H NMR (500 MHz, DMSO-$d_6$) δ 9.91 (s, 1H), 8.14-8.06 (m, 2H), 7.97-7.90 (m, 3H), 7.51-7.46 (m, 2H), 7.44-7.39 (m, 2H), 7.27 (dd, J=3.5, 0.8 Hz, 1H), 6.67 (dd, J=3.5, 1.8 Hz, 1H); $^{13}$C NMR (126 MHz, DMSO) δ 183.05, 180.58, 156.12, 148.24, 148.22, 146.48, 146.27, 139.61, 139.09, 134.65, 134.31, 131.66, 131.59, 131.31, 130.90, 126.47, 126.12, 123.81, 120.14, 115.82, 112.22; HRMS (ESI-TOF) m/z: [M+H]$^+$ Calcd for $C_{22}H_{13}F_3NO_5$ 428.3373. Found 428.0736.

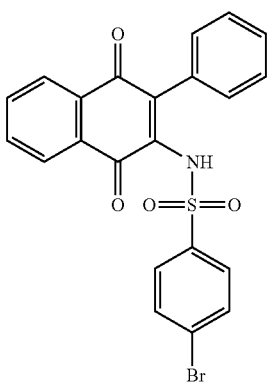

KSC-279-088-1

4-bromo-N-(1,4-dioxo-3-phenyl-1,4-dihydronaphthalen-2-yl)benzenesulfonamide (KSC-279-088-1)

Compound was prepared according to the procedures of Blagg et al.[1] $^1$H NMR (500 MHz, DMSO-$d_6$) δ 10.01 (s, 1H), 8.01 (ddd, J=7.3, 6.2, 2.0 Hz, 2H), 7.92-7.85 (m, 2H), 7.72-7.67 (m, 2H), 7.59-7.54 (m, 2H), 7.39-7.33 (m, 3H), 7.30-7.24 (m, 2H); $^{13}$C NMR (126 MHz, DMSO) δ 183.39, 181.26, 141.37, 140.00, 138.62, 134.57, 134.16, 131.67, 131.50, 131.21, 130.59, 130.26, 128.40, 127.90, 127.49, 126.30, 126.07, 125.86; HRMS (ESI-TOF) m/z: [M+H]$^+$ Calcd for $C_{22}H_{15}BrNO_4S$ 467.9900. Found 467.9882.

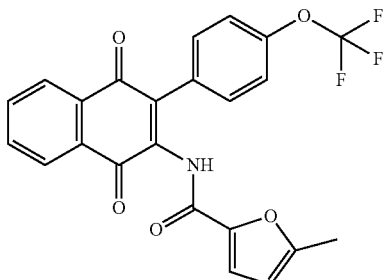

KSC-279-081-1

N-(1,4-dioxo-3-(4-(trifluoromethoxy)phenyl)-1,4-dihydronaphthalen-2-yl)-5-methylfuran-2-carboxamide (KSC-279-081-1)

Compound was prepared according to the procedures of Blagg et al.[1] $^1$H NMR (500 MHz, DMSO-$d_6$) δ 9.72 (s, 1H), 8.13-8.05 (m, 2H), 7.99-7.87 (m, 2H), 7.52-7.44 (m, 2H), 7.44-7.38 (m, 2H), 7.18 (d, J=3.4 Hz, 1H), 6.29 (dd, J=3.4, 1.0 Hz, 1H), 2.34 (s, 3H); $^{13}$C NMR (126 MHz, DMSO) δ 183.04, 180.69, 155.93, 155.82, 148.17, 148.16, 145.02, 139.67, 138.49, 134.63, 134.26, 131.64, 131.58, 131.48, 130.88, 126.44, 126.08, 123.80, 122.40, 122.04, 121.03, 120.11, 118.99, 117.19, 109.45, 108.70, 13.47; HRMS (ESI-TOF) m/z: [M+H]$^+$ Calcd for $C_{23}H_{15}F_3NO_5$ 442.3633. Found 442.0893.

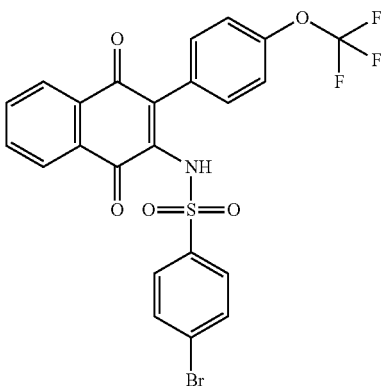

KSC-279-083-1

4-bromo-N-(1,4-dioxo-3-(4-(trifluoromethoxy)phenyl)-1,4-dihydronaphthalen-2-yl)benzenesulfonamide (KSC-279-083-1)

Compound was prepared according to the procedures of Blagg et al.[1] $^1$H NMR (500 MHz, DMSO-$d_6$) δ 10.13 (s, 1H), 8.05-7.99 (m, 2H), 7.94-7.86 (m, 2H), 7.72-7.67 (m, 2H), 7.61-7.55 (m, 2H), 7.41-7.35 (m, 2H), 7.34-7.28 (m, 2H); $^{13}$C NMR (126 MHz, DMSO) δ 183.14, 181.13, 148.34, 148.33, 141.19, 138.81, 138.72, 134.63, 134.21, 133.03, 132.41, 131.69, 131.51, 130.58, 130.44, 130.14, 127.83, 126.31, 126.11, 126.00, 124.16, 121.04, 119.78, 119.00; HRMS (ESI-TOF) m/z: [M+H]$^+$ Calcd for $C_{23}H_{14}BrF_3NO_5S$ 551.9723; Found 551.9707.

Synthetic Protocols for KSC-288-025-1 to KSC-288-031-1

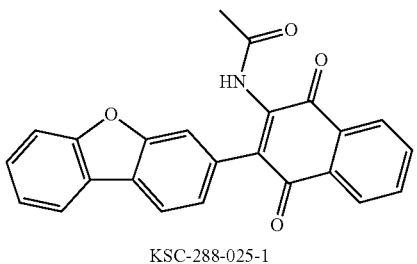 [SMILES: CC(=O)NC1=C(c2ccc3c(c2)oc2ccccc23)C(=O)c2ccccc2C1=O]

KSC-288-025-1

N-(3-(dibenzo[b,d]furan-3-yl)-1,4-dioxo-1,4-dihydronaphthalen-2-yl)acetamide (KSC-288-025-1)

Compound was prepared according to the procedures of Blagg et al.[1] $^1$H NMR (500 MHz, DMSO-$d_6$) δ 9.77 (s, 1H), 8.21-8.16 (m, 2H), 8.15-8.11 (m, 1H), 8.11-8.07 (m, 1H), 7.98-7.91 (m, 2H), 7.62 (d, J=8.2 Hz, 1H), 7.55-7.48 (m, 1H), 7.47-7.40 (m, 2H), 7.36 (dd, J=7.5, 1.3 Hz, 1H), 1.77 (s, 3H); $^{13}$C NMR (126 MHz, DMSO) δ 180.79, 155.27, 153.19, 134.60, 134.20, 131.15, 127.72, 127.54, 126.34, 126.21, 123.65, 123.48, 123.06, 122.48, 121.42, 121.07, 111.53, 22.80; HRMS (ESI-TOF) m/z: [M+H]$^+$ Calcd for $C_{24}H_{16}NO_4$ 382.1074. Found 382.1074.

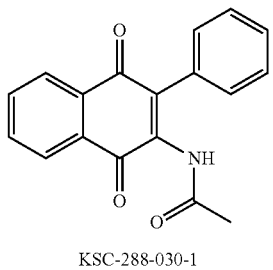 [SMILES: CC(=O)NC1=C(c2ccccc2)C(=O)c2ccccc2C1=O]

KSC-288-030-1

N-(1,4-dioxo-3-phenyl-1,4-dihydronaphthalen-2-yl)acetamide (KSC-288-030-1)

Compound was prepared according to the procedures of Blagg et al.[1] $^1$H NMR (500 MHz, DMSO-$d_6$) δ 9.62 (s, 1H), 8.12-8.01 (m, 2H), 7.97-7.87 (m, 2H), 7.50-7.35 (m, 3H), 7.33-7.25 (m, 2H), 1.87 (s, 3H); $^{13}$C NMR (126 MHz, DMSO) δ 183.41, 180.95, 168.62, 140.20, 134.39, 134.09, 132.19, 131.62, 131.10, 129.46, 128.31, 127.56, 126.27, 125.95, 22.61; HRMS (ESI-TOF) m/z: [M+H]$^+$ Calcd for $C_{18}H_{14}NO_3$ 292.0968. Found 292.0969.

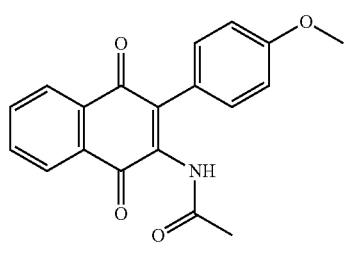

KSC-288-021-1

N-(3-(4-methoxyphenyl)-1,4-dioxo-1,4-dihydronaphthalen-2-yl)acetamide (KSC-288-021-1)

Compound was prepared according to the procedures of Blagg et al.[1] $^1$H NMR (500 MHz, DMSO-$d_6$) δ 9.59 (s, 1H), 8.09-8.01 (m, 2H), 7.94-7.86 (m, 2H), 7.30-7.21 (m, 2H), 7.03-6.96 (m, 2H), 3.34 (s, 3H), 1.89 (s, 3H); $^{13}$C NMR (126 MHz, DMSO) δ 183.66, 180.88, 168.67, 159.37, 139.73, 139.29, 134.28, 134.05, 131.64, 131.12, 131.10, 126.28, 125.88, 124.08, 113.13, 55.09, 22.63; HRMS (ESI-TOF) [M+H]$^+$ Calcd for $C_{19}H_{16}NO_4$ 322.1074. Found 322.1077.

KSC-288-034-1

N-(3-(4-chlorophenyl)-1,4-dioxo-1,4-dihydronaphthalen-2-yl)acetamide (KSC-288-034-1)

Compound was prepared according to the procedures of Blagg et al.[1] $^1$H NMR (500 MHz, DMSO-$d_6$) δ 9.69 (s, 1H), 8.11-8.00 (m, 2H), 7.96-7.87 (m, 2H), 7.53-7.46 (m, 2H), 7.35-7.27 (m, 2H), 1.89 (s, 3H); $^{13}$C NMR (126 MHz, DMSO) δ 183.08, 180.96, 168.31, 140.04, 134.46, 134.09, 132.94, 131.58, 131.43, 131.33, 131.02, 127.68, 126.28, 125.96, 22.78; HRMS (ESI-TOF) m/z: [M+H]$^+$ Calcd for $C_{18}H_{13}ClNO_3$ 326.0579. Found 326.0561.

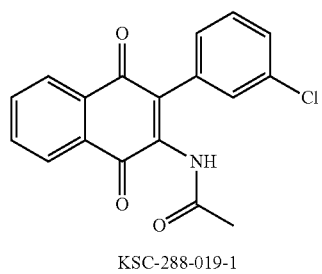 [SMILES: CC(=O)NC1=C(c2cccc(Cl)c2)C(=O)c2ccccc2C1=O]

KSC-288-019-1

N-(3-(3-chlorophenyl)-1,4-dioxo-1,4-dihydronaphthalen-2-yl)acetamide (KSC-288-019-1)

Compound was prepared according to the procedures of Blagg et al.[1] $^1$H NMR (500 MHz, DMSO-$d_6$) δ 9.72 (s, 1H), 8.10-8.02 (m, 2H), 7.95-7.88 (m, 2H), 7.47-7.42 (m, 2H), 7.37-7.33 (m, 1H), 7.26-7.20 (m, 1H), 1.88 (s, 3H); $^{13}$C NMR (126 MHz, DMSO) δ 182.96, 180.96, 168.28, 140.14, 136.94, 134.67, 134.49, 134.10, 132.10, 131.57, 130.99, 129.49, 129.38, 128.04, 127.85, 126.28, 125.98, 22.77; HRMS (ESI-TOF) m/z: [M+H]$^+$ Calcd for $C_{18}H_{13}ClNO_3$ 326.0579. Found 326.0566.

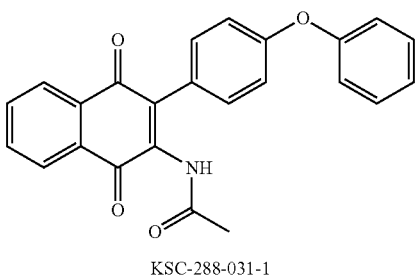 [SMILES: CC(=O)NC1=C(c2ccc(Oc3ccccc3)cc2)C(=O)c2ccccc2C1=O]

KSC-288-031-1

N-(1,4-dioxo-3-(4-phenoxyphenyl)-1,4-dihydronaphthalen-2-yl)acetamide (KSC-288-031-1)

Compound was prepared according to the procedures of Blagg et al.[1] $^1$H NMR (500 MHz, DMSO-$d_6$) δ 9.65 (s, 1H), 8.09-8.03 (m, 2H), 7.95-7.86 (m, 2H), 7.48-7.42 (m, 2H), 7.34-7.29 (m, 2H), 7.20 (tt, J=7.6, 1.1 Hz, 1H), 7.12-7.06 (m, 2H), 7.06-7.00 (m, 2H), 1.91 (s, 3H); $^{13}$C NMR (126 MHz, DMSO) δ 183.42, 180.90, 168.61, 156.91, 156.05, 140.07, 134.36, 134.07, 131.62, 131.46, 131.11, 130.13, 127.03, 126.28, 125.92, 123.87, 119.11, 117.30, 22.70; HRMS (ESI-TOF) m/z: [M+H]$^+$ Calcd for $C_{24}H_{18}NO_4$ 384.1230. Found 384.1234.

Synthetic Protocols for KSC-288-076-1 to KSC-292-044-1

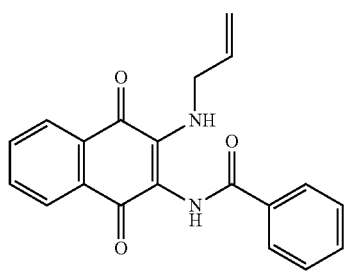

KSC-288-076-1

N-(3-(allylamino)-1,4-dioxo-1,4-dihydronaphthalen-2-yl)benzamide (KSC-288-076-1)

Allylamine (20.7 mg, 0.363 mmol), KSC-279-067-1 (51.6 mg, 0.166 mmol) (pp. 51), and 1-pentanol (1 mL) were combined in a microwave vial, capped with a headspace of air, and held at 150° C. in a Biotage Initiator™ microwave reactor for 5 minutes. Upon cooling, the solution was concentrated in vacuo. The resulting residue was purified according to the preparative RP HPLC methods described in the General Experimental Section (pp. 41). Yield: 36.5 mg; 66%. $^1$H NMR (500 MHz, DMSO-$d_6$) δ 9.51 (s, 1H), 8.06-8.01 (m, 1H), 7.98 (ddd, J=8.5, 5.5, 1.3 Hz, 3H), 7.86 (td, J=7.6, 1.3 Hz, 1H), 7.77 (td, J=7.5, 1.3 Hz, 1H), 7.63-7.56 (m, 1H), 7.56-7.49 (m, 2H), 7.44 (t, J=6.6 Hz, 1H), 5.87 (ddt, J=17.1, 10.3, 5.2 Hz, 1H), 5.10-4.99 (m, 2H), 4.18-3.88 (m, 2H); $^{13}$C NMR (126 MHz, DMSO) δ 182.18, 178.20, 166.58, 144.14, 135.08, 134.99, 134.01, 132.53, 132.27, 131.52, 129.98, 128.33, 127.66, 126.11, 125.64, 115.89, 111.53, 45.23; HRMS (ESI-TOF) m/z: [M+H]$^+$ Calcd for $C_{20}H_{17}N_2O_3$ 333.1234. Found 333.1233.

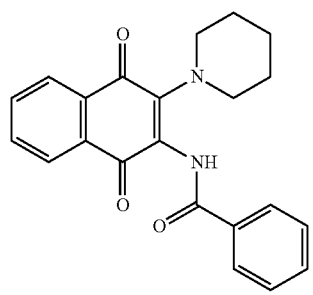

KSC-288-061-1

N-(1,4-dioxo-3-(piperidin-1-yl)-1,4-dihydronaphthalen-2-yl)benzamide (KSC-288-061-1)

This compound was prepared using the same protocol described for KSC-288-076-1 (pp. 66) using KSC-279-067-1 (pp. 51) and the appropriate amine. Yield: 85.3 mg; 92%. $^1$H NMR (400 MHz, CDCl$_3$) δ 8.27 (s, 1H), 7.96-7.86 (m, 2H), 7.86-7.79 (m, 2H), 7.53 (dd, J=5.7, 3.3 Hz, 2H), 7.49-7.42 (m, 1H), 7.42-7.34 (m, 2H), 3.43-3.30 (m, 4H), 1.60 (p, J=6.2 Hz, 4H), 1.55-1.46 (m, 2H); $^{13}$C NMR (101 MHz, CDCl$_3$) δ 183.04, 180.99, 165.11, 144.63, 133.87, 133.50, 133.08, 132.28, 132.15, 130.94, 128.79, 127.61, 126.73, 125.60, 120.29, 50.29, 26.56, 24.05; HRMS (ESI-TOF) m/z: [M+H]$^+$ Calcd for $C_{22}H_{21}N_2O_3$ 361.1547. Found 361.1565.

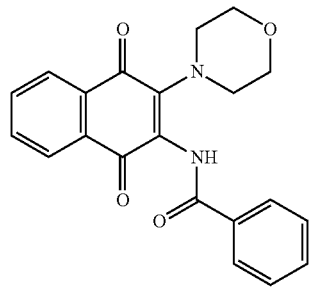

KSC-288-063-1

N-(3-morpholino-1,4-dioxo-1,4-dihydronaphthalen-2-yl)benzamide (KSC-288-063-1)

This compound was prepared using the same protocol described for KSC-288-076-1 (pp. 66) using KSC-279-067-1 (pp. 51) and the appropriate amine. Yield: 74.0 mg; 85%. $^1$H NMR (400 MHz, CDCl$_3$) δ 8.40 (s, 1H), 8.09-7.99 (m, 2H), 7.99-7.92 (m, 2H), 7.71-7.64 (m, 2H), 7.63-7.56 (m, 1H), 7.55-7.47 (m, 2H), 3.89-3.76 (m, 4H), 3.60-3.49 (m, 4H); $^{13}$C NMR (101 MHz, CDCl$_3$) δ 182.94, 181.28, 165.07, 143.33, 133.69, 133.44, 133.40, 132.39, 132.15, 130.71, 128.87, 127.63, 126.80, 125.76, 121.08, 67.29, 49.19; HRMS (ESI-TOF) m/z: [M+H]$^+$ Calcd for $C_{21}H_{19}N_2O_4$ 363.1339. Found 363.1350.

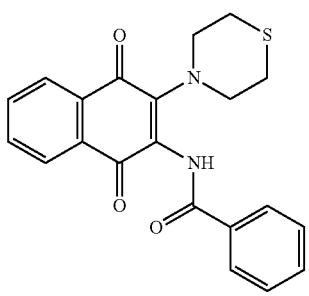

KSC-288-074-1

N-(1,4-dioxo-3-thiomorpholino-1,4-dihydronaphthalen-2-yl)benzamide (KSC-288-074-1)

This compound was prepared using the same protocol described for KSC-288-076-1 (pp. 66) using KSC-279-067-1 (pp. 51) and the appropriate amine. Yield: 34.0 mg; 54%. $^1$H NMR (500 MHz, DMSO-$d_6$) δ 9.69 (s, 1H), 8.06-7.99 (m, 3H), 7.99-7.95 (m, 1H), 7.87-7.78 (m, 2H), 7.66-7.60 (m, 1H), 7.59-7.53 (m, 2H), 3.64-3.44 (m, 4H), 2.81-2.62 (m, 4H); $^{13}$C NMR (126 MHz, DMSO) δ 182.66, 179.91, 165.01, 148.52, 134.21, 133.51, 133.40, 131.87, 131.39, 130.84, 128.51, 127.77, 126.41, 125.41, 123.18, 51.80, 27.17; HRMS (ESI-TOF) m/z: [M+H]$^+$ Calcd for $C_{21}H_{19}N_2O_3S$ 379.1111. Found 379.1117.

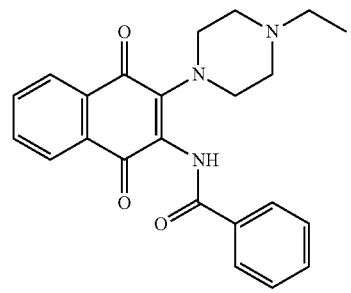

KSC-288-075-1

N-(3-(4-ethylpiperazin-1-yl)-1,4-dioxo-1,4-dihydronaphthalen-2-yl)benzamide (KSC-288-075-1)

This compound was prepared using the same protocol described for KSC-288-076-1 (pp. 66) using KSC-279-067-1 (pp. 51) and the appropriate amine. Yield: 51.5 mg; 80%. $^1$H NMR (500 MHz, DMSO-$d_6$) δ 9.65 (s, 1H), 8.06-7.94 (m, 4H), 7.81 (dtd, J=13.8, 7.4, 1.7 Hz, 2H), 7.65-7.59 (m, 1H), 7.58-7.51 (m, 2H), 3.46-3.31 (m, 4H), 2.49-2.39 (m, 4H), 2.30 (q, J=7.1 Hz, 2H), 0.95 (t, J=7.1 Hz, 3H); $^{13}$C NMR (126 MHz, DMSO) δ 182.68, 179.64, 164.98, 148.04, 134.21, 133.58, 133.22, 131.77, 131.48, 130.95, 128.47, 127.73, 126.36, 125.34, 121.82, 52.65, 51.59, 49.36, 11.83; HRMS (ESI-TOF) m/z: [M+H]$^+$ Calcd for $C_{23}H_{24}N_3O_3$ 390.1812. Found 390.1832.

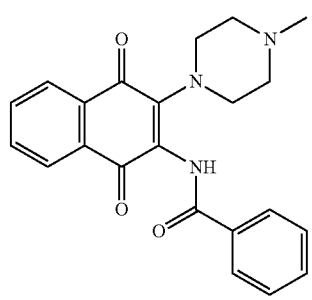

KSC-288-064-1

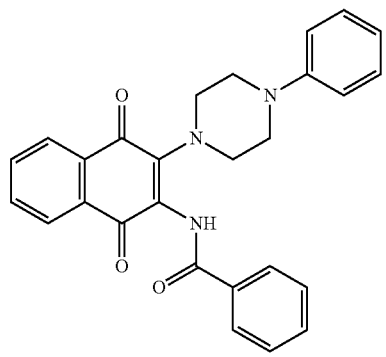

KSC-288-073-1

N-(3-(4-methylpiperazin-1-yl)-1,4-dioxo-1,4-dihydronaphthalen-2-yl)benzamide (KSC-288-064-1)

This compound was prepared using the same protocol described for KSC-288-076-1 (pp. 66) using KSC-279-067-1 (pp. 51) and the appropriate amine. Yield: 80.8 mg; 96%. $^1$H NMR (400 MHz, Chloroform-d) δ 8.36 (s, 1H), 8.07-7.98 (m, 2H), 7.97-7.90 (m, 2H), 7.66 (dt, J=7.4, 4.2 Hz, 2H), 7.61-7.53 (m, 1H), 7.53-7.45 (m, 2H), 3.64-3.48 (m, 4H), 2.54 (t, J=5.0 Hz, 4H), 2.30 (s, 3H); $^{13}$C NMR (101 MHz, CDCl$_3$) δ 182.99, 181.20, 164.81, 143.99, 133.59, 133.50, 133.25, 132.20, 130.82, 128.74, 127.64, 126.75, 125.69, 121.23, 55.38, 48.76, 46.23; HRMS (ESI-TOF) m/z: [M+H]$^+$ Calcd for $C_{22}H_{22}N_3O_3$ 376.1656. Found 376.1687.

N-(1,4-dioxo-3-(4-phenylpiperazin-1-yl)-1,4-dihydronaphthalen-2-yl)benzamide (KSC-288-073-1)

This compound was prepared using the same protocol described for KSC-288-076-1 (pp. 66) using KSC-279-067-1 (pp. 51) and the appropriate amine. Yield: 51.6 mg; 71%. $^1$H NMR (500 MHz, DMSO-$d_6$) δ 9.72 (s, 1H), 8.07-8.00 (m, 3H), 8.00-7.95 (m, 1H), 7.82 (dtd, J=13.2, 7.4, 1.7 Hz, 2H), 7.65-7.60 (m, 1H), 7.60-7.52 (m, 2H), 7.23-7.16 (m, 2H), 6.93 (dt, J=7.9, 1.0 Hz, 2H), 6.78 (tt, J=7.3, 1.0 Hz, 1H), 3.55 (t, J=4.9 Hz, 4H), 3.25 (dd, J=6.4, 3.6 Hz, 4H); $^{13}$C NMR (126 MHz, DMSO) δ 182.70, 179.64, 165.16, 150.79, 147.88, 134.25, 133.56, 133.27, 131.82, 131.48, 130.96, 128.89, 128.49, 127.77, 126.41, 125.39, 122.10, 119.11, 115.62, 49.19, 48.83; HRMS (ESI-TOF) m/z: [M+H]$^+$ Calcd for C$_{27}$H$_{24}$N$_3$O$_3$ 438.1812. Found 438.1820.

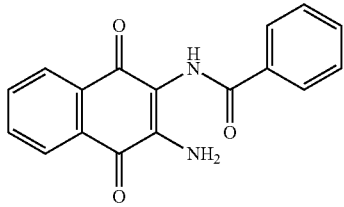

N-(3-amino-1,4-dioxo-1,4-dihydronaphthalen-2-yl) benzamide (KSC-292-066-1)

This compound was prepared using the same protocol described for KSC-279-067-1 (pp. 51) using KSC-292-065-1 (pp. 50) and the appropriate acyl chloride. Yield: 22.9 mg; 15%. $^1$H NMR (400 MHz, Chloroform-d) δ 8.93 (s, 1H), 8.09 (ddd, J=7.2, 5.8, 1.1 Hz, 2H), 8.02-7.92 (m, 2H), 7.72 (td, J=7.5, 1.3 Hz, 1H), 7.66 (td, J=7.5, 1.3 Hz, 1H), 7.63-7.57 (m, 1H), 7.57-7.49 (m, 2H), 7.27 (s, OH), 6.38 (s, 2H); $^{13}$C NMR (101 MHz, CDCl$_3$) δ 181.35, 179.10, 165.40, 137.76, 134.54, 133.59, 132.93, 132.46, 131.67, 130.52, 128.91, 127.60, 126.51, 126.36, 115.43; HRMS (ESI-TOF) m/z: [M+H]$^+$ Calcd for C$_{17}$H$_{12}$N$_2$O$_3$ 293.0921. Found 293.0913.

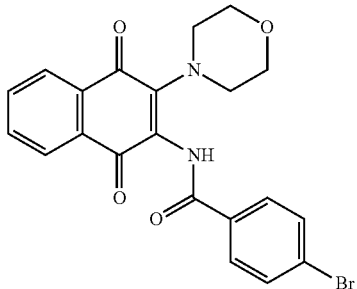

4-bromo-N-(3-morpholino-1,4-dioxo-1,4-dihydronaphthalen-2-yl)benzamide (KSC-292-041-1)

This compound was prepared using the same protocol described for KSC-288-076-1 (pp. 66) using KSC-292-034-1 (pp. 52) and the appropriate amine. Yield: 15.4 mg; 45%. $^1$H NMR (500 MHz, DMSO-d$_6$) δ 9.79 (s, 1H), 8.04-7.98 (m, 1H), 7.98-7.92 (m, 3H), 7.87-7.79 (m, 2H), 7.79-7.75 (m, 2H), 3.72-3.62 (m, 4H), 3.42-3.35 (m, 4H); $^{13}$C NMR (126 MHz, DMSO) δ 182.59, 179.56, 164.24, 147.76, 134.28, 133.31, 132.64, 131.55, 131.47, 130.90, 129.86, 126.41, 125.68, 125.38, 121.62, 66.48, 49.88; HRMS (ESI-TOF) m/z: [M+H]$^+$ Calcd for C$_{21}$H$_{18}$BrN$_2$O$_4$ 441.0444. Found 441.0431.

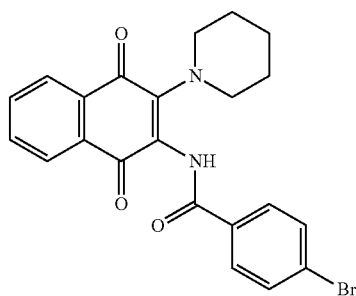

4-bromo-N-(1,4-dioxo-3-(piperidin-1-yl)-1,4-dihydronaphthalen-2-yl)benzamide (KSC-292-040-1)

This compound was prepared using the same protocol described for KSC-288-076-1 (pp. 66) using KSC-292-034-1 (pp. 52) and the appropriate amine. Yield: 13.3 mg; 45%. $^1$H NMR (500 MHz, DMSO-d$_6$) δ 9.72 (s, 1H), 8.02-7.98 (m, 1H), 7.98-7.93 (m, 3H), 7.85-7.74 (m, 4H), 3.40-3.27 (m, 4H), 1.67-1.57 (m, 4H), 1.57-1.50 (m, 2H); $^{13}$C NMR (126 MHz, DMSO) δ 182.82, 179.34, 164.02, 148.88, 134.21, 133.12, 132.82, 131.52, 131.03, 129.81, 126.38, 125.54, 125.29, 120.95, 50.82, 26.14, 23.55; HRMS (ESI-TOF) m/z: [M+H]$^+$ Calcd for C$_{22}$H$_{20}$BrN$_2$O$_3$ 439.0652. Found 439.0656.

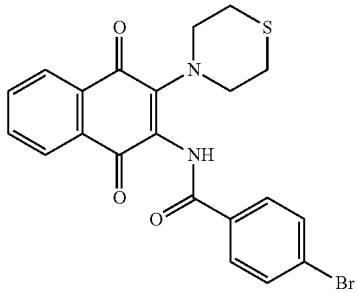

4-bromo-N-(1,4-dioxo-3-thiomorpholino-1,4-dihydronaphthalen-2-yl)benzamide (KSC-292-045-1)

This compound was prepared using the same protocol described for KSC-288-076-1 (pp. 66) using KSC-292-034-1 (pp. 52) and the appropriate amine. Yield: 16.6 mg; 41%. $^1$H NMR (500 MHz, DMSO-d$_6$) δ 9.80 (s, 1H), 8.03-7.99 (m, 1H), 7.99-7.95 (m, 3H), 7.86-7.81 (m, 2H), 7.81-7.76 (m, 2H), 3.60-3.45 (m, 4H), 2.77-2.64 (m, 4H); $^{13}$C NMR (126 MHz, DMSO) δ 182.61, 179.78, 164.17, 148.65, 134.24, 133.41, 132.61, 131.57, 131.41, 130.83, 129.89, 126.43, 125.73, 125.41, 122.90, 51.84, 27.16; HRMS (ESI-TOF) m/z: [M+H]$^+$ Calcd for C$_{21}$H$_{18}$BrN$_2$O$_3$S 457.0216. Found 457.0207.

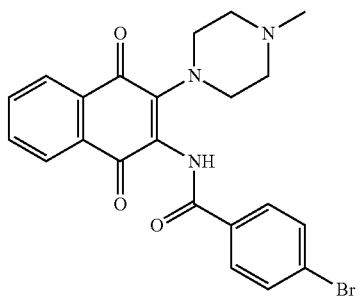

4-bromo-N-(3-(4-methylpiperazin-1-yl)-1,4-dioxo-1,4-dihydronaphthalen-2-yl)benzamide (KSC-292-042-1)

This compound was prepared using the same protocol described for KSC-288-076-1 (pp. 66) using KSC-292-034-1 (pp. 52) and the appropriate amine. Yield: 26.7 mg; 67%. $^1$H NMR (500 MHz, DMSO-d$_6$) δ 9.79 (s, 1H), 8.03-7.93 (m, 4H), 7.87-7.74 (m, 4H), 3.48-3.34 (m, 4H), 2.59-2.51 (m, 4H), 2.25 (s, 3H); $^{13}$C NMR (126 MHz, DMSO) δ 182.57, 179.56, 164.23, 163.32, 148.00, 134.27, 133.32, 132.67, 131.53, 131.46, 130.89, 129.86, 126.40, 125.66, 125.38, 121.98, 54.49, 48.76, 45.20; HRMS (ESI-TOF) m/z: [M+H]$^+$ Calcd for $C_{22}H_{21}BrN_3O_3$ 454.0761. Found 454.0765.

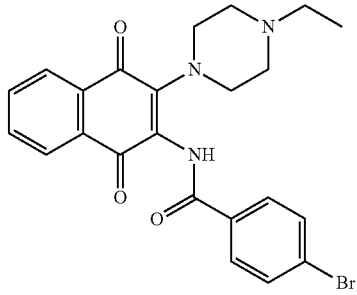

4-bromo-N-(3-(4-ethylpiperazin-1-yl)-1,4-dioxo-1,4-dihydronaphthalen-2-yl)benzamide (KSC-292-044-1)

This compound was prepared using the same protocol described for KSC-288-076-1 (pp. 66) using KSC-292-034-1 (pp. 52) and the appropriate amine. Yield: 26.8 mg; 58%. $^1$H NMR (500 MHz, DMSO-d$_6$) δ 9.80 (s, 1H), 8.02-7.93 (m, 4H), 7.86-7.75 (m, 4H), 3.46-3.34 (m, 4H), 2.59 (s, 4H), 2.44 (q, J=7.2 Hz, 2H), 1.00 (t, J=7.2 Hz, 3H); $^{13}$C NMR (126 MHz, DMSO) δ 182.57, 179.57, 164.18, 163.35, 147.92, 134.27, 133.31, 132.64, 131.53, 131.46, 130.89, 129.87, 126.39, 125.67, 125.38, 121.85, 52.30, 51.45, 48.83, 11.30; HRMS (ESI-TOF) m/z: [M+H]$^+$ Calcd for $C_{23}H_{23}BrN_3O_3$ 468.0917. Found 468.0910.

Synthetic Protocols for KSC-288-086-1 to KSC-292-015-1

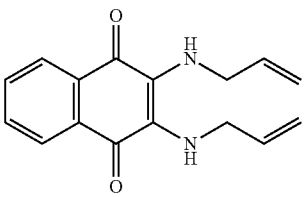

2,3-bis(allylamino)naphthalene-1,4-dione (KSC-288-086-1)

KSC-288-079-1 (50.0 mg, 0.144 mmol) (pp. 42), allylamine (35.8 mg, 0.627 mmol), and 1-pentanol (2 mL) were combined in a microwave vial, capped with a headspace of air, and held at 150° C. in a Biotage Initiator™ microwave reactor for 5 minutes. Upon cooling, the solution was concentrated in vacuo. To the crude residue was added trifluoroacetic acid (1 mL) and the solution was allowed to stir at room temperature under air for 2 h, after which time the solution was again concentrated in vacuo. The resulting residue was diluted with sat. aq. NaHCO$_3$ (ca. 2 mL) and extracted with dichloromethane (3×2 mL). The combined organic layers were combined, dried (Na$_2$SO$_4$), and concentrated in vacuo. The resulting residue was purified according to the preparative RP HPLC methods described in the General Experimental Section (pp. 41). Yield: 19.0 mg; 49%. $^1$H NMR (500 MHz, DMSO) δ 7.91-7.86 (m, 2H), 7.73-7.68 (m, 2H), 5.82 (ddt, J=17.1, 10.3, 5.6 Hz, 2H), 5.47 (t, J=7.2 Hz, 2H), 5.10 (dq, J=17.2, 1.6 Hz, 2H), 5.03 (dq, J=10.2, 1.3 Hz, 2H), 3.76-3.67 (m, 4H); $^{13}$C NMR (126 MHz, DMSO) δ 180.87, 136.10, 133.44, 131.33, 130.68, 125.38, 115.64, 44.49; HRMS (ESI-TOF) m/z: [M+H]$^+$ Calcd for $C_{16}H_{17}N_2O_2$ 269.1285. Found 269.1301.

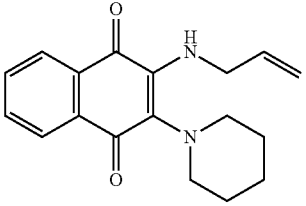

2-(allylamino)-3-(piperidin-1-yl)naphthalene-1,4-dione (KSC-288-078-1)

This compound was prepared using the same protocol described for KSC-288-086-1 (pp. 71) using KSC-288-079-1 (pp. 42) and the appropriate amine. Yield: 20.5 mg; 47%. $^1$H NMR (400 MHz, CDCl$_3$) δ 8.02 (dd, J=7.7, 1.2 Hz, 1H), 7.96 (dd, J=7.7, 1.2 Hz, 1H), 7.67 (td, J=7.6, 1.4 Hz, 1H), 7.55 (td, J=7.5, 1.3 Hz, 1H), 6.13 (t, J=6.6 Hz, 1H), 5.98 (ddt, J=17.2, 10.4, 5.2 Hz, 1H), 5.26-5.14 (m, 2H), 4.51 (ddt, J=6.7, 5.2, 1.7 Hz, 2H), 3.20-3.08 (m, 4H), 1.65-1.54 (m, 6H); $^{13}$C NMR (101 MHz, CDCl$_3$) δ 183.96, 181.39, 144.45, 135.37, 134.29, 133.56, 131.62, 130.48, 128.53, 125.77, 125.72, 115.63, 51.46, 46.84, 26.50, 24.10; HRMS (ESI-TOF) m/z: [M+H]$^+$ Calcd for $C_{18}H_{21}N_2O_2$ 297.1597579. Found 297.1591.

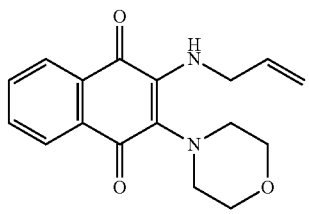

2-(allylamino)-3-morpholinonaphthalene-1,4-dione (KSC-288-087-1)

This compound was prepared using the same protocol described for KSC-288-086-1 (pp. 71) using KSC-288-079-1 (pp. 42) and the appropriate amine. Yield: 21.4 mg; 50%. $^1$H NMR (500 MHz, DMSO) δ 7.94-7.88 (m, 2H), 7.80 (td, J=7.6, 1.3 Hz, 1H), 7.68 (td, J=7.5, 1.3 Hz, 1H), 7.15 (t, J=6.7 Hz, 1H), 6.06-5.93 (m, 1H), 5.12-5.03 (m, 2H), 4.50-4.41 (m, 2H), 3.62 (t, J=4.6 Hz, 4H), 3.08 (s, 4H); $^{13}$C NMR (126 MHz, DMSO) δ 183.24, 180.14, 144.97, 136.20, 134.70, 132.92, 132.02, 129.90, 125.57, 125.20, 124.76, 114.05, 66.28, 50.20, 45.81; HRMS (ESI-TOF) m/z: [M+H]$^+$ Calcd for $C_{17}H_{19}N_2O_3$ 299.1390. Found 299.1417.

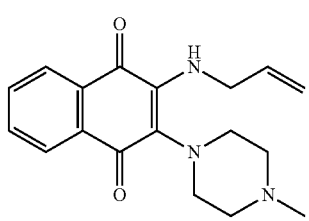

2-(allylamino)-3-thiomorpholinonaphthalene-1,4-dione (KSC-288-090-1)

This compound was prepared using the same protocol described for KSC-288-086-1 (pp. 71) using KSC-288-079-1 (pp. 42) and the appropriate amine. Yield: 22.3 mg; 49%. $^1$H NMR (500 MHz, DMSO) δ 7.93-7.86 (m, 2H), 7.79 (td, J=7.6, 1.3 Hz, 1H), 7.68 (td, J=7.5, 1.3 Hz, 1H), 7.10 (t, J=6.7 Hz, 1H), 5.98 (ddt, J=17.1, 10.5, 4.5 Hz, 1H), 5.13-5.03 (m, 2H), 4.47-4.38 (m, 2H), 3.40-3.20 (m, 4H), 2.74-2.56 (m, 4H)$^{13}$C NMR (126 MHz, DMSO) δ 183.38, 180.11, 144.54, 136.19, 134.64, 132.78, 132.01, 130.00, 126.67, 125.54, 125.18, 114.12, 52.25, 45.76, 27.19; HRMS (ESI-TOF) m/z: [M+H]$^+$ Calcd for $C_{17}H_{19}N_2O_2S$ 315.1162. Found 315.1191.

KSC-288-088-1

2-(allylamino)-3-(4-methylpiperazin-1-yl)naphthalene-1,4-dione (KSC-288-088-1)

This compound was prepared using the same protocol described for KSC-288-086-1 (pp. 71) using KSC-288-079-1 (pp. 42) and the appropriate amine. Yield: 17.2 mg; 38%. $^1$H NMR (500 MHz, DMSO) δ 7.93-7.88 (m, 2H), 7.79 (td, J=7.6, 1.3 Hz, 1H), 7.68 (td, J=7.5, 1.3 Hz, 1H), 7.02 (t, J=6.7 Hz, 1H), 5.96 (ddt, J=16.9, 10.6, 4.7 Hz, 1H), 5.12-5.02 (m, 2H), 4.48-4.39 (m, 2H), 3.10 (s, 4H), 2.35 (s, 4H), 2.19 (s, 3H); $^{13}$C NMR (126 MHz, DMSO) δ 183.24, 180.18, 144.62, 136.15, 134.65, 132.96, 131.99, 129.89, 125.53, 125.33, 125.21, 114.20, 54.94, 49.66, 46.13, 45.74; HRMS (ESI-TOF) m/z: [M+H]$^+$ Calcd for $C_{18}H_{22}N_3O_2$ 312.1707. Found 312.1729.

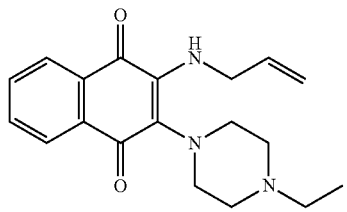

2-(allylamino)-3-(4-ethylpiperazin-1-yl)naphthalene-1,4-dione (KSC-288-089-1)

This compound was prepared using the same protocol described for KSC-288-086-1 (pp. 71) using KSC-288-079-1 (pp. 42) and the appropriate amine. Yield: 20.9 mg; 45%. $^1$H NMR (500 MHz, DMSO) δ 7.93-7.88 (m, 2H), 7.78 (td, J=7.6, 1.3 Hz, 1H), 7.67 (td, J=7.5, 1.3 Hz, 1H), 7.02 (t, J=6.7 Hz, 1H), 5.95 (ddt, J=16.8, 10.7, 4.7 Hz, 1H), 5.12-5.01 (m, 2H), 4.48-4.39 (m, 2H), 3.10 (s, 4H), 2.49-2.26 (m, 6H), 1.01 (t, J=7.2 Hz, 3H); $^{13}$C NMR (126 MHz, DMSO) δ 183.24, 180.16, 144.62, 136.16, 134.64, 132.95, 131.98, 129.88, 125.52, 125.36, 125.21, 114.18, 52.66, 51.90, 49.76, 45.74, 12.04; HRMS (ESI-TOF) m/z: [M+H]$^+$ Calcd for $C_{19}H_{24}N_3O_2$ 326.1863. Found 326.1895.

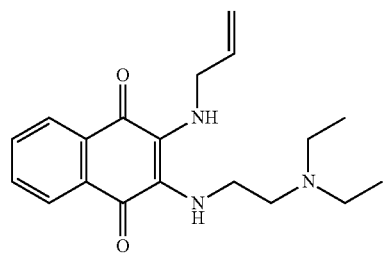

2-(allylamino)-3-((2-(diethylamino)ethyl)amino)naphthalene-1,4-dione (KSC-288-085-1)

This compound was prepared using the same protocol described for KSC-288-086-1 (pp. 71) using KSC-288-079-1 (pp. 42) and the appropriate amine. Yield: 18.4 mg; 39%. $^1$H NMR (500 MHz, DMSO) δ 7.90-7.85 (m, 2H), 7.73-7.67 (m, 2H), 5.82 (ddt, J=17.1, 10.3, 5.7 Hz, 1H), 5.65

(t, J=5.8 Hz, 1H), 5.26 (t, J=6.8 Hz, 1H), 5.10 (dq, J=17.1, 1.5 Hz, 1H), 5.02 (dq, J=10.2, 1.2 Hz, 1H), 3.67 (t, J=5.6 Hz, 2H), 3.18 (q, J=5.4 Hz, 2H), 2.49-2.40 (m, 6H), 0.90 (t, J=7.1 Hz, 6H); $^{13}$C NMR (126 MHz, DMSO) δ 180.95, 180.56, 136.23, 133.47, 133.33, 133.17, 130.93, 130.67, 130.30, 125.31, 125.26, 115.59, 52.29, 46.29, 45.00, 11.69; HRMS (ESI-TOF) m/z: [M+H]$^+$ Calcd for $C_{19}H_{26}N_3O_2$ 328.2020. Found 328.2042.

KSC-288-091-1

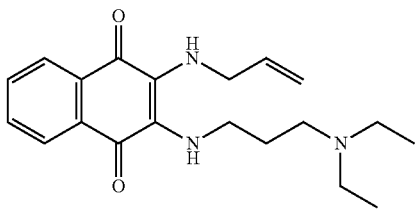

2-(allylamino)-3-((3-(diethylamino)propyl)amino) naphthalene-1,4-dione (KSC-288-091-1)

This compound was prepared using the same protocol described for KSC-288-086-1 (pp. 71) using KSC-288-079-1 (pp. 42) and the appropriate amine. Yield: 31.4 mg; 64%. $^1$H NMR (500 MHz, DMSO) δ 7.91-7.82 (m, 2H), 7.75-7.65 (m, 2H), 5.89-5.68 (m, 2H), 5.25 (t, J=7.1 Hz, 1H), 5.10 (dq, J=17.1, 1.5 Hz, 1H), 5.02 (dd, J=10.2, 1.7 Hz, 1H), 3.65 (t, J=6.2 Hz, 2H), 3.27-3.09 (m, 2H), 2.49-2.36 (m, 6H), 1.57 (p, J=6.7 Hz, 2H), 0.92 (t, J=7.1 Hz, 6H); $^{13}$C NMR (126 MHz, DMSO) δ 181.07, 180.56, 136.20, 133.50, 133.17, 132.84, 130.91, 130.62, 130.15, 125.33, 125.28, 115.57, 49.98, 46.11, 45.06, 41.14, 26.70, 11.28; HRMS (ESI-TOF) m/z: [M+H]$^+$ Calcd for $C_{20}H_{28}N_3O_2$ 342.2176. Found 342.2198.

KSC-288-084-1

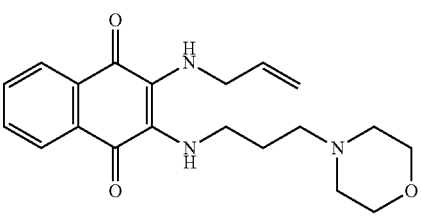

2-(allylamino)-3-((3-morpholinopropyl)amino)naphthalene-1,4-dione (KSC-288-084-1)

This compound was prepared using the same protocol described for KSC-288-086-1 (pp. 71) using KSC-288-079-1 (pp. 42) and the appropriate amine. Yield: 17.3 mg; 34%. $^1$H NMR (500 MHz, DMSO) δ 7.91-7.83 (m, 2H), 7.75-7.66 (m, 2H), 5.87-5.76 (m, 2H), 5.23 (t, J=7.2 Hz, 1H), 5.10 (dq, J=17.2, 1.6 Hz, 1H), 5.02 (dq, J=10.2, 1.2 Hz, 1H), 3.69-3.61 (m, 2H), 3.56 (t, J=4.6 Hz, 4H), 3.20 (q, J=6.0 Hz, 2H), 2.30 (t, J=6.7 Hz, 6H), 1.61 (p, J=6.7 Hz, 2H); $^{13}$C NMR (126 MHz, DMSO) δ 181.12, 180.56, 136.21, 133.53, 133.18, 132.98, 130.91, 130.63, 130.05, 125.36, 125.29, 115.60, 66.04, 56.16, 53.32, 45.08, 41.09, 26.07; HRMS (ESI-TOF) m/z: [M+H]$^+$ Calcd for $C_{20}H_{26}N_3O_3$ 356.1969. Found 356.2000.

Synthetic Protocols for KSC-292-015-1 to KSC-292-017-1

KSC-292-015-1

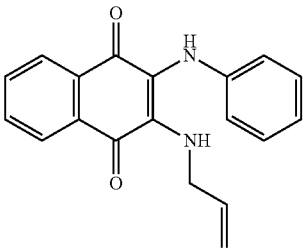

2-(allylamino)-3-(phenylamino)naphthalene-1,4-dione (KSC-292-015-1)

This compound was prepared using the same protocol described for KSC-288-086-1 (pp. 71) using KSC-292-002-1 (pp. 43) and the appropriate amine. Yield: 16.7 mg; 47%. $^1$H NMR (500 MHz, DMSO) δ 8.01-7.96 (m, 1H), 7.96-7.91 (m, 1H), 7.79 (td, J=7.5, 1.4 Hz, 1H), 7.73 (td, J=7.5, 1.4 Hz, 1H), 7.37 (s, 1H), 7.18-7.11 (m, 2H), 6.82 (t, J=6.9 Hz, 1H), 6.74-6.67 (m, 3H), 5.69 (ddt, J=17.1, 10.2, 5.6 Hz, 1H), 5.02-4.92 (m, 2H), 3.71-3.59 (m, 2H); $^{13}$C NMR (126 MHz, DMSO) δ 181.85, 180.03, 145.13, 139.41, 135.64, 134.39, 132.71, 131.87, 130.43, 128.64, 125.77, 125.43, 118.28, 118.22, 115.58, 114.95, 44.49; HRMS (ESI-TOF) m/z: [M+H]$^+$ Calcd for $C_{19}H_{17}N_2O_2$ 305.1285. Found 305.1285.

KSC-292-006-1

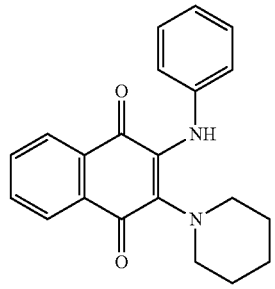

2-(phenylamino)-3-(piperidin-1-yl)naphthalene-1,4-dione (KSC-292-006-1)

This compound was prepared using the same protocol described for KSC-288-086-1 (pp. 71) using KSC-292-002-1 (pp. 43) and the appropriate amine. Yield: 18.2 mg; 47%. $^1$H NMR (500 MHz, DMSO) δ 8.07 (s, 1H), 7.92 (dd, J=7.3, 1.6 Hz, 2H), 7.74 (dtd, J=21.0, 7.4, 1.6 Hz, 2H), 7.24-7.16 (m, 2H), 6.97-6.86 (m, 3H), 3.10-2.96 (m, 4H), 1.35-1.16 (m, 6H); $^{13}$C NMR (126 MHz, DMSO) δ 181.59, 181.09, 140.49, 135.24, 133.56, 132.88, 132.22, 130.34, 129.79, 127.77, 125.84, 124.98, 120.72, 119.29, 49.23, 25.38, 23.81; HRMS (ESI-TOF) m/z: [M+H]$^+$ Calcd for $C_{21}H_{21}N_2O_2$ 333.1598. Found 333.1601.

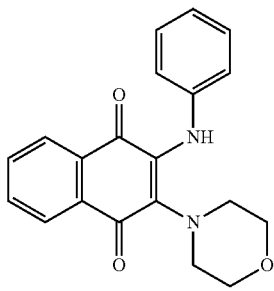

KSC-292-005-1

2-morpholino-3-(phenylamino)naphthalene-1,4-dione (KSC-292-005-1)

This compound was prepared using the same protocol described for KSC-288-086-1 (pp. 71) using KSC-292-002-1 (pp. 43) and the appropriate amine. Yield: 18.9 mg; 48%. $^1$H NMR (500 MHz, DMSO) δ 8.27 (s, 1H), 7.97-7.91 (m, 2H), 7.79 (td, J=7.5, 1.5 Hz, 1H), 7.73 (td, J=7.4, 1.5 Hz, 1H), 7.28-7.21 (m, 2H), 7.02-6.93 (m, 3H), 3.20-3.11 (m, 4H), 3.11-3.02 (m, 4H); $^{13}$C NMR (126 MHz, DMSO) δ 181.90, 181.00, 139.79, 133.83, 132.87, 132.65, 132.24, 131.49, 130.19, 127.75, 125.81, 125.10, 121.49, 120.52, 65.71, 48.36; HRMS (ESI-TOF) m/z: [M+H]$^+$ Calcd for $C_{20}H_{19}N_2O_3$ 335.1390. Found 335.1393.

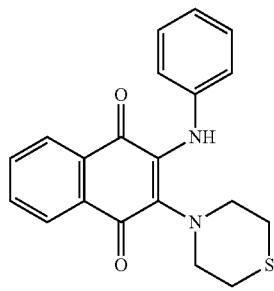

KSC-292-012-1

2-(phenylamino)-3-thiomorpholinonaphthalene-1,4-dione (KSC-292-012-1)

This compound was prepared using the same protocol described for KSC-288-086-1 (pp. 71) using KSC-292-002-1 (pp. 43) and the appropriate amine. Yield: 12.9 mg; 31%. $^1$H NMR (500 MHz, DMSO) δ 8.29 (s, 1H), 7.98-7.91 (m, 2H), 7.79 (td, J=7.5, 1.4 Hz, 1H), 7.73 (td, J=7.5, 1.4 Hz, 1H), 7.29-7.21 (m, 2H), 7.03-6.95 (m, 3H), 3.24-3.11 (m, 4H), 2.36-2.28 (m, 4H); $^{13}$C NMR (126 MHz, DMSO) δ 182.16, 180.99, 140.08, 133.91, 133.67, 132.83, 132.28, 132.14, 130.20, 127.78, 125.84, 125.16, 121.66, 120.49, 50.43, 26.46; HRMS (ESI-TOF) m/z: [M+H]$^+$ Calcd for $C_{20}H_{19}N_2O_2S$ 351.1162. Found 351.1161.

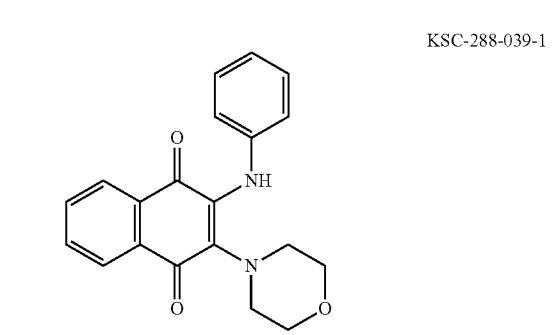 [SMILES: O=C1C(Nc2ccccc2)=C(N2CCOCC2)C(=O)c2ccccc21]

KSC-288-039-1

2-morpholino-3-(phenylamino)naphthalene-1,4-dione (KSC-288-039-1)

This compound was prepared using the same protocol described for KSC-288-086-1 (pp. 71) using KSC-292-002-1 (pp. 43) and the appropriate amine. Yield: 26.0 mg; 18%. $^1$H NMR (500 MHz, DMSO) δ 8.27 (s, 1H), 7.98-7.90 (m, 2H), 7.78 (td, J=7.5, 1.5 Hz, 1H), 7.73 (td, J=7.4, 1.5 Hz, 1H), 7.28-7.21 (m, 2H), 7.03-6.93 (m, 3H), 3.18-3.12 (m, 4H), 3.10-3.03 (m, 4H); $^{13}$C NMR (126 MHz, DMSO) δ 181.90, 181.00, 139.79, 133.83, 132.87, 132.64, 132.23, 131.49, 130.19, 127.75, 125.81, 125.10, 121.49, 120.52, 65.71, 48.36; HRMS (ESI-TOF) m/z: [M+H]$^+$ Calcd for $C_{20}H_{19}N_2O_3$ 335.1390. Found 335.1406.

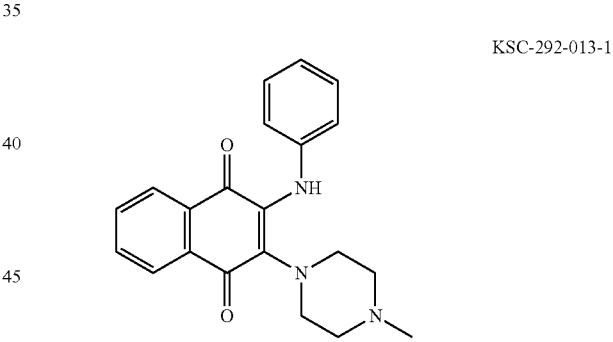

KSC-292-013-1

2-(4-methylpiperazin-1-yl)-3-(phenylamino)naphthalene-1,4-dione (KSC-292-013-1)

This compound was prepared using the same protocol described for KSC-288-086-1 (pp. 71) using KSC-292-002-1 (pp. 43) and the appropriate amine. Yield: 18.8 mg; 46%. $^1$H NMR (500 MHz, DMSO) δ 8.14 (s, 1H), 7.96-7.90 (m, 2H), 7.75 (dtd, J=22.6, 7.4, 1.4 Hz, 2H), 7.24-7.18 (m, 2H), 6.96-6.88 (m, 3H), 3.07 (t, J=4.7 Hz, 4H), 1.96 (s, 7H); $^{13}$C NMR (126 MHz, DMSO) δ 181.68, 180.99, 140.19, 134.01, 133.67, 132.89, 132.20, 130.35, 130.26, 127.82, 125.83, 125.03, 120.91, 119.74, 54.20, 47.72, 45.80; HRMS (ESI-TOF) m/z: [M+H]$^+$ Calcd for $C_{21}H_{22}N_3O_2$ 348.1707. Found 348.1716.

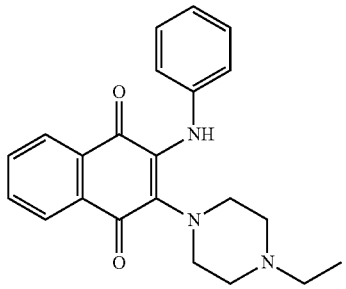

KSC-292-008-1

2-(4-ethylpiperazin-1-yl)-3-(phenylamino)naphthalene-1,4-dione (KSC-292-008-1)

This compound was prepared using the same protocol described for KSC-288-086-1 (pp. 71) using KSC-292-002-1 (pp. 43) and the appropriate amine. Yield: 20.3 mg; 48%. $^1$H NMR (500 MHz, DMSO) δ 8.13 (s, 1H), 7.96-7.89 (m, 2H), 7.74 (dtd, J=22.1, 7.4, 1.4 Hz, 2H), 7.24-7.17 (m, 2H), 6.97-6.87 (m, 3H), 3.08 (t, J=4.7 Hz, 4H), 2.10 (q, J=7.1 Hz, 2H), 2.01 (s, 4H), 0.86 (t, J=7.2 Hz, 3H); $^{13}$C NMR (126 MHz, DMSO) δ 181.65, 181.00, 140.20, 134.06, 133.65, 132.90, 132.19, 130.27, 130.17, 127.82, 125.83, 125.02, 120.88, 119.69, 51.94, 51.61, 47.88, 11.67; HRMS (ESI-TOF) m/z: [M+H]$^+$ Calcd for $C_{22}H_{24}N_3O_2$ 362.1863. Found 362.1877.

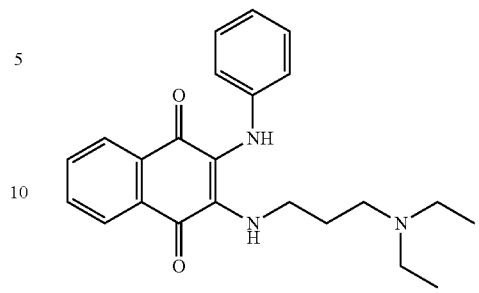

KSC-292-011-1

2-((3-(diethylamino)propyl)amino)-3-(phenylamino)naphthalene-1,4-dione (KSC-292-011-1)

This compound was prepared using the same protocol described for KSC-288-086-1 (pp. 71) using KSC-292-002-1 (pp. 43) and the appropriate amine. Yield: 36.5 mg; 82%. $^1$H NMR (500 MHz, DMSO) δ 8.00-7.96 (m, 1H), 7.96-7.92 (m, 1H), 7.79 (td, J=7.5, 1.4 Hz, 1H), 7.72 (td, J=7.5, 1.3 Hz, 1H), 7.30 (s, 1H), 7.23-7.08 (m, 3H), 6.73-6.61 (m, 3H), 3.19 (q, J=6.6 Hz, 2H), 2.43 (q, J=7.1 Hz, 4H), 2.31 (t, J=6.8 Hz, 2H), 1.47 (p, J=6.7 Hz, 2H), 0.90 (t, J=7.1 Hz, 6H); $^{13}$C NMR (126 MHz, DMSO) δ 182.03, 179.70, 164.26, 145.91, 140.74, 134.44, 132.50, 132.15, 130.40, 128.62, 125.75, 125.39, 117.93, 117.07, 114.62, 49.96, 45.99, 41.67, 26.27, 10.96; HRMS (ESI-TOF) m/z: [M+H]$^+$ Calcd for $C_{23}H_{28}N_3O_2$ 378.2176. Found 378.2189.

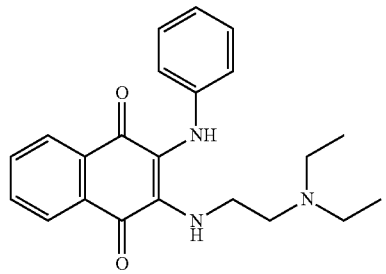

KSC-292-009-1

2-(2-(diethylamino)ethyl)amino)-3-(phenylamino)naphthalene-1,4-dione (KSC-292-009-1)

This compound was prepared using the same protocol described for KSC-288-086-1 (pp. 71) using KSC-292-002-1 (pp. 43) and the appropriate amine. Yield: 23.9 mg; 56%. $^1$H NMR (500 MHz, DMSO) δ 8.00-7.91 (m, 2H), 7.78 (td, J=7.5, 1.4 Hz, 1H), 7.72 (td, J=7.5, 1.4 Hz, 1H), 7.34 (s, 1H), 7.17-7.10 (m, 2H), 6.72-6.61 (m, 4H), 3.15 (q, J=6.3 Hz, 2H), 2.42-2.27 (m, 6H), 0.84 (t, J=7.1 Hz, 6H); $^{13}$C NMR (126 MHz, DMSO) δ 181.86, 179.67, 145.41, 140.34, 134.39, 132.54, 132.08, 130.42, 128.58, 125.72, 125.39, 118.08, 117.63, 114.81, 51.74, 46.09, 11.76; HRMS (ESI-TOF) m/z: [M+H]$^+$ Calcd for $C_{22}H_{26}N_3O_2$ 364.2020. Found 364.2046.

KSC-292-014-1

2-((4-(diethylamino)butyl)amino)-3-(phenylamino)naphthalene-1,4-dione (KSC-292-014-1)

This compound was prepared using the same protocol described for KSC-288-086-1 (pp. 71) using KSC-292-002-1 (pp. 43) and the appropriate amine. Yield: 32.7 mg; 71%. $^1$H NMR (500 MHz, DMSO) δ 9.25 (s, OH), 7.99 (dd, J=7.6, 1.0 Hz, 1H), 7.95 (dd, J=7.6, 0.9 Hz, 1H), 7.80 (td, J=7.5, 1.4 Hz, 1H), 7.74 (td, J=7.5, 1.3 Hz, 1H), 7.34 (s, 1H), 7.14 (dd, J=8.4, 7.4 Hz, 2H), 6.93 (t, J=6.8 Hz, 1H), 6.73-6.65 (m, 3H), 3.14 (q, J=6.2 Hz, 2H), 3.03 (q, J=7.1 Hz, 4H), 2.93-2.80 (m, 2H), 1.47-1.33 (m, 4H), 1.13 (t, J=7.3 Hz, 6H); $^{13}$C NMR (126 MHz, DMSO) δ 182.04, 179.88, 146.06, 140.64, 134.51, 132.59, 132.10, 130.42, 128.76, 125.80, 125.43, 118.01, 117.05, 114.51, 50.31, 46.12, 41.60, 26.94, 20.34, 8.44; HRMS (ESI-TOF) m/z: [M+H]$^+$ Calcd for $C_{24}H_{30}N_3O_2$ 392.2333. Found 392.2351.

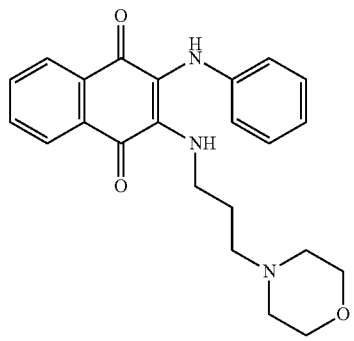

KSC-292-007-1

2-((3-morpholinopropyl)amino)-3-(phenylamino)naphthalene-1,4-dione (KSC-292-007-1)

This compound was prepared using the same protocol described for KSC-288-086-1 (pp. 71) using KSC-292-002-1 (pp. 43) and the appropriate amine. Yield: 23.5 mg; 51%. $^1$H NMR (500 MHz, DMSO) δ 8.01-7.96 (m, 1H), 7.96-7.91 (m, 1H), 7.78 (td, J=7.5, 1.4 Hz, 1H), 7.72 (td, J=7.5, 1.3 Hz, 1H), 7.30 (s, 1H), 7.16-7.06 (m, 3H), 6.72-6.63 (m, 3H), 3.52 (t, J=4.5 Hz, 4H), 3.20 (q, J=6.7 Hz, 2H), 2.21 (s, 4H), 2.15 (t, J=6.5 Hz, 2H), 1.48 (p, J=6.6 Hz, 2H); $^{13}$C NMR (126 MHz, DMSO) δ 182.05, 179.72, 145.88, 140.67, 134.44, 132.50, 132.14, 130.40, 128.62, 125.76, 125.39, 117.96, 117.11, 114.65, 66.00, 56.31, 53.21, 41.67, 26.09; HRMS (ESI-TOF) m/z: [M+H]$^+$ Calcd for $C_{23}H_{26}N_3O_3$ 392.1969. Found 392.1979.

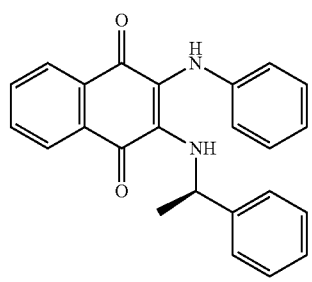

KSC-292-106-1

(R)-2-(phenylamino)-3-((1-phenylethyl)amino)naphthalene-1,4-dione (KSC-292-016-1)

This compound was prepared using the same protocol described for KSC-288-086-1 (pp. 71) using KSC-292-002-1 (pp. 43) and the appropriate amine. Yield: 11.1 mg; 26%. $^1$H NMR (500 MHz, DMSO) δ 7.97-7.93 (m, 1H), 7.93-7.88 (m, 1H), 7.75 (td, J=7.4, 1.6 Hz, 1H), 7.74-7.72 (m, 1H), 7.71 (td, J=7.4, 1.5 Hz, 1H), 7.26-7.18 (m, 4H), 7.17-7.09 (m, 3H), 6.85-6.78 (m, 3H), 6.37 (d, J=10.2 Hz, 1H), 4.57-4.45 (m, 1H), 1.13 (d, J=6.8 Hz, 3H); $^{13}$C NMR (126 MHz, DMSO) δ 181.41, 180.42, 144.57, 143.04, 135.73, 134.26, 133.07, 131.38, 130.30, 128.52, 128.28, 126.88, 125.77, 125.49, 120.41, 119.12, 116.14, 50.79, 22.34; HRMS (ESI-TOF) m/z: [M+H]$^+$ Calcd for $C_{24}H_{21}N_2O_2$ 369.1598. Found 369.1608.

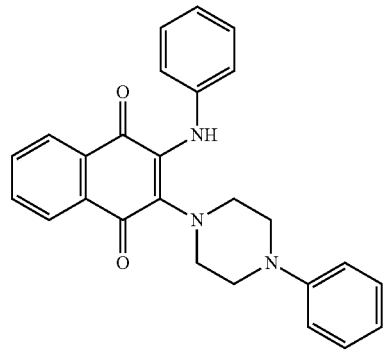

KSC-292-017-1

2-(phenylamino)-3-(4-phenylpiperazin-1-yl)naphthalene-1,4-dione (KSC-292-017-1)

This compound was prepared using the same protocol described for KSC-288-086-1 (pp. 71) using KSC-292-002-1 (pp. 43) and the appropriate amine. Yield: 5.8 mg; 12%. $^1$H NMR (500 MHz, DMSO) δ 8.27 (s, 1H), 7.99-7.92 (m, 2H), 7.77 (dtd, J=24.3, 7.4, 1.4 Hz, 2H), 7.25-7.18 (m, 2H), 7.18-7.10 (m, 2H), 7.01 (d, J=7.6 Hz, 2H), 6.91-6.83 (m, 1H), 6.83-6.76 (m, 2H), 6.76-6.69 (m, 1H), 3.26-3.18 (m, 4H), 2.82-2.74 (m, 4H); $^{13}$C NMR (126 MHz, DMSO) δ 181.83, 181.07, 151.00, 139.99, 133.80, 133.32, 132.91, 132.27, 131.20, 130.26, 128.81, 127.76, 125.85, 125.11, 121.22, 120.17, 118.74, 115.43, 48.10, 47.83; HRMS (ESI-TOF) m/z: [M+H]$^+$ Calcd for $C_{26}H_{24}N_3O_2$ 410.1863. Found 410.1879.

Synthetic Protocols for KSC-307-013-1 to KSC-307-016-1

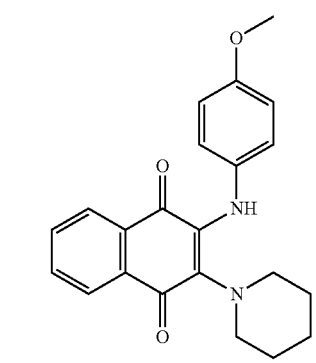

KSC-307-013-1

2-((4-methoxyphenyl)amino)-3-(piperidin-1-yl)naphthalene-1,4-dione (KSC-307-013-1)

This compound was prepared using the same protocol described for KSC-288-086-1 (pp. 71) using KSC-307-001-1 (pp. 43) and the appropriate amine. Yield: 65.5 mg; 72%. $^1$H NMR (400 MHz, DMSO) δ 8.06 (s, 1H), 7.96-7.88 (m, 2H), 7.74 (dtd, J=23.7, 7.4, 1.4 Hz, 2H), 6.97-6.77 (m, 4H), 3.73 (s, 3H), 3.01-2.91 (m, 4H), 1.32-1.23 (m, 2H), 1.23-1.13 (m, 4H); $^{13}$C NMR (126 MHz, DMSO) δ 181.95, 180.65, 154.49, 133.76, 133.05, 132.59, 132.42, 132.31, 132.26, 130.21, 125.69, 124.98, 121.90, 112.93, 55.22, 49.30, 25.21, 23.80; HRMS (ESI-TOF) m/z: [M+H]$^+$ Calcd for $C_{22}H_{23}N_2O_3$ 363.1703. Found 363.1735.

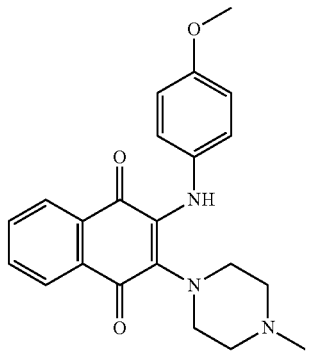

KSC-307-015-1

2-((4-methoxyphenyl)amino)-3-(4-methylpiperazin-1-yl)naphthalene-1,4-dione (KSC-307-015-1)

This compound was prepared using the same protocol described for KSC-288-086-1 (pp. 71) using KSC-307-001-1 (pp. 43) and the appropriate amine. Yield: 32.1 mg; 34%. $^1$H NMR (500 MHz, DMSO) δ 8.15 (s, 1H), 7.94-7.88 (m, 2H), 7.77 (td, J=7.5, 1.4 Hz, 1H), 7.70 (td, J=7.5, 1.4 Hz, 1H), 6.94-6.89 (m, 2H), 6.85-6.79 (m, 2H), 3.73 (s, 3H), 2.99 (t, J=4.8 Hz, 4H), 1.94 (d, J=22.0 Hz, 7H); $^{13}$C NMR (126 MHz, DMSO) δ 182.02, 180.56, 154.75, 133.86, 132.84, 132.75, 132.60, 132.41, 130.98, 130.13, 125.68, 125.04, 122.39, 113.04, 55.28, 54.07, 47.80, 45.90; HRMS (ESI-TOF) m/z: [M+H]$^+$ Calcd for $C_{22}H_{24}N_3O_3$ 378.1812. Found 378.1830.

KSC-307-016-1

2-(4-isopropylpiperazin-1-yl)-3-((4-methoxyphenyl)amino)naphthalene-1,4-dione (KSC-307-016-1)

This compound was prepared using the same protocol described for KSC-288-086-1 (pp. 71) using KSC-307-001-1 (pp. 43) and the appropriate amine. Yield: 48.5 mg; 48%. $^1$H NMR (500 MHz, DMSO) δ 8.14 (s, 1H), 7.93-7.86 (m, 2H), 7.75 (td, J=7.5, 1.4 Hz, 1H), 7.69 (td, J=7.5, 1.3 Hz, 1H), 6.94-6.87 (m, 2H), 6.85-6.77 (m, 2H), 3.70 (s, 3H), 3.06-2.93 (m, 4H), 2.45 (p, J=6.5 Hz, 1H), 1.95 (s, 4H), 0.77 (d, J=6.6 Hz, 6H); $^{13}$C NMR (126 MHz, DMSO) δ 182.01, 180.61, 154.75, 133.82, 132.71, 132.54, 132.40, 130.75, 130.09, 125.67, 124.99, 122.70, 112.83, 55.04, 53.63, 48.41, 46.95, 17.58; HRMS (ESI-TOF) m/z: [M+H]$^+$ Calcd for $C_{24}H_{28}N_3O_3$ 406.2125. Found 406.2131.

Synthetic Protocols for KSC-307-038-1 to KSC-307-047-1

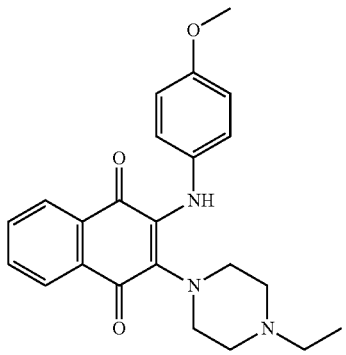

KSC-307-014-1

2-(4-ethylpiperazin-1-yl)-3-((4-methoxyphenyl)amino)naphthalene-1,4-dione (KSC-307-014-1)

This compound was prepared using the same protocol described for KSC-288-086-1 (pp. 71) using KSC-307-001-1 (pp. 43) and the appropriate amine. Yield: 33.5 mg; 34%. $^1$H NMR (500 MHz, DMSO) δ 8.13 (s, 1H), 7.94-7.88 (m, 2H), 7.76 (td, J=7.5, 1.4 Hz, 1H), 7.70 (td, J=7.5, 1.4 Hz, 1H), 6.93-6.89 (m, 2H), 6.84-6.80 (m, 2H), 3.72 (s, 3H), 3.06-2.92 (m, 4H), 2.10 (q, J=7.2 Hz, 2H), 1.95 (s, 4H), 0.86 (t, J=7.2 Hz, 3H); $^{13}$C NMR (126 MHz, DMSO) δ 181.99, 180.57, 154.70, 133.83, 132.72, 132.64, 132.59, 132.39, 131.03, 130.13, 125.68, 125.02, 122.35, 113.00, 55.24, 51.70, 51.69, 47.97, 11.53; HRMS (ESI-TOF) m/z: [M+H]$^+$ Calcd for $C_{23}H_{26}N_3O_3$ 392.1969. Found 392.1977.

KSC-307-038-1

2-((4-fluorophenyl)amino)-3-(piperidin-1-yl)naphthalene-1,4-dione (KSC-307-038-1)

This compound was prepared using the same protocol described for KSC-288-086-1 (pp. 71) using KSC-307-006-1 (pp. 44) and the appropriate amine. Yield: 53.5 mg; 61%. $^1$H NMR (400 MHz, DMSO) δ 8.16 (s, 1H), 7.93 (dt, J=7.3, 1.6 Hz, 2H), 7.75 (dtd, J=19.3, 7.4, 1.5 Hz, 2H), 7.09-7.01 (m, 2H), 7.00-6.93 (m, 2H), 3.05-2.96 (m, 4H), 1.36-1.26 (m, 2H), 1.27-1.17 (m, 4H); $^{13}$C NMR (126 MHz, DMSO) δ 181.69, 181.02, 158.02, 156.13, 136.61, 136.60, 134.20, 133.66, 132.82, 132.27, 130.77, 130.25, 125.80, 124.99, 121.25, 121.19, 114.26, 114.08, 49.24, 25.35, 23.75; HRMS (ESI-TOF) m/z: [M+H]$^+$ Calcd for $C_{21}H_{20}FN_2O_2$ 351.1503. Found 351.1542.

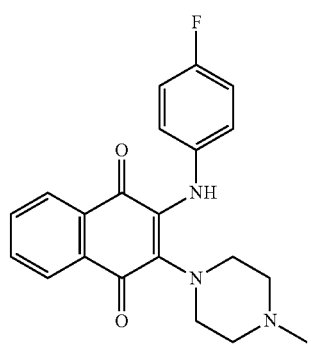

KSC-307-040-1

2-((4-fluorophenyl)amino)-3-(4-methylpiperazin-1-yl)naphthalene-1,4-dione (KSC-307-040-1)

This compound was prepared using the same protocol described for KSC-288-086-1 (pp. 71) using KSC-307-006-1 (pp. 44) and the appropriate amine. Yield: 54.7 mg; 60%. $^1$H NMR (500 MHz, DMSO) δ 8.23 (s, 1H), 7.94-7.89 (m, 2H), 7.74 (dtd, J=25.5, 7.4, 1.4 Hz, 2H), 7.08-7.02 (m, 2H), 6.99-6.93 (m, 2H), 3.03 (t, J=4.8 Hz, 4H), 1.97 (s, 3H), 1.94 (s, 4H); $^{13}$C NMR (126 MHz, DMSO) δ 181.76, 180.91, 158.26, 156.37, 136.25, 136.24, 133.74, 132.83, 132.79, 132.23, 131.42, 130.16, 125.78, 125.03, 121.78, 121.72, 114.29, 114.11, 54.19, 47.73, 45.86; HRMS (ESI-TOF) m/z: [M+H]$^+$ Calcd for $C_{21}H_{21}FN_3O_2$ 366.1612. Found 366.1626.

KSC-307-041-1

2-((4-fluorophenyl)amino)-3-(4-isopropylpiperazin-1-yl)naphthalene-1,4-dione (KSC-307-041-1)

This compound was prepared using the same protocol described for KSC-288-086-1 (pp. 71) using KSC-307-006-1 (pp. 44) and the appropriate amine. Yield: 64.9 mg; 48%. $^1$H NMR (400 MHz, DMSO) δ 8.26 (s, 1H), 7.98-7.89 (m, 2H), 7.76 (dtd, J=20.6, 7.4, 1.5 Hz, 2H), 7.12-7.02 (m, 2H), 7.02-6.95 (m, 2H), 3.11-2.98 (m, 4H), 2.51 (dt, J=3.7, 1.8 Hz, 1H), 2.14-1.96 (m, 4H), 0.83 (d, J=6.5 Hz, 6H); $^{13}$C NMR (126 MHz, DMSO) δ 181.81, 180.99, 158.34, 156.45, 136.01, 135.99, 133.79, 132.81, 132.25, 130.15, 125.79, 125.04, 122.17, 122.11, 114.26, 114.08, 53.81, 48.21, 47.17, 17.56; HRMS (ESI-TOF) m/z: [M+H]$^+$ Calcd for $C_{23}H_{25}FN_3O_2$ 394.1925. Found 394.1980.

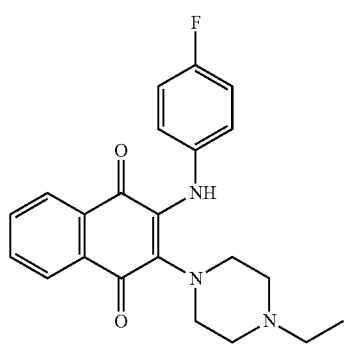

KSC-307-039-1

2-(4-ethylpiperazin-1-yl)-3-((4-fluorophenyl)amino) naphthalene-1,4-dione (KSC-307-039-1)

This compound was prepared using the same protocol described for KSC-288-086-1 (pp. 71) using KSC-307-006-1 (pp. 44) and the appropriate amine. Yield: 38.1 mg; 40%. $^1$H NMR (500 MHz, DMSO) δ 8.23 (s, 1H), 7.94-7.89 (m, 2H), 7.74 (dtd, J=24.9, 7.4, 1.4 Hz, 2H), 7.08-7.02 (m, 2H), 6.98-6.93 (m, 2H), 3.04 (t, J=4.8 Hz, 4H), 2.11 (q, J=7.2 Hz, 2H), 1.98 (s, 4H), 0.87 (t, J=7.2 Hz, 3H); $^{13}$C NMR (126 MHz, DMSO) δ 181.75, 180.93, 158.23, 156.34, 136.24, 136.22, 133.74, 132.86, 132.80, 132.23, 131.27, 130.16, 125.79, 125.03, 121.77, 121.71, 114.29, 114.11, 51.85, 51.67, 47.89, 11.55; HRMS (ESI-TOF) m/z: [M+H]$^+$ Calcd for $C_{22}H_{23}FN_3O_2$ 380.1769. Found 380.1776.

KSC-307-042-1

2-((4-fluorophenyl)amino)-3-(pyrrolidin-1-yl)naphthalene-1,4-dione (KSC-307-042-1)

This compound was prepared using the same protocol described for KSC-288-086-1 (pp. 71) using KSC-307-006-1 (pp. 44) and the appropriate amine. Yield: 51.9 mg; 62%. $^1$H NMR (500 MHz, DMSO) δ 7.90 (dd, J=6.9, 2.0 Hz, 2H), 7.76-7.68 (m, 3H), 7.01-6.95 (m, 2H), 6.71-6.65 (m, 2H), 3.44-3.37 (m, 4H), 1.58-1.50 (m, 4H); $^{13}$C NMR (126 MHz, DMSO) δ 182.71, 179.54, 156.64, 154.77, 139.49, 139.48, 138.40, 133.47, 132.69, 131.45, 131.23, 125.63, 124.82, 122.34, 116.55, 116.49, 114.78, 114.61, 50.60, 24.87; HRMS (ESI-TOF) m/z: [M+H]$^+$ Calcd for $C_{20}H_{18}FN_2O_2$ 337.1347. Found 337.1370.

KSC-307-043-1

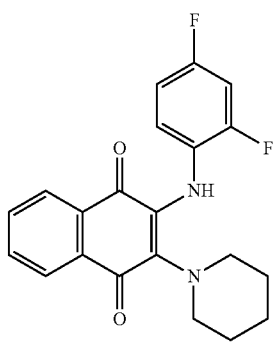

2-((2,4-difluorophenyl)amino)-3-(piperidin-1-yl)naphthalene-1,4-dione (KSC-307-043-1)

This compound was prepared using the same protocol described for KSC-288-086-1 (pp. 71) using KSC-307-007-1 (pp. 44) and the appropriate amine. Yield: 13.4 mg; 15%. $^1$H NMR (500 MHz, DMSO) δ 7.91 (s, 1H), 7.90-7.83 (m, 2H), 7.73 (td, J=7.5, 1.4 Hz, 1H), 7.67 (td, J=7.5, 1.4 Hz, 1H), 7.18 (ddd, J=11.6, 9.1, 2.8 Hz, 1H), 7.08 (td, J=9.2, 6.1 Hz, 1H), 6.97-6.91 (m, 1H), 2.87 (t, J=5.2 Hz, 4H), 1.25-1.14 (m, 2H), 1.10-0.98 (m, 4H); $^{13}$C NMR (126 MHz, DMSO) δ 181.77, 181.33, 159.06, 158.97, 157.13, 157.04, 156.08, 155.98, 154.11, 154.01, 135.42, 134.15, 132.80, 132.70, 132.30, 129.98, 125.69, 125.43, 125.40, 125.34, 125.31, 125.26, 124.87, 124.85, 124.79, 124.77, 110.29, 110.26, 110.11, 110.09, 103.65, 103.46, 103.43, 103.24, 49.82, 25.14, 23.51; HRMS (ESI-TOF) m/z: [M+H]$^+$ Calcd for $C_{21}H_{19}F_2N_2O_2$ 369.1409; Found 369.1434.

KSC-307-045-1

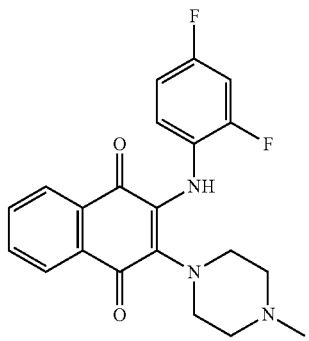

2-((2,4-difluorophenyl)amino)-3-(4-methylpiperazin-1-yl)naphthalene-1,4-dione (KSC-307-045-1)

This compound was prepared using the same protocol described for KSC-288-086-1 (pp. 71) using KSC-307-007-1 (pp. 44) and the appropriate amine. Yield: 42.2 mg; 44%. $^1$H NMR (400 MHz, DMSO) δ 8.20 (s, 1H), 8.00-7.91 (m, 2H), 7.82 (td, J=7.5, 1.4 Hz, 1H), 7.75 (td, J=7.5, 1.4 Hz, 1H), 7.34-7.17 (m, 2H), 7.08-6.99 (m, 1H), 3.01 (t, J=4.5 Hz, 4H), 2.18-1.99 (m, 7H); $^{13}$C NMR (126 MHz, DMSO) δ 181.82, 181.20, 159.53, 159.44, 157.60, 157.50, 156.49, 156.38, 154.51, 154.41, 137.07, 134.36, 132.83, 132.36, 132.24, 130.37, 130.17, 129.93, 125.73, 125.66, 125.41, 125.18, 125.15, 125.08, 125.06, 110.47, 110.45, 110.30, 110.27, 103.79, 103.60, 103.58, 103.39, 53.81, 47.78, 45.17; HRMS (ESI-TOF) m/z: [M+H]$^+$ Calcd for $C_{21}H_{20}F_2N_3O_2$ 384.1518. Found 384.1530.

KSC-307-044-1

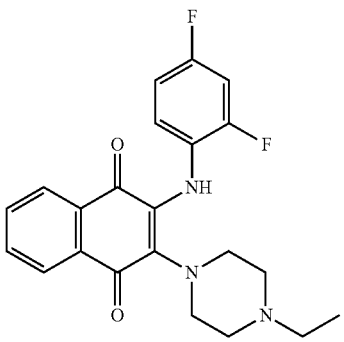

2-((2,4-difluorophenyl)amino)-3-(4-ethylpiperazin-1-yl)naphthalene-1,4-dione (KSC-307-044-1)

This compound was prepared using the same protocol described for KSC-288-086-1 (pp. 71) using KSC-307-007-1 (pp. 44) and the appropriate amine. Yield: 57.8 mg; 58%. $^1$H NMR (400 MHz, DMSO) δ 8.12 (s, 1H), 7.99-7.88 (m, 2H), 7.81 (td, J=7.5, 1.4 Hz, 1H), 7.74 (td, J=7.5, 1.4 Hz, 1H), 7.31-7.13 (m, 2H), 7.08-6.96 (m, 1H), 2.99 (t, J=4.7 Hz, 4H), 2.16 (q, J=7.1 Hz, 2H), 1.93 (s, 4H), 0.90 (t, J=7.2 Hz, 3H); $^{13}$C NMR (126 MHz, DMSO) δ 181.80, 181.24, 159.39, 159.30, 157.46, 157.37, 156.42, 156.32, 154.45, 154.35, 136.37, 134.26, 132.77, 132.27, 130.91, 129.89, 125.67, 125.44, 125.42, 125.32, 125.15, 125.12, 125.06, 125.03, 110.37, 110.34, 110.20, 110.17, 103.72, 103.53, 103.51, 103.32, 51.69, 51.59, 48.36, 11.33; HRMS (ESI-TOF) m/z: [M+H]$^+$ Calcd for $C_{22}H_{22}F_2N_3O_2$ 398.1675. Found 398.1699.

KSC-307-046-1

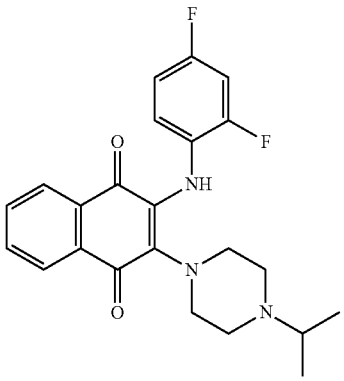

2-((2,4-difluorophenyl)amino)-3-(4-isopropylpiperazin-1-yl)naphthalene-1,4-dione (KSC-307-046-1)

This compound was prepared using the same protocol described for KSC-288-086-1 (pp. 71) using KSC-307-007-1 (pp. 44) and the appropriate amine. Yield: 63.0 mg; 61%. $^1$H NMR (400 MHz, DMSO) δ 8.15 (s, 1H), 8.00-7.88 (m, 2H), 7.80 (td, J=7.5, 1.4 Hz, 1H), 7.74 (td, J=7.5, 1.4 Hz, 1H), 7.30-7.14 (m, 2H), 7.07-6.97 (m, 1H), 3.04-2.88 (m, 4H), 2.58-2.46 (m, 1H), 1.95 (s, 4H), 0.82 (d, J=6.5 Hz, 6H); $^{13}$C NMR (126 MHz, DMSO) δ 181.85, 181.28, 159.52, 159.43, 157.59, 157.50, 156.64, 156.54, 154.67, 154.56, 136.48, 134.27, 132.73, 132.28, 130.72, 129.85, 125.66, 125.62, 125.31, 125.02, 124.99, 124.93, 124.90, 110.31, 110.29, 110.14, 110.11, 103.70, 103.51, 103.49, 103.30, 53.74, 48.82, 46.93, 17.46; HRMS (ESI-TOF) m/z: [M+H]$^+$ Calcd for $C_{23}H_{24}F_2N_3O_2$ 412.1831. Found 412.1889.

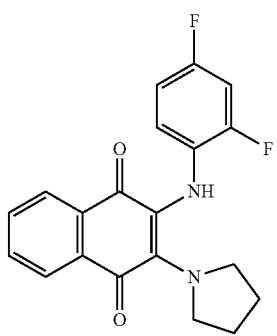

KSC-307-047-1

2-((2,4-difluorophenyl)amino)-3-(pyrrolidin-1-yl)naphthalene-1,4-dione (KSC-307-047-1)

This compound was prepared using the same protocol described for KSC-288-086-1 (pp. 71) using KSC-307-007-1 (pp. 44) and the appropriate amine. Yield: 35.9 mg; 41%. $^1$H NMR (500 MHz, DMSO) δ 7.93-7.88 (m, 2H), 7.74 (dtd, J=16.5, 7.4, 1.5 Hz, 2H), 7.20 (ddd, J=11.7, 8.9, 2.9 Hz, 1H), 6.97 (s, 1H), 6.89-6.84 (m, 1H), 6.49 (td, J=9.4, 5.8 Hz, 1H), 3.51-3.42 (m, 4H), 1.66-1.56 (m, 4H); $^{13}$C NMR (126 MHz, DMSO) δ 182.99, 179.02, 155.76, 155.67, 153.87, 153.78, 151.92, 151.82, 149.98, 149.88, 141.09, 133.70, 132.71, 131.53, 131.22, 129.14, 129.11, 129.05, 129.03, 125.80, 125.68, 124.88, 120.69, 116.45, 116.42, 116.38, 116.34, 110.50, 110.47, 110.32, 110.30, 103.70, 103.52, 103.49, 103.30, 51.07, 24.93; HRMS (ESI-TOF) m/z: [M+H]$^+$ Calcd for $C_{20}H_{17}F_2N_2O_2$ 355.1253. Found 355.1289.

Synthetic Protocols for KSC-307-023-1 to KSC-307-037-1

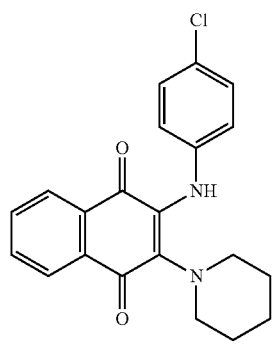

KSC-307-023-1

2-((4-chlorophenyl)amino)-3-(piperidin-1-yl)naphthalene-1,4-dione (KSC-307-023-1)

This compound was prepared using the same protocol described for KSC-288-086-1 (pp. 71) using KSC-307-003-1 (pp. 45) and the appropriate amine. Yield: 42.0 mg; 46%. $^1$H NMR (500 MHz, DMSO-d$_6$) δ 8.13 (s, 1H), 7.88-7.83 (m, 2H), 7.67 (dtd, J=18.7, 7.4, 1.5 Hz, 2H), 7.18-7.12 (m, 2H), 6.89-6.83 (m, 2H), 3.01-2.94 (m, 4H), 1.30-1.24 (m, 2H), 1.24-1.17 (m, 4H); $^{13}$C NMR (126 MHz, DMSO) δ 181.35, 181.20, 139.80, 136.24, 133.50, 132.98, 132.13, 130.36, 128.84, 127.56, 125.89, 124.98, 123.82, 120.24, 49.28, 25.56, 23.76; HRMS (ESI-TOF) m/z: [M+H]$^+$ Calcd for $C_{21}H_{20}ClN_2O_2$ 367.1208. Found 367.1248.

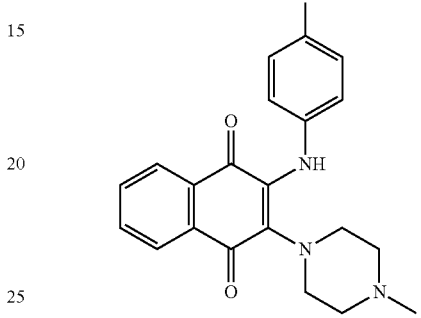

KSC-307-025-1

2-((4-chlorophenyl)amino)-3-(4-methylpiperazin-1-yl)naphthalene-1,4-dione (KSC-307-025-1)

This compound was prepared using the same protocol described for KSC-288-086-1 (pp. 71) using KSC-307-003-1 (pp. 45) and the appropriate amine. Yield: 41.8 mg; 44%. $^1$H NMR (500 MHz, DMSO-d$_6$) δ 8.29 (s, 1H), 7.95-7.89 (m, 3H), 7.74 (dtd, J=21.1, 7.4, 1.4 Hz, 2H), 7.27-7.21 (m, 2H), 6.96-6.91 (m, 2H), 3.07 (t, J=4.7 Hz, 6H), 2.05-1.68 (m, 4H); $^{13}$C NMR (126 MHz, DMSO) δ 181.52, 181.06, 139.29, 134.65, 133.64, 132.96, 132.13, 130.24, 129.70, 127.56, 125.87, 125.03, 124.29, 120.98, 54.28, 47.75, 45.86; HRMS (ESI-TOF) m/z: [M+H]$^+$ Calcd for $C_{21}H_{21}ClN_3O_2$ 382.1317. Found 382.1353.

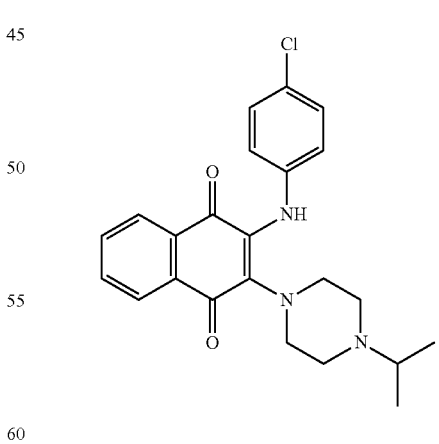

KSC-307-026-1

2-((4-chlorophenyl)amino)-3-(4-isopropylpiperazin-1-yl)naphthalene-1,4-dione (KSC-307-026-1)

This compound was prepared using the same protocol described for KSC-288-086-1 (pp. 71) using KSC-307-003-1 (pp. 45) and the appropriate amine. Yield: 52.3 mg;

45%. $^1$H NMR (500 MHz, DMSO-d$_6$) δ 8.30 (s, 1H), 7.95-7.89 (m, 2H), 7.74 (dtd, J=20.7, 7.4, 1.5 Hz, 2H), 7.26-7.20 (m, 2H), 6.96-6.91 (m, 2H), 3.14-3.02 (m, 4H), 2.52-2.45 (m, 2H), 2.06 (s, 4H), 0.81 (d, J=6.6 Hz, 6H); $^{13}$C NMR (126 MHz, DMSO) δ 181.54, 181.13, 138.95, 134.39, 133.63, 132.95, 132.14, 130.22, 129.60, 127.52, 125.86, 125.00, 124.42, 121.28, 53.65, 48.37, 47.27, 17.61; HRMS (ESI-TOF) m/z: [M+H]$^+$ Calcd for C$_{23}$H$_{25}$ClN$_3$O$_2$ 410.1630. Found 410.1653.

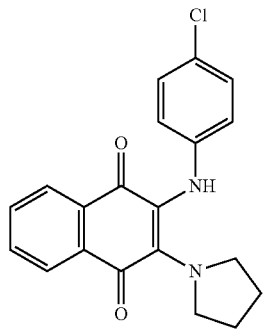

KSC-307-027-1

2-((4-chlorophenyl)amino)-3-(pyrrolidin-1-yl)naphthalene-1,4-dione (KSC-307-027-1)

This compound was prepared using the same protocol described for KSC-288-086-1 (pp. 71) using KSC-307-003-1 (pp. 45) and the appropriate amine. Yield: 33.6 mg; 38%. $^1$H NMR (400 MHz, DMSO-d$_6$) δ 7.91 (dt, J=7.0, 1.9 Hz, 2H), 7.81 (s, 1H), 7.74 (pd, J=7.4, 1.6 Hz, 2H), 7.22-7.11 (m, 2H), 6.72-6.59 (m, 2H), 3.51-3.39 (m, 4H), 1.60 (p, J=3.8 Hz, 4H); $^{13}$C NMR (126 MHz, DMSO) δ 183.02, 179.21, 142.79, 140.47, 133.64, 132.58, 131.43, 131.39, 128.12, 125.68, 124.83, 121.59, 120.50, 116.23, 51.03, 24.96; HRMS (ESI-TOF) m/z: [M+H]$^+$ Calcd for C$_{20}$H$_{18}$ClN$_2$O$_2$ 353.1051. Found 353.1077.

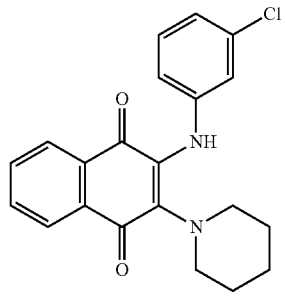

KSC-307-048-1

2-((3-chlorophenyl)amino)-3-(piperidin-1-yl)naphthalene-1,4-dione (KSC-307-048-1)

This compound was prepared using the same protocol described for KSC-288-086-1 (pp. 71) using KSC-307-008-1 (pp. 46) and the appropriate amine. Yield: 34.5 mg; 38%. $^1$H NMR (500 MHz, DMSO) δ 8.17 (s, 1H), 7.89-7.83 (m, 2H), 7.68 (dtd, J=16.4, 7.4, 1.4 Hz, 2H), 7.12 (t, J=8.0 Hz, 1H), 6.88-6.78 (m, 3H), 3.03 (t, J=5.5 Hz, 4H), 1.31-1.25 (m, 2H), 1.25-1.17 (m, 4H); $^{13}$C NMR (126 MHz, DMSO) δ 181.40, 181.27, 142.56, 137.25, 133.42, 133.02, 132.52, 132.18, 130.37, 129.28, 128.04, 125.94, 124.97, 119.49, 117.91, 116.99, 49.29, 25.56, 23.79; HRMS (ESI-TOF) m/z: [M+H]$^+$ Calcd for C$_{21}$H$_{20}$ClN$_2$O$_2$ 367.1208. Found 367.1219.

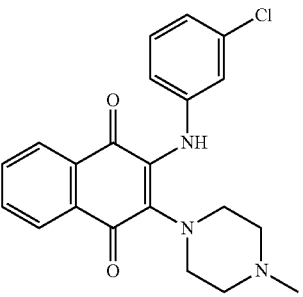

KSC-307-050-1

2-((3-chlorophenyl)amino)-3-(4-methylpiperazin-1-yl)naphthalene-1,4-dione (KSC-307-050-1)

This compound was prepared using the same protocol described for KSC-288-086-1 (pp. 71) using KSC-307-008-1 (pp. 46) and the appropriate amine. Yield: 44.8 mg; 47%. $^1$H NMR (500 MHz, DMSO) δ 8.30 (s, 1H), 7.95-7.91 (m, 2H), 7.75 (dtd, J=18.5, 7.4, 1.5 Hz, 2H), 7.20 (t, J=8.1 Hz, 1H), 6.97-6.92 (m, 1H), 6.92-6.87 (m, 2H), 3.13 (t, J=4.6 Hz, 4H), 2.10-2.01 (m, 4H), 2.00 (s, 3H); $^{13}$C NMR (126 MHz, DMSO) δ 181.40, 181.29, 142.23, 135.99, 133.54, 133.03, 132.59, 132.18, 130.28, 129.32, 128.63, 125.92, 125.02, 119.74, 118.40, 117.44, 54.35, 47.75, 45.80; HRMS (ESI-TOF) m/z: [M+H]$^+$ Calcd for C$_{21}$H$_{21}$ClN$_3$O$_2$ 382.1317. Found 382.1359.

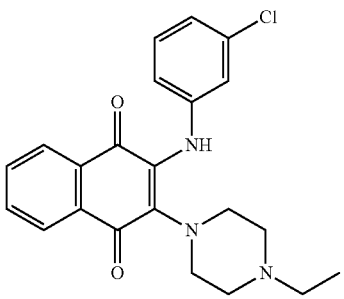

KSC-307-049-1

2-((3-chlorophenyl)amino)-3-(4-ethylpiperazin-1-yl)naphthalene-1,4-dione (KSC-307-049-1)

This compound was prepared using the same protocol described for KSC-288-086-1 (pp. 71) using KSC-307-008-1 (pp. 46) and the appropriate amine. Yield: 39.1 mg; 40%. $^1$H NMR (500 MHz, DMSO) δ 8.29 (s, 1H), 7.95-7.91 (m, 2H), 7.75 (dtd, J=18.0, 7.4, 1.5 Hz, 2H), 7.22-7.17 (m, 1H), 6.96-6.92 (m, 1H), 6.91-6.87 (m, 2H), 3.14 (t, J=4.5 Hz, 4H), 2.14 (q, J=7.1 Hz, 2H), 2.11-2.02 (m, 4H), 0.88 (t, J=7.2 Hz, 3H); $^{13}$C NMR (126 MHz, DMSO) δ 181.37, 181.30, 142.21, 135.99, 133.52, 133.03, 132.58, 132.16, 130.28, 129.31, 128.44, 125.92, 125.01, 119.71, 118.37, 117.39, 52.04, 51.62, 47.91, 11.57; HRMS (ESI-TOF) m/z: [M+H]⁺ Calcd for $C_{22}H_{23}ClN_3O_2$ 396.1473. Found 396.1516.

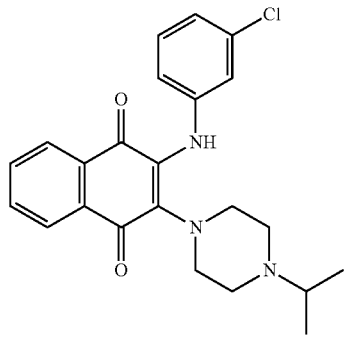

2-((3-chlorophenyl)amino)-3-(4-isopropylpiperazin-1-yl)naphthalene-1,4-dione (KSC-307-051-1)

This compound was prepared using the same protocol described for KSC-288-086-1 (pp. 71) using KSC-307-008-1 (pp. 46) and the appropriate amine. Yield: 50.8 mg; 50%. ¹H NMR (500 MHz, DMSO) δ 8.30 (s, 1H), 7.94-7.90 (m, 2H), 7.74 (dtd, J=17.9, 7.4, 1.5 Hz, 2H), 7.20 (t, J=8.0 Hz, 1H), 6.98-6.94 (m, 1H), 6.89-6.83 (m, 2H), 3.13 (t, J=4.2 Hz, 4H), 2.50-2.44 (m, 1H), 2.14-2.05 (m, 4H), 0.81 (d, J=6.6 Hz, 6H); ¹³C NMR (126 MHz, DMSO) δ 181.37, 181.32, 141.90, 135.72, 133.49, 132.99, 132.54, 132.15, 130.25, 129.23, 128.37, 125.91, 124.97, 119.79, 118.64, 117.59, 53.71, 48.37, 47.48, 17.68; HRMS (ESI-TOF) m/z: [M+H]⁺ Calcd for $C_{23}H_{25}ClN_3O_2$ 410.1630. Found 410.1663.

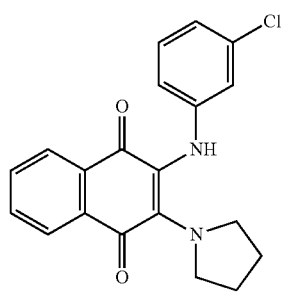

2-((3-chlorophenyl)amino)-3-(pyrrolidin-1-yl)naphthalene-1,4-dione (KSC-307-052-1)

This compound was prepared using the same protocol described for KSC-288-086-1 (pp. 71) using KSC-307-008-1 (pp. 46) and the appropriate amine. Yield: 43.9 mg; 50%. ¹H NMR (400 MHz, DMSO) δ 7.97-7.85 (m, 3H), 7.80-7.68 (m, 2H), 7.18-7.09 (m, 1H), 6.72 (ddd, J=7.9, 1.9, 0.9 Hz, 1H), 6.67-6.59 (m, 2H), 3.55-3.40 (m, 4H), 1.71-1.55 (m, 4H); ¹³C NMR (126 MHz, DMSO) δ 183.18, 179.14, 145.65, 141.23, 133.68, 133.05, 132.55, 131.48, 131.42, 129.92, 125.73, 124.86, 119.76, 117.43, 113.97, 113.22, 51.17, 24.97; HRMS (ESI-TOF) m/z: [M+H]⁺ Calcd for $C_{20}H_{18}ClN_2O_2$ 353.1051. Found 353.1083.

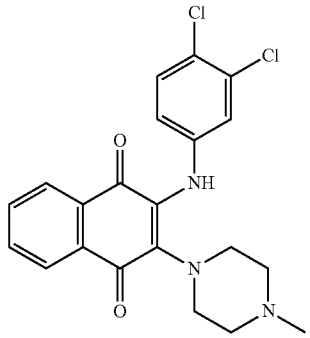

2-((3,4-dichlorophenyl)amino)-3-(4-methylpiperazin-1-yl)naphthalene-1,4-dione (KSC-307-035-1)

This compound was prepared using the same protocol described for KSC-288-086-1 (pp. 71) using KSC-307-005-1 (pp. 46) and the appropriate amine. Yield: 52.8 mg; 51%. ¹H NMR (500 MHz, DMSO) δ 8.42 (s, 1H), 7.93 (dt, J=7.1, 1.7 Hz, 2H), 7.75 (dtd, J=17.9, 7.4, 1.6 Hz, 2H), 7.40 (d, J=8.7 Hz, 1H), 7.04 (d, J=2.6 Hz, 1H), 6.99 (dd, J=8.8, 2.6 Hz, 1H), 3.13 (t, J=4.5 Hz, 4H), 2.04 (s, 4H), 2.01 (s, 3H); ¹³C NMR (126 MHz, DMSO) δ 181.32, 181.31, 140.95, 136.41, 133.53, 133.06, 132.18, 130.36, 130.26, 129.46, 128.19, 125.94, 125.02, 121.28, 119.95, 118.92, 54.42, 47.80, 45.87; HRMS (ESI-TOF) m/z: [M+H]⁺ Calcd for $C_{21}H_{20}Cl_2N_3O_2$ 416.0927. Found 416.0958.

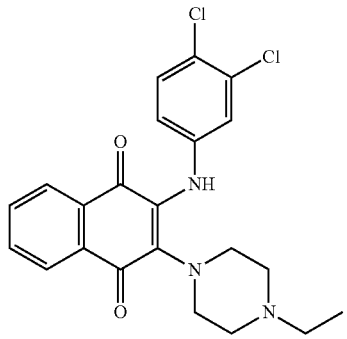

2-((3,4-dichlorophenyl)amino)-3-(4-ethylpiperazin-1-yl)naphthalene-1,4-dione (KSC-307-034-1)

This compound was prepared using the same protocol described for KSC-288-086-1 (pp. 71) using KSC-307-005-1 (pp. 46) and the appropriate amine. Yield: 35.5 mg; 33%. ¹H NMR (500 MHz, DMSO) δ 8.41 (s, 1H), 7.96-7.91 (m, 2H), 7.76 (dtd, J=17.6, 7.4, 1.5 Hz, 2H), 7.40 (d, J=8.7 Hz, 1H), 7.04 (d, J=2.6 Hz, 1H), 6.99 (dd, J=8.8, 2.6 Hz, 1H), 3.15 (t, J=4.5 Hz, 4H), 2.16 (q, J=7.1 Hz, 2H), 2.09 (s, 4H), 0.89 (t, J=7.2 Hz, 3H); ¹³C NMR (126 MHz, DMSO) δ 181.35, 181.30, 140.92, 136.43, 133.52, 133.07, 132.18, 130.35, 130.27, 129.46, 128.02, 125.95, 125.02, 121.24, 119.94, 118.90, 52.03, 51.67, 47.97, 11.42; HRMS (ESI-TOF) m/z: [M+H]⁺ Calcd for $C_{22}H_{22}Cl_2N_3O_2$ 430.1084. Found 430.1091.

Synthetic Protocols for KSC-307-028-1 to KSC-307-057-1

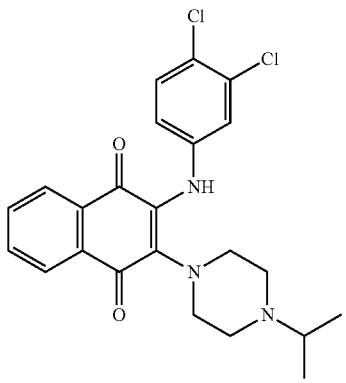

KSC-307-036-1

2-((3,4-dichlorophenyl)amino)-3-(4-isopropylpiperazin-1-yl)naphthalene-1,4-dione (KSC-307-036-1)

This compound was prepared using the same protocol described for KSC-288-086-1 (pp. 71) using KSC-307-005-1 (pp. 46) and the appropriate amine. Yield: 42.0 mg; 38%. $^1$H NMR (500 MHz, DMSO) δ 8.38 (s, 1H), 7.89-7.84 (m, 2H), 7.69 (dtd, J=18.0, 7.4, 1.5 Hz, 2H), 7.37-7.33 (m, 1H), 6.96-6.92 (m, 2H), 3.08 (t, J=4.3 Hz, 4H), 2.48-2.44 (m, 1H), 2.08-1.96 (m, 4H), 0.75 (d, J=6.6 Hz, 6H); $^{13}$C NMR (126 MHz, DMSO) δ 181.39, 181.35, 140.45, 135.95, 133.53, 133.03, 132.18, 130.29, 130.22, 129.38, 128.13, 125.94, 124.98, 121.48, 120.40, 119.29, 53.62, 48.42, 47.30, 17.45; HRMS (ESI-TOF) m/z: [M+H]$^+$ Calcd for $C_{23}H_{24}Cl_2N_3O_2$ 444.1240. Found 444.1251.

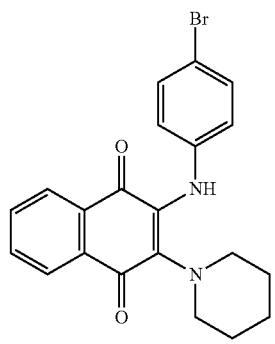

KSC-307-028-1

2-((4-bromophenyl)amino)-3-(piperidin-1-yl)naphthalene-1,4-dione (KSC-307-028-1)

This compound was prepared using the same protocol described for KSC-288-086-1 (pp. 71) using KSC-307-004-1 (pp. 47) and the appropriate amine. Yield: 25.8 mg; 25%. $^1$H NMR (400 MHz, DMSO) δ 8.19 (s, 1H), 7.99-7.88 (m, 2H), 7.76 (pd, J=7.4, 1.5 Hz, 2H), 7.38-7.31 (m, 2H), 6.91-6.83 (m, 2H), 3.11-2.99 (m, 4H), 1.42-1.19 (m, 6H); $^{13}$C NMR (126 MHz, DMSO) δ 181.31, 181.26, 140.36, 136.62, 133.50, 133.04, 132.13, 130.46, 130.39, 128.59, 125.91, 125.00, 120.57, 111.50, 49.31, 25.59, 23.76; HRMS (ESI-TOF) m/z: [M+H]$^+$ Calcd for $C_{21}H_{20}BrN_2O_2$ 411.0703. Found 411.0727.

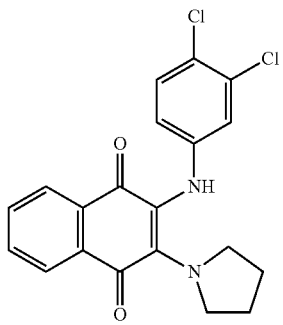

KSC-307-037-1

2-((3,4-dichlorophenyl)amino)-3-(pyrrolidin-1-yl)naphthalene-1,4-dione (KSC-307-037-1)

This compound was prepared using the same protocol described for KSC-288-086-1 (pp. 71) using KSC-307-005-1 (pp. 46) and the appropriate amine. Yield: 62.8 mg; 65%. $^1$H NMR (500 MHz, DMSO) δ 7.94 (s, 1H), 7.84 (dd, J=7.6, 1.3 Hz, 2H), 7.66 (dtd, J=20.4, 7.4, 1.3 Hz, 2H), 7.25 (d, J=8.8 Hz, 1H), 6.72 (d, J=2.7 Hz, 1H), 6.60 (dd, J=8.8, 2.7 Hz, 1H), 3.43-3.37 (m, 4H), 1.60-1.53 (m, 4H); $^{13}$C NMR (126 MHz, DMSO) δ 183.13, 179.00, 144.45, 141.70, 133.67, 132.49, 131.46, 131.41, 130.76, 130.04, 125.73, 124.85, 119.23, 118.72, 115.48, 114.77, 51.34, 25.02; HRMS (ESI-TOF) m/z: [M+H]$^+$ Calcd for $C_{20}H_{17}Cl_2N_2O_2$ 387.0662; Found 387.0685.

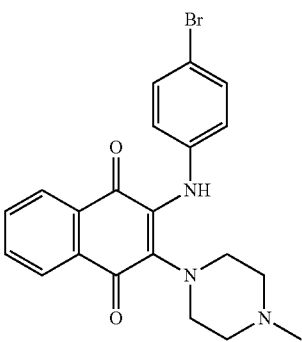

KSC-307-030-1

2-((4-bromophenyl)amino)-3-(4-methylpiperazin-1-yl)naphthalene-1,4-dione (KSC-307-030-1)

This compound was prepared using the same protocol described for KSC-288-086-1 (pp. 71) using KSC-307-004-1 (pp. 47) and the appropriate amine. Yield: 7.8 mg; 7%. $^1$H NMR (500 MHz, DMSO) δ 8.30 (s, 1H), 7.96-7.90 (m, 2H), 7.76 (dtd, J=20.3, 7.4, 1.5 Hz, 2H), 7.39-7.34 (m, 2H), 6.92-6.86 (m, 2H), 3.09 (t, J=4.4 Hz, 4H), 2.10-1.93 (m, 7H); $^{13}$C NMR (126 MHz, DMSO) δ 181.52, 181.11, 139.78, 134.85, 133.68, 133.02, 132.14, 130.46, 130.27, 129.59, 125.89, 125.06, 121.41, 112.05, 54.24, 47.69, 45.78; HRMS (ESI-TOF) m/z: [M+H]$^+$ Calcd for $C_{21}H_{21}BrN_3O_2$ 426.0812. Found 426.0855.

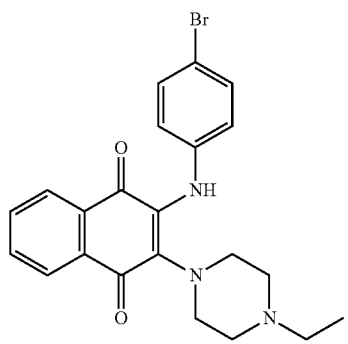

KSC-307-029-1

2-((4-bromophenyl)amino)-3-(4-ethylpiperazin-1-yl) naphthalene-1,4-dione (KSC-307-029-1)

This compound was prepared using the same protocol described for KSC-288-086-1 (pp. 71) using KSC-307-004-1 (pp. 47) and the appropriate amine. Yield: 23.9 mg; 22%. $^1$H NMR (500 MHz, DMSO) δ 8.22 (s, 1H), 7.90-7.83 (m, 2H), 7.69 (dtd, J=19.8, 7.4, 1.5 Hz, 2H), 7.33-7.25 (m, 2H), 6.84-6.79 (m, 2H), 3.03 (t, J=4.6 Hz, 4H), 2.09 (q, J=7.1 Hz, 2H), 1.99 (s, 4H), 0.82 (t, J=7.2 Hz, 3H); $^{13}$C NMR (126 MHz, DMSO) δ 181.47, 181.12, 139.76, 134.93, 133.63, 133.01, 132.12, 130.45, 130.27, 129.32, 125.88, 125.03, 121.33, 111.99, 51.94, 51.67, 47.92, 11.53; HRMS (ESI-TOF) m/z: [M+H]$^+$ Calcd for $C_{22}H_{23}BrN_3O_2$ 440.0968. Found 440.0978.

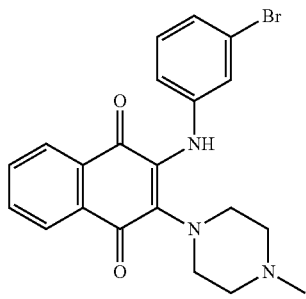

KSC-307-055-1

2-((3-bromophenyl)amino)-3-(4-methylpiperazin-1-yl)naphthalene-1,4-dione (KSC-307-055-1)

This compound was prepared using the same protocol described for KSC-288-086-1 (pp. 71) using KSC-307-009-1 (pp. 47) and the appropriate amine. Yield: 55.9 mg; 53%. $^1$H NMR (500 MHz, DMSO) δ 8.28 (s, 1H), 7.94-7.90 (m, 2H), 7.74 (dtd, J=18.5, 7.4, 1.5 Hz, 2H), 7.13 (t, J=7.9 Hz, 1H), 7.05-6.97 (m, 3H), 3.12 (t, J=4.6 Hz, 4H), 2.07-2.01 (m, 4H), 2.00 (s, 3H); $^{13}$C NMR (126 MHz, DMSO) δ 181.38, 181.26, 142.37, 135.87, 133.52, 133.01, 132.17, 130.26, 129.65, 128.62, 125.92, 125.01, 122.63, 121.20, 121.17, 117.84, 54.35, 47.75, 45.80; HRMS (ESI-TOF) m/z: [M+H]$^+$ Calcd for $C_{21}H_{21}BrN_3O_2$ 426.0812. Found 426.0857.

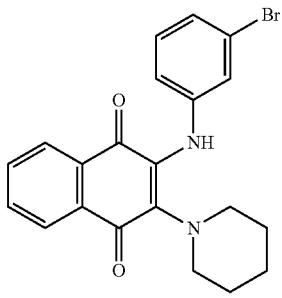

KSC-307-053-1

2-((3-bromophenyl)amino)-3-(piperidin-1-yl)naphthalene-1,4-dione (KSC-307-053-1)

This compound was prepared using the same protocol described for KSC-288-086-1 (pp. 71) using KSC-307-009-1 (pp. 47) and the appropriate amine. Yield: 47.6 mg; 46%. $^1$H NMR (500 MHz, DMSO) δ 8.16 (s, 1H), 7.89-7.84 (m, 2H), 7.68 (dtd, J=16.6, 7.4, 1.5 Hz, 2H), 7.08-7.03 (m, 1H), 6.97-6.93 (m, 2H), 6.92-6.88 (m, 1H), 3.03 (t, J=5.3 Hz, 4H), 1.33-1.16 (m, 6H); $^{13}$C NMR (126 MHz, DMSO) δ 181.40, 181.27, 142.71, 137.19, 133.43, 133.03, 132.19, 130.36, 129.62, 128.03, 125.94, 124.97, 122.37, 121.12, 120.70, 117.39, 49.30, 25.57, 23.80; HRMS (ESI-TOF) m/z: [M+H]$^+$ Calcd for $C_{21}H_{20}BrN_2O_2$ 411.0703. Found 411.0747.

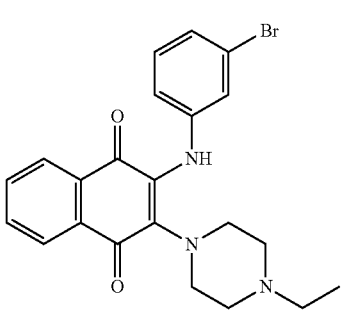

KSC-307-054-1

2-((3-bromophenyl)amino)-3-(4-ethylpiperazin-1-yl) naphthalene-1,4-dione (KSC-307-054-1)

This compound was prepared using the same protocol described for KSC-288-086-1 (pp. 71) using KSC-307-009-1 (pp. 47) and the appropriate amine. Yield: 52.5 mg; 48%. $^1$H NMR (500 MHz, DMSO) δ 8.28 (s, 1H), 7.95-7.91 (m, 2H), 7.75 (dtd, J=18.1, 7.4, 1.5 Hz, 2H), 7.14 (t, J=7.9 Hz, 1H), 7.04-6.97 (m, 3H), 3.14 (t, J=4.5 Hz, 4H), 2.15 (q, J=7.1 Hz, 2H), 2.09 (s, 4H), 0.88 (t, J=7.2 Hz, 3H); $^{13}$C NMR (126 MHz, DMSO) δ 181.36, 181.28, 142.37, 135.93, 133.52, 133.02, 132.17, 130.28, 129.65, 128.43, 125.93, 125.00, 122.60, 121.20, 121.14, 117.80, 52.04, 51.63, 47.92, 11.57; HRMS (ESI-TOF) m/z: [M+H]$^+$ Calcd for $C_{22}H_{23}BrN_3O_2$ 440.0968. Found 440.0993.

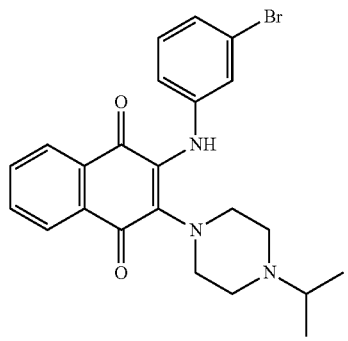

2-((3-bromophenyl)amino)-3-(4-isopropylpiperazin-1-yl)naphthalene-1,4-dione (KSC-307-056-1)

This compound was prepared using the same protocol described for KSC-288-086-1 (pp. 71) using KSC-307-009-1 (pp. 47) and the appropriate amine. Yield: 56.8 mg; 50%. $^1$H NMR (500 MHz, DMSO) δ 8.30 (s, 1H), 7.94-7.90 (m, 2H), 7.74 (dtd, J=18.1, 7.4, 1.5 Hz, 2H), 7.14 (t, J=8.1 Hz, 1H), 7.03-6.95 (m, 3H), 3.14 (t, J=4.4 Hz, 4H), 2.54-2.45 (m, 1H), 2.17-2.06 (m, 4H), 0.81 (d, J=6.6 Hz, 6H); $^{13}$C NMR (126 MHz, DMSO) δ 181.38, 181.32, 142.05, 135.66, 133.50, 133.00, 132.17, 130.25, 129.58, 128.39, 125.92, 124.98, 122.69, 121.44, 121.18, 118.02, 53.73, 48.37, 47.47, 17.70; HRMS (ESI-TOF) m/z: [M+H]$^+$ Calcd for $C_{23}H_{25}BrN_3O_2$ 454.1125. Found 454.1184.

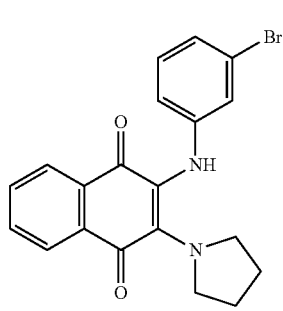

2-((3-bromophenyl)amino)-3-(pyrrolidin-1-yl)naphthalene-1,4-dione (KSC-307-057-1)

This compound was prepared using the same protocol described for KSC-288-086-1 (pp. 71) using KSC-307-009-1 (pp. 47) and the appropriate amine. Yield: 51.6 mg; 52%. $^1$H NMR (500 MHz, DMSO) δ 7.93-7.87 (m, 3H), 7.73 (dtd, J=18.9, 7.4, 1.6 Hz, 2H), 7.07 (t, J=8.0 Hz, 1H), 6.84 (ddd, J=7.8, 1.9, 0.8 Hz, 1H), 6.75 (t, J=2.0 Hz, 1H), 6.68 (ddd, J=8.3, 2.2, 0.8 Hz, 1H), 3.50-3.41 (m, 4H), 1.66-1.56 (m, 4H); $^{13}$C NMR (126 MHz, DMSO) δ 183.12, 179.15, 145.63, 140.92, 133.66, 132.55, 131.45, 131.38, 130.22, 125.72, 124.85, 121.67, 120.33, 119.89, 116.87, 113.66, 51.14, 24.97; HRMS (ESI-TOF) m/z: [M+H]$^+$ Calcd for $C_{20}H_{18}BrN_2O_2$ 397.0546. Found 397.0594.

Synthetic Protocols for KSC-307-018-1 to KSC-307-021-1

2-((4-iodophenyl)amino)-3-(piperidin-1-yl)naphthalene-1,4-dione (KSC-307-018-1)

This compound was prepared using the same protocol described for KSC-288-086-1 (pp. 71) using KSC-307-002-1 (pp. 48) and the appropriate amine. Yield: 24.5 mg; 21%. $^1$H NMR (500 MHz, DMSO-d$_6$) δ 8.09 (s, 1H), 7.88-7.83 (m, 2H), 7.73-7.62 (m, 3H), 7.44-7.39 (m, 2H), 6.71-6.64 (m, 2H), 3.03-2.92 (m, 4H), 1.31-1.19 (m, 6H); $^{13}$C NMR (126 MHz, DMSO) δ 181.25, 140.96, 136.85, 136.29, 133.47, 133.05, 132.11, 130.41, 128.34, 125.91, 125.00, 120.91, 82.47, 49.32, 25.61, 23.77; HRMS (ESI-TOF) m/z: [M+H]$^+$ Calcd for $C_{21}H_{20}IN_2O_2$ 459.0564. Found 459.0589.

2-((4-iodophenyl)amino)-3-(4-methylpiperazin-1-yl)naphthalene-1,4-dione (KSC-307-020-1)

This compound was prepared using the same protocol described for KSC-288-086-1 (pp. 71) using KSC-307-002-1 (pp. 48) and the appropriate amine. Yield: 20.8 mg; 18%. $^1$H NMR (500 MHz, DMSO-d$_6$) δ 8.22 (s, 1H), 7.86 (ddt, J=7.3, 1.7, 1.0 Hz, 2H), 7.69 (dtd, J=20.1, 7.4, 1.5 Hz, 2H), 7.47-7.41 (m, 2H), 6.73-6.66 (m, 2H), 3.02 (t, J=4.6 Hz, 4H), 1.95 (s, 7H); $^{13}$C NMR (126 MHz, DMSO) δ 181.50, 181.10, 140.27, 136.27, 134.96, 133.66, 133.02, 132.14, 130.27, 129.37, 128.49, 125.89, 125.05, 121.87, 83.17, 54.23, 47.76, 45.86; HRMS (ESI-TOF) m/z: [M+H]$^+$ Calcd for $C_{21}H_{21}IN_3O_2$ 474.0673. Found 474.0692.

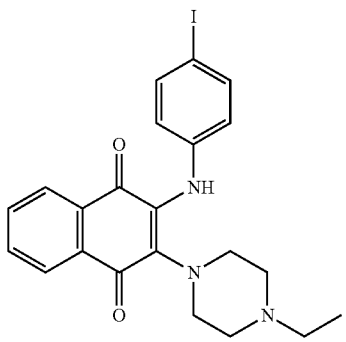

2-(4-ethylpiperazin-1-yl)-3-((4-iodophenyl)amino)naphthalene-1,4-dione (KSC-307-019-1)

This compound was prepared using the same protocol described for KSC-288-086-1 (pp. 71) using KSC-307-002-1 (pp. 48) and the appropriate amine. Yield: 35.8 mg; 29%. $^1$H NMR (500 MHz, DMSO-$d_6$) δ 8.21 (s, 1H), 7.86 (dt, J=7.3, 1.8 Hz, 2H), 7.69 (dtd, J=19.8, 7.4, 1.5 Hz, 2H), 7.47-7.39 (m, 2H), 6.73-6.66 (m, 2H), 3.03 (t, J=4.6 Hz, 6H), 2.11 (s, 2H), 2.01 (s, 4H), 0.84 (t, J=7.1 Hz, 3H); $^{13}$C NMR (126 MHz, DMSO) δ 181.47, 181.12, 140.27, 136.27, 133.64, 133.03, 132.13, 130.28, 128.50, 125.89, 125.05, 121.81, 51.88, 51.67, 47.89, 30.15, 18.50, 13.39, 11.67, 11.51; HRMS (ESI-TOF) m/z: [M+H]$^+$ Calcd for $C_{22}H_{23}IN_3O_2$ 488.0829. Found 488.0814.

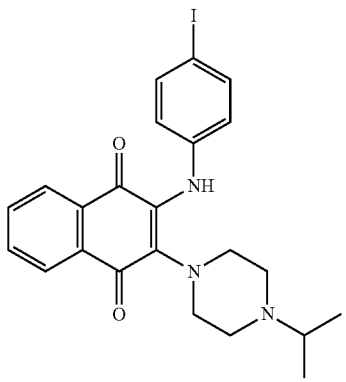

2-((4-iodophenyl)amino)-3-(4-isopropylpiperazin-1-yl)naphthalene-1,4-dione (KSC-307-021-1)

This compound was prepared using the same protocol described for KSC-288-086-1 (pp. 71) using KSC-307-002-1 (pp. 48) and the appropriate amine. Yield: 28.7 mg; 23%. $^1$H NMR (500 MHz, DMSO-$d_6$) δ 8.24 (s, 1H), 7.90-7.84 (m, 2H), 7.70 (dtd, J=20.0, 7.4, 1.5 Hz, 2H), 7.49-7.43 (m, 2H), 6.74-6.68 (m, 2H), 3.08-3.01 (m, 4H), 2.49-2.41 (m, 1H), 2.10-1.94 (m, 4H), 0.78 (d, J=6.6 Hz, 6H); $^{13}$C NMR (126 MHz, DMSO) δ 181.49, 181.16, 139.86, 136.24, 134.68, 133.62, 132.98, 132.12, 130.23, 129.23, 125.88, 125.01, 122.06, 83.41, 53.66, 48.38, 47.25, 17.73; HRMS (ESI-TOF) m/z: [M+H]$^+$ Calcd for $C_{23}H_{25}IN_3O_2$ 502.0986. Found 502.0986.

Synthetic Protocols for KSC-292-037-1 to KSC-292-078-1

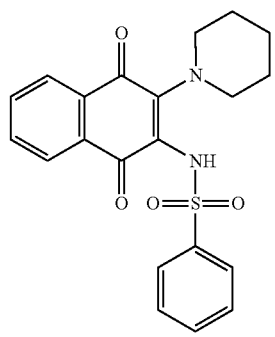

N-(1,4-dioxo-3-(piperidin-1-yl)-1,4-dihydronaphthalen-2-yl)benzenesulfonamide (KSC-292-037-1)

This compound was prepared using the same protocol described for KSC-288-076-1 (pp. 66) using KSC-292-029-1 (pp. 48) and the appropriate amine. Yield: 12.6 mg; 32%. $^1$H NMR (500 MHz, DMSO-$d_6$) δ 9.28 (s, 1H), 7.94-7.89 (m, 1H), 7.74-7.62 (m, 5H), 7.54-7.48 (m, 1H), 7.45-7.39 (m, 2H), 3.42-3.25 (m, 4H), 1.72-1.52 (m, 6H); $^{13}$C NMR (126 MHz, DMSO) δ 182.63, 179.94, 133.65, 132.95, 131.80, 130.66, 128.41, 126.53, 126.10, 124.97, 52.05, 26.02, 23.77; HRMS (ESI-TOF) m/z: [M+H]$^+$ Calcd for $C_{21}H_{21}N_2O_4S$ 397.1217. Found 397.1234.

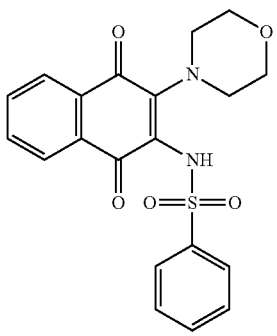

N-(3-morpholino-1,4-dioxo-1,4-dihydronaphthalen-2-yl)benzenesulfonamide (KSC-292-035-1)

This compound was prepared using the same protocol described for KSC-288-076-1 (pp. 66) using KSC-292-029-1 (pp. 48) and the appropriate amine. Yield: 9.5 mg; 25%. $^1$H NMR (500 MHz, DMSO-$d_6$) δ 9.29 (s, 1H), 7.99-7.90 (m, 1H), 7.78-7.69 (m, 4H), 7.67-7.62 (m, 1H), 7.56 (tt, J=7.0, 1.2 Hz, 1H), 7.48-7.41 (m, 2H), 3.81-3.70 (m, 4H), 3.51-3.40 (m, 4H); $^{13}$C NMR (126 MHz, DMSO) δ 182.81, 179.60, 149.39, 140.36, 134.15, 133.20, 132.52, 131.55, 130.33, 128.64, 126.80, 126.41, 125.08, 119.35, 66.31, 51.29; HRMS (ESI-TOF) m/z: [M+H]$^+$ Calcd for $C_{20}H_{19}N_2O_5S$ 399.1009. Found 399.1032.

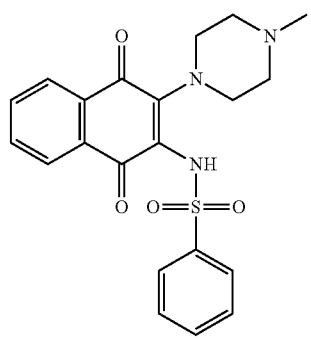

KSC-292-036-1

N-(3-(4-methylpiperazin-1-yl)-1,4-dioxo-1,4-dihydronaphthalen-2-yl)benzenesulfonamide (KSC-292-036-1)

This compound was prepared using the same protocol described for KSC-288-076-1 (pp. 66) using KSC-292-029-1 (pp. 48) and the appropriate amine. Yield: 13.2 mg; 33%. $^1$H NMR (500 MHz, DMSO-$d_6$) δ 7.94-7.89 (m, 1H), 7.76-7.64 (m, 5H), 7.55-7.49 (m, 1H), 7.46-7.40 (m, 2H), 3.46-3.37 (m, 5H), 2.56-2.52 (m, 4H), 2.27 (s, 3H); $^{13}$C NMR (126 MHz, DMSO) δ 182.38, 180.34, 133.61, 133.11, 131.88, 131.79, 130.59, 128.96, 128.45, 126.49, 126.08, 125.83, 125.05, 66.98, 54.80, 50.27, 45.60; HRMS (ESI-TOF) m/z: [M+H]$^+$ Calcd for $C_{21}H_{22}N_3O_4S$ 412.1326. Found 412.1322.

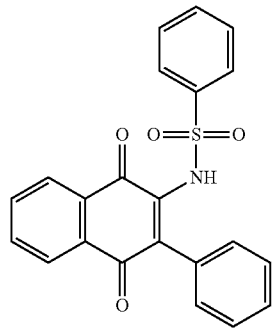

KSC-292-073-2

N-(1,4-dioxo-3-phenyl-1,4-dihydronaphthalen-2-yl)benzenesulfonamide (KSC-292-073-2)

This compound was prepared using the same protocol described for KSC-279-067-1 (pp. 51) using the appropriate sulfonyl chloride and KSC-279-070-1 (pp. 53). Yield: 50 mg; 30%. $^1$H NMR (500 MHz, DMSO-$d_6$) δ 9.84 (s, 1H), 8.06-7.96 (m, 2H), 7.89 (pd, J=7.4, 1.6 Hz, 2H), 7.69-7.63 (m, 2H), 7.59 (tt, J=8.7, 1.2 Hz, 1H), 7.52-7.44 (m, 2H), 7.39-7.31 (m, 3H), 7.31-7.23 (m, 2H); $^{13}$C NMR (126 MHz, DMSO) δ 183.41, 181.21, 141.98, 134.55, 134.13, 132.11, 131.51, 131.34, 130.63, 130.28, 128.58, 128.36, 127.47, 126.27, 126.04, 125.91; HRMS (ESI-TOF) m/z: [M+H]$^+$ Calcd for $C_{22}H_{16}NO_4S$ 390.0795. Found 390.0789.

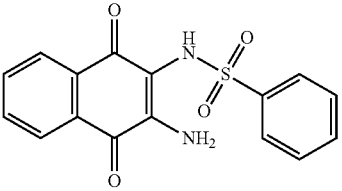

KSC-292-075-1

N-(3-amino-1,4-dioxo-1,4-dihydronaphthalen-2-yl)benzenesulfonamide (KSC-292-075-1)

This compound was prepared using the same protocol described for KSC-279-067-1 (pp. 51) using KSC-292-065-1 (pp. 50) and the appropriate sulfonyl chloride. Yield: 34.4 mg; 19%. $^1$H NMR (500 MHz, DMSO-$d_6$) δ 9.14 (s, 1H), 7.98-7.90 (m, 1H), 7.81-7.78 (m, 1H), 7.78-7.76 (m, 1H), 7.76-7.72 (m, 1H), 7.72-7.70 (m, 1H), 7.70-7.66 (m, 1H), 7.57 (tt, J=8.6, 1.2 Hz, 2H), 7.52-7.43 (m, 2H), 7.06 (s, 2H); $^{13}$C NMR (126 MHz, DMSO) δ 181.31, 176.77, 147.19, 140.32, 134.86, 132.46, 132.44, 131.74, 129.89, 128.56, 126.94, 125.77, 125.50, 110.36; HRMS (ESI-TOF) m/z: [M+H]$^+$ Calcd for $C_{16}H_{13}N_2O_4S$ 329.0591. Found 329.0577.

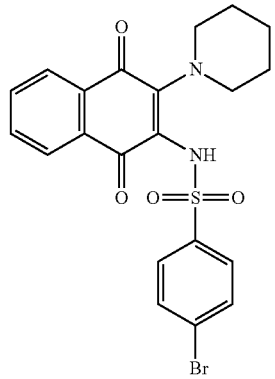

KSC-288-065-1

4-bromo-N-(1,4-dioxo-3-(piperidin-1-yl)-1,4-dihydronaphthalen-2-yl)benzenesulfonamide (KSC-288-065-1)

This compound was prepared using the same protocol described for KSC-288-076-1 (pp. 66) using KSC-288-054-1 (pp. 49) and the appropriate amine. Yield: 71.9 mg; 75%. $^1$H NMR (400 MHz, Chloroform-d) δ 8.00-7.93 (m, 1H), 7.71-7.65 (m, 1H), 7.62-7.54 (m, 4H), 7.45-7.39 (m, 2H), 6.83 (s, 1H), 3.69-3.54 (m, 4H), 1.84-1.74 (m, 4H), 1.74-1.65 (m, 2H); $^{13}$C NMR (101 MHz, CDCl$_3$) δ 183.05, 179.77, 148.30, 137.71, 133.93, 133.06, 131.96, 131.91, 130.43, 129.07, 128.15, 126.91, 125.54, 117.46, 52.93, 26.51, 23.99; HRMS (ESI-TOF) m/z: [M+H]$^+$ Calcd for $C_{21}H_{20}BrN_2O_4S$ 475.0322. Found 477.0324.

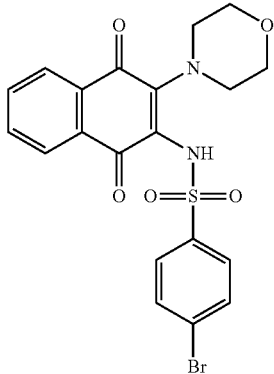

KSC-288-070-1

4-bromo-N-(3-morpholino-1,4-dioxo-1,4-dihydronaphthalen-2-yl)benzenesulfonamide (KSC-288-070-1)

This compound was prepared using the same protocol described for KSC-288-076-1 (pp. 66) using KSC-288-054-1 (pp. 49) and the appropriate amine. Yield: 19.9 mg; 37%. $^1$H NMR (500 MHz, DMSO-$d_6$) δ 9.46 (s, 1H), 7.98-7.91 (m, 1H), 7.75 (dtd, J=11.5, 7.3, 1.8 Hz, 2H), 7.70-7.63 (m, 5H), 3.84-3.69 (m, 4H), 3.47 (t, J=4.6 Hz, 4H); $^{13}$C NMR (126 MHz, DMSO) δ 182.75, 179.59, 149.65, 139.85, 134.19, 133.24, 131.68, 131.56, 130.35, 128.86, 126.43, 126.27, 125.12, 66.30, 51.36; HRMS (ESI-TOF) m/z: [M+H]$^+$ Calcd for $C_{20}H_{18}BrN_2O_5S$ 477.0114. Found 477.0099.

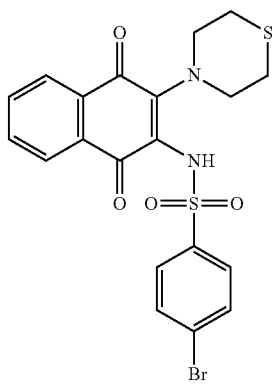

KSC-288-072-1

4-bromo-N-(1,4-dioxo-3-thiomorpholino-1,4-dihydronaphthalen-2-yl)benzenesulfonamide (KSC-288-072-1)

This compound was prepared using the same protocol described for KSC-288-076-1 (pp. 66) using KSC-288-054-1 (pp. 49) and the appropriate amine. Yield: 21.0 mg; 38%. $^1$H NMR (400 MHz, Chloroform-d) δ 8.05-8.00 (m, 1H), 8.00-7.94 (m, 1H), 7.67 (td, J=7.6, 1.4 Hz, 1H), 7.55 (td, J=7.5, 1.3 Hz, 1H), 6.20-6.06 (m, 1H), 5.98 (ddt, J=17.2, 10.4, 5.2 Hz, 1H), 5.26-5.14 (m, 2H), 4.51 (ddt, J=6.7, 5.2, 1.7 Hz, 2H), 3.20-3.08 (m, 4H), 1.65-1.54 (m, 6H); $^{13}$C NMR (126 MHz, DMSO) δ 182.71, 179.88, 134.82, 134.11, 133.33, 132.59, 131.68, 131.50, 130.30, 128.81, 126.43, 126.21, 125.81, 125.16, 53.41, 27.03; HRMS (ESI-TOF) m/z: [M+H]$^+$ Calcd for $C_{20}H_{18}BrN_2O_4S_2$ 492.9886. Found 492.9864.

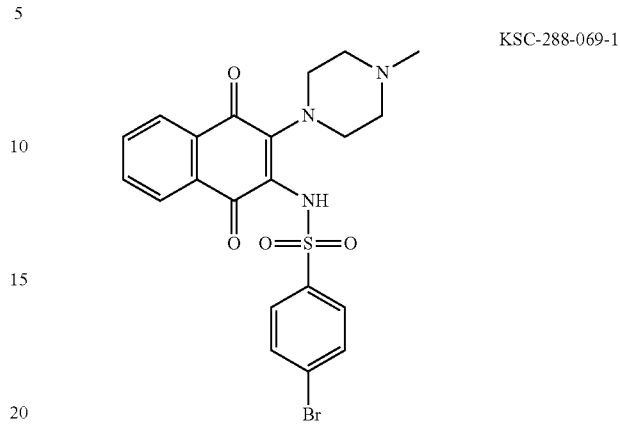

4-bromo-N-(3-(4-methylpiperazin-1-yl)-1,4-dioxo-1,4-dihydronaphthalen-2-yl)benzenesulfonamide (KSC-288-069-1)

This compound was prepared using the same protocol described for KSC-288-076-1 (pp. 66) using KSC-288-054-1 (pp. 49) and the appropriate amine. Yield: 11.8 mg; 21%. $^1$H NMR (500 MHz, DMSO-$d_6$) δ 7.91-7.85 (m, 1H), 7.73-7.66 (m, 5H), 7.65-7.60 (m, 2H), 3.40-3.26 (m, 5H), 2.54 (s, 4H), 2.29 (s, 3H); $^{13}$C NMR (126 MHz, DMSO) δ 181.87, 133.06, 132.19, 131.97, 131.18, 130.89, 128.23, 127.68, 125.67, 125.04, 124.35, 54.88, 49.79, 45.45; HRMS (ESI-TOF) m/z: [M+H]$^+$ Calcd for $C_{21}H_{21}BrN_3O_4S$ 490.0431. Found 490.0420.

KSC-288-077-1

N-(3-(allylamino)-1,4-dioxo-1,4-dihydronaphthalen-2-yl)-4-bromobenzenesulfonamide (KSC-288-077-1)

This compound was prepared using the same protocol described for KSC-288-076-1 (pp. 66) using KSC-288-054-1 (pp. 49) and the appropriate amine. Yield: 7.9 mg; 14%. $^1$H NMR (500 MHz, DMSO-$d_6$) δ 9.27 (s, 1H), 8.02-7.94 (m, 1H), 7.84-7.54 (m, 8H), 5.93 (ddt, J=17.2, 10.6, 5.4 Hz, 1H), 5.21-5.06 (m, 2H), 4.37 (s, 2H); $^{13}$C NMR (126 MHz, DMSO) δ 182.11, 177.93, 135.08, 134.71, 132.52, 131.83, 131.50, 129.85, 129.05, 126.13, 126.02, 125.46, 116.12, 45.49; HRMS (ESI-TOF) m/z: [M+H]$^+$ Calcd for $C_{19}H_{16}BrN_2O_4S$ 447.0009. Found 446.9986.

KSC-288-071-1

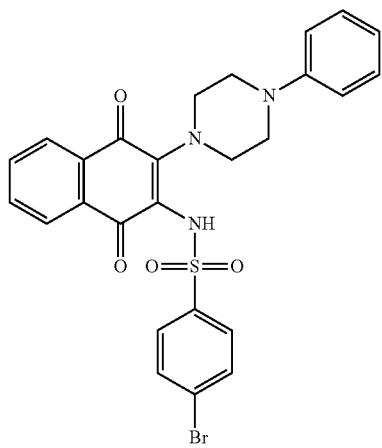

4-bromo-N-(1,4-dioxo-3-(4-phenylpiperazin-1-yl)-1,4-dihydronaphthalen-2-yl)benzenesulfonamide (KSC-288-071-1)

This compound was prepared using the same protocol described for KSC-288-076-1 (pp. 66) using KSC-288-054-1 (pp. 49) and the appropriate amine. Yield: 5.7 mg; 9%. $^1$H NMR (500 MHz, DMSO-$d_6$) δ 9.48 (s, 1H), 7.98-7.93 (m, 1H), 7.79-7.61 (m, 7H), 7.25 (dd, J=8.7, 7.2 Hz, 2H), 7.00 (d, J=8.0 Hz, 2H), 6.85-6.78 (m, 1H), 3.65-3.53 (m, 4H), 3.33-3.28 (m, 4H); $^{13}$C NMR (126 MHz, DMSO) δ 182.57, 150.93, 133.89, 133.18, 131.75, 131.54, 130.54, 128.95, 128.70, 126.25, 125.09, 119.00, 115.60, 50.53, 48.66; HRMS (ESI-TOF) m/z: [M+H]$^+$ Calcd for $C_{26}H_{23}BrN_3O_4S$ 552.0587. Found 552.0564.

KSC-292-076-1

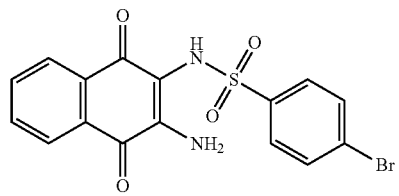

N-(3-amino-1,4-dioxo-1,4-dihydronaphthalen-2-yl)-4-bromobenzenesulfonamide (KSC-292-076-1)

This compound was prepared using the same protocol described for KSC-279-067-1 (pp. 51) using KSC-292-065-1 (pp. 50) and the appropriate sulfonyl chloride. Yield: 42.9 mg; 19%. $^1$H NMR (500 MHz, DMSO-$d_6$) δ 9.27 (s, 1H), 7.95 (d, J=7.5 Hz, 1H), 7.83-7.64 (m, 7H), 7.17 (s, 2H); $^{13}$C NMR (126 MHz, DMSO) δ 181.32, 176.85, 147.74, 139.95, 134.94, 132.47, 131.80, 131.62, 129.92, 129.02, 126.19, 125.82, 125.55, 109.74; HRMS (ESI-TOF) m/z: [M+H]$^+$ Calcd for $C_{16}H_{12}BrN_2O_4S$ 406.9696. Found 406.9640.

KSC-293-027-1

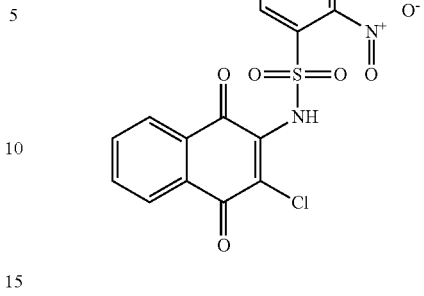

N-(3-chloro-1,4-dioxo-1,4-dihydronaphthalen-2-yl)-2-nitrobenzenesulfonamide (KSC-293-027-1)

2,3-dichloronaphthalene-1,4-dione (228 mg, 1.0 mmol), 2-nitrobenzenesulfonamide (264 mg, 1.3 mmol), and cesium carbonate (425 mg, 1.3 mmol) were stirred in toluene (5 mL) at reflux for 17 h, after which time 1 M aq. citric acid (10 mL) was added. The solids were collected via vacuum filtration, washed with water, and dried in vacuo. Yield: 366 mg, 93%. $^1$H NMR (400 MHz, DMSO-$d_6$) δ 8.20-8.15 (m, 1H), 8.08-8.04 (m, 1H), 7.95-7.79 (m, 7H).

KSC-293-031

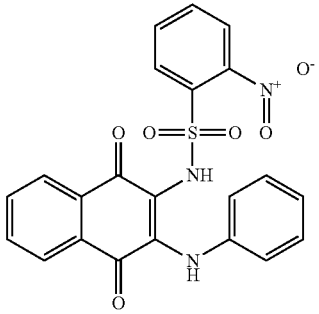

N-(1,4-dioxo-3-(phenylamino)-1,4-dihydronaphthalen-2-yl)-2-nitrobenzenesulfonamide (KSC-293-031)

Aniline (25 μL, 0.27 mmol) was added to a suspension of Error! Reference source not found. (52 mg, 0.13 mmol; pp. Error! Bookmark not defined.) in absolute EtOH (2 mL) and stirred at 75° C. for 48 h. The mixture was then diluted with sat. aq. NaHCO$_3$ (10 mL) and extracted 3 times with dichloromethane. The combined organic layers were washed once with water, dried (MgSO$_4$), filtered through a plug of silica with 10:1 CH$_2$Cl$_2$/MeOH, and concentrated in vacuo. The residue was then purified via MPLC (silica, 0-100% CH$_2$Cl$_2$/hexanes). Yield: 39 mg, 66%. $^1$H NMR (400 MHz, DMSO-$d_6$) δ 9.21-9.09 (m, 2H), 8.06 (dd, J=6.5, 1.8 Hz, 1H), 7.90-7.67 (m, 7H), 7.28-7.19 (m, 2H), 7.12-7.00 (m, 3H); $^{13}$C NMR (126 MHz, DMSO) δ 182.41, 178.74, 147.04, 142.72, 138.10, 135.01, 133.77, 133.45, 132.96, 132.22, 131.76, 130.31, 130.01, 127.49, 126.24, 125.75, 123.99, 123.71, 111.83; HRMS (ESI-TOF) m/z: [M+H]$^+$ Calcd for $C_{22}H_{16}N_3O_6S$ 450.0754. Found 450.0769.

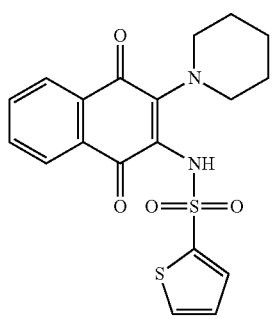

KSC-292-039-1

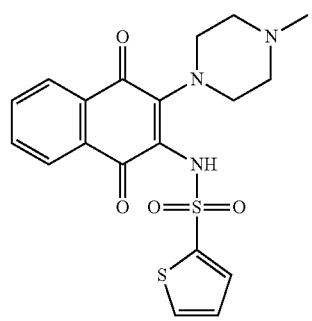

KSC-288-080-1

N-(1,4-dioxo-3-(piperidin-1-yl)-1,4-dihydronaphthalen-2-yl)thiophene-2-sulfonamide (KSC-292-039-1)

This compound was prepared using the same protocol described for KSC-288-086-1 (pp. 71) using KSC-292-031-1 (pp. 49) and the appropriate amine. Yield: 23.1 mg; 61%. $^1$H NMR (500 MHz, DMSO-$d_6$) δ 9.38 (s, 1H), 7.99-7.92 (m, 1H), 7.81 (dd, J=5.0, 1.4 Hz, 1H), 7.79-7.68 (m, 3H), 7.47 (dd, J=3.7, 1.4 Hz, 1H), 7.03 (dd, J=5.0, 3.7 Hz, 1H), 3.45-3.35 (m, 4H), 1.76-1.66 (m, 4H), 1.66-1.57 (m, 2H); $^{13}$C NMR (126 MHz, DMSO) δ 181.83, 178.30, 149.37, 139.59, 133.03, 131.93, 131.73, 130.97, 130.46, 129.38, 126.13, 125.30, 123.94, 116.96, 51.18, 24.82, 22.50; HRMS (ESI-TOF) m/z: [M+H]$^+$ Calcd for $C_{19}H_{19}N_2O_4S_2$ 403.0781. Found 403.0795.

N-(3-(4-methylpiperazin-1-yl)-1,4-dioxo-1,4-dihydronaphthalen-2-yl)thiophene-2-sulfonamide (KSC-288-080-1)

This compound was prepared using the same protocol described for KSC-288-086-1 (pp. 71) using KSC-292-031-1 (pp. 49) and the appropriate amine. Yield: 6.6 mg; 20%. $^1$H NMR (500 MHz, DMSO-$d_6$) δ 9.43 (s, 1H), 7.98-7.90 (m, 1H), 7.84-7.65 (m, 4H), 7.46 (dd, J=3.7, 1.3 Hz, 1H), 7.02 (dd, J=5.0, 3.7 Hz, 1H), 3.42 (s, 4H), 2.70 (s, 4H), 2.38 (s, 3H); $^{13}$C NMR (126 MHz, DMSO) δ 182.21, 166.51, 133.60, 133.25, 131.97, 130.64, 127.00, 126.88, 126.07, 125.17, 100.09, 99.49, 76.06, 54.54, 50.88, 49.83, 45.03; HRMS (ESI-TOF) m/z: [M+H]$^+$ Calcd for $C_{19}H_{20}N_3O_4S_2$ 418.0890. Found 418.0913.

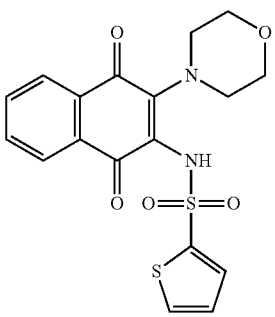

KSC-288-083-1

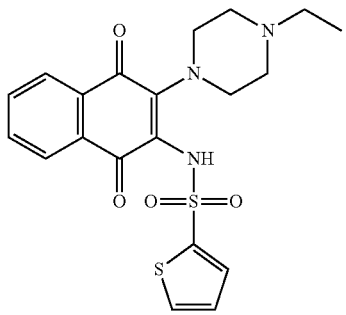

KSC-288-081-1

N-(3-morpholino-1,4-dioxo-1,4-dihydronaphthalen-2-yl)thiophene-2-sulfonamide (KSC-288-083-1)

This compound was prepared using the same protocol described for KSC-288-086-1 (pp. 71) using KSC-292-031-1 (pp. 49) and the appropriate amine. Yield: 23.9 mg; 75%. $^1$H NMR (500 MHz, DMSO-$d_6$) δ 9.46 (s, 1H), 8.01-7.92 (m, 1H), 7.83 (dd, J=5.0, 1.4 Hz, 1H), 7.81-7.69 (m, 3H), 7.51 (dd, J=3.7, 1.4 Hz, 1H), 7.04 (dd, J=5.0, 3.8 Hz, 1H), 3.76 (t, J=4.4 Hz, 6H), 3.46 (t, J=4.5 Hz, 6H); $^{13}$C NMR (126 MHz, DMSO) δ 182.81, 179.63, 149.50, 140.55, 134.25, 133.24, 133.04, 132.29, 131.57, 130.38, 127.34, 126.47, 125.14, 118.78, 66.27, 51.33; HRMS (ESI-TOF) m/z: [M+H]$^+$ Calcd for $C_{18}H_{17}N_2O_5S_2$ 405.0573. Found 405.0601.

N-(3-(4-ethylpiperazin-1-yl)-1,4-dioxo-1,4-dihydronaphthalen-2-yl)thiophene-2-sulfonamide (KSC-288-081-1)

This compound was prepared using the same protocol described for KSC-288-086-1 (pp. 71) using KSC-292-031-1 (pp. 49) and the appropriate amine. Yield: 15.5 mg; 45%. $^1$H NMR (500 MHz, DMSO-$d_6$) δ 9.36 (s, 1H), 7.97-7.90 (m, 1H), 7.80-7.67 (m, 4H), 7.45 (dd, J=3.7, 1.3 Hz, 1H), 7.02 (dd, J=5.0, 3.7 Hz, 1H), 3.43 (s, 4H), 2.78 (s, 4H), 2.67-2.56 (m, 2H), 1.10 (t, J=7.2 Hz, 3H); $^{13}$C NMR (126 MHz, DMSO) δ 182.05, 133.44, 133.25, 132.07, 131.42, 130.70, 126.92, 125.95, 125.18, 52.27, 51.45, 49.74, 11.01; HRMS (ESI-TOF) [M+H]$^+$ Calcd for $C_{20}H_{22}N_3O_4S_2$ 432.1046. Found 432.1081.

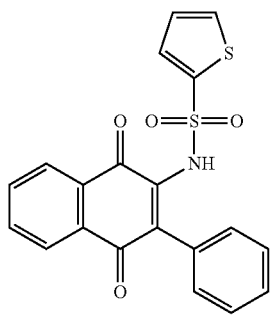

N-(1,4-dioxo-3-phenyl-1,4-dihydronaphthalen-2-yl)thiophene-2-sulfonamide (KSC-292-074-1)

Compound was prepared according to the procedures of Blagg et al.[1] $^1$H NMR (500 MHz, DMSO-$d_6$) δ 10.02 (s, 1H), 8.07-8.00 (m, 2H), 7.95-7.88 (m, 2H), 7.86 (dd, J=5.0, 1.4 Hz, 1H), 7.42 (dd, J=3.7, 1.4 Hz, 1H), 7.40-7.34 (m, 3H), 7.31-7.25 (m, 2H), 7.06 (dd, J=5.0, 3.8 Hz, 1H); $^{13}$C NMR (126 MHz, DMSO) δ 183.53, 181.21, 134.54, 134.20, 132.70, 132.04, 131.57, 131.39, 130.70, 130.29, 128.36, 127.38, 127.07, 126.33, 126.03; HRMS (ESI-TOF) m/z: [M+H]$^+$ Calcd for $C_{26}H_{14}NO_4S_2$ 396.0359. Found 396.0359.

N-(3-(allylamino)-1,4-dioxo-1,4-dihydronaphthalen-2-yl)thiophene-2-sulfonamide (KSC-288-082-1)

This compound was prepared using the same protocol described for KSC-288-086-1 (pp. 71) using KSC-292-031-1 (pp. 49) and the appropriate amine. Yield: 6.2 mg; 21%. $^1$H NMR (500 MHz, DMSO-$d_6$) δ 9.26 (s, 1H), 8.04-7.96 (m, 1H), 7.83 (dd, J=5.0, 1.4 Hz, 1H), 7.81-7.75 (m, 1H), 7.75-7.69 (m, 2H), 7.65-7.56 (m, 1H), 7.49 (dd, J=3.7, 1.4 Hz, 1H), 7.05 (dd, J=5.0, 3.7 Hz, 1H), 5.91 (ddt, J=17.1, 10.4, 5.2 Hz, 1H), 5.13 (qq, J=13.3, 1.5 Hz, 3H), 4.33 (s, 2H); $^{13}$C NMR (126 MHz, DMSO) δ 182.17, 177.93, 145.44, 140.68, 135.10, 134.61, 132.95, 132.53, 132.28, 131.85, 129.83, 127.23, 126.16, 125.48, 116.24, 108.66, 45.46; HRMS (ESI-TOF) m/z: [M+H]$^+$ Calcd for $C_{17}H_{15}N_2O_4S_2$ 375.0468. Found 375.0480.

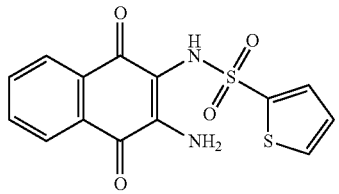

N-(3-amino-1,4-dioxo-1,4-dihydronaphthalen-2-yl)thiophene-2-sulfonamide (KSC-292-077-1)

This compound was prepared using the same protocol described for KSC-279-067-1 (pp. 51) using KSC-292-065-1 (pp. 50) and the appropriate sulfonyl chloride. Yield: 79.3 mg; 43%. $^1$H NMR (500 MHz, DMSO-$d_6$) δ 9.28 (s, 1H), 8.00-7.93 (m, 1H), 7.85 (dd, J=5.0, 1.4 Hz, 1H), 7.80-7.75 (m, 2H), 7.72 (dt, J=7.6, 4.4 Hz, 1H), 7.55 (dd, J=3.7, 1.4 Hz, 1H), 7.38-6.71 (m, 2H), 7.07 (dd, J=5.0, 3.8 Hz, 1H); $^{13}$C NMR (126 MHz, DMSO) δ 181.34, 176.87, 147.45, 140.53, 134.94, 132.99, 132.48, 132.22, 131.81, 129.91, 127.30, 125.84, 125.56, 109.88; HRMS (ESI-TOF) m/z: [M+H]$^+$ Calcd for $C_{14}H_{11}N_2O_4S_2$ 335.0155. Found 335.0161.

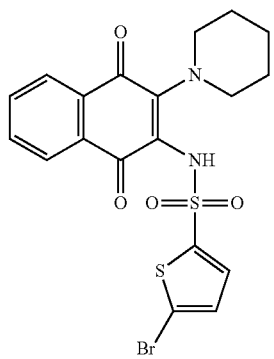

5-bromo-N-(1,4-dioxo-3-(piperidin-1-yl)-1,4-dihydronaphthalen-2-yl)thiophene-2-sulfonamide (KSC-292-047-1)

This compound was prepared using the same protocol described for KSC-288-086-1 (pp. 71) using KSC-292-032-1 (pp. 49) and the appropriate amine. Yield: 18.4 mg; 62%. $^1$H NMR (400 MHz, DMSO-$d_6$) δ 9.61 (s, 1H), 8.01-7.94 (m, 1H), 7.79-7.74 (m, 3H), 7.32 (d, J=4.0 Hz, 1H), 7.21 (d, J=4.0 Hz, 1H), 3.47-3.36 (m, 4H), 1.76-1.67 (m, 4H), 1.67-1.57 (m, 2H); $^{13}$C NMR (101 MHz, DMSO) δ 182.89, 179.47, 150.91, 142.00, 134.20, 133.10, 132.63, 131.66, 130.91, 130.61, 126.48, 125.08, 118.37, 52.39, 25.94, 23.60; HRMS (ESI-TOF) m/z: [M+H]$^+$ Calcd for $C_{19}H_{18}BrN_2O_4S_2$ 480.9886. Found 480.9886.

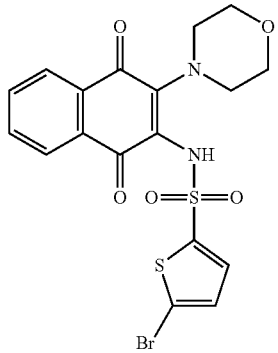

KSC-292-046-1

5-bromo-N-(3-morpholino-1,4-dioxo-1,4-dihydronaphthalen-2-yl)thiophene-2-sulfonamide (KSC-292-046-1)

This compound was prepared using the same protocol described for KSC-288-086-1 (pp. 71) using KSC-292-032-1 (pp. 49) and the appropriate amine. Yield: 19.8 mg; 66%. $^1$H NMR (400 MHz, DMSO-$d_6$) δ 9.69 (s, 1H), 8.02-7.93 (m, 1H), 7.83-7.73 (m, 3H), 7.35 (d, J=4.0 Hz, 1H), 7.22 (d, J=4.0 Hz, 1H), 3.86-3.68 (m, 4H), 3.55-3.38 (m, 4H); $^{13}$C NMR (101 MHz, DMSO) δ 182.71, 179.71, 149.74, 141.95, 134.24, 133.27, 132.75, 131.65, 130.96, 130.48, 126.49, 125.14, 118.50, 66.28, 51.39; HRMS (ESI-TOF) m/z: [M+H]$^+$ Calcd for $C_{18}H_{16}BrN_2O_5S_2$ 482.9679. Found 482.9662.

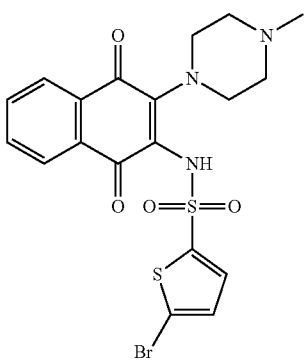

KSC-292-048-1

5-bromo-N-(3-(4-methylpiperazin-1-yl)-1,4-dioxo-1,4-dihydronaphthalen-2-yl)thiophene-2-sulfonamide (KSC-292-048-1)

This compound was prepared using the same protocol described for KSC-288-086-1 (pp. 71) using KSC-292-032-1 (pp. 49) and the appropriate amine. Yield: 27.2 mg; 81%. $^1$H NMR (400 MHz, DMSO-$d_6$) δ 8.16 (s, 1H), 7.96-7.90 (m, 1H), 7.84-7.79 (m, 1H), 7.73 (dtd, J=19.2, 7.4, 1.6 Hz, 2H), 7.26 (d, J=3.9 Hz, 1H), 7.16 (d, J=3.9 Hz, 1H), 3.50-3.36 (m, 4H), 3.10-2.95 (m, 4H), 2.61 (s, 3H); $^{13}$C NMR (101 MHz, DMSO) δ 182.19, 181.49, 163.17, 133.38, 132.94, 132.36, 130.90, 130.26, 129.31, 125.62, 125.27, 115.76, 54.14, 48.53, 43.85; HRMS (ESI-TOF) m/z: [M+H]$^+$ Calcd for $C_{19}H_{19}BrN_3O_4S_2$ 495.9995. Found 495.9980.

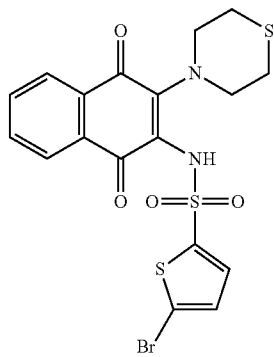

KSC-292-055-1

5-bromo-N-(1,4-dioxo-3-thiomorpholino-1,4-dihydronaphthalen-2-yl)thiophene-2-sulfonamide (KSC-292-055-1)

This compound was prepared using the same protocol described for KSC-288-086-1 (pp. 71) using KSC-292-032-1 (pp. 49) and the appropriate amine. Yield: 16.0 mg; 50%. $^1$H NMR (400 MHz, DMSO-$d_6$) δ 9.72 (s, 1H), 8.02-7.94 (m, 1H), 7.82-7.74 (m, 3H), 7.36 (d, J=4.0 Hz, 1H), 7.22 (d, J=4.0 Hz, 1H), 3.65-3.57 (m, 4H), 2.85-2.77 (m, 4H); $^{13}$C NMR (101 MHz, DMSO) δ 182.71, 179.93, 150.77, 141.84, 134.23, 133.38, 132.84, 131.56, 130.97, 130.39, 126.54, 125.19, 118.58, 53.49, 27.01; HRMS (ESI-TOF) m/z: [M+H]$^+$ Calcd for $C_{18}H_{16}BrN_2O_4S_3$ 498.9450. Found 498.9439.

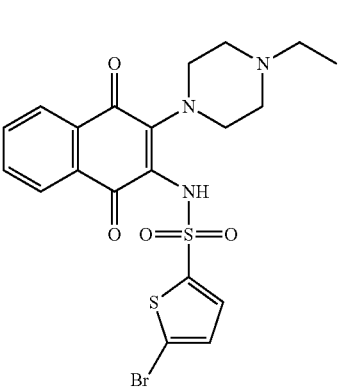

KSC-292-049-1

5-bromo-N-(3-(4-ethylpiperazin-1-yl)-1,4-dioxo-1,4-dihydronaphthalen-2-yl)thiophene-2-sulfonamide (KSC-292-049-1)

This compound was prepared using the same protocol described for KSC-288-086-1 (pp. 71) using KSC-292-032-1 (pp. 49) and the appropriate amine. Yield: 22.1 mg; 74.9%. $^1$H NMR (400 MHz, DMSO-$d_6$) δ 8.16 (s, 1H), 7.95-7.89 (m, 1H), 7.84-7.78 (m, 1H), 7.73 (dtd, J=20.9, 7.4, 1.5 Hz, 2H), 7.25 (d, J=3.9 Hz, 1H), 7.16 (d, J=3.9 Hz, 1H), 3.56-3.33 (m, 4H), 3.18-3.00 (m, 4H), 2.91 (q, J=7.1 Hz, 2H), 1.18 (t, J=7.2 Hz, 3H); $^{13}$C NMR (101 MHz, DMSO) δ 181.32, 163.16, 133.40, 132.77, 132.47, 130.96, 130.18, 125.51, 125.29, 51.88, 51.25, 48.37, 9.86; HRMS (ESI-TOF) m/z: [M+H]$^+$ Calcd for $C_{20}H_{21}BrN_3O_4S_2$ 510.0151. Found 510.0145.

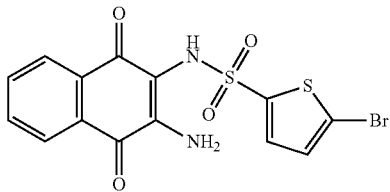

KSC-292-078-1

N-(3-amino-1,4-dioxo-1,4-dihydronaphthalen-2-yl)-5-bromothiophene-2-sulfonamide (KSC-292-078-1)

This compound was prepared using the same protocol described for KSC-279-067-1 (pp. 51) using KSC-292-065-1 (pp. 50) and the appropriate sulfonyl chloride. Yield: 43.5 mg; 19%. $^1$H NMR (500 MHz, DMSO-d$_6$) δ 9.47 (s, 1H), 8.01-7.92 (m, 1H), 7.85-7.76 (m, 2H), 7.73 (td, J=7.3, 1.8 Hz, 1H), 7.37 (d, J=4.0 Hz, 1H), 7.23 (d, J=4.0 Hz, 1H), 7.22 (s, 2H); $^{13}$C NMR (126 MHz, DMSO) δ 181.29, 176.99, 147.87, 142.21, 134.98, 132.65, 132.50, 131.91, 130.91, 129.96, 125.87, 125.58, 118.32, 109.51; HRMS (ESI-TOF) m/z: [M+H]$^+$ Calcd for C$_{14}$H$_{10}$BrN$_2$O$_4$S$_2$ 412.9260. Found 412.9243.

Synthetic Protocols for KSC-292-020-1 to KSC-292-025-1

KSC-292-020-1

N-(3-(allylamino)-1,4-dioxo-1,4-dihydronaphthalen-2-yl)-N-methylacetamide (KSC-292-020-1)

This compound was prepared using the same protocol described for KSC-288-086-1 (pp. 71) using KSC-292-004-1 (pp. 50) and the appropriate amine. Yield: 8.0 mg; 38%. $^1$H NMR (500 MHz, DMSO-d$_6$) δ 8.06-7.96 (m, 2H), 7.86 (td, J=7.5, 1.3 Hz, 1H), 7.77 (td, J=7.5, 1.3 Hz, 1H), 7.64 (t, J=6.7 Hz, 1H), 5.91 (ddt, J=17.1, 10.1, 4.9 Hz, 1H), 5.18-5.06 (m, 2H), 4.13-3.91 (m, 2H), 2.89 (s, 3H), 1.78 (s, 3H); $^{13}$C NMR (126 MHz, DMSO) δ 182.03, 171.54, 135.29, 135.00, 132.59, 132.09, 130.35, 126.18, 125.74, 115.57, 44.90, 21.57; HRMS (ESI-TOF) m/z: [M+H]$^+$ Calcd for C$_{16}$H$_{17}$N$_2$O$_3$ 285.1234. Found 285.1237.

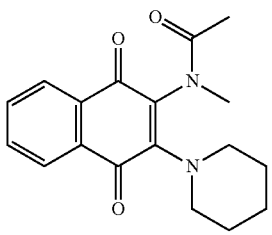

KSC-292-022-1

N-(1,4-dioxo-3-(piperidin-1-yl)-1,4-dihydronaphthalen-2-yl)-N-methylacetamide (KSC-292-022-1)

This compound was prepared using the same protocol described for KSC-288-086-1 (pp. 71) using KSC-292-004-1 (pp. 50) and the appropriate amine. Yield: 27.4 mg; 71%. $^1$H NMR (500 MHz, DMSO-d$_6$) δ 8.00-7.90 (m, 2H), 7.80 (dtd, J=18.8, 7.4, 1.3 Hz, 2H), 3.45-3.36 (m, 2H), 3.36-3.27 (m, 2H), 2.91 (s, 3H), 1.85 (s, 3H), 1.77-1.54 (m, 6H); $^{13}$C NMR (126 MHz, DMSO) δ 182.97, 179.08, 170.89, 150.13, 134.06, 132.97, 132.06, 131.00, 126.83, 126.28, 125.46, 51.07, 35.62, 26.31, 23.37, 21.59; HRMS (ESI-TOF) m/z: [M+H]$^+$ Calcd for C$_{18}$H$_{21}$N$_2$O$_3$ 313.1547. Found 313.1558.

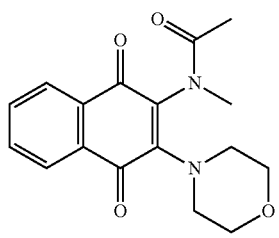

KSC-292-021-1

N-methyl-N-(3-morpholino-1,4-dioxo-1,4-dihydronaphthalen-2-yl)acetamide (KSC-292-021-1)

This compound was prepared using the same protocol described for KSC-288-086-1 (pp. 71) using KSC-292-004-1 (pp. 50) and the appropriate amine. Yield: 28.4 mg; 73%. $^1$H NMR (500 MHz, DMSO-d$_6$) δ 8.00-7.96 (m, 2H), 7.82 (dtd, J=16.5, 7.4, 1.4 Hz, 2H), 3.82-3.69 (m, 4H), 3.48 (ddd, J=13.1, 6.2, 3.0 Hz, 2H), 3.38-3.30 (m, 2H), 2.91 (s, 3H), 1.86 (s, 3H); $^{13}$C NMR (126 MHz, DMSO) δ 182.72, 179.28, 170.96, 149.13, 134.13, 133.13, 132.05, 130.87, 127.04, 126.31, 125.53, 66.68, 50.22, 35.55, 21.66; HRMS (ESI-TOF) m/z: [M+H]$^+$ Calcd for C$_{17}$H$_{19}$N$_2$O$_4$ 315.1339. Found 315.1346.

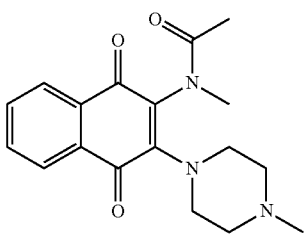

KSC-292-023-1

N-methyl-N-(3-(4-methylpiperazin-1-yl)-1,4-dioxo-1,4-dihydronaphthalen-2-yl)acetamide (KSC-292-023-1)

This compound was prepared using the same protocol described for KSC-288-086-1 (pp. 71) using KSC-292-004-1 (pp. 50) and the appropriate amine. Yield: 29.5 mg; 73%. $^1$H NMR (500 MHz, DMSO-d$_6$) δ 8.00-7.94 (m, 2H), 7.81 (dtd, J=17.4, 7.4, 1.5 Hz, 2H), 3.46 (ddd, J=12.5, 6.5, 3.1 Hz, 2H), 3.33 (ddd, J=12.7, 6.4, 3.1 Hz, 2H), 2.91 (s, 3H), 2.53-2.38 (m, 4H), 2.22 (s, 3H), 1.85 (s, 3H); $^{13}$C NMR (126 MHz, DMSO) δ 182.79, 179.24, 170.91, 149.52, 134.08, 133.08, 132.07, 130.89, 127.24, 126.30, 125.50, 55.05, 49.71, 45.71, 35.65, 21.66; HRMS (ESI-TOF) m/z: [M+H]⁺ Calcd for $C_{18}H_{22}N_3O_3$ 328.1656. Found 328.1654.

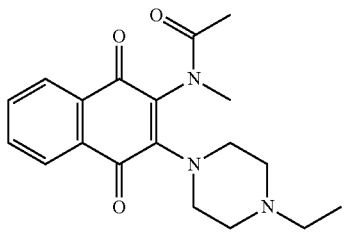

KSC-292-024-1

N-(3-(4-ethylpiperazin-1-yl)-1,4-dioxo-1,4-dihydronaphthalen-2-yl)-N-methylacetamide (KSC-292-024-1)

This compound was prepared using the same protocol described for KSC-288-086-1 (pp. 71) using KSC-292-004-1 (pp. 50) and the appropriate amine. Yield: 29.1 mg; 69%. ¹H NMR (500 MHz, DMSO-d₆) δ 8.00-7.94 (m, 2H), 7.81 (dtd, J=17.7, 7.4, 1.5 Hz, 3H), 3.47 (ddd, J=12.4, 6.4, 3.1 Hz, 2H), 3.34 (ddd, J=12.6, 6.3, 3.1 Hz, 2H), 2.91 (s, 3H), 2.59-2.43 (m, 3H), 2.38 (q, J=7.0 Hz, 2H), 1.85 (s, 3H), 1.02 (t, J=7.2 Hz, 3H); ¹³C NMR (126 MHz, DMSO) δ 182.79, 179.23, 170.90, 149.46, 134.09, 133.07, 132.08, 130.90, 127.11, 126.30, 125.49, 52.83, 51.56, 49.84, 35.67, 21.66, 11.80; HRMS (ESI-TOF) m/z: [M+H]⁺ Calcd for $C_{19}H_{24}N_3O_3$ 342.1812. Found 342.1823.

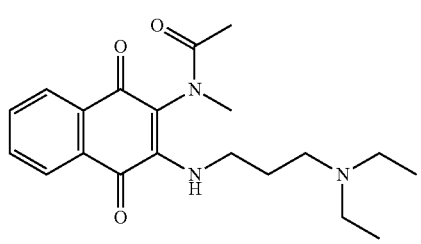

KSC-292-025-1

N-(3-((3-(diethylamino)propyl)amino)-1,4-dioxo-1,4-dihydronaphthalen-2-yl)-N-methylacetamide (KSC-292-025-1)

This compound was prepared using the same protocol described for KSC-288-086-1 (pp. 71) using KSC-292-004-1 (pp. 50) and the appropriate amine. Yield: 8.6 mg; 20%. ¹H NMR (500 MHz, DMSO-d₆) δ 8.22 (s, 1H), 8.05-7.96 (m, 2H), 7.89-7.82 (m, 1H), 7.75 (tdd, J=7.5, 2.6, 1.3 Hz, 1H), 2.92 (s, 3H), 2.53-2.37 (m, 10H), 1.83 (s, 3H), 1.05-0.90 (m, 6H); ¹³C NMR (126 MHz, DMSO) δ 171.21, 135.05, 132.47, 126.13, 125.75, 46.21, 46.09, 45.82, 45.59, 21.44, 11.37, 11.22; HRMS (ESI-TOF) m/z: [M+H]⁺ Calcd for $C_{20}H_{28}N_3O_3$ 358.2125. Found 358.2129.

Synthetic Protocols for KSC-293-046 to KSC-293-087

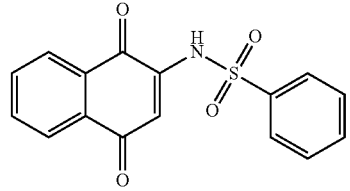

KSC-293-046

N-(1,4-dioxo-1,4-dihydronaphthalen-2-yl)benzenesulfonamide (KSC-293-046)

This compound was prepared using the same protocol described for KSC-279-067-1 (pp. 51) using the appropriate sulfonyl chloride and 2-aminonaphthalene-1,4-dione (87 mg, 0.50 mmol). Yield: 97 mg; 62%. ¹H NMR (400 MHz, DMSO-d₆) δ 10.88 (s, 1H), 8.08-7.96 (m, 3H), 7.94-7.88 (m, 1H), 7.83 (pd, J=7.3, 1.6 Hz, 2H), 7.76-7.70 (m, 1H), 7.70-7.62 (m, 2H), 6.56 (s, 1H); ¹³C NMR (126 MHz, DMSO) δ 183.47, 179.37, 142.07, 138.65, 134.81, 133.98, 133.72, 131.20, 130.38, 129.62, 127.14, 126.36, 125.56, 113.60; HRMS (ESI-TOF) m/z: [M+H]⁺ Calcd for $C_{16}H_{12}NO_4S$ 314.0482. Found 314.0482.

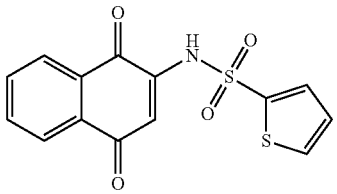

KSC-293-051

N-(1,4-dioxo-1,4-dihydronaphthalen-2-yl)thiophene-2-sulfonamide (KSC-293-051)

This compound was prepared using the same protocol described for KSC-279-067-1 (pp. 51) using the appropriate sulfonyl chloride and 2-aminonaphthalene-1,4-dione (87 mg, 0.50 mmol). Yield: 69 mg; 43%. ¹H NMR (400 MHz, DMSO-d₆) δ 8.06 (dd, J=5.0, 1.4 Hz, 1H), 8.02-7.98 (m, 1H), 7.96-7.92 (m, 1H), 7.91-7.79 (m, 4H), 7.23 (dd, J=5.0, 3.8 Hz, 1H), 6.67 (s, 1H); ¹³C NMR (126 MHz, DMSO) δ 183.50, 179.34, 141.86, 138.58, 135.12, 134.84, 134.33, 133.78, 131.22, 130.41, 128.05, 126.40, 125.60, 114.07; HRMS (ESI-TOF) m/z: [M-H]⁻ Calcd for $C_{14}H_8NO_4S_2$ 317.9900. Found 317.9915.

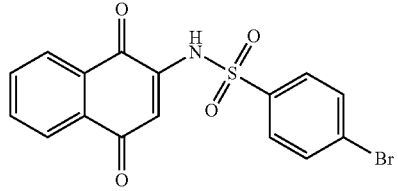

KSC-293-052

4-bromo-N-(1,4-dioxo-1,4-dihydronaphthalen-2-yl)benzenesulfonamide (KSC-293-052)

This compound was prepared using the same protocol described for KSC-279-067-1 (pp. 51) using the appropriate sulfonyl chloride and 2-aminonaphthalene-1,4-dione (87 mg, 0.50 mmol). Yield: 11 mg; 6%. $^1$H NMR (400 MHz, DMSO-$d_6$) δ 8.04-7.77 (m, 9H), 6.56 (s, 1H); $^{13}$C NMR (126 MHz, DMSO) δ 183.48, 179.39, 137.99, 134.76, 133.70, 132.67, 131.25, 130.44, 129.17, 127.95, 126.34, 125.54, 113.76; HRMS (ESI-TOF) m/z: [M+H]$^+$ Calcd for $C_{16}H_{11}BrNO_4S$ 391.9587. Found 391.9443.

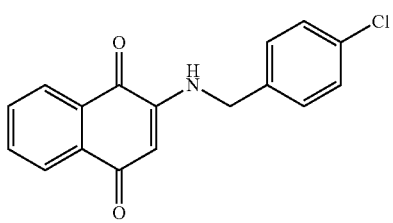

KSC-293-083

2-((4-chlorobenzyl)amino)naphthalene-1,4-dione (KSC-293-083)

Cerium(III) chloride heptahydrate (7.5 mg, 20 μmol), followed by 4-chlorobenzylamine (114 mg, 0.81 mmol), was added to a suspension of naphthalene-1,4-dione (64 mg, 0.41 mmol) in absolute ethanol (1.5 mL). The mixture was held at 75° C. for 72 h after which time it was cooled to room temperature and 10 mL of 1.0 M aq. citric acid was added with vigorous stirring. The insoluble material was collected by filtration, washed with water, and dried in vacuo at 45° C. Yield: 108 mg; 88%. $^1$H NMR (400 MHz, DMSO-$d_6$) δ 8.21 (t, J=6.5 Hz, 1H), 8.00 (dd, J=7.6, 0.9 Hz, 1H), 7.90 (dd, J=7.6, 1.0 Hz, 1H), 7.82 (td, J=7.5, 1.4 Hz, 1H), 7.73 (td, J=7.5, 1.4 Hz, 1H), 7.46-7.32 (m, 4H), 5.56 (s, 1H), 4.44 (d, J=6.6 Hz, 2H); $^{13}$C NMR (126 MHz, DMSO) δ 181.54, 181.44, 148.39, 136.51, 134.84, 132.96, 132.29, 131.63, 130.43, 129.03, 128.43, 125.91, 125.34, 100.51, 44.34; HRMS (ESI-TOF) m/z: [M+H]$^+$ Calcd for $C_{17}H_{13}ClNO_2$ 298.0629; Found 298.0651.

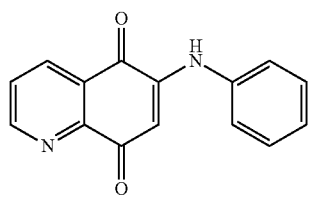

KSC-293-084

6-(phenylamino)quinoline-5,8-dione (KSC-293-084)

KSC-293-084 was purchased from Santa Cruz Biotechnology (Dallas, Tex.) and used without further purification. $^1$H NMR (400 MHz, DMSO-$d_6$) δ 9.33 (s, 1H), 8.99 (dd, J=4.7, 1.7 Hz, 1H), 8.42 (dd, J=7.9, 1.7 Hz, 1H), 7.78 (dd, J=7.9, 4.7 Hz, 1H), 7.51-7.43 (m, 2H), 7.43-7.36 (m, 2H), 7.24 (tt, J=7.2, 1.2 Hz, 1H), 6.21 (s, 1H); $^{13}$C NMR (126 MHz, DMSO) δ 181.62, 181.23, 154.60, 148.19, 145.89, 137.96, 134.16, 129.37, 127.69, 126.88, 125.41, 123.77, 103.08; HRMS (ESI-TOF) m/z: [M+H]$^+$ Calcd for $C_{15}H_{11}N_2O_2$ 251.0815. Found 251.0806.

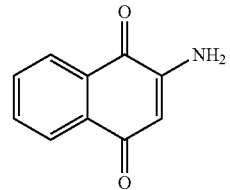

KSC-293-036B 2-aminonaphthalene-1,4-dione (KSC-293-036B)

To a suspension of naphthalene-1,4-dione (159 mg, 1.0 mmol) was sequentially added triethylamine (182 μL, 1.3 mmol) and O-benzylhydroxylamine hydrochloride (193 mg, 1.2 mmol). The mixture was stirred at room temperature for 20 h then concentrated in vacuo and purified via MPLC (silica, 0-10% MeOH/CH$_2$Cl$_2$). Yield: 111 mg, 63%. $^1$H NMR (400 MHz, DMSO-$d_6$) δ 7.96 (ddd, J=7.6, 1.3, 0.4 Hz, 1H), 7.93-7.89 (m, 1H), 7.81 (td, J=7.5, 1.4 Hz, 1H), 7.72 (td, J=7.5, 1.4 Hz, 1H), 7.21 (s, 2H), 5.82 (s, 1H); $^{13}$C NMR (126 MHz, CDCl$_3$) δ 181.95, 181.74, 150.38, 134.64, 133.14, 132.12, 130.39, 125.71, 125.20, 102.22; HRMS (ESI-TOF) m/z: [M+H]$^+$ Calcd for $C_{10}H_8NO_2$ 174.0550. Found 174.0549.

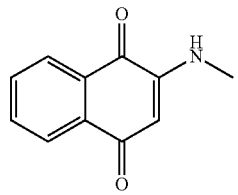

KSC-293-047A 2-(methylamino)naphthalene-1,4-dione (KSc-293-047A)

This compound was prepared using the same protocol described for KSC-293-036B (pp. 115) using N,O-dimethylhydroxylamine hydrochloride (1.18 g, 12.1 mmol). Yield: 1.24 g, 66%. $^1$H NMR (400 MHz, DMSO-$d_6$) δ 8.01-7.93 (m, 2H), 7.83 (td, J=7.5, 1.3 Hz, 1H), 7.72 (td, J=7.5, 1.4 Hz, 1H), 7.70-7.63 (m, 1H), 5.60 (d, J=0.5 Hz, 2H), 2.80 (d, J=4.9 Hz, 3H); $^{13}$C NMR (126 MHz, DMSO) δ 181.48, 181.13, 149.54, 134.84, 133.32, 132.14, 130.40, 125.88, 125.39, 99.19, 28.93; HRMS (ESI-TOF) m/z: [M+H]$^+$ Calcd for $C_{11}H_{10}NO_2$ 188.0706. Found 188.0709.

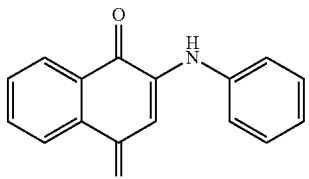

KSC-293-058

2-(phenylamino)naphthalene-1,4-dione (KSC-293-058)

This compound was prepared using the same protocol described for KSC-293-083 (pp. 115) using the appropriate amine. Yield: 133 mg, 97%. $^1$H NMR (400 MHz, DMSO-$d_6$) δ 9.25 (s, 1H), 8.07 (dd, J=7.5, 0.9 Hz, 1H), 7.95 (dd, J=7.6, 1.0 Hz, 1H), 7.87 (td, J=7.5, 1.3 Hz, 1H), 7.79 (td, J=7.5, 1.4 Hz, 1H), 7.51-7.42 (m, 2H), 7.42-7.35 (m, 2H), 7.23 (tt, J=7.2, 1.1 Hz, 1H), 6.11 (s, 1H); $^{13}$C NMR (126 MHz, DMSO) δ 182.57, 181.59, 146.20, 138.07, 134.90, 132.64, 132.57, 130.43, 129.30, 126.13, 125.27, 125.26, 123.71, 101.92; HRMS (ESI-TOF) m/z: [M+H]$^+$ Calcd for $C_{16}H_{12}NO_2$ 250.0863. Found 250.0882.

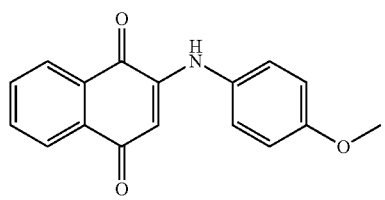

KSC-293-061

2-((4-methoxyphenyl)amino)naphthalene-1,4-dione (KSC-293-061)

This compound was prepared using the same protocol described for KSC-293-083 (pp. 115) using the appropriate amine. Yield: 110 mg, 96%. $^1$H NMR (400 MHz, DMSO-$d_6$) δ 9.16 (s, 1H), 8.05 (d, J=7.4 Hz, 1H), 7.94 (d, J=7.4 Hz, 1H), 7.85 (t, J=7.1 Hz, 1H), 7.78 (t, J=7.1 Hz, 1H), 7.30 (d, J=8.8 Hz, 2H), 7.02 (d, J=8.8 Hz, 2H), 5.92 (s, 1H), 3.78 (s, 3H); $^{13}$C NMR (126 MHz, DMSO) δ 182.25, 181.68, 156.95, 146.92, 134.91, 132.76, 132.51, 130.59, 130.45, 126.08, 125.63, 125.27, 114.54, 101.03, 55.34; HRMS (ESI-TOF) m/z: [M+H]$^+$ Calcd for $C_{17}H_{14}NO_3$ 280.0968. Found 280.0956.

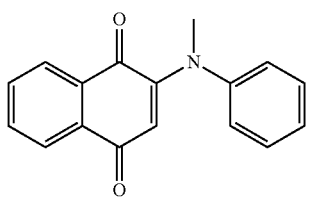

KSC-293-064

2-(methyl(phenyl)amino)naphthalene-1,4-dione (KSC-293-064)

This compound was prepared using the same protocol described for KSC-293-083 (pp. 115) using the appropriate amine. Yield: 101 mg, 94%. $^1$H NMR (400 MHz, DMSO-$d_6$) δ 7.95 (d, J=6.9 Hz, 1H), 7.88-7.69 (m, 3H), 7.43-7.31 (m, 2H), 7.27-7.15 (m, 3H), 6.16 (s, 1H), 3.35 (s, 3H); $^{13}$C NMR (126 MHz, DMSO) δ 182.50, 181.60, 151.98, 148.01, 134.22, 132.88, 132.18, 132.04, 129.29, 126.31, 125.58, 125.03, 125.01, 111.72, 42.97; HRMS (ESI-TOF) m/z: [M+H]$^+$ Calcd for $C_{17}H_{14}NO_2$ 264.1019. Found 264.1031.

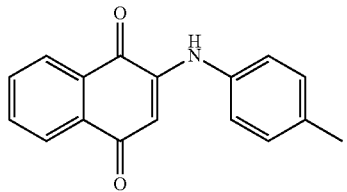

KSC-293-062

2-(p-tolylamino)naphthalene-1,4-dione (KSC-293-062)

This compound was prepared using the same protocol described for KSC-293-083 (pp. 115) using the appropriate amine. Yield: 98 mg, 92%. $^1$H NMR (400 MHz, DMSO-$d_6$) δ 9.19 (s, 1H), 8.06 (dd, J=7.6, 1.0 Hz, 1H), 7.95 (dd, J=7.6, 1.0 Hz, 1H), 7.86 (td, J=7.5, 1.4 Hz, 1H), 7.78 (td, J=7.5, 1.4 Hz, 1H), 7.32-7.21 (m, 4H), 6.04 (s, 1H), 2.32 (s, 3H); $^{13}$C NMR (126 MHz, DMSO) δ 182.41, 181.63, 146.40, 135.39, 134.90, 134.67, 132.66, 132.57, 130.43, 129.75, 126.11, 125.27, 123.75, 101.57, 20.60; HRMS (ESI-TOF) m/z: [M+H]$^+$ Calcd for $C_{17}H_{14}NO_2$ 264.1019. Found 264.1035.

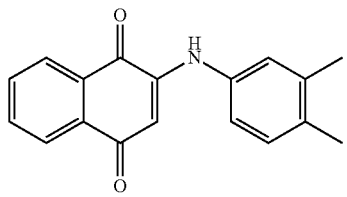

KSC-293-074

2-((3,4-dimethylphenyl)amino)naphthalene-1,4-dione (KSC-293-074)

This compound was prepared using the same protocol described for KSC-293-083 (pp. 115) using the appropriate amine. Yield: 102 mg, 91%. $^1$H NMR (400 MHz, DMSO-$d_6$) δ 9.12 (s, 1H), 8.05 (d, J=7.4 Hz, 1H), 7.94 (d, J=7.4 Hz, 1H), 7.86 (t, J=7.2 Hz, 1H), 7.78 (t, J=7.2 Hz, 1H), 7.25-7.04 (m, 3H), 6.03 (s, 1H), 2.24 (d, J=6.5 Hz, 6H); $^{13}$C NMR (126 MHz, DMSO) δ 182.37, 181.64, 146.45, 137.26, 135.56, 134.90, 133.58, 132.69, 132.54, 130.41, 130.15, 126.10, 125.26, 124.80, 121.25, 101.51, 19.50, 18.94; HRMS (ESI-TOF) m/z: [M+H]$^+$ Calcd for $C_{18}H_{16}NO_2$ 278.1176. Found 278.1191.

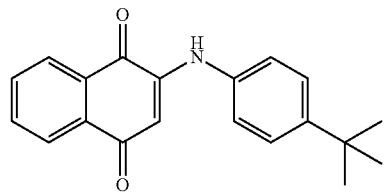

KSC-293-077

2-((4-(tert-butyl)phenyl)amino)naphthalene-1,4-dione (KSC-293-077)

This compound was prepared using the same protocol described for KSC-293-083 (pp. 115) using the appropriate amine. Yield: 110 mg, 89%. $^1$H NMR (400 MHz, DMSO-$d_6$) δ 9.22 (s, 1H), 8.06 (d, J=7.4 Hz, 1H), 7.95 (d, J=7.5 Hz, 1H), 7.86 (t, J=7.3 Hz, 1H), 7.78 (t, J=7.3 Hz, 1H), 7.46 (d, J=8.4 Hz, 2H), 7.31 (d, J=8.4 Hz, 2H), 6.07 (s, 1H), 1.30 (s, 9H); $^{13}$C NMR (126 MHz, DMSO) δ 182.43, 181.66, 147.82, 146.33, 135.38, 134.91, 132.64, 132.58, 130.44, 126.12, 126.01, 125.26, 123.43, 101.58, 34.27, 31.13; HRMS (ESI-TOF) m/z: [M+H]$^+$ Calcd for $C_{20}H_{20}NO_2$ 306.1489. Found 306.1507.

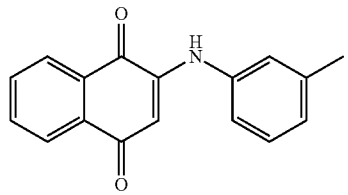

2-(m-tolylamino)naphthalene-1,4-dione (KSC-293-081)

This compound was prepared using the same protocol described for KSC-293-083 (pp. 115) using the appropriate amine. Yield: 101 mg, 94%. $^1$H NMR (400 MHz, DMSO-$d_6$) δ 9.17 (s, 1H), 8.06 (dd, J=7.5, 0.9 Hz, 1H), 7.95 (dd, J=7.6, 1.0 Hz, 1H), 7.86 (td, J=7.5, 1.3 Hz, 1H), 7.79 (td, J=7.5, 1.3 Hz, 1H), 7.33 (t, J=7.7 Hz, 1H), 7.24-7.15 (m, 2H), 7.05 (d, J=7.5 Hz, 1H), 6.10 (s, 1H), 2.34 (s, 3H); $^{13}$C NMR (126 MHz, DMSO) δ 182.54, 181.59, 146.23, 138.76, 137.96, 134.91, 132.62, 132.60, 130.41, 129.13, 126.13, 126.04, 125.27, 124.13, 120.86, 101.92, 21.02; HRMS (ESI-TOF) m/z: [M+H]$^+$ Calcd for $C_{17}H_{14}NO_2$ 264.1019. Found 264.1044.

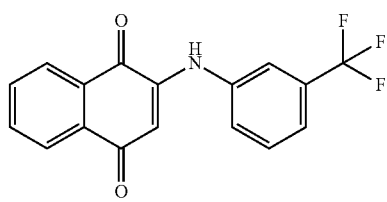

2-((3-(trifluoromethyl)phenyl)amino)naphthalene-1,4-dione (KSC-293-082)

This compound was prepared using the same protocol described for KSC-293-083 (pp. 115) using the appropriate amine. Yield: 117 mg, 91%. $^1$H NMR (400 MHz, DMSO-$d_6$) δ 9.43 (s, 1H), 8.08 (dd, J=7.6, 1.0 Hz, 1H), 7.97 (dd, J=7.6, 1.0 Hz, 1H), 7.88 (td, J=7.5, 1.4 Hz, 1H), 7.81 (td, J=7.5, 1.4 Hz, 1H), 7.77-7.71 (m, 2H), 7.68 (t, J=7.8 Hz, 1H), 7.55 (d, J=7.6 Hz, 1H), 6.18 (s, 1H); $^{13}$C NMR (126 MHz, DMSO) δ 182.91, 181.32, 145.75, 139.23, 134.95, 132.86, 132.40, 130.55, 130.41, 130.15, 129.89, 126.98, 126.21, 125.34, 124.99, 122.83, 121.32, 121.29, 120.03, 120.00, 119.97, 103.06; HRMS (ESI-TOF) m/z: [M+H]$^+$ Calcd for $C_{17}H_{11}F_3NO_2$ 318.0736; Found 318.0758.

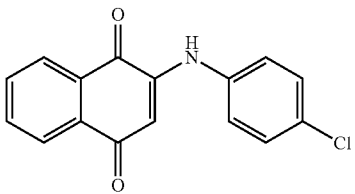

2-((4-chlorophenyl)amino)naphthalene-1,4-dione (KSC-293-060)

This compound was prepared using the same protocol described for KSC-293-083 (pp. 115) using the appropriate amine. Yield: 113 mg, 98%. $^1$H NMR (400 MHz, DMSO-$d_6$) δ 9.30 (s, 1H), 8.07 (dd, J=7.6, 1.0 Hz, 1H), 7.96 (dd, J=7.6, 1.0 Hz, 1H), 7.84 (dtd, J=29.0, 7.4, 1.3 Hz, 2H), 7.55-7.46 (m, 2H), 7.46-7.40 (m, 2H), 6.13 (s, 1H); $^{13}$C NMR (126 MHz, DMSO) δ 182.73, 181.46, 145.90, 137.18, 134.95, 132.77, 132.50, 130.44, 129.26, 128.96, 126.19, 125.33, 125.21, 102.55; HRMS (ESI-TOF) m/z: [M+H]$^+$ Calcd for $C_{16}H_{11}ClNO_2$ 284.0473. Found 284.0459.

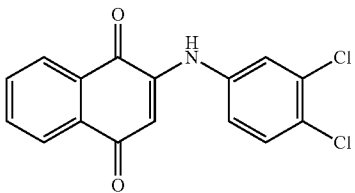

2-((3,4-dichlorophenyl)amino)naphthalene-1,4-dione (KSC-293-063)

This compound was prepared using the same protocol described for KSC-293-083 (pp. 115) using the appropriate amine. Yield: 124 mg, 96%. $^1$H NMR (400 MHz, DMSO-$d_6$) δ 9.35 (s, 1H), 8.08 (dd, J=7.5, 0.7 Hz, 1H), 7.97 (dd, J=7.7, 1.0 Hz, 1H), 7.88 (td, J=7.4, 1.1 Hz, 1H), 7.81 (td, J=7.5, 1.3 Hz, 1H), 7.68 (dd, J=5.6, 3.1 Hz, 2H), 7.43 (dd, J=8.7, 2.5 Hz, 1H), 6.21 (s, 1H); $^{13}$C NMR (126 MHz, DMSO) δ 182.92, 181.28, 145.49, 138.63, 134.97, 132.90, 132.37, 131.54, 131.10, 130.39, 126.64, 126.22, 125.35, 124.91, 123.26, 103.68; HRMS (ESI-TOF) m/z: [M+H]$^+$ Calcd for $C_{16}H_{10}Cl_2NO_2$ 318.0083. Found 318.0071.

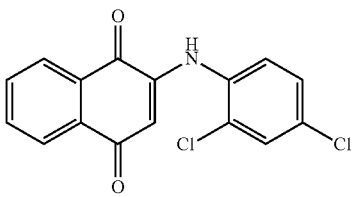

2-((2,4-dichlorophenyl)amino)naphthalene-1,4-dione (KSC-293-068)

This compound was prepared using the same protocol described for KSC-293-083 (pp. 115) using the appropriate amine. Yield: 115 mg, 89%. $^1$H NMR (400 MHz, DMSO-d$_6$) δ 9.09 (s, 1H), 8.08 (dd, J=7.5, 0.9 Hz, 2H), 7.95 (dd, J=7.6, 1.1 Hz, 2H), 7.87 (td, J=7.5, 1.3 Hz, 1H), 7.84-7.78 (m, 2H), 7.58-7.49 (m, 2H), 5.50 (s, 1H); $^{13}$C NMR (126 MHz, DMSO) δ 182.47, 181.08, 146.49, 135.06, 134.15, 132.89, 132.45, 131.70, 130.95, 130.30, 129.85, 129.35, 128.56, 126.18, 125.45, 103.39; HRMS (ESI-TOF) m/z: [M+H]$^+$ Calcd for C$_{16}$H$_{10}$Cl$_2$NO$_2$ 318.0083. Found 318.0069.

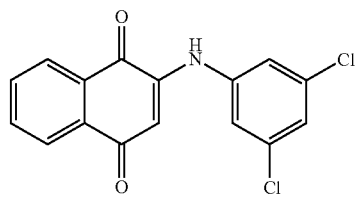

KSC-293-069

2-((3,5-dichlorophenyl)amino)naphthalene-1,4-dione (KSC-293-069)

This compound was prepared using the same protocol described for KSC-293-083 (pp. 115) using the appropriate amine. Yield: 89 mg, 69%. $^1$H NMR (400 MHz, DMSO-d$_6$) δ 9.36 (s, 1H), 8.07 (dd, J=7.6, 1.0 Hz, 1H), 7.97 (dd, J=7.6, 1.0 Hz, 1H), 7.88 (td, J=7.5, 1.4 Hz, 1H), 7.81 (td, J=7.5, 1.4 Hz, 1H), 7.48 (d, J=1.8 Hz, 2H), 7.41 (t, J=1.8 Hz, 1H), 6.24 (s, 1H); $^{13}$C NMR (126 MHz, DMSO) δ 183.03, 181.18, 145.26, 141.12, 134.97, 134.49, 132.97, 132.28, 130.36, 126.23, 125.36, 124.07, 121.50, 104.48; HRMS (ESI-TOF) m/z: [M+H]$^+$ Calcd for C$_{16}$H$_{10}$Cl$_2$NO$_2$ 318.0083. Found 318.0072.

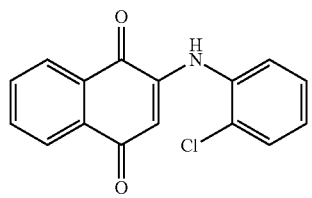

KSC-293-078

2-((2-chlorophenyl)amino)naphthalene-1,4-dione (KSC-293-078)

This compound was prepared using the same protocol described for KSC-293-083 (pp. 115) using the appropriate amine. Yield: 103 mg, 90%. $^1$H NMR (400 MHz, DMSO-d$_6$) δ 9.10 (s, 1H), 8.08 (dd, J=7.6, 1.0 Hz, 1H), 7.95 (dd, J=7.6, 1.1 Hz, 1H), 7.87 (td, J=7.5, 1.4 Hz, 1H), 7.81 (td, J=7.5, 1.5 Hz, 1H), 7.67-7.62 (m, 1H), 7.51-7.45 (m, 2H), 7.39 (ddd, J=8.1, 6.7, 2.4 Hz, 1H), 5.47 (s, 1H); $^{13}$C NMR (126 MHz, DMSO) δ 182.39, 181.19, 146.65, 135.04, 134.83, 132.82, 132.50, 130.33, 130.31, 129.81, 128.42, 128.41, 128.10, 126.16, 125.42, 102.93; HRMS (ESI-TOF) m/z: [M+H]$^+$ Calcd for C$_{16}$H$_{11}$ClNO$_2$ 284.0473. Found 284.0490.

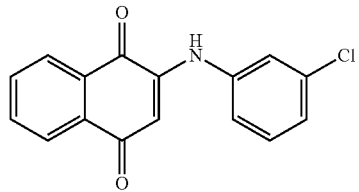

KSC-293-079

2-((3-chlorophenyl)amino)naphthalene-1,4-dione (KSC-293-079)

This compound was prepared using the same protocol described for KSC-293-083 (pp. 115) using the appropriate amine. Yield: 110 mg, 96%. $^1$H NMR (400 MHz, DMSO-d$_6$) δ 9.31 (s, 1H), 8.07 (dd, J=7.6, 1.0 Hz, 1H), 7.96 (dd, J=7.6, 1.0 Hz, 1H), 7.87 (td, J=7.5, 1.4 Hz, 1H), 7.80 (td, J=7.5, 1.4 Hz, 1H), 7.50-7.44 (m, 2H), 7.42-7.36 (m, 1H), 7.27 (ddd, J=7.9, 2.0, 1.0 Hz, 1H), 6.17 (s, 1H); $^{13}$C NMR (126 MHz, DMSO) δ 182.82, 181.36, 145.73, 139.86, 134.94, 133.51, 132.82, 132.41, 130.91, 130.40, 126.19, 125.32, 124.81, 123.15, 121.86, 103.10; HRMS (ESI-TOF) m/z: [M+H]$^+$ Calcd for C$_{16}$H$_{11}$ClNO$_2$ 284.0473. Found 284.0484.

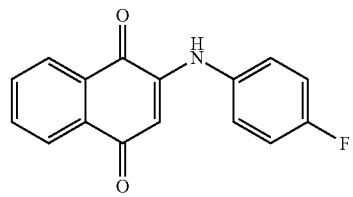

KSC-293-080

2-((4-fluorophenyl)amino)naphthalene-1,4-dione (KSC-293-080)

This compound was prepared using the same protocol described for KSC-293-083 (pp. 115) using the appropriate amine. Yield: 105 mg, 97%. $^1$H NMR (400 MHz, DMSO-d$_6$) δ 9.25 (s, 1H), 8.10-8.02 (m, 1H), 7.99-7.91 (m, 1H), 7.86 (td, J=7.5, 1.2 Hz, 1H), 7.79 (td, J=7.5, 1.3 Hz, 1H), 7.46-7.38 (m, 2H), 7.34-7.24 (m, 2H), 6.00 (s, 1H); $^{13}$C NMR (126 MHz, DMSO) δ 182.54, 181.52, 160.35, 158.42, 146.58, 134.92, 134.37, 134.34, 132.66, 132.58, 130.42, 126.13, 126.07, 126.00, 125.29, 116.19, 116.01, 101.74; HRMS (ESI-TOF) m/z: [M+H]$^+$ Calcd for C$_{16}$H$_{11}$FNO$_2$ 268.0768; Found 268.0791.

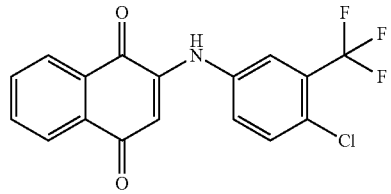

KSC-293-070

2-((4-chloro-3-(trifluoromethyl)phenyl)amino)naphthalene-1,4-dione (KSC-293-070)

This compound was prepared using the same protocol described for KSC-293-083 (pp. 115) using the appropriate amine. Yield: 131 mg, 92%. $^1$H NMR (400 MHz, DMSO-$d_6$) δ 9.45 (s, 1H), 8.08 (dd, J=7.5, 0.9 Hz, 2H), 7.97 (dd, J=7.6, 1.0 Hz, 1H), 7.93-7.70 (m, 5H), 6.25 (s, 1H); $^{13}$C NMR (126 MHz, DMSO) δ 183.01, 181.20, 145.37, 138.05, 134.96, 132.93, 132.54, 132.33, 130.38, 127.79, 126.23, 125.57, 125.35, 122.53, 122.49, 103.78; HRMS (ESI-TOF) m/z: [M+H]$^+$ Calcd for $C_{17}H_{10}ClF_3NO_2$ 352.0347. Found 352.0354.

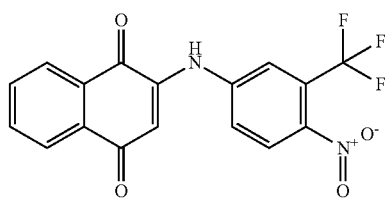

KSC-293-071

2-((4-nitro-3-(trifluoromethyl)phenyl)amino)naphthalene-1,4-dione (KSC-293-071)

This compound was prepared using the same protocol described for KSC-293-083 (pp. 115) using the appropriate amine. Yield: 48 mg, 33%. $^1$H NMR (400 MHz, DMSO-$d_6$) δ 9.76 (s, 1H), 8.24 (d, J=8.9 Hz, 1H), 8.13-8.06 (m, 2H), 8.02-7.81 (m, 4H), 6.57 (s, 1H); $^{13}$C NMR (126 MHz, DMSO) δ 184.11, 183.54, 182.63, 181.00, 144.26, 144.02, 143.45, 141.43, 137.60, 134.99, 134.65, 133.25, 132.09, 131.56, 131.52, 130.41, 128.02, 126.44, 126.35, 125.98, 125.43, 124.53, 123.44, 123.17, 123.09, 121.15, 121.10, 107.07; HRMS (ESI-TOF) m/z: [M+H]$^+$ Calcd for $C_{17}H_8F_3N_2O_4$ 361.0442. Found 361.0446.

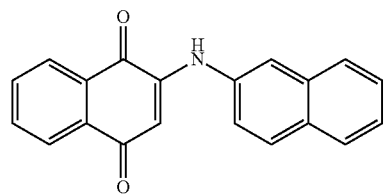

KSC-293-076

2-(naphthalen-2-ylamino)naphthalene-1,4-dione (KSC-293-076)

This compound was prepared using the same protocol described for KSC-293-083 (pp. 115) using the appropriate amine. Yield: 115 mg, 95%. $^1$H NMR (400 MHz, DMSO-$d_6$) δ 9.43 (s, 1H), 8.10 (dd, J=7.6, 1.0 Hz, 1H), 8.01-7.85 (m, 6H), 7.81 (td, J=7.5, 1.4 Hz, 1H), 7.60 (dd, J=8.8, 2.2 Hz, 1H), 7.57-7.46 (m, 2H), 6.30 (s, 1H); $^{13}$C NMR (126 MHz, DMSO) δ 182.74, 181.60, 145.97, 135.79, 134.95, 133.32, 132.71, 132.60, 130.56, 130.46, 129.01, 127.62, 127.51, 126.72, 126.19, 125.70, 125.32, 123.07, 120.21, 102.39; HRMS (ESI-TOF) m/z: [M+H]$^+$ Calcd for $C_{20}H_{14}NO_2$ 300.1019. Found 300.1040.

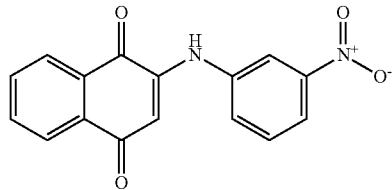

KSC-293-072

2-((3-nitrophenyl)amino)naphthalene-1,4-dione (KSC-293-072)

This compound was prepared using the same protocol described for KSC-293-083 (pp. 115) using the appropriate amine. Yield: 44 mg, 37%. $^1$H NMR (400 MHz, DMSO-$d_6$) δ 9.54 (s, 1H), 8.24 (t, J=2.1 Hz, 1H), 8.09 (dd, J=7.5, 1.0 Hz, 1H), 8.05-7.94 (m, 2H), 7.85 (dtd, J=26.6, 7.4, 1.4 Hz, 3H), 7.71 (t, J=8.2 Hz, 1H), 6.30 (s, 1H); $^{13}$C NMR (126 MHz, DMSO) δ 183.08, 181.25, 148.38, 145.56, 139.74, 134.96, 132.94, 132.35, 130.69, 130.44, 129.29, 126.25, 125.36, 119.21, 117.67, 103.65; HRMS (ESI-TOF) m/z: [M+H]$^+$ Calcd for $C_{16}H_{11}N_2O_4$ 295.0713. Found 295.0693.

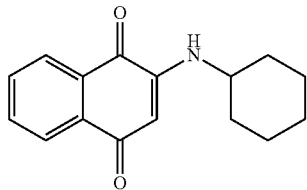

KSC-293-066-1

2-(cyclohexylamino)naphthalene-1,4-dione (KSC-293-066-1)

This compound was prepared using the same protocol described for KSC-293-083 (pp. 115) using the appropriate amine. Yield: 82 mg, 80%. $^1$H NMR (400 MHz, DMSO-$d_6$) δ 7.96 (dd, J=16.3, 7.5 Hz, 2H), 7.83 (t, J=7.1 Hz, 1H), 7.72 (t, J=7.1 Hz, 1H), 7.12 (d, J=8.3 Hz, 1H), 5.74 (s, 1H), 1.79 (d, J=50.2 Hz, 4H), 1.66-1.04 (m, 7H); $^{13}$C NMR (126 MHz, DMSO) δ 181.76, 181.35, 147.33, 134.88, 133.14, 132.16, 130.43, 125.92, 125.30, 99.42, 50.80, 31.07, 25.14, 24.48; HRMS (ESI-TOF) m/z: [M+H]$^+$ Calcd for $C_{16}H_{18}NO_2$ 256.1332. Found 256.1324.

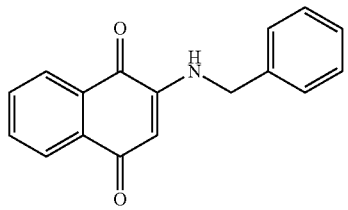

KSC-293-067

2-(benzylamino)naphthalene-1,4-dione (KSC-293-067)

This compound was prepared using the same protocol described for KSC-293-083 (pp. 115) using the appropriate amine. Yield: 102 mg, 95%. ¹H NMR (400 MHz, DMSO-d₆) δ 8.20 (t, J=6.4 Hz, 1H), 8.00 (dd, J=7.6, 0.9 Hz, 2H), 7.90 (dd, J=7.6, 1.0 Hz, 1H), 7.81 (td, J=7.5, 1.3 Hz, 1H), 7.73 (td, J=7.5, 1.4 Hz, 1H), 7.39-7.30 (m, 4H), 7.30-7.22 (m, 1H), 5.57 (s, 1H), 4.45 (d, J=6.5 Hz, 2H); ¹³C NMR (126 MHz, DMSO) δ 181.60, 181.37, 148.47, 137.40, 134.84, 133.00, 132.26, 130.42, 128.50, 127.09, 125.91, 125.33, 100.41, 45.08; HRMS (ESI-TOF) m/z: [M+H]⁺ Calcd for C₁₇H₁₄NO₂ 264.1019. Found 264.0993.

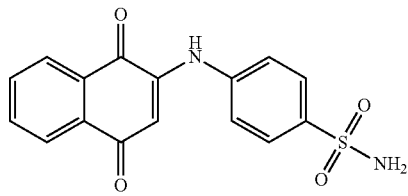

KSC-293-087

4-((1,4-dioxo-1,4-dihydronaphthalen-2-yl)amino)benzenesulfonamide (KSC-293-087)

This compound was prepared using the same protocol described for KSC-293-083 (pp. 115) using the appropriate amine. Yield: 281 mg, 43%. ¹H NMR (400 MHz, DMSO-d₆) δ 9.45 (s, 1H), 8.12-8.06 (m, 1H), 8.01-7.95 (m, 1H), 7.92-7.84 (m, 3H), 7.82 (td, J=7.5, 1.4 Hz, 1H), 7.64-7.56 (m, 2H), 7.37 (s, 2H), 6.33 (s, 1H); ¹³C NMR (101 MHz, DMSO) δ 182.96, 181.33, 145.20, 141.46, 139.63, 134.92, 132.87, 132.33, 130.40, 126.98, 126.22, 125.31, 122.71, 103.82; HRMS (ESI-TOF) m/z: [M+H]⁺ Calcd for C₁₆H₁₃N₂O₄S 329.0591. Found 329.0593.

Synthetic Protocols for KSC-293-025 to KSC-293-050

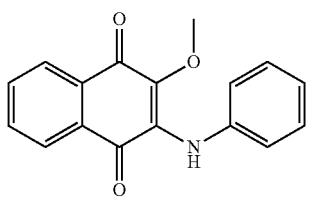

KSC-293-025

2-methoxy-3-(phenylamino)naphthalene-1,4-dione (KSC-293-025)

To a solution of 0.5 M sodium methoxide in methanol (8 mL) was added 2,3-dichloronaphthalene-1,4-dione (228 mg, 1.0 mmol) and the mixture stirred at room temperature for 2.5 h. To the resulting suspension was then added aniline (123 mg, 1.3 mmol) and the mixture then stirred at 60° C. for 3 h, after which time the mixture was concentrated in vacuo, diluted with 1 M aq. citric acid (6 mL) and extracted 3 times with dichloromethane. The combined organic extracts were dried (MgSO₄), filtered through a plug of silica, washing with 10:1 CH₂Cl₂:MeOH. The filtrate was concentrated in vacuo and purified via MPLC (silica, 0-5% MeOH/CH₂Cl₂). Yield: 74 mg, 26%. ¹H NMR (400 MHz, DMSO-d₆) δ 8.51 (s, 1H), 8.03-7.93 (m, 2H), 7.80 (dtd, J=27.1, 7.5, 1.4 Hz, 2H), 7.32-7.22 (m, 2H), 7.10-6.97 (m, 3H), 3.48 (s, 3H); ¹³C NMR (126 MHz, DMSO) δ 182.70, 178.70, 140.27, 140.13, 134.56, 134.53, 132.99, 131.70, 130.22, 127.79, 125.79, 125.49, 122.77, 121.88, 59.24; HRMS (ESI-TOF) m/z: [M+H]⁺ Calcd for C₁₇H₁₄NO₃ 280.0968. Found 280.0972.

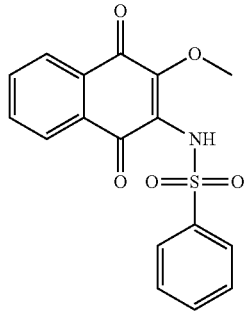

KSC-293-030

N-(3-methoxy-1,4-dioxo-1,4-dihydronaphthalen-2-yl)benzenesulfonamide (KSC-293-030)

This compound was prepared using the same protocol described for KSC-293-025 (pp. 124) using the appropriate amine. Yield: 258 mg, 75%. ¹H NMR (400 MHz, DMSO-d₆) δ 9.80 (s, 1H), 8.02-7.94 (m, 1H), 7.94-7.78 (m, 5H), 7.69-7.54 (m, 3H), 3.78 (s, 3H); ¹³C NMR (126 MHz, CDCl₃) δ 180.86, 180.75, 152.14, 141.93, 134.29, 134.21, 132.42, 130.87, 130.15, 128.82, 126.88, 126.26, 126.00, 125.91, 60.36; HRMS (ESI-TOF) m/z: [M+H]⁺ Calcd for C₁₇H₁₄NO₅S 344.0587. Found 344.0582.

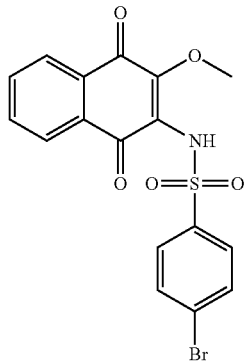

KSC-293-042

4-bromo-N-(3-methoxy-1,4-dioxo-1,4-dihydronaphthalen-2-yl)benzenesulfonamide (KSC-293-042)

This compound was prepared using the same protocol described for KSC-293-025 (pp. 124) using the appropriate amine. Yield: 124 mg, 59%. ¹H NMR (400 MHz, DMSO-d₆) δ 9.95 (s, 1H), 8.00-7.95 (m, 1H), 7.95-7.89 (m, 1H), 7.87-7.79 (m, 6H), 3.85 (s, 3H); ¹³C NMR (126 MHz, DMSO) δ 180.86, 180.72, 152.49, 141.32, 134.32, 134.21, 131.90, 130.89, 130.14, 128.32, 126.51, 126.13, 126.03, 125.91, 60.50; HRMS (ESI-TOF) m/z: [M+H]⁺ Calcd for C₁₇H₁₂BrNO₅S 421.9692. Found 421.9682.

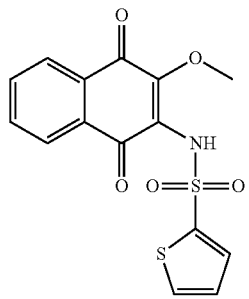

KSC-293-050

N-(3-methoxy-1,4-dioxo-1,4-dihydronaphthalen-2-yl)thiophene-2-sulfonamide (KSC-293-050)

This compound was prepared using the same protocol described for KSC-293-025 (pp. 124) using the appropriate amine. Yield: 100 mg, 57%. $^1$H NMR (400 MHz, DMSO-d$_6$) δ 9.89 (s, 1H), 8.03-7.96 (m, 1H), 7.94-7.89 (m, 2H), 7.87-7.82 (m, 2H), 7.65 (dd, J=3.8, 1.4 Hz, 1H), 7.14 (dd, J=5.0, 3.8 Hz, 1H), 3.98 (s, 3H); $^{13}$C NMR (126 MHz, DMSO) δ 180.90, 180.80, 154.31, 141.80, 134.41, 134.14, 133.00, 132.29, 130.88, 130.22, 127.36, 126.09, 125.88, 125.20, 60.77; HRMS (ESI-TOF) m/z: [M+H]$^+$ Calcd for C$_{15}$H$_{12}$NO$_5$S$_2$ 350.0151. Found 350.0134.

Synthetic Protocols for KSC-293-057 to KSC-304-029-1

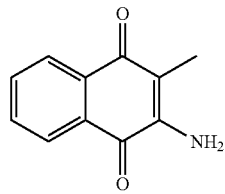

KSC-293-057

2-amino-3-methylnaphthalene-1,4-dione (KSC-293-057)

So a suspension of 2-methylnaphthalene-1,4-dione (173 mg, 1.0 mmol) was added azidotrimethylsilane (134 µL, 1.0 mmol) and the mixture was stirred at room temperature for 9 days, after which time 0.2 M aq. citric acid (10 mL) was added and stirred 30 min. The insoluble material was collected via vacuum filtration and the solids washed with water and dried in vacuo and purified via MPLC (silica, 0-6% MeOH/CH$_2$Cl$_2$). Yield: 66 mg, 35%. $^1$H NMR (400 MHz, DMSO-d$_6$) δ 7.93 (dd, J=7.6, 1.4 Hz, 2H), 7.77 (td, J=7.6, 1.3 Hz, 1H), 7.68 (td, J=7.5, 1.4 Hz, 1H), 6.78 (s, 2H), 1.92 (s, 3H); $^{13}$C NMR (126 MHz, DMSO) δ 181.30, 146.91, 134.39, 132.97, 132.03, 130.20, 125.39, 110.38, 9.62; HRMS (ESI-TOF) m/z: [M+H]$^+$ Calcd for C$_{11}$H$_{10}$NO$_2$ 188.0706. Found 188.0695.

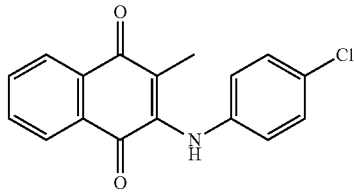

KSC-304-028-1

2-((4-chlorophenyl)amino)-3-methylnaphthalene-1,4-dione (KSC-304-028-1)

2-Methylnaphthalene-1,4-dione (172.0 mg, 0.999 mmol) and copper(II) acetate, monohydrate (19.6 mg, 0.098 mmol) were dissolved into glacial AcOH (2 mL) with the help of sonication. To this solution was added 4-chloroaniline (130.7 mg, 1.025 mmol) and the reaction mixture was stirred at 70° C. under air for 16 h, after which time the reaction mixture was concentrated in vacuo. The crude residue was re-dissolved in dichloromethane and passed through a plug of silica and the silica was further washed with 10% MeOH/ dichloromethane. The filtrate was then concentrated in vacuo and the crude residue was purified according to the preparative RP HPLC methods described in the General Experimental Section (pp. 41). Yield: 3.1 mg; 1%. $^1$H NMR (500 MHz, DMSO-d$_6$) δ 8.76 (s, 1H), 8.00 (td, J=6.4, 1.0 Hz, 3H), 7.84 (td, J=7.5, 1.4 Hz, 1H), 7.78 (td, J=7.5, 1.4 Hz, 1H), 7.33 (dt, J=9.8, 3.1 Hz, 3H), 7.02 (dt, J=11.8, 3.3 Hz, 3H); $^{13}$C NMR (126 MHz, DMSO) δ 183.61, 181.80, 142.99, 140.01, 134.34, 132.87, 132.45, 130.59, 128.23, 126.03, 125.79, 125.54, 122.72, 120.29, 13.73; HRMS (ESI-TOF) m/z: [M+H]$^+$ Calcd for C$_{17}$H$_{13}$ClNO$_2$ 298.0629. Found 298.0621.

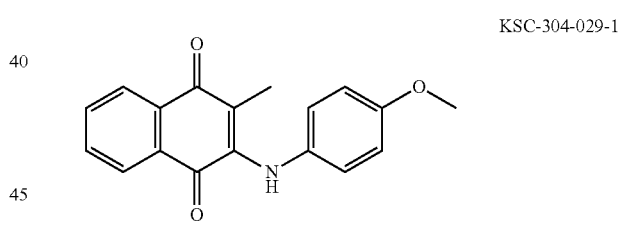

KSC-304-029-1

2-((4-methoxyphenyl)amino)-3-methylnaphthalene-1,4-dione (KSC-304-029-1)

This compound was prepared using the same protocol described for KSC-304-028-1 (pp. 127) using 4-methoxyaniline. Yield: 15.3 mg; 5%. $^1$H NMR (500 MHz, DMSO-d$_6$) δ 8.51 (s, 1H), 7.92 (ddd, J=12.1, 7.6, 0.9 Hz, 2H), 7.75 (td, J=7.5, 1.4 Hz, 1H), 7.68 (td, J=7.5, 1.3 Hz, 1H), 6.96 (dt, J=10.2, 2.6 Hz, 2H), 6.83 (dt, J=10.2, 2.6 Hz, 2H), 3.68 (s, 3H), 1.51 (s, 3H); $^{13}$C NMR (126 MHz, DMSO) δ 183.12, 182.00, 155.63, 143.80, 134.37, 133.50, 132.70, 132.50, 130.35, 125.68, 125.45, 124.36, 115.68, 113.59, 55.18, 13.15; HRMS (ESI-TOF) m/z: [M+H]$^+$ Calcd for C$_{18}$H$_{16}$NO$_3$ 294.1125. Found 294.1119.

REFERENCES

1. Kyle Hadden, M.; Hill, S. A.; Davenport, J.; Matts, R. L.; Blagg, B. S. J., Synthesis and evaluation of Hsp90 inhibitors that contain the 1,4-naphthoquinone scaffold. *Bioorganic & Medicinal Chemistry* 2009, 17 (2), 634-640.

Example 3: Other Compounds of the Invention

The following compound was synthesized in analogy to the above Examples and data collected as shown in FIG. 13:

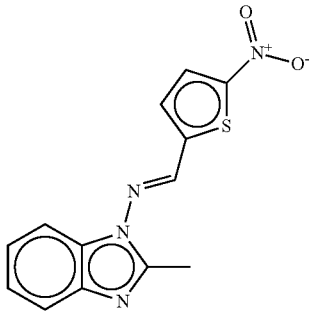

According to the FIG. 13, the compound of this Example. was tested in two MITF-dependent melanoma cell viability assays, SK-MEL-5 and MALME-3M plus an MITF-independent cell line, A-375. The compound showed specific activity against the MITF-dependent cells and no impairment of viability in A-375 cells. The compound reduced the expression of multiple MITF target genes, including the cell cycle regulator CDK2.

Example 4: Mechanism of Action Studies

Figure 2B:
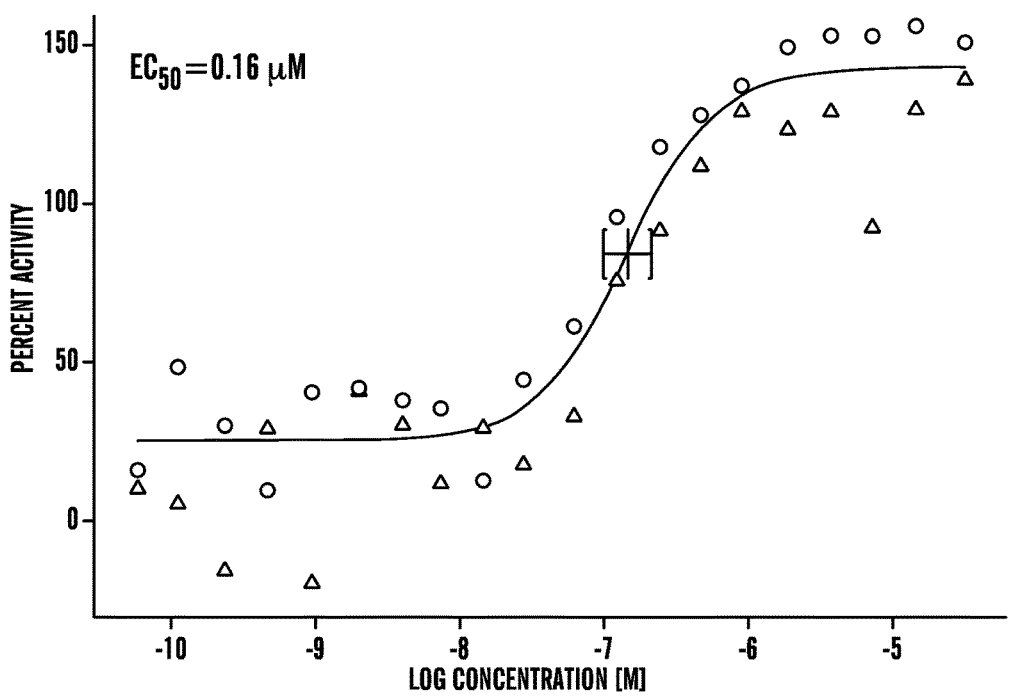
Figure 2C:
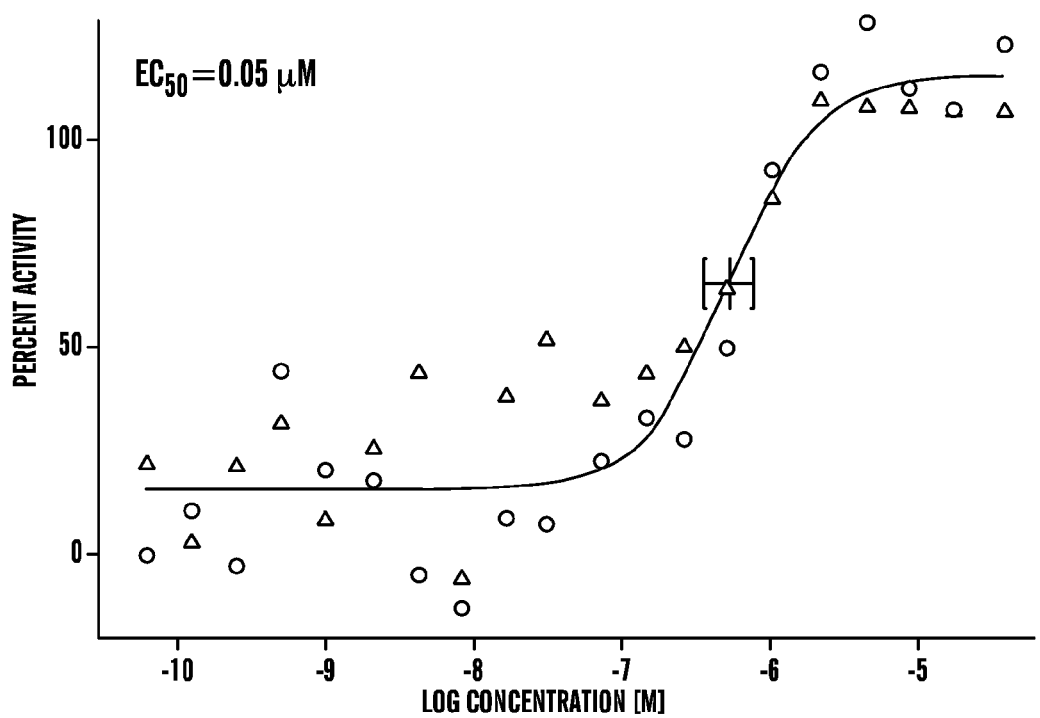
Figure 2D:
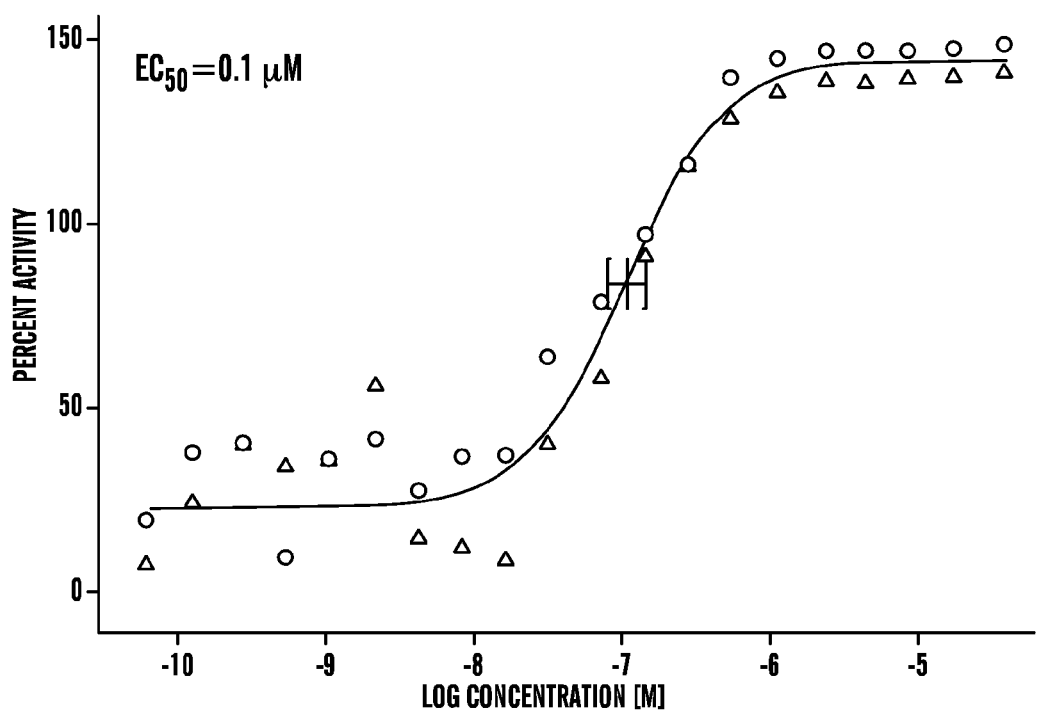
Figure 2E:
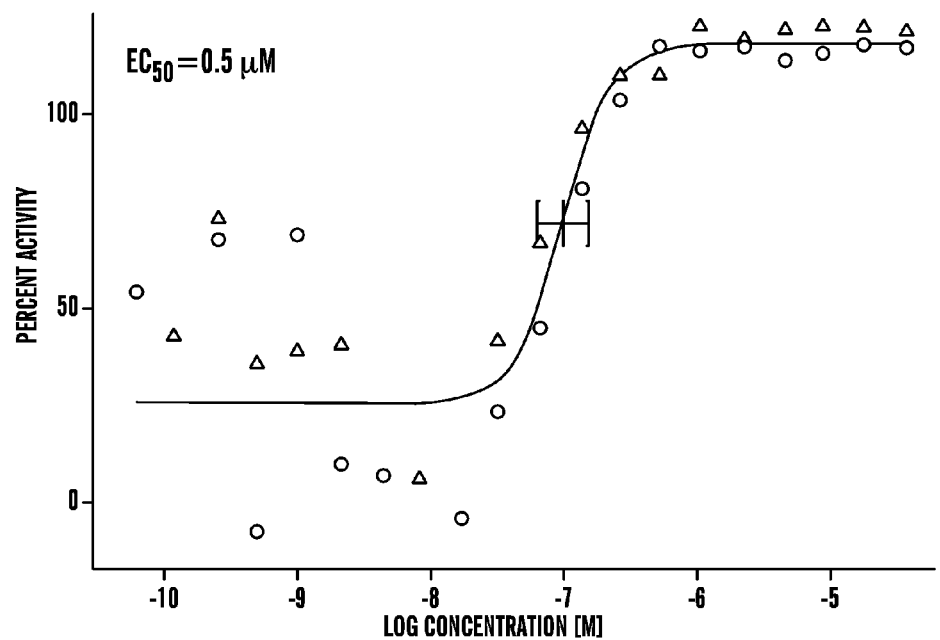
Figure 3:
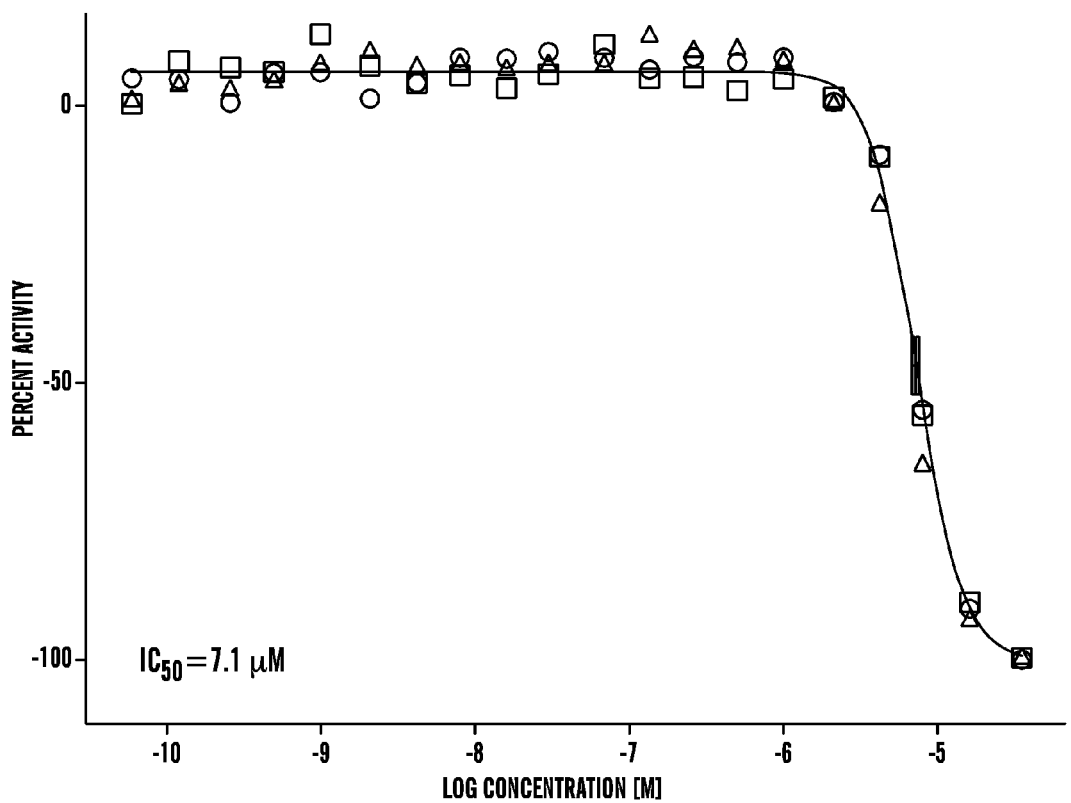
FIG. 3 provides primary melanocyte viability assay data for 4-((1,4-dioxo-1,4-dihydronaphthalen-2-yl)amino)benzenesulfonamide. The compound was tested across a range of concentrations up to 35 µM in a primary human melanocyte assay. Compounds were incubated for 24 hours and viability measured with CellTiter-Glo (PubChem AID 651920). Concentration response curves were generated with Genedata Screener Condeseo and show normalized percent activity for the individual doses. $IC_{50}$=7.14 µM. □=replicate 1, ∆=replicate 2, □=replicate 3.
Figure 4A:
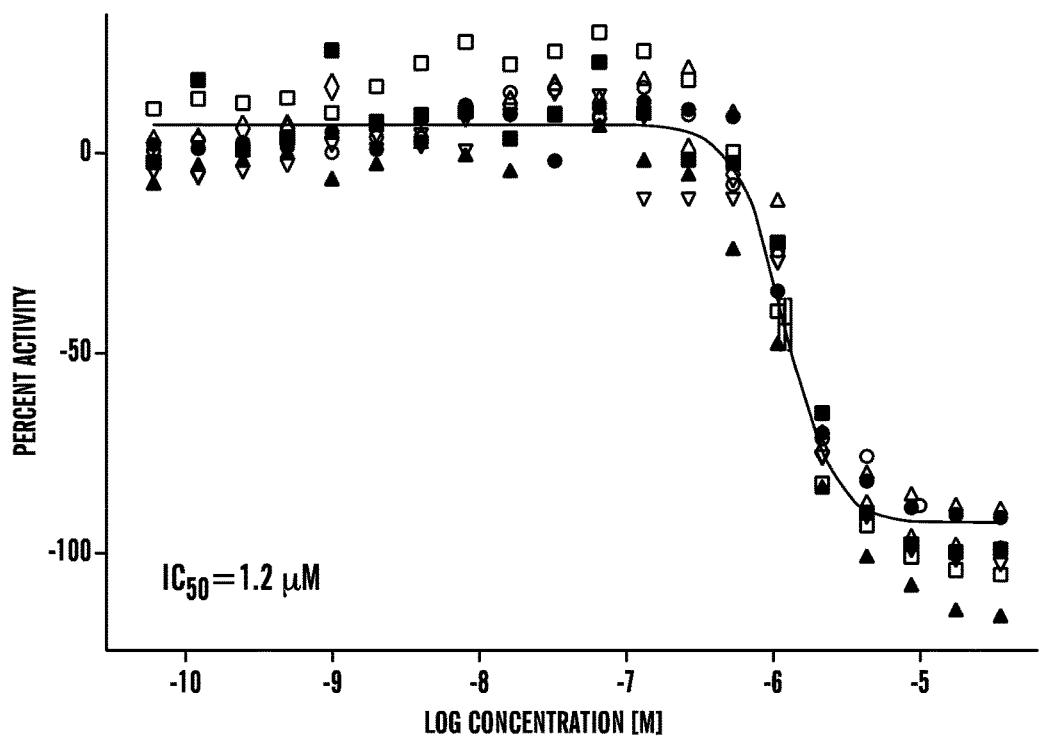
FIG. 4 shows dose response curves for 4-((1,4-dioxo-1,4-dihydronaphthalen-2-yl)amino)benzenesulfonamide. The compound was tested across a range of concentrations up to 35 µM in the primary assay and several secondary assays. Concentration response curves were generated with Genedata Screener Condeseo and show normalized percent activity for the individual doses. TRPM-1 promoter assay (PubChem AID 651588), $IC_{50}$=1.2 µM (A); A375 cytotoxicity assay (PubChem AID 651591), $IC_{50}$>35 µM (B); SK-MEL-5 CellTiter-Glo (PubChem AID 651586), $IC_{50}$=0.75 µM (C) and MALME-3M CellTiter-Glo (PubChem AID 651585), $IC_{50}$=0.88 µM (D). □=replicate 1, ∆=replicate 2, □=replicate 3, ◊=replicate 4
Figure 4B:
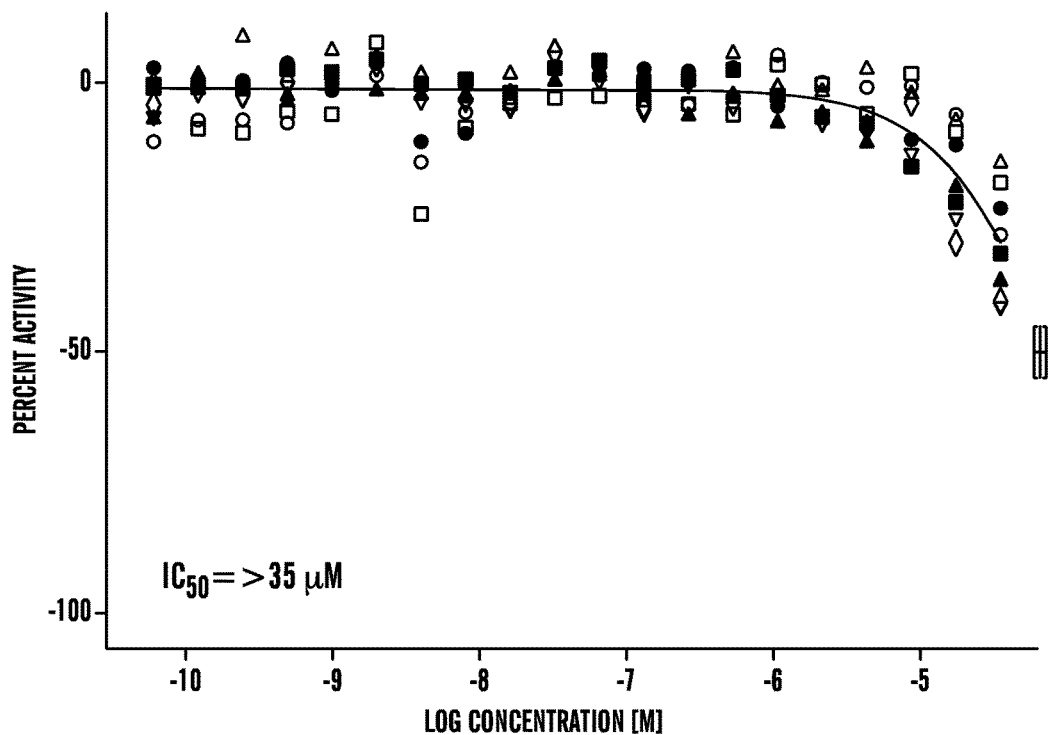
Figure 4C:
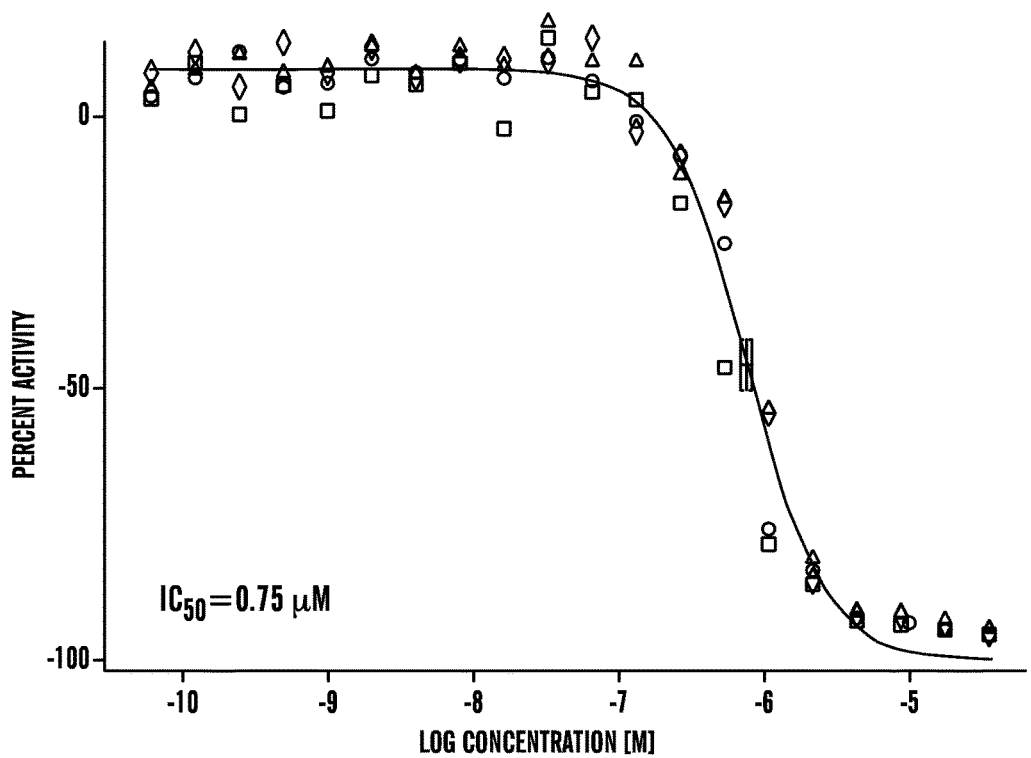
Figure 4D:
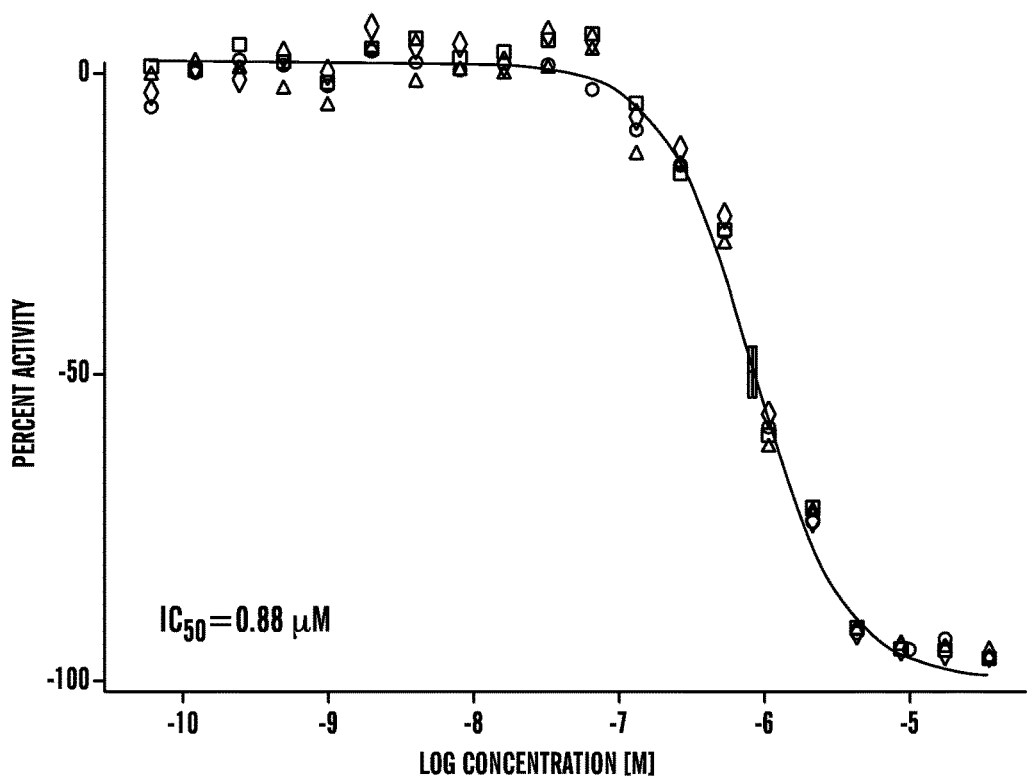
Figure 5A:
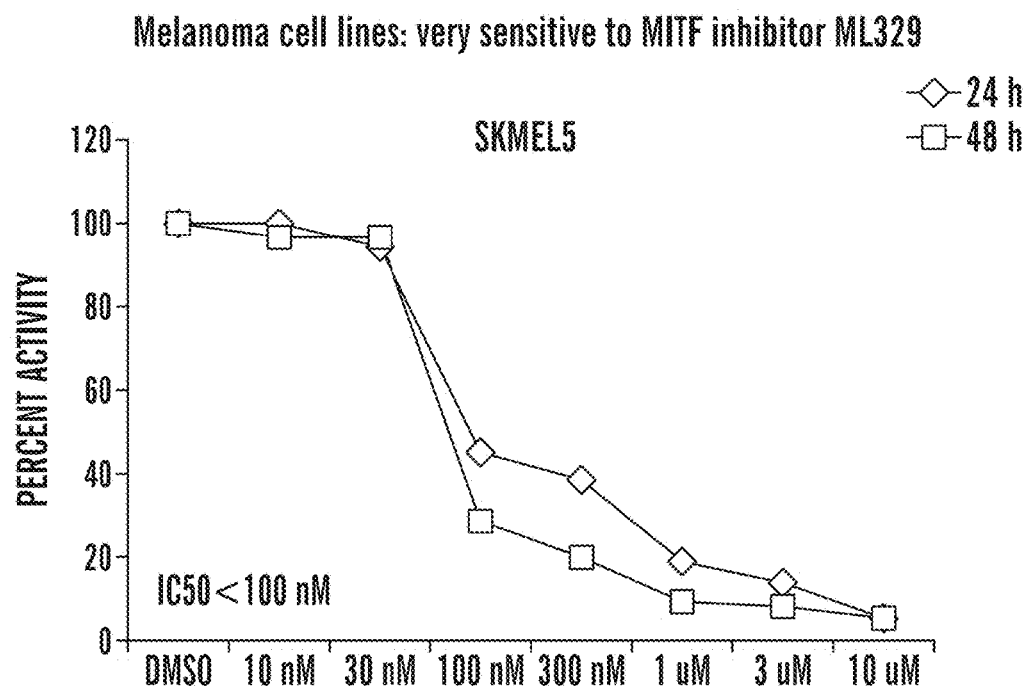
FIGS. 5A-5D shows that melanoma cell lines SKMEL5, IST MEL, MALME-3M and 501 MEL are very sensitive to MITF inhibitor ML329.
Figure 5B:
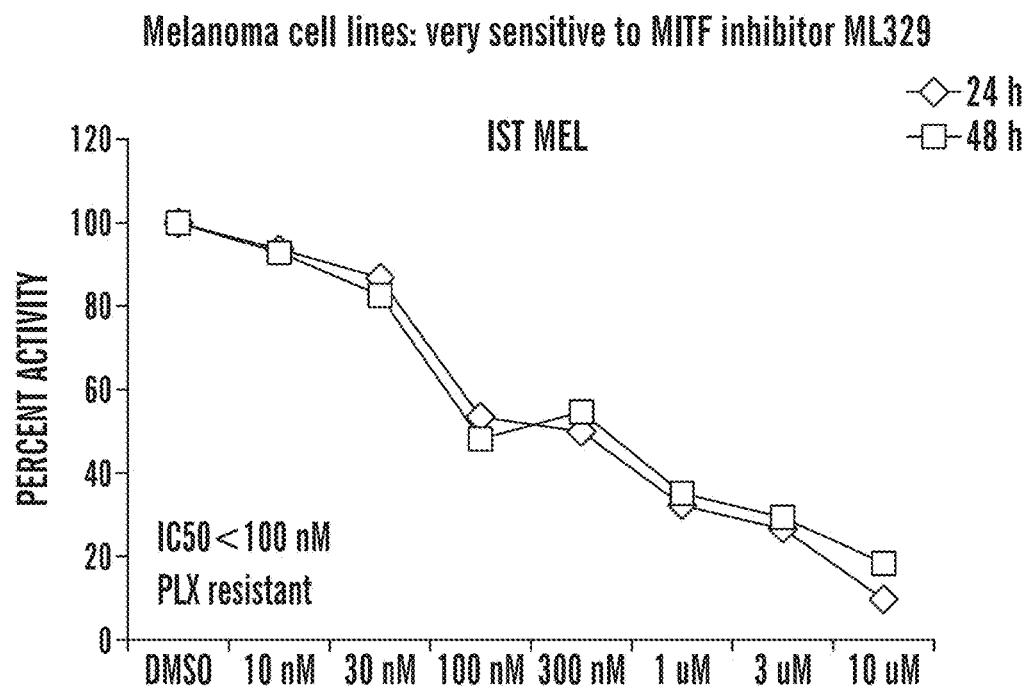
Figure 5C:
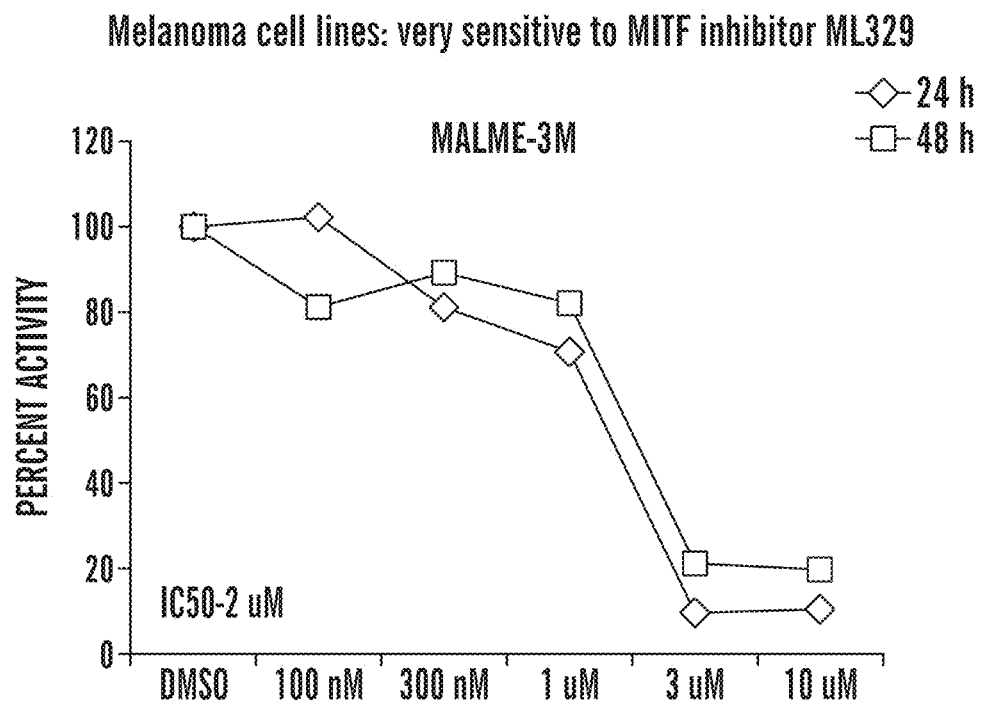
Figure 5D:
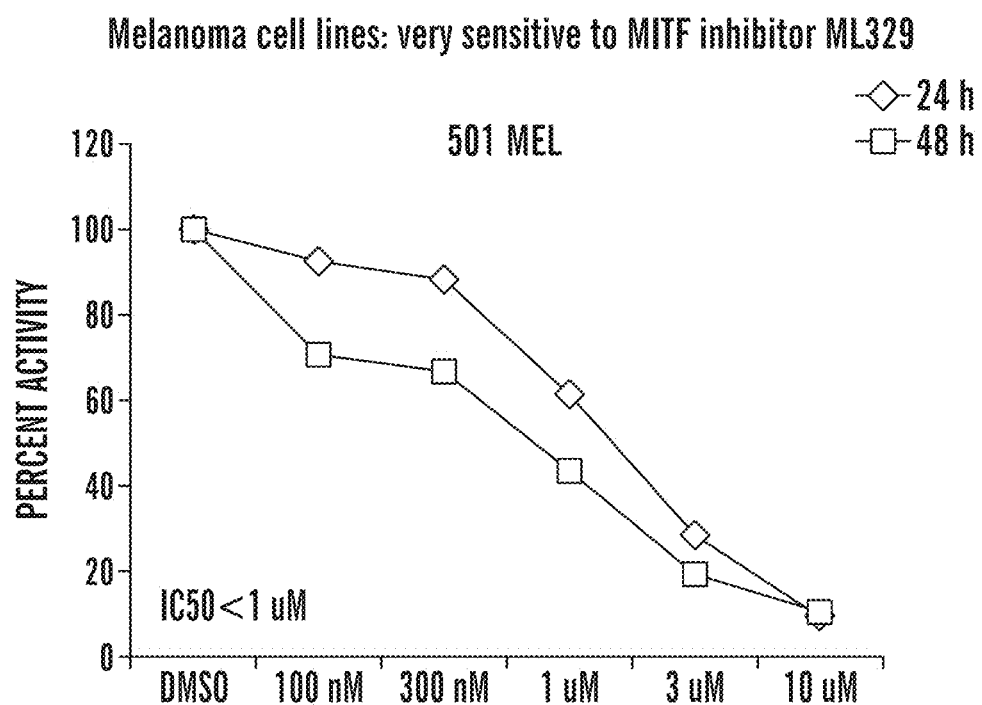
Figure 6A:
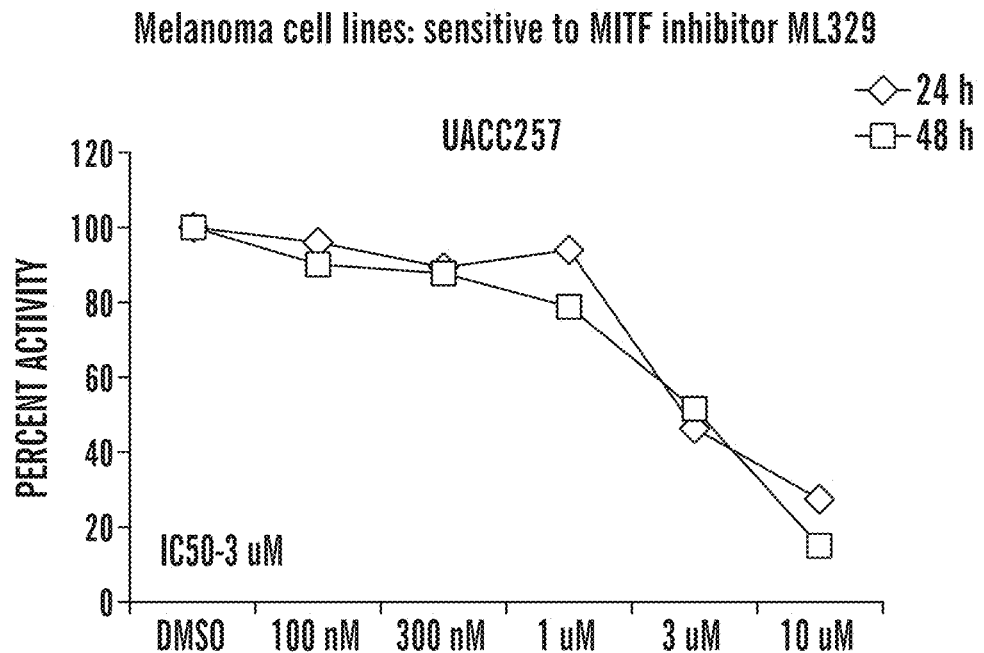
FIGS. 6A-6D shows that melanoma cell lines UACC257, C32, COLO800 and MZ2MEL are sensitive to MITF inhibitor ML329.
Figure 6B:
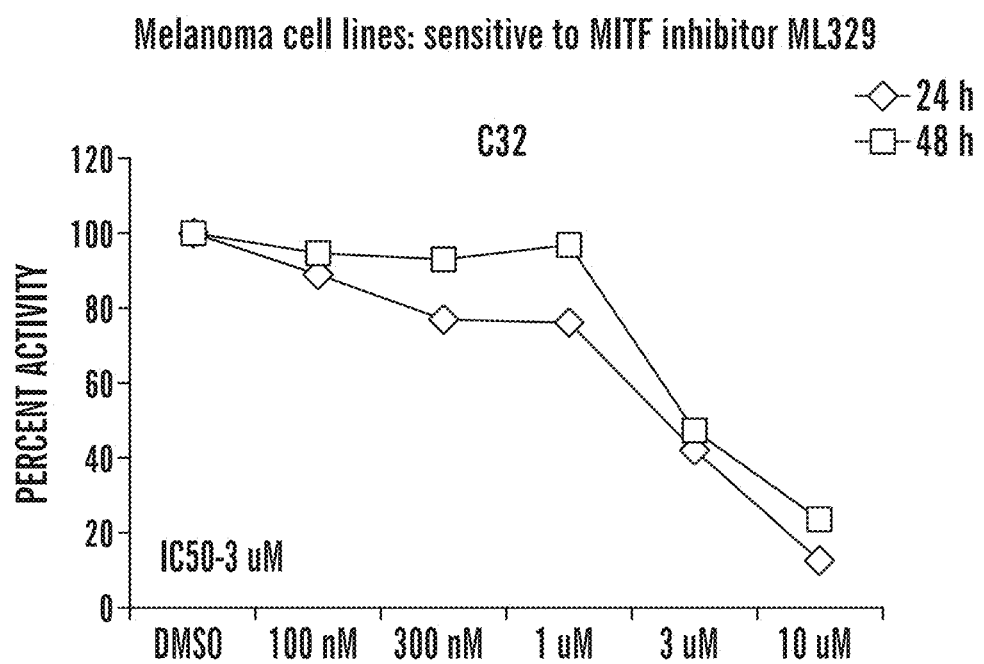
Figure 6C:
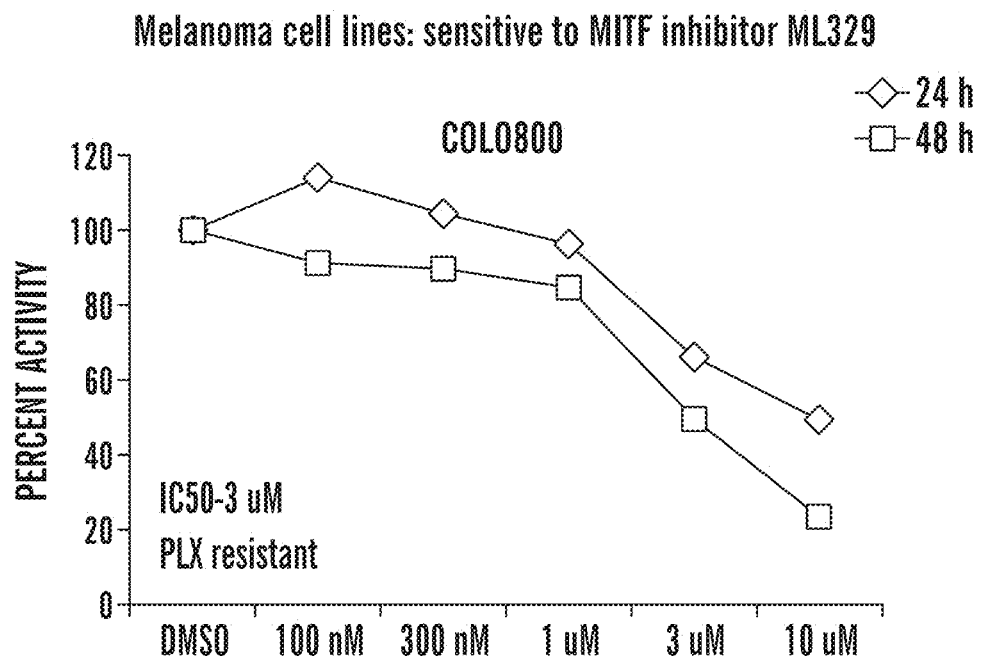
Figure 6D:
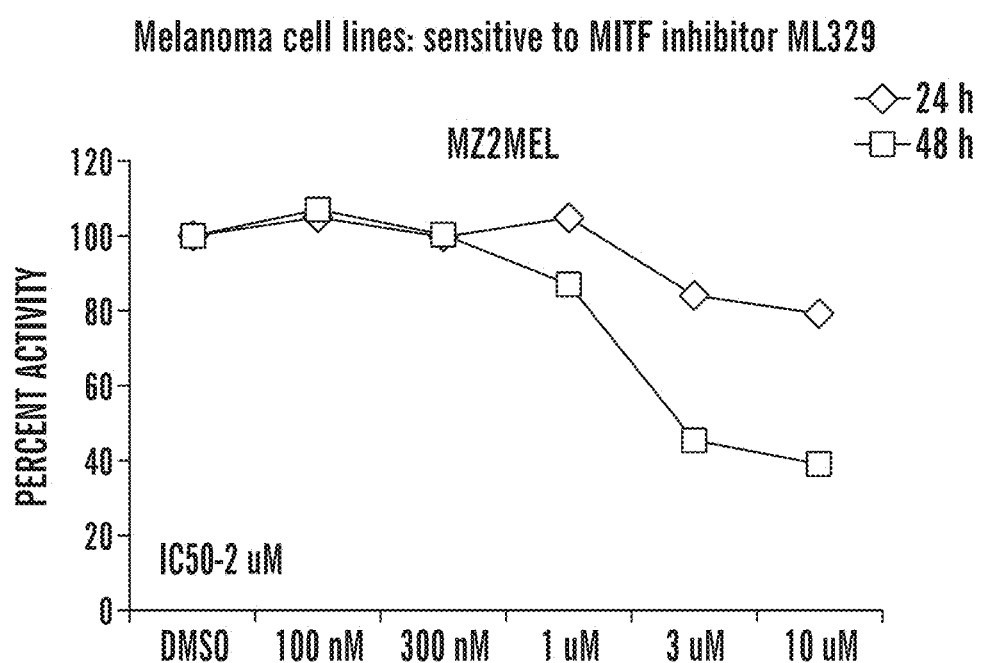
Figure 7A:
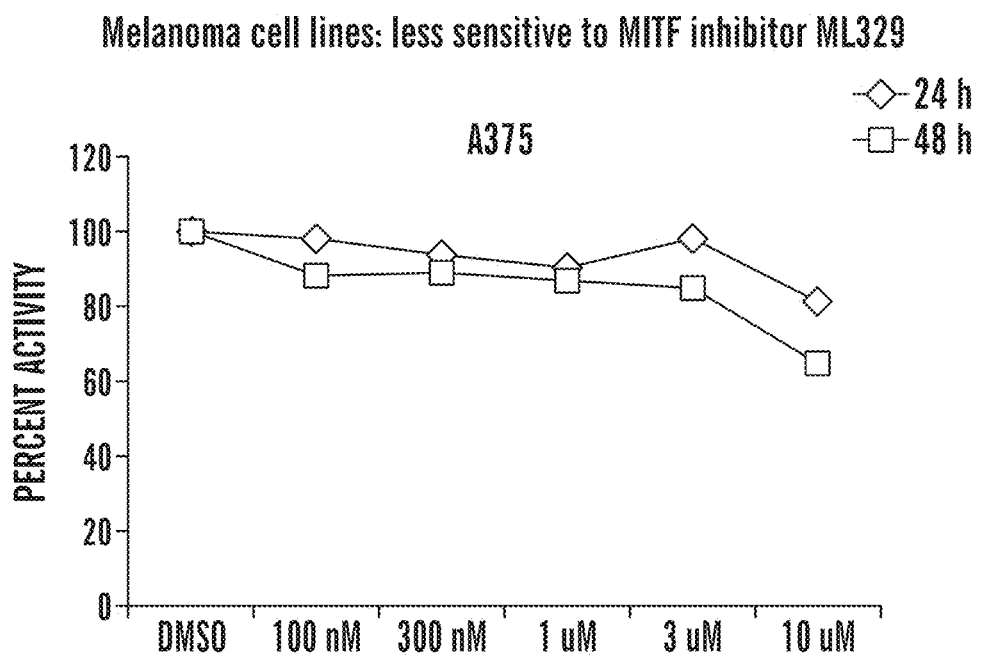
FIGS. 7A-7D shows that melanoma cell lines A375, SKMEL2, IPC298 and SK30 are less sensitive to MITF inhibitor ML329.
Figure 7B:
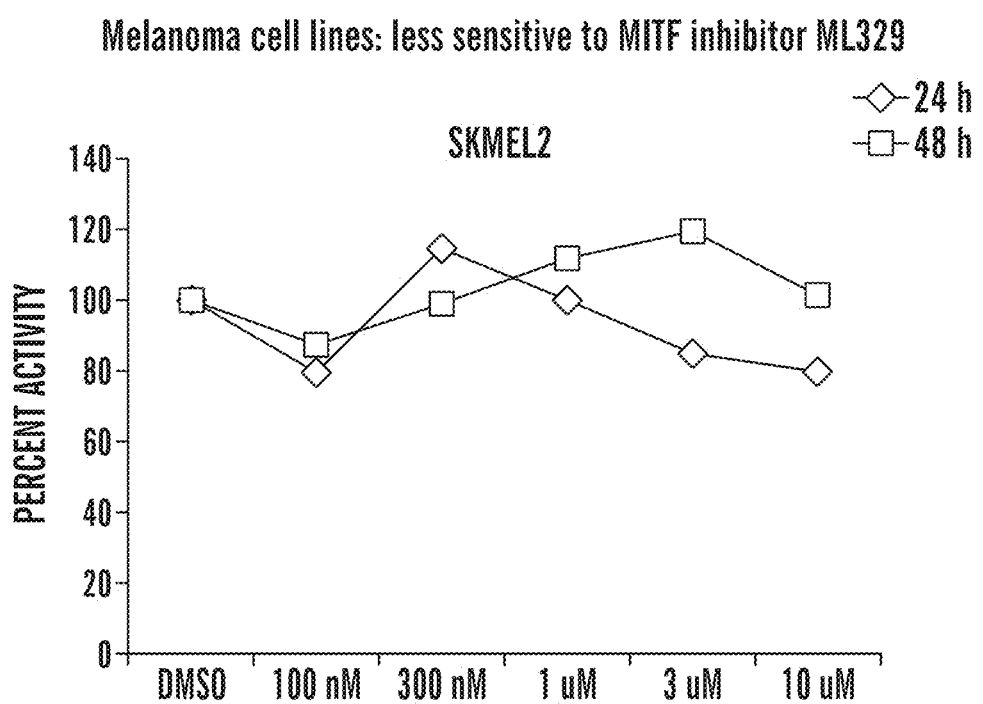
Figure 7C:
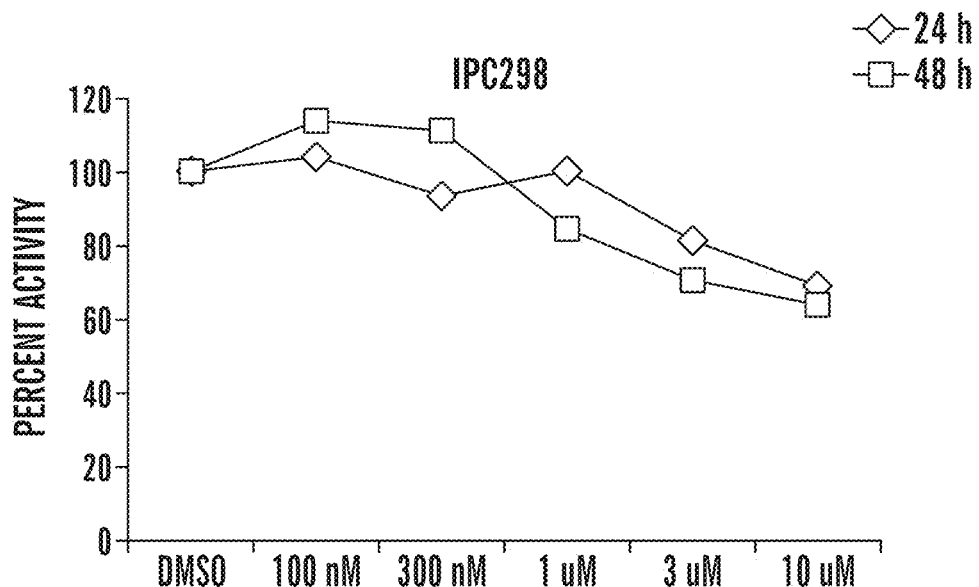
Figure 7D:
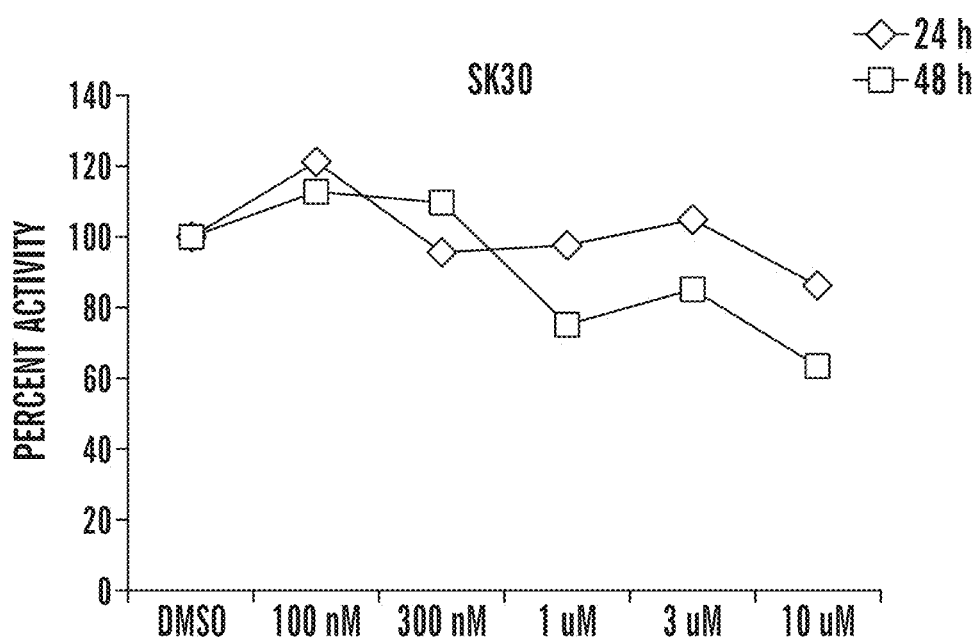
Figure 8A:
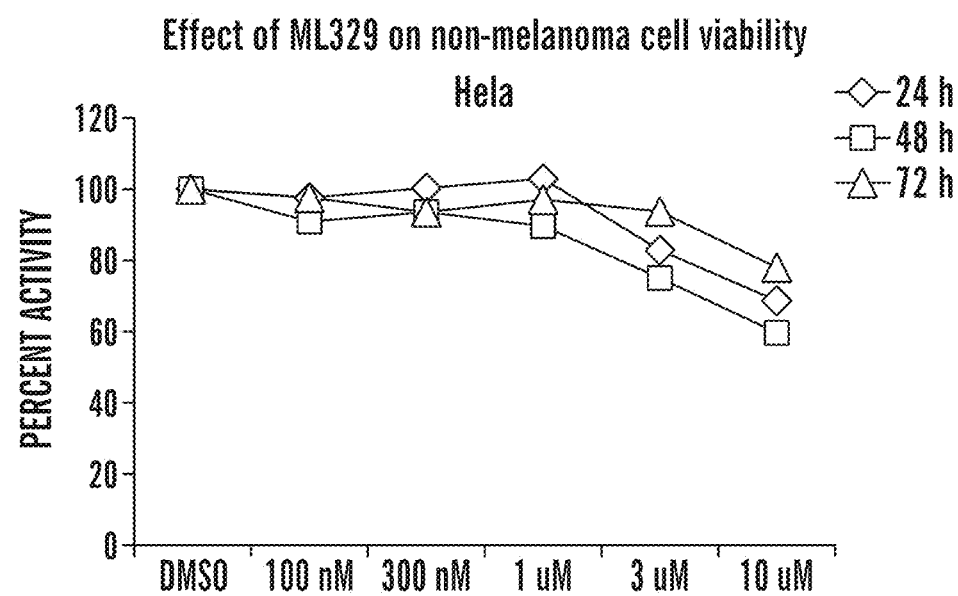
FIGS. 8A-8E shows the effect of ML329 on non-melanoma cell viability.
Figure 8B:
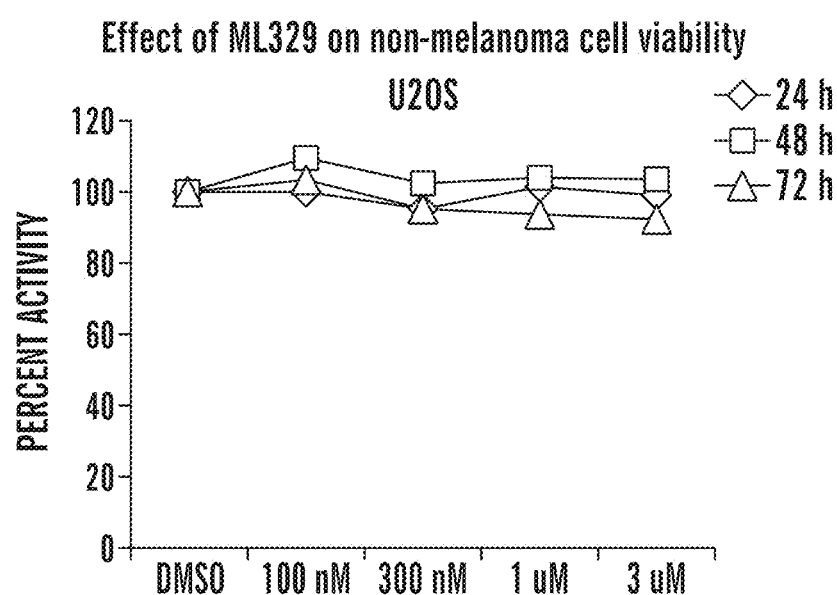
Figure 8C:
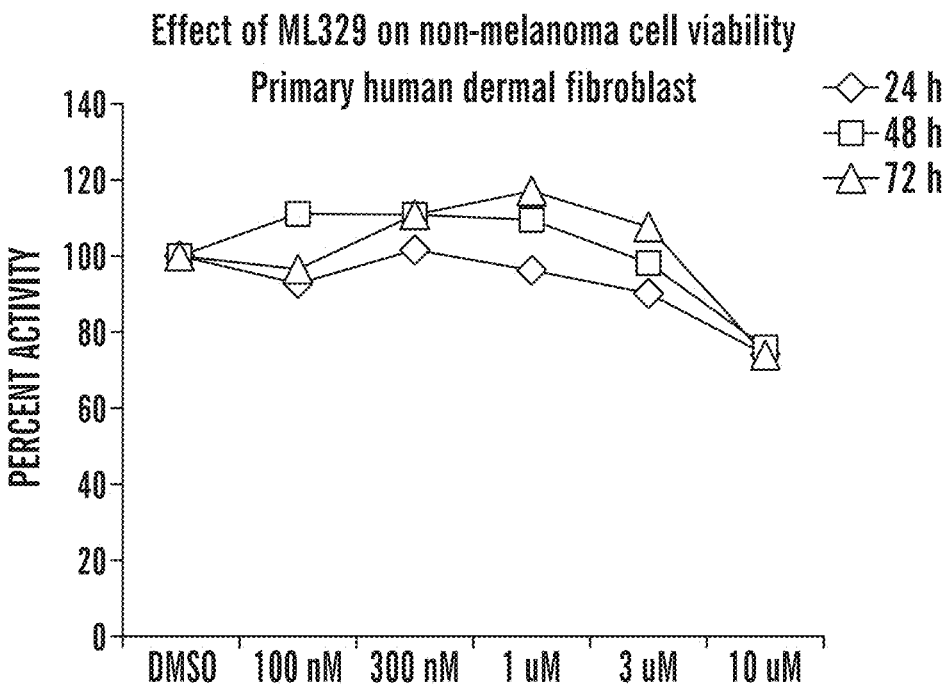
Figure 8D:
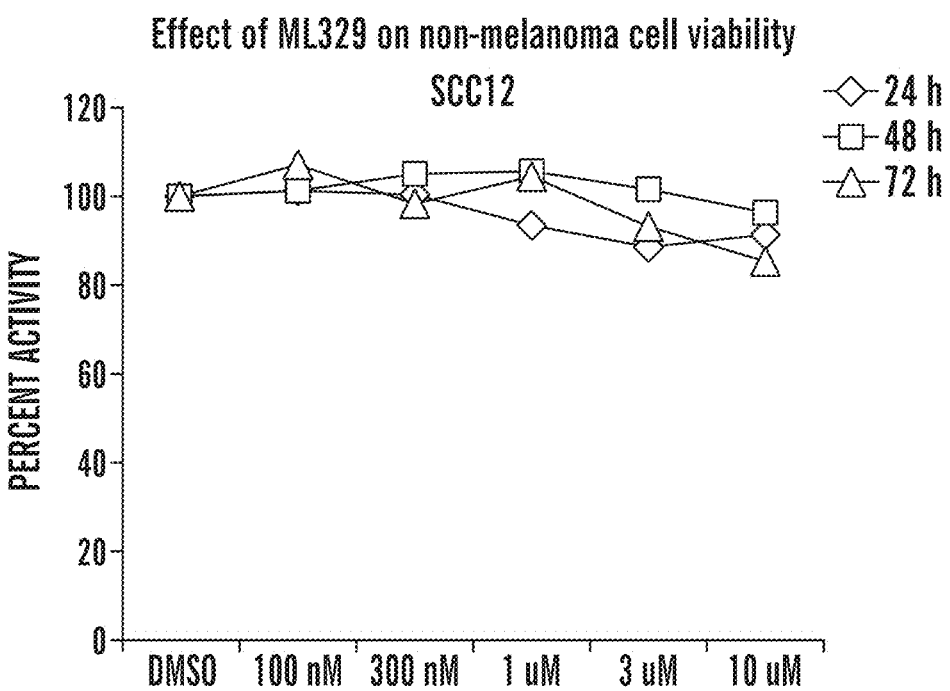
Figure 8E:
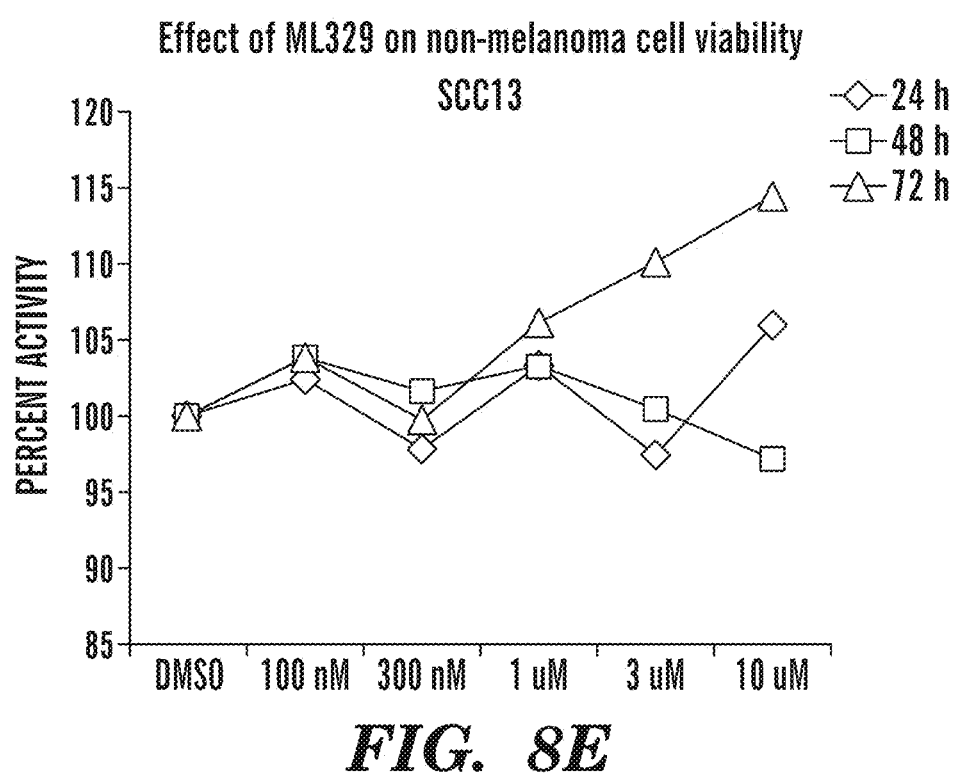

The assays utilized in this project were phenotypic, cell-based assays that leave some ambiguity to how the compound of Example 1 works in cells. The assays used in this project show circumstantial evidence of the compound of Example 1 regulating MITF and its molecular pathways. The compound could be acting on an upstream activator of MITF since a reduction of MITF transcription and several of its target genes by qPCR was observed (FIG. 2B, PubChem AID 651773). MITF expression is regulated by a number of transcriptional regulators including: MITF itself, BRAF, WNT signaling, SOX10, CREB, and Pax3 (2). The compound of Example 1 reduced the expression of multiple MITF target genes suggesting a mechanism that impacts a broader profile of MITF targets, including both melanogenesis and cell cycle genes such as CDK2 (FIG. 2C). The compound of Example 1 consistently lowered the expression of several MITF target genes including: melastatin (TRPM-1), dopachrome tautomerase/tyrosinase-related protein-2 (DCT), the cell cycle regulator cyclin-dependent kinase-2 (CDK2) and melan-A (MLANA/MART1). The primary screen was carried out in a BRAF(V600E) mutated melanoma cell line, SK-MEL-5. It is quite clear that the compound of Example 1's activities are very different from those of BRAF inhibitors, something studied in the Fisher lab quite extensively. BRAF-MEK-MAPK lead to proteolysis of MITF, and thus MAPK pathway suppression leads to MITF stabilization/up-regulation. It was observed (and published) that multiple MITF target genes are up-regulated following BRAF inhibitor treatments. In contrast it was found that the compound of Example 1 suppresses both MITF and multiple of its transcriptional target genes. It is believed that MITF up-regulation following BRAF suppression represents a survival mechanism that limits efficacy of BRAF targeted therapies. Therefore, it is plausible that concurrent use of MITF antagonists (like the compound of Example 1) may offer significant benefit in combination with BRAF inhibitors. Proper determination of mechanism of action will require a number of different studies, some of which are outlined in Section 4.3.

Example 5: Analytical Assays for Compounds of the Invention

Solubility.

Solubility was determined in phosphate buffered saline (PBS) pH 7.4 with 1% DMSO. Each compound was prepared in duplicate at 100 µM in both 100% DMSO and PBS with 1% DMSO. Compounds were allowed to equilibrate at room temperature with a 250 rpm orbital shake for 24 hours. After equilibration, samples were analyzed by UPLC-MS (Waters, Milford, Mass.) with compounds detected by SIR detection on a single quadrupole mass spectrometer. The DMSO samples were used to create a two-point calibration curve to which the response in PBS was fit.

PBS Stability.

Stability was determined in the presence of PBS pH 7.4 with 0.1% DMSO. Each compound was prepared in duplicate on six separate plates and allowed to equilibrate at room temperature with a 250-rpm orbital shake for 48 hours. One plate was removed at each time point (0, 2, 4, 8, 24, and 48 hours). An aliquot was removed from each well and analyzed by UPLC-MS (Waters, Milford, Mass.) with compounds detected by SIR detection on a single quadrupole mass spectrometer. Additionally, to the remaining material at each time point, acetonitrile was added to force dissolution of compound (to test for recovery of compound). An aliquot of this was also analyzed by UPLC-MS.

GSH Stability.

Stability was determined in the presence of PBS pH 7.4, 10 µM compound and 50 µM glutathione with 0.1% DMSO. Each compound was prepared in duplicate on six separate plates and allowed to equilibrate at room temperature with a 250-rpm orbital shake for 48 hours. One plate was removed at each time point (0, 2, 4, 8, 24, and 48 hours). An aliquot was removed from each well and analyzed by UPLC-MS (Waters, Milford, Mass.) with compounds detected by SIR detection on a single quadrupole mass spectrometer. Additionally, to the remaining material at each time point, acetonitrile was added to force dissolution of compound (to test for recovery of compound). An aliquot of this was also analyzed by UPLC-MS.

DTT Stability.

Compound was dissolved at 10 µM in PBS/acetonitrile (1/1) at pH 7.4 (1% DMSO) and incubated at room temperature with either no thiol source as a negative control or 50 µM dithiothreitol (DTT). The mixtures were sampled every hour for eight hours or every 8 hours for 48 hours and analyzed by RP HPLC/UV/HRMS. The analytical RP HPLCUV/HRMS system utilized for the analysis was a Waters Acquity system with UV-detection and mass-detection (Waters LCT Premier). The analytical method conditions included a Waters Acquity HSS T3 C18 column (2.1×50 mm, 1.8 um) and elution with a linear gradient of 99% water to 100% CH3CN at 0.6 mL/min flow rate. Peaks on chromatograms were integrated using the Waters OpenLynx software. Absolute areas under the curve (214 nm) were compared at each time point to determine relative percent compound remaining in supernatant. The masses of potential adducts were searched for in the samples to determine if any detectable adduct formed. All samples were prepared in duplicate. Ethacrynic acid, a known Michael acceptor, was used as a positive control and was tested in PBS/acetonitrile (1/1).

Plasma Protein Binding.

Plasma protein binding was determined by equilibrium dialysis using the Rapid Equilibrium Dialysis (RED) device (Pierce Biotechnology, Rockford, Ill.) for both human and mouse plasma. Each compound was prepared in duplicate at 5 µM in plasma (0.95% acetonitrile, 0.05% DMSO) and added to one side of the membrane (200 uL) with PBS pH 7.4 added to the other side (350 uL). Compounds were incubated at 37° C. for 5 hours with a 250-rpm orbital shake. After incubation, samples were analyzed by UPLC-MS (Waters, Milford, Mass.) with compounds detected by SIR detection on a single quadrupole mass spectrometer.

Plasma Stability.

Plasma stability was determined at 37° C. at 5 hours in both human and mouse plasma. Each compound was prepared in duplicate at 5 µM in plasma diluted 50/50 (v/v) with PBS pH 7.4 (0.95% acetonitrile, 0.05% DMSO). Compounds were incubated at 37° C. for 5 hours with a 250-rpm orbital shake with time points taken at 0 hours and 5 hours. Samples were analyzed by UPLC-MS (Waters, Milford, Mass.) with compounds detected by SIR detection on a single quadrupole mass spectrometer.

Example 6: Biological Assays of Certain Compounds of the Invention

Materials and Reagents:

Steady-Glo® Luciferase Assay System was purchased from Promega (Catalog No. E2550; Madison, Wis.); Cell-Titer-Glo® Luminescent Cell Viability Assay was purchased from Promega (Catalog No. G7573; Madison, Wis.); Cells to CT Bulk Lysis reagents purchased from Ambion (Catalog No. 4391851C; Grand Island, N.Y.); Cells to CT Bulk RT reagents purchased from Ambion (Catalog No. 4391852C; Grand Island, N.Y.); Light Cycler 480 Probes Master purchased from Roche (Catalog No. 4887301001); Human GAPD (GAPDH) Endogenous Control VIC/MGB probe/primer limited purchased from Applied Biosystems (Catalog No. 4326317E; Grand Island, N.Y.); Human MITF FAM probe/primer set purchased from Applied Biosystems (Catalog No. 4331182 Hs01117294_m1; Grand Island, N.Y.); Human TRPM1 probe/primer set purchased from Applied Biosystems (Catalog No. 4331182 Hs00170127_m1; Grand Island, N.Y.); Human CDK2 probe/primer set purchased from Applied Biosystems (Catalog No. 4331182 Hs01548894_m1; Grand Island, N.Y.); Human DCT probe/primer set purchased from Applied Biosystems (Catalog No. 4331182 Hs01098278_m1; Grand Island, N.Y.); and Human MLANA probe/primer set purchased from Applied Biosystems (Catalog No. 4331182 Hs00194133_m1; Grand Island, N.Y.).

Cell Lines:

The following cell lines were used in this study: (i) TRPM-1:luc is a SK-MEL-5 melanoma cell line that expresses firefly luciferase under the control of the melastatin (TRPM-1) promoter. This cell line was used in the primary HTS campaign and generated by the Fisher Lab; (ii) SK-MEL-5 is the parental cell line to SKMEL5 TRPM-1:luc cells, and does not contain the luciferase reporter. This cell line was obtained from ATCC (Catalog Number HTB-70; Manassas, Va.); (iii) A375 obtained from ATCC (Catalog Number CRL-1619; Manassas, Va.) is a melanoma cell line characterized to be independent of MITF for growth and survival; and (iv) MALME-3M was obtained from ATCC (Catalog Number HTB-64; Manassas, Va.) is a melanoma cell line dependent upon MITF activity for growth and survival.

Assays

SK-MEL-5 TRPM-1 Luciferase Reporter:

The TRPM1 luciferase promoter construct was transfected into the SK-MEL-5 melanoma cell line and a stable cell line was generated. This promoter is exquisitely sensitive to MITF over-expression and suppression and contains three canonical E-box motifs within the cloned promoter fragment (17). On day 0, cells were plated at 2,000 cells per well into white, opaque 384 well plates in phenol red-free media. On day 1, cells were treated with compounds or positive control for 24 hours. On day 2, 20 uL of SteadyGlo (Promega) was added per well and luminescence signal was determined with the Perkin-Elmer EnVision plate reader. Primary HTS data were analyzed in Genedata Screener Assay Analyzer. All values were normalized against DMSO treated samples and the positive control (18 µM parthenolide, CID 6473881). For the HTS, the average of two replicates was used to rank order activity and to choose compounds for retests. For dose studies, percent (%) activity was determined for each concentration and the concentration response curves (CRCs) were generated with Genedata Screener's Condoseo.

SK-MEL-5 Cell Cytotoxicity Assay:

SK-MEL-5 cells were treated with compounds for 24 hours, and then cell viability was measured using the CellTiter-Glo Assay (Promega), a luciferase-based reagent that measures cellular ATP levels. The compounds were tested at different concentrations to determine $IC_{50}$ values. Compounds that were active in the primary assay and toxic below 30 µM at 24 hours were considered for probe development. Data were normalized against DMSO in Genedata Screener's Assay Analyzer. Curves were generated with Genedata Screener's Condoseo and showed percent (%) activity for the individual doses.

A-375 Cell Cytotoxicity Assay:

A375 cells were treated with compounds for 24 hours, and then cell viability was measured using the CellTiter-Glo Assay (Promega), a luciferase-based reagent that measures cellular ATP levels. The compounds were tested at different concentrations to determine $IC_{50}$ values. Compounds that were active in the primary assay and were not toxic below 30 µM at 24 hours were considered for probe development. Data were normalized against DMSO in Genedata Screener's Assay Analyzer. Curves were generated with Genedata Screener's Condoseo and showed percent (%) activity for the individual doses.

MALME-3M Cell Cytotoxicity Assay:

MALME-3M cells were treated with compounds for 24 hours, and then cell viability was measured using the CellTiter-Glo Assay (Promega), a luciferase-based reagent that measures cellular ATP levels. The compounds were tested at different concentrations to determine $IC_{50}$ values. Compounds that were active in the primary assay and toxic below 30 µM at 24 hours were considered for probe development. Data were normalized against DMSO in Genedata Screener's Assay Analyzer. Curves were generated with Genedata Screener's Condoseo and showed percent (%) activity for the individual doses.

qPCR Assay for MITF Expression:

SK-MEL-5 cells were treated with compounds for 24 hours. Next, cells were lysed with DNase I (Ambion, from Cell to CT Lysis Mix). Lysed cells were delivered to a RT-PCR plate (Ambion, Cells to CT RT Mix) and the plates were then processed for reverse transcription to create cDNA. qPCR was performed by transferring cDNA from the RT-PCR plate to a qPCR plate containing PCR master mix (Roche, Probes Master), FAM Taqman probe/primer set for the target gene (human MITF, Applied Biosystem, 4331182 Hs01117294_m1), VIC Taqman probe/primer set for a house keeping gene (human GAPDH, Applied Biosystems C10228) and water. qPCR plates were cycled using a real-time PCR instrument (Roche, Light Cycler). Using the instrument software, a cycle call was generated when each well enters log phase amplification (Ct). The delta Ct value was determined by subtracting the Ct value of the control gene (GAPDH) from the Ct value of the target gene (MITF) in each well. The delta delta Ct value of each compound treatment was determined by averaging the delta Ct values of the mock well on each plate and subtracting that average from the delta Ct value of each compound well. The compounds were tested at different concentrations to determine $IC_{50}$ values. Data were normalized against DMSO in Genedata Screener's Assay Analyzer. Curves were generated with Genedata Screener's Condoseo and showed percent (%) activity for the individual doses.

qPCR Assay for TRPM1 Expression (SAI: PubChem AID No. 651770):

Protocol is the same as for the qPCR assay for MITF expression except the following primers and probes were used: FAM Taqman probe/primer set for the target gene (human TRPM1, Applied Biosystem, 4331182 Hs00170127_m1), VIC Taqman probe/primer set for a house keeping gene (human GAPDH, Applied Biosystems C10228).

qPCR Assay for CDK2 Expression:

Protocol is the same as the qPCR assay for MITF expression except the following primers and probes were used: FAM Taqman probe/primer set for the target gene (human CDK2, Applied Biosystem, 4331182 Hs01548894_m1), VIC Taqman probe/primer set for a house keeping gene (human GAPDH, Applied Biosystems C10228)

qPCR Assay for DCT Expression:

Protocol is the same as the qPCR assay for MITF expression except the following primers and probes were used: FAM Taqman probe/primer set for the target gene (human DCT, Applied Biosystem, 4331182 Hs01098278_m1), VIC Taqman probe/primer set for a house keeping gene (human GAPDH, Applied Biosystems C10228)

qPCR Assay for MLANA Expression:

Protocol is the same as the qPCR assay for MITF expression except the following primers and probes were used: FAM Taqman probe/primer set for the target gene (human MLANA, Applied Biosystem, 4331182 Hs00194133_m1), VIC Taqman probe/primer set for a house keeping gene (human GAPDH, Applied Biosystems C10228)

Cell Proliferation Assay of Primary Human Melanocytes:

Primary human neonatal melanocytes were isolated from discarded foreskins by gentle dispase treatment and grown in Ham's F10 media supplemented with 7% FBS, penicillin/streptomycin/glutamine, 0.1 mM methyl-3-(2-methylpropyl)-7H-1-purine-2,6-dione (IBMX), 50 ng/mL 12-tetradecanoylphorbol 13-acetate (TPA), 1 µM $Na_3VO_4$ and 1 µM N(6),2'-O-dibutyryladenosine 3':5' cyclic monophosphate (dbcAMP). Cells were plated at 4,000 cells per well of a 384 well plate. On the following day, 10 nL of compound was added per well and incubated for 24 hours. The compounds were tested at different concentrations to determine $IC_{50}$ values. At the end of compound treatment, cell viability was measured with CellTiter-Glo (Promega) and luminescence measured with the PerkinElmer EnVision plate reader. Data were normalized against DMSO in Genedata Screener's Assay Analyzer. Curves were generated with Genedata Screener's Condoseo and showed percent (%) activity for the individual doses.

TABLE 1

Summary of Completed Assays and AIDs

| PubChem AID No. | Type | Target | Concentration Range (µM) | Samples Tested |
|---|---|---|---|---|
| 488944 | Summary | MITF Inhibitor project | NA | NA |
| 488899 | Cell-based | TRPM-1 promoter activity assay | 12.5 | 331,578 |
| 493177 | Cell-based | TRPM-1 promoter activity assay | 0.015-35 | 1,241 |
| 493073 | Cell-based | TRPM-1 promoter activity assay | 0.015-35 | 1,241 |
| 493102 | Cell-based | TRPM-1 promoter activity assay | 0.015-35 | 1,241 |
| 493240 | Cell-based | SK-MEL-5 cytotoxicity assay | 0.015-35 | 1,280 |
| 540335 | Cell-based | A375 cytotoxicity assay | 0.015-35 | 1,280 |
| 493191 | Cell-based | MALME-3M cytotoxicity assay | 0.015-35 | 1,280 |
| 540348 | Cell-based | TRPM-1 promoter activity assay | 0.015-35 | 29 |
| 624290 | Cell-based | TRPM-1 promoter activity assay | 0.00006-35 | 70 |
| 624259 | Cell-based | TRPM-1 promoter activity assay | 0.00006-35 | 70 |
| 624316 | Cell-based | TRPM-1 promoter activity assay | 0.00006-35 | 107 |
| 624363 | Cell-based | TRPM-1 promoter activity assay | 0.00006-35 | 57 |
| 624440 | Cell-based | TRPM-1 promoter activity assay | 0.00006-35 | 26 |
| 624426 | Cell-based | TRPM-1 promoter activity assay | 0.00006-35 | 26 |
| 624430 | Cell-based | TRPM-1 promoter activity assay | 0.00006-35 | 62 |
| 651588 | Cell-based | TRPM-1 promoter activity assay | 0.00006-35 | 37 |
| 651753 | Cell-based | TRPM-1 promoter activity assay | 0.00006-35 | 20 |
| 540347 | Cell-based | SK-MEL-5 cytotoxicity assay | 0.015-35 | 30 |
| 624289 | Cell-based | SK-MEL-5 cytotoxicity assay | 0.00006-35 | 107 |
| 624315 | Cell-based | SK-MEL-5 cytotoxicity assay | 0.00006-35 | 107 |
| 624366 | Cell-based | SK-MEL-5 cytotoxicity assay | 0.00006-35 | 57 |
| 624427 | Cell-based | SK-MEL-5 cytotoxicity assay | 0.00006-35 | 26 |
| 624429 | Cell-based | SK-MEL-5 cytotoxicity assay | 0.00006-35 | 26 |
| 624428 | Cell-based | SK-MEL-5 cytotoxicity assay | 0.00006-35 | 62 |
| 651586 | Cell-based | SK-MEL-5 cytotoxicity assay | 0.00006-35 | 37 |
| 540346 | Cell-based | A375 cytotoxicity assay | 0.015-35 | 1,280 |
| 624489 | Cell-based | A375 cytotoxicity assay | 0.00006-35 | 107 |
| 624324 | Cell-based | A375 cytotoxicity assay | 0.00006-35 | 107 |
| 624364 | Cell-based | A375 cytotoxicity assay | 0.00006-35 | 120 |

TABLE 1-continued

Summary of Completed Assays and AIDs

| PubChem AID No. | Type | Target | Concentration Range (µM) | Samples Tested |
|---|---|---|---|---|
| 624368 | Cell-based | A375 cytotoxicity assay | 0.00006-35 | 57 |
| 624488 | Cell-based | A375 cytotoxicity assay | 0.00006-35 | 26 |
| 624490 | Cell-based | A375 cytotoxicity assay | 0.00006-35 | 26 |
| 624492 | Cell-based | A375 cytotoxicity assay | 0.00006-35 | 62 |
| 651591 | Cell-based | A375 cytotoxicity assay | 0.00006-35 | 37 |
| 540339 | Cell-based | MALME-3M cytotoxicity assay | 0.015-35 | 30 |
| 624299 | Cell-based | MALME-3M cytotoxicity assay | 0.00006-35 | 107 |
| 624362 | Cell-based | MALME-3M cytotoxicity assay | 0.00006-35 | 16 |
| 651584 | Cell-based | MALME-3M cytotoxicity assay | 0.00006-35 | 26 |
| 651585 | Cell-based | MALME-3M cytotoxicity assay | 0.00006-35 | 37 |
| 651773 | Cell-based | SK-MEL-5 qPCR for MITF | 0.00006-35 | 35 |
| 651770 | Cell-based | SK-MEL-5 qPCR for TRPM-1 | 0.00006-35 | 35 |
| 651772 | Cell-based | SK-MEL-5 qPCR for CDK2 | 0.00006-35 | 35 |
| 651771 | Cell-based | SK-MEL-5 qPCR for DCT | 0.00006-35 | 35 |
| 651795 | Cell-based | SK-MEL-5 qPCR for MLANA | 0.00006-35 | 35 |
| 651920 | Cell-based | Primary melanocyte cell viability | 0.00006-35 | 33 |

NA = not applicable

Detailed Assay Protocols
SK-MEL-5 TRPM-1 Luciferase Reporter Assay (2084-01)
SK-MEL-5/TRPM1Luc Culture Medium:
DMEM (High Glucose, HEPES, Phenol Red), Invitrogen Catalog No. 12430-047; Fetal Bovine Serum (10%), Thermo-Hyclone Catalog No. SH30071.03; Pen-Strep-Glutamine (1%), Invitrogen Catalog No. 10378-016; and Hygromycin (250 ug/mL), Invitrogen 10687-010.
SK-MEL-5/TRPM1Luc Plating Medium:
DMEM (High Glucose, no Phenol Red), Invitrogen Catalog No. 31053-036, Fetal Bovine Serum (10%), Thermo-Hyclone Catalog No. SH30071.03, Pen-Strep-Glutamine (1%), Invitrogen Catalog No. 10378-016; Steady Glo Promega Catalog No. E2550; and Parthenolide Enzo Catalog No. BML-T113-0250.

SK-MEL-5/TRPM1Luc cells were maintained in DMEM (10% FBS, 1% Pen-Strep-Glutamine, 250 ug/mL Hygromycin). Cells were fluid changed every 3 days and/or split upon reaching 100% confluency. For the primary HTS, cells were thawed at 4 million cells per Falcon T175 flask. After 3 days, the cells were fluid changed. After 3 more days, the cells were passed to a Corning triple flask (10-15 million cells) and plated after 3 days in the triple flask.
Protocol:
Day 1
1. Plate TRPM-1 luc/SKMEL5 cells at 2000 per well in 30 uL media (phenol red free DMEM/10% Fetal Bovine Serum/Penicillin/Streptomycin/L-Glutamine)
2. Use Corning white 384-well, square, opaque-bottomed plates (Corning Catalog No. 8867BC)
Day 2
3. Pin 100 nL compound/DMSO solution (Cybi Well) into assay plates. (For HTS, required sentinel pinning with the positive control, parthenolide (6 mM))
4. Incubate 24 hours at 37° C. in Liconic incubator.
Day 3
5. Add 20 uL 100% Promega SteadyGlo per well with Thermo Combi fluid transfer apparatus.
6. Shake 15 seconds on "big bear" plate shaker and incubate at room temperature for 5 minutes.
7. Read on the Perkin-Elmer EnVision plate reader with ultra-sensitive luminescence (US LUM) settings for 0.5 sec per well SK-MEL-5 Cytotoxicity Assay (2084-02)
SK-MEL-5 Cells:
ATCC Catalog No. HTB-70, lot 58483232, passage 28
SK-MEL-5 Culture Medium:
DMEM (High Glucose, HEPES, Phenol Red), Invitrogen Catalog No. 12430-047; Fetal Bovine Serum (10%), Thermo-Hyclone Catalog No. SH30071.03; and Pen-Strep-Glutamine (1%), Invitrogen Catalog No. 10378-016.
SK-MEL-5 Plating Medium:
DMEM (High Glucose, no Phenol Red), Invitrogen Catalog No. 31053-036; Fetal Bovine Serum (10%), Thermo-Hyclone Catalog No. SH30071.03; and Pen-Strep-Glutamine (1%), Invitrogen Catalog No. 10378-016

SK-MEL-5 cells were maintained in DMEM (10% FBS, 1% Pen-Strep-Glutamine). Cells were fluid changed every 3 days and/or split upon reaching 100% confluency. For secondary assays, cells were thawed at 4 million cells per Falcon T175 flask. After 3 days, the cells were fluid changed, after 3 more days cells were passed to a Corning Triple flask (10-15 million cells) and plated after 3 days in the triple flask.
Protocol:
Day 1
1. Plate SK-MEL-5 cells at 3,000 per well in 30 uL media (phenol red free DMEM/10% Fetal Bovine Serum/Penicillin/Streptomycin/L-Glutamine)
2. Use Corning white 384-well, square, opaque-bottomed plates (Corning Catalog No. 8867BC)
Day 2
3. Pin 100 nL compound/DMSO solution (Cybi Well) into assay plates. (For HTS, required sentinel pinning with the positive control, parthenolide (6 mM))
4. Incubate 24 hours at 37° C. in Liconic incubator.
Day 3
5. Add 20 uL 100% Cell Titer GLO per well with Thermo Combi fluid transfer apparatus.
6. Shake 15 seconds on "big bear" plate shaker and incubate at room temperature for 5 minutes.
7. Read on the Perkin-Elmer EnVision plate reader with luminescence (LUM) settings for 0.1 sec per well.
A-375 Cytotoxicity Assay (2084-03)
A-375 Cells ATCC Catalog No. CRL-1619, Lot No. 58463364, passage 166
A-375 Culture Medium: DMEM (High Glucose, HEPES, Phenol Red), Invitrogen Catalog No. 12430-047; Fetal Bovine Serum (10%), Thermo-Hyclone Catalog No. SH30071.03; and Pen-Strep-Glutamine (1%), Invitrogen Catalog No. 10378-016.

A-375 Plating Medium: DMEM (High Glucose, no Phenol Red), Invitrogen Catalog No. 31053-036; Fetal Bovine Serum (10%), Thermo-Hyclone Catalog No. SH30071.03; and Pen-Strep-Glutamine (1%), Invitrogen Catalog No. 10378-016.

A-375 cells were maintained in DMEM (10% FBS, 1% Pen-Strep-Glutamine). Cells were fluid changed every 3 days and/or split upon reaching 90% confluency. For secondary assays, cells were thawed at 2 million cells per Falcon T175 flask. After 3 days, cells were passed to a Corning Triple flask (6-8 million cells) and plated after 3 days in the triple flask.

Protocol:
Day 1
1. Plate A-375 cells at 3,000 per well in 30 uL media (phenol red free DMEM/10% Fetal Bovine Serum/Penicillin/Streptomycin/L-Glutamine)
2. Use Corning white 384-well, square, opaque-bottomed plates (Corning Catalog No. 8867BC)

Day 2
3. Pin 100 nL compound/DMSO solution (Cybi Well) into assay plates. (For HTS, required sentinel pinning with the positive control, parthenolide (6 mM))
4. Incubate 24 hours at 37° C. in Liconic incubator.

Day 3
5. Add 20 uL 100% Promega Cell Titer GLO per well with Thermo Combi fluid transfer apparatus.
6. Shake 15 seconds on "big bear" plate shaker and incubate at room temperature for 5 minutes.
7. Read on the Perkin-Elmer EnVision plate reader with luminescence (LUM) settings for 0.1 sec per well.

MALME-3M Cytotoxicity Assay (2084-04)

MALME-3M Cells ATCC Catalog No. HTB-64, Lot No. 58483222, passage 26

MALME-3M Culture Medium: IMDM (High Glucose, Phenol Red), ATCC Catalog No. 30-2005; Fetal Bovine Serum (20%), Thermo-Hyclone Catalog No. SH30071.03; and Pen-Strep-Glutamine (1%), Invitrogen Catalog No. 10378-016.

MALME-3M Plating Medium: IMDM (no Phenol Red), Gibco Catalog No. 21056-02; Fetal Bovine Serum (10%), Thermo-Hyclone Catalog No. SH30071.03; and Pen-Strep-Glutamine (1%), Invitrogen Catalog No. 10378-016.

MALME-3M cells were maintained in IMDM (20% FBS, 1% Pen-Strep-Glutamine). Cells were fluid changed every 3 days and/or split upon reaching 100% confluency. For secondary assays, cells were thawed at 6 million cells per Falcon T175 flask. After 3 days, cells were fluid changed, after 3 more days cells were passed to a Corning Triple flask (15-18 million cells) and plated after 3 days in the triple flask.

Protocol:
Day 1
1. Plate MALME-3M cells at 3,000 per well in 30 uL media (phenol red free IMDM/10% Fetal Bovine Serum/Penicillin/Streptomycin/L-Glutamine)
2. Use Corning white 384-well, square, opaque-bottomed plates (Corning Catalog No. 8867BC)

Day 2
3. Pin 100 nL compound/DMSO solution (Cybi Well) into assay plates, including the positive control.
4. Incubate 24 hours at 37° C. in Liconic incubator.

Day 3
5. Add 20 uL 100% Promega Cell Titer GLO per well with Thermo Combi fluid transfer apparatus.
6. Shake 15 seconds on "big bear" plate shaker and incubate at room temperature for 5 minutes.
7. Read on the Perkin-Elmer EnVision plate reader with luminescence (LUM) settings for 0.1 sec per well.

Cell Proliferation Assay with Primary Human Melanocytes (2084-06)

Primary human neonatal melanocytes were isolated from discarded foreskins by gentle dispase treatment and grown in TIVA media (Ham's F10 media supplemented with 7% FBS, penicillin/streptomycin/glutamine, 0.1 mM IBMX, 50 ng/mL TPA, 104 $Na_3VO_4$ and 104 dbcAMP). Cells were passaged using Accutase (Sigma Catalog #A6964-100ML) for gentle treatment and generation of a single cell suspension.

Protocol
Day 1
1. Plate primary melanocytes at 3,000 per well in 30 uL media (TIVA media)
2. Use Corning white 384-well, square, opaque-bottomed plates (Corning Catalog No. 8867BC)

Day 2
3. Pin 100 nL compound/DMSO solution (Cybi Well) into assay plates. (pinning with the positive control, parthenolide (18 µM final concentration))
4. Incubate 24 hours at 37° C. in Liconic incubator.

Day 3
5. Add 20 uL 100% Promega Cell Titer GLO per well with Thermo Combi fluid transfer apparatus.
6. Shake 15 seconds on "big bear" plate shaker and incubate at room temperature for 5 minutes.
7. Read on the Perkin-Elmer EnVision plate reader with luminescence (LUM) settings for 0.1 sec per well.

qPCR Assay for Target Gene Expression (MITF: 2084-05, TRPM1: 2084-09, CDK2: 2084-11, DCT: 2084-12, MLANA: 2084-13)

SK-MEL-5 Cells ATCC Catalog No. HTB-70, lot 58483232, passage 28

SK-MEL-5 Culture/Plating Medium: DMEM (High Glucose, HEPES, Phenol Red), Invitrogen Catalog No. 12430-047; Fetal Bovine Serum (10%), Thermo-Hyclone Catalog No. SH30071.03; and Pen-Strep-Glutamine (1%), Invitrogen Catalog No. 10378-016.

Parthenolide Enzo Catalog No. BML-T113-0250.

Cells to CT Bulk Lysis Solution Ambion Catalog No. 4391851C. Cells to CT Bulk RT Reagents Ambion Catalog No. 4391852C. Light Cycler 480 Probes Master Roche Catalog No. 4887301001. Human GAPD (GAPDH) Endogenous Control VIC/MGB probe/primer limited Applied Biosystems Catalog No. 4326317E.

Target Gene FAM Probe/Primer Sets:

Human MITF FAM probe/primer Applied Biosystems Catalog No. 4331182 Hs01117294_m1; Human TRPM1 probe/primer Applied Biosystems Catalog No. 4331182 Hs00170127_m1; Human CDK2 probe/primer Applied Biosytems Catalog No. 4331182 Hs01548894_m1; Human DCT probe/primer Applied Biosystems Catalog No. 4331182 Hs01098278_m1; and Human MLANA probe/primer Applied Biosystems Catalog No. 4331182 Hs00194133_m1.

SK-MEL-5 cells were maintained in DMEM (10% FBS, 1% Pen-Strep-Glutamine). Cells were fluid changed every 3 days and/or split upon reaching 100% confluency. For secondary assays, cells were thawed at 4 million cells per Falcon T175 flask. After 3 days, the cells were fluid changed, after 3 more days cells were passed to a Corning triple flask (10-15 million cells) and plated after 3 days in the triple flask.

Protocol:

Day 1

1. Plate SK-MEL-5 cells at 4,000 per well in 30 uL media (DMEM/10% Fetal Bovine Serum/Penicillin/Streptomycin/L-Glutamine)
2. Use Corning white 384-well, square, opaque-bottomed plates (Corning Catalog No. 8867BC)

Day 2

3. Pin 100 nL compound/DMSO solution (Cybi Well) into assay plates. (in plate positive control, parthenolide (6 mM))
4. Incubate 24 hours at 37° C. in Liconic incubator Day 3

Cell Lysis

5. The medium is aspirated from assay plates and the cells are washed twice (100 uL PBS) using the ELX405 Plate Washer (Biotek).
6. The assay plates are flipped upside down and centrifuged at 1000 rpm for 2 minutes to remove the excess liquid.
7. 10 uL of Lysis solution with DNase I (Ambion, from Cell to CT Lysis Mix) is added to each well using the MultiDrop Combi/Standard tube dispensing cassette (Thermo Scientific).
8. Each assay plate is then shaken for 2 minutes and incubated for an additional 8 minutes at room temperature.
9. 1 uL of stop solution (Ambion, from Cell to CT Lysis Mix) is added with the Multidrop Combi-nL (Thermo Scientific) and the assay plate is centrifuged at 1000 rpm for 2 minutes.

TABLE 1

Reverse Transcription (RT) Mix

| Component | Amount per reaction |
|---|---|
| 2X RT Buffer | 5 uL |
| 20X RT Enzyme Mix | 0.5 uL |
| Nuclease-Free Water | 2.5 uL |

10. 8 uL of RT mix is dispensed into each well of a RT assay plate (Axygen, PCR-384 RGD C).
11. 2 uL of the lysed cells are transferred into RT assay plate using Vario transfer unit (Cybi Well).
12. The RT assay plates are incubated at 37° C. for 1 hour and the reverse transcriptase is inactivated by incubating the plates for 1 minute at 95° C.
13. cDNA is stored at −80° C. until ready for qPCR analysis Day 4

TABLE 2 qPCR Master Mix

| Component | Amount per reaction |
|---|---|
| 2X Roche Master Mix | 2.5 uL |
| 20X FAM Target Gene Taqman probe/primer | 0.125 uL |
| 20X VIC GAPDH Taqman probe/primer | 0.125 uL |
| PCR water | 1.25 uL |

14. 4 uL/well of qPCR master mix is dispensed in PCR plate (Roche Light Cycler 480 Multiwell Plate 384, Catalog No. 04 729 749 001) using the Multidrop Combi-nL (Thermo Scientific).
15. 1 uL/well of RT DNA is transferred in the 4 uL/well PCR plate.
16. The PCR plates are centrifuged for 2 minutes at 1000 rpm.
17. PCR is performed using Thermo Cycler (Roche Light Cycler 480 II) with Macro Protocol:

TABLE 3

| PCR cycle | | |
|---|---|---|
| Step | Temperature | Time |
| 1. | 95° C. | 10 minutes |
| 2. | 95° C. | 10 seconds |
| 3. | 60° C. | 30 seconds |
| | Step 2 and 3 (55 cycles) | |
| 4. | 40° C. | 30 seconds |

Data Analysis

For the primary screen and other assays, negative-control (NC) wells and positive-control (PC) wells were included on every plate. The raw signals of the plate wells were normalized using the 'Stimulators Minus Neutral Controls' or the 'Neutral Controls' method (when no positive control was available) in GeneData Screener Assay Analyzer (v7.0.3 & v10.0.2). The median raw signal of the intra-plate NC wells was set to a normalized activity value of 0, while the median raw signal of the intra-plate PC wells was set to a normalized activity value of 100. Experimental wells were scaled to this range, resulting in an activity score representing the percent change in signal relative to the intra-plate controls. The mean of the replicate percent activities were presented as the final 'PubChem Activity Score'. The 'PubChem Activity Outcome' class was assigned as described below, based on an activity threshold of 70%:

Activity_Outcome=1 (inactive), less than half of the replicates fell outside the threshold.

Activity_Outcome=2 (active), all of the replicates fell outside the threshold, OR at least half of the replicates fell outside the threshold AND the 'PubChem Activity Score' fell outside the threshold.

Activity_Outcome=3 (inconclusive), at least half of the replicates fell outside the threshold AND the 'PubChem Activity Score did not fall outside the threshold.

Eurofins Panlabs LeadProfiling Screen Report for the compound of Example 1

The following text was provided along with the study results in the report for the LeadProfilingScreen for the compound of Example 1

Study Objective:

To evaluate, in radioligand binding assays, the activity of the compound of Example 1 across a panel of 67 receptors.

Methods:

Methods employed in this study have been adapted from the scientific literature to maximize reliability and reproducibility. Reference standards were run as an integral part of each assay to ensure the validity of the results obtained.

Where presented, $IC_{50}$ values were determined by a non-linear, least squares regression analysis using MathIQ™ (ID Business Solutions Ltd., UK). Where inhibition constant ($K_i$) are presented, the Ki values were calculated using the equation of Cheng and Prusoff (Cheng. Y., Prusoff, W. H., Biochem. Pharmacol. 22:3099-3108, 1973) using the observed $IC_{50}$ of the tested compound, the concentration of radioligand employed in the assay, and the historical values of the KD of the ligand (obtained experimentally at Eurofins Panlabs, Inc.). Where presented, the Hill coefficient ($n_H$), defining the slope of the competitive binding curve, was calculated using MathIQ™. Hill coefficients significantly different than 1.0, may suggest that the binding displacement does not follow the laws of mass action with a single binding site. Where $IC_{50}$, $K_i$, and/or nH data are presented without Standard Error of the Mean (SEM), data are insufficient to be quantitative, and the values presented (Ki, $IC_{50}$, $n_H$) should be interpreted with caution.

TABLE 4

| Cat # | Assay Name | Batch* | Spec. | Rep. | Conc. | % Inh. |
|---|---|---|---|---|---|---|
| 200510 | Adenosine A1 | 324045 | human | 2 | 10 μM | 46 |
| 200610 | Adenosine A2A | 324044 | human | 2 | 10 μM | 50 |
| 200720 | Adenosine A3 | 324012 | human | 2 | 10 μM | 15 |
| 203100 | Adrenergic α1A | 324046 | rat | 2 | 10 μM | 28 |
| 203200 | Adrenergic α1B | 324024 | rat | 2 | 10 μM | 16 |
| 203400 | Adrenergic α1D | 324047 | human | 2 | 10 μM | 21 |
| 203620 | Adrenergic α2A | 324048 | human | 2 | 10 μM | 33 |
| 204010 | Adrenergic β1 | 324027 | human | 2 | 10 μM | 20 |
| 204110 | Adrenergic β2 | 324042 | human | 2 | 10 μM | 10 |
| 285010 | Androgen (Testosterone) AR | 324064 | rat | 2 | 10 μM | 14 |
| 212510 | Bradykinin B1 | 324141 | human | 2 | 10 μM | 29 |
| 212620 | Bradykinin B2 | 324310 | human | 2 | 10 μM | 11 |
| 214510 | Calcium Channel L-Type, Benzothiazepine | 324113 | rat | 2 | 10 μM | 20 |
| 214600 | Calcium Channel L-Type, Dihydropyridine | 324317 | rat | 2 | 10 μM | 30 |
| 216000 | Calcium Channel N-Type | 323997 | rat | 2 | 10 μM | −3 |
| 217030 | Cannabinoid CB1 | 324041 | human | 2 | 10 μM | 31 |
| 219500 | Dopamine D1 | 324037 | human | 2 | 10 μM | 21 |
| 219700 | Dopamine D2S | 324038 | human | 2 | 10 μM | 0 |
| 219800 | Dopamine D3 | 324039 | human | 2 | 10 μM | 9 |
| 219900 | Dopamine D4.2 | 324230 | human | 2 | 10 μM | 4 |
| 224010 | Endothelin ETA | 324347 | human | 2 | 10 μM | 17 |
| 224110 | Endothelin ETB | 324349 | human | 2 | 10 μM | 17 |
| 225510 | Epidermal Growth Factor (EGF) | 324350 | human | 2 | 10 μM | 11 |
| 226010 | Estrogen ERα | 324351 | human | 2 | 10 μM | 5 |
| 226600 | GABAA, Flunitrazepam, Central | 324035 | rat | 2 | 10 μM | 20 |
| 226500 | GABAA, Muscimol, Central | 324034 | rat | 2 | 10 μM | 4 |
| 228610 | GABAB1A | 324354 | human | 2 | 10 μM | 11 |
| 232030 | Glucocorticoid | 324040 | human | 2 | 10 μM | 5 |
| 232700 | Glutamate, Kainate | 324324 | rat | 2 | 10 μM | 43 |
| 232810 | Glutamate, NMDA, Agonism | 324326 | rat | 2 | 10 μM | 29 |
| 232910 | Glutamate, NMDA, Glycine | 324329 | rat | 2 | 10 μM | 9 |
| 233000 | Glutamate, NMDA, Phencyclidine | 324036 | rat | 2 | 10 μM | 0 |
| 239610 | Histamine H1 | 324052 | human | 2 | 10 μM | −5 |
| 239710 | Histamine H2 | 324083 | human | 2 | 10 μM | −5 |
| 239820 | Histamine H3 | 324131 | human | 2 | 10 μM | −5 |
| 241000 | Imidazoline I2, Central | 324053 | rat | 2 | 10 μM | −5 |
| 243520 | Interleukin IL-1 | 324013 | mouse | 2 | 10 μM | 6 |
| 250460 | Leukotriene, Cysteinyl CysLT1 | 324130 | human | 2 | 10 μM | 5 |
| 251600 | Melatonin MT1 | 324356 | human | 2 | 10 μM | 9 |
| 252610 | Muscarinic M1 | 324054 | human | 2 | 10 μM | 7 |
| 252710 | Muscarinic M2 | 324055 | human | 2 | 10 μM | 15 |
| 252810 | Muscarinic M3 | 324056 | human | 2 | 10 μM | 22 |
| 257010 | Neuropeptide Y Y1 | 324363 | human | 2 | 10 μM | −6 |
| 257110 | Neuropeptide Y Y2 | 324365 | human | 2 | 10 μM | 5 |
| 258590 | Nicotinic Acetylcholine | 324018 | human | 2 | 10 μM | 9 |
| 258700 | Nicotinic Acetylcholine α1, Bungarotoxin | 324019 | human | 2 | 10 μM | −2 |
| 260130 | Opiate δ1 (OP1, DOP) | 324366 | human | 2 | 10 μM | −6 |
| 260210 | Opiate κ (OP2, KOP) | 324124 | human | 2 | 10 μM | 19 |
| 260410 | Opiate μ (OP3, MOP) | 324058 | human | 2 | 10 μM | 1 |
| 264500 | Phorbol Ester | 324067 | mouse | 2 | 10 μM | 18 |
| 265010 | Platelet Activating Factor (PAF) | 324114 | human | 2 | 10 μM | 3 |
| 265600 | Potassium Channel [KATP] | 324068 | hamster | 2 | 10 μM | 10 |
| 265900 | Potassium Channel hERG | 324069 | human | 2 | 10 μM | −4 |
| 268420 | Prostanoid EP4 | 324070 | human | 2 | 10 μM | 11 |
| 268700 | Purinergic P2X | 324103 | rabbit | 2 | 10 μM | −2 |
| 268810 | Purinergic P2Y | 324128 | rat | 2 | 10 μM | −7 |
| 270000 | Rolipram | 324059 | rat | 2 | 10 μM | 15 |
| 271110 | Serotonin (5-Hydroxytryptamine) 5-HT1A | 324121 | human | 2 | 10 μM | 21 |
| 271700 | Serotonin (5-Hydroxytryptamine) 5-HT2B | 324061 | human | 2 | 10 μM | 37 |
| 271910 | Serotonin (5-Hydroxytryptamine) 5-HT3 | 324005 | human | 2 | 10 μM | 5 |
| 278110 | Sigma σ1 | 324062 | human | 2 | 10 μM | 15 |
| 279510 | Sodium Channel, Site 2 | 324063 | rat | 2 | 10 μM | 6 |
| 255520 | Tachykinin NK1 | 324358 | human | 2 | 10 μM | 37 |
| 285900 | Thyroid Hormone | 324137 | rat | 2 | 10 μM | −4 |
| 220320 | Transporter, Dopamine (DAT) | 324015 | human | 2 | 10 μM | 2 |

TABLE 4-continued

| Cat # | Assay Name | Batch* | Spec. | Rep. | Conc. | % Inh. |
|---|---|---|---|---|---|---|
| 226400 | Transporter, GABA | 324353 | rat | 2 | 10 μM | 9 |
| 204410 | Transporter, Norepinephrine (NET) | 324014 | human | 2 | 10 μM | 8 |
| 274030 | Transporter, Serotonin (5-Hydroxytryptamine) (SERT) | 324370 | human | 2 | 10 μM | −5 |

*Batch: Represents compounds tested concurrently in the same assay(s).

Results of Examples 4-6 are summarized in Tables 5-10.

TABLE 5

Round 1 SAR and Anilino-substituted Naphthoquinone Compounds

Structure

| | | | | | | Target Potency IC50 (μM) | | | | | | Antitarget Potency IC50 (μM) | Fold Selectivity A375/ |
|---|---|---|---|---|---|---|---|---|---|---|---|---|---|
| Entry | * | R1 | R2 | R3 | n | TRPM1 | n | SKMEL5 | n | MALME-3M | n | A375 | TRPM1 |
| 1 | S | —Cl | ⸻NH-allyl | —H | 1 | 2.7 | 1 | 9.5 | 1 | 7.9 | 1 | 62.3 | 23 |
| | | | Purity (UPLC): 100% | | | | | | | | | | |
| 2 | S | N-methylpiperazinyl | —Ph | —H | 1 | 6.1 | 1 | 23.9 | 1 | 16.4 | 1 | 45.7 | 7 |
| | | | Purity (UPLC): 95% | | | | | | | | | | |
| 3 | S | piperidinyl | —Ph | —H | 1 | 6.3 | 1 | 17.4 | 1 | 5.8 | 1 | 44.3 | 7 |
| | | | Purity (UPLC): 92% | | | | | | | | | | |
| 4 | S | —H | —Ph | —H | 1 | 4.7 | 1 | 2.8 | 1 | 3.4 | 1 | 59.3 | 13 |
| | | | Purity (UPLC): 99% | | | | | | | | | | |
| 5 | S | —OMe | —Ph | —H | 1 | 6.3 | 1 | 3.2 | 1 | 8.2 | 1 | 59.0 | 9 |
| | | | Purity (UPLC): 91% | | | | | | | | | | |
| 6 | S | morpholinyl | —Ph | —H | 1 | 6.4 | 1 | 37.2 | 1 | 24.9 | 1 | 68.9 | 11 |
| | | | Purity (UPLC): 96% | | | | | | | | | | |
| 7 | S | thiomorpholinyl | —Ph | —H | 1 | 9.8 | 1 | 62.4 | 1 | 70.0 | 1 | 69.8 | 7 |
| | | | Purity (UPLC): 93% | | | | | | | | | | |

TABLE 5-continued

Round 1 SAR and Anilino-substituted Naphthoquinone Compounds

Structure:

A naphthoquinone core with substituents R1 (at position 3), and an amino group at position 2 bearing R2 and R3 (N-R2/R3).

| Entry | * | R1 | R2 | R3 | n | TRPM1 | n | SKMEL5 | n | MALME-3M | n | A375 | Fold Selectivity A375/TRPM1 |
|---|---|---|---|---|---|---|---|---|---|---|---|---|---|
| 8 | S | (R)-NH-CH(CH3)-Ph | —Ph | —H | 1 | 10.8 | 1 | 70.0 | 1 | 70.0 | 1 | 64.6 | 6 |
| | | Purity (UPLC): 95% | | | | | | | | | | | |
| 9 | S | N-piperazinyl-N'-Ph | —Ph | —H | 1 | 20.8 | 1 | 70.0 | 1 | 70.0 | 1 | 70.0 | 3 |
| | | Purity (UPLC): 95% | | | | | | | | | | | |
| 10 | S | —Ph | —Ph | —H | 1 | 11.3 | 1 | 30.0 | 1 | 41.9 | 1 | 70.0 | 6 |
| | | Purity (UPLC): 100% | | | | | | | | | | | |
| 11 | S | —H | —Ph | —Me | 1 | 16.2 | 1 | 2.3 | 1 | ND | 1 | 70.0 | 4 |
| | | Purity (UPLC): 94% | | | | | | | | | | | |
| 12 | S | —H | —Me | —H | 1 | 12.6 | 1 | 61.8 | 1 | 44.9 | 1 | 70.0 | 6 |
| | | Purity (UPLC): 96% | | | | | | | | | | | |
| 13 | S | —H | —H | —H | 1 | 3.2 | 1 | 8.5 | 1 | 7.3 | 1 | 64.0 | 20 |
| | | Purity (UPLC): 92% | | | | | | | | | | | |
| 14 | S | —H | —NH—CH2—(4-Cl-C6H4) | —H | 1 | 70.0 | 1 | 53.3 | 1 | ND | 1 | 70.0 | 1 |
| | | Purity (UPLC): 94% | | | | | | | | | | | |
| 15 | S | —Me | —NH—(4-Cl-C6H4) | —H | 1 | 40.7 | 1 | 0.8 | 1 | ND | 1 | 70.0 | 2 |
| | | Purity (UPLC): 100% | | | | | | | | | | | |

*P = purchased; S = synthesized

TABLE 6

Round 1 SAR and N-methylacetamide-subsituted Naphthoquinone Compounds

Structure

[Naphthoquinone core with N(Me)Ac substituent and R group]

| Entry | * | R | n | TRPM1 | n | SKMEL5 | n | MALME-3M | n | A375 | Fold Selectivity A375/TRPM1 |
|---|---|---|---|---|---|---|---|---|---|---|---|
| | | | | Target Potency IC50 (μM) | | | | | | Antitarget Potency IC50 (μM) | |
| 1 | S | 4-methylpiperazinyl | 1 | 0.4 | 1 | 4.4 | 1 | 2.0 | 1 | 14.4 | 36 |
| | | Purity (UPLC): 100% | | | | | | | | | |
| 2 | S | 4-ethylpiperazinyl | 1 | 0.4 | 1 | 4.9 | 1 | 2.5 | 1 | 11.3 | 27 |
| | | Purity (UPLC): 100% | | | | | | | | | |
| 3 | S | piperidinyl | 1 | 0.7 | 1 | 4.6 | 1 | 4.9 | 1 | 29.0 | 40 |
| | | Purity (UPLC): 99% | | | | | | | | | |
| 4 | S | morpholinyl | 1 | 2.1 | 1 | 7.8 | 1 | 7.4 | 1 | 26.3 | 12 |
| | | Purity (UPLC): 99% | | | | | | | | | |
| 5 | S | NH-allyl | 1 | 0.1 | 1 | 0.6 | 1 | 0.7 | 1 | 11.0 | 119 |
| | | Purity (UPLC): 92% | | | | | | | | | |
| 6 | S | NH-(CH2)3-NEt2 | 1 | 0.4 | 1 | 4.4 | 1 | 3.1 | 1 | 4.8 | 11 |
| | | Purity (UPLC): 100% | | | | | | | | | |

*P = purchased; S = synthesized

TABLE 7
Round 1 SAR and Benzoyl-substituted Naphthoquinone compounds
Structure
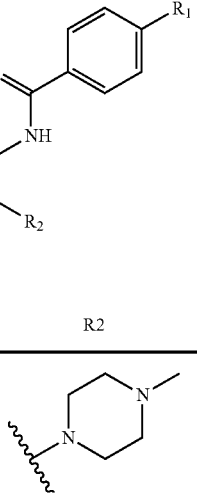
| Entry | * | R1 | R2 | n | Target Potency IC50 (µM) TRPM1 | n | SKMEL5 | n | MALME-3M | n | Antitarget Potency IC50 (µM) A375 | Fold Selectivity A375/TRPM1 |
|---|---|---|---|---|---|---|---|---|---|---|---|---|
| 1 | S | —H | 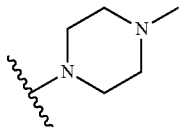 [SMILES: *N1CCN(C)CC1] Purity (UPLC): 97% | 1 | 0.8 | 1 | 8.5 | 1 | 3.6 | 1 | 29.8 | 37 |
| 2 | S | —Br | 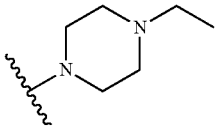 [SMILES: *N1CCN(CC)CC1] Purity (UPLC): 99% | 1 | 1.0 | 1 | 5.9 | 1 | 1.9 | 1 | 20.0 | 21 |
| 3 | S | —H | 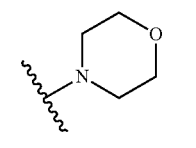 Purity (UPLC): 100% | 1 | 0.9 | 1 | 7.2 | 1 | 3.8 | 1 | 23.6 | 25 |
| 4 | S | —H | —NH2 Purity (UPLC): 100% | 1 | 6.6 | 1 | 11.7 | 1 | 12.2 | 1 | 67.2 | 10 |
| 5 | S | —H | morpholine Purity (UPLC): 97% | 1 | 7.8 | 1 | 28.2 | 1 | 18.6 | 1 | 40.2 | 5 |
| 6 | S | —H | N-phenylpiperazine Purity (UPLC): 98% | 1 | 41.7 | 1 | 70.0 | 1 | 64.0 | 1 | 70.0 | 2 |
*P = purchased; S = synthesized TABLE 8
Round 1 SAR Benzene- and Thiophene-substituted Naphthoquinone Compounds
Structure
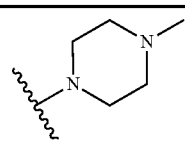
| Entry | * | R1 | R2 | n | Target Potency IC50 (μM) | | | | | Antitarget Potency IC50 (μM) | Fold Selectivity |
| | | | | | TRPM1 | n | SKMEL5 | n | MALME-3M | n | A375 | TA375/RPM1 |
|---|---|---|---|---|---|---|---|---|---|---|---|---|
| 1 | S | 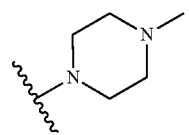 | —Ph | 1 | 0.9 | 1 | 14.6 | 1 | 7.3 | 1 | 37.5 | 42 |
| | | Purity (UPLC): 98% | | | | | | | | | | |
| 2 | S | 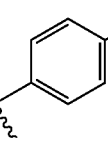 | 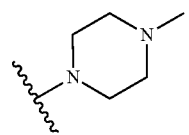 | 1 | 3.4 | 1 | 45.1 | 1 | 70.0 | 1 | 60.5 | 18 |
| | | Purity (UPLC): 96% | | | | | | | | | | |
| 3 | S | 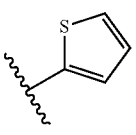 [SMILES: *c1cccs1] | 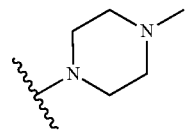 [SMILES: *N1CCN(C)CC1] | 1 | 2.6 | 1 | 42.2 | 1 | 11.7 | 1 | 65.8 | 25 |
| | | Purity (UPLC): 96% | | | | | | | | | | |
| 4 | S | 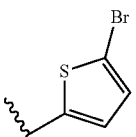 | 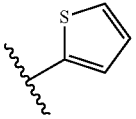 [SMILES: *c1cccs1] | 1 | 3.0 | 1 | 28.7 | 1 | 9.8 | 1 | 59.8 | 20 |
| | | Purity (UPLC): 99% | | | | | | | | | | |
| 5 | S | —H | —Ph | 1 | 7.1 | 1 | 8.9 | 1 | 13.6 | 1 | 70.0 | 10 |
| | | Purity (UPLC): 99% | | | | | | | | | | |
| 6 | S | —H | 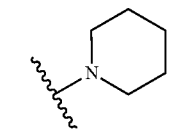 [SMILES: *N1CCCCC1] | 1 | 6.5 | 1 | 12.8 | 1 | 27.8 | 1 | 70.0 | 11 |
| | | Purity (UPLC): 99% | | | | | | | | | | |
| 7 | S | 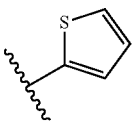 | 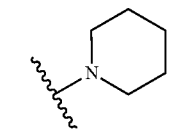 [SMILES: *N1CCCCC1] | 1 | 21.8 | 1 | 50.3 | 1 | 48.8 | 1 | 70.0 | 3 |
| | | Purity (UPLC): 96% | | | | | | | | | | |
| 8 | S | —NH2 | —Ph | 1 | 7.2 | 1 | 15.4 | 1 | 15.5 | 1 | 66.2 | 9 |
| | | Purity (UPLC): 100% | | | | | | | | | | |

TABLE 8-continued

Round 1 SAR Benzene- and Thiophene-substituted Naphthoquinone Compounds

Structure

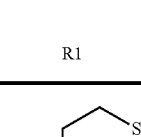

| Entry | * | R1 | R2 | n | TRPM1 | n | SKMEL5 | n | MALME-3M | n | A375 | Antitarget Potency IC50 (μM) | Fold Selectivity TA375/RPM1 |
|---|---|---|---|---|---|---|---|---|---|---|---|---|---|
| 9 | S | 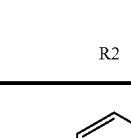 | 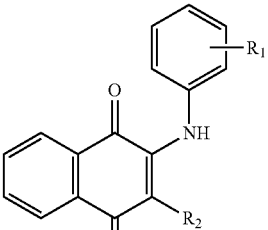Br | 1 | 25.3 | 1 | 55.5 | 1 | 51.7 | 1 | 70.0 | | 3 |
| | | Purity (UPLC): 97% | | | | | | | | | | | |
| 10 | S | —OMe | —Ph | | 7.7 | | 14.1 | | 18.6 | | 70.0 | | 9 |
| | | Purity (UPLC): 98% | | | | | | | | | | | |

*P = purchased; S = synthesized

TABLE 9

Round 2 SAR and Anilino- and Nitrogen-heterocycle-substituted Naphthoquinone Compounds Structure

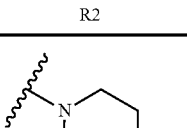

| Entry | Previous Entry | * | R1 | R2 | n | TRPM1 | n | SKMEL5 | n | MALME-3M | n | A375 | Antitarget Potency IC50 (μM) | Fold Selectivity A375/TRPM1 |
|---|---|---|---|---|---|---|---|---|---|---|---|---|---|---|
| 1 | Table 3/Entry 2 | S | —H | (N-methylpiperazine) | 1 | 6.1 | 1 | 23.9 | 1 | 16.4 | 1 | 45.7 | | 7 |
| | | | Purity (UPLC): 95% | | | | | | | | | | | |
| 2 | — | S | 2,4-diF | (N-methylpiperazine) | 1 | 11.4 | 1 | 9.9 | 1 | 25.4 | 1 | 70.0 | | 6 |
| | | | Purity (UPLC): 97% | | | | | | | | | | | |

TABLE 9-continued
Round 2 SAR and Anilino- and Nitrogen-heterocycle-substituted Naphthoquinone Compounds
Structure
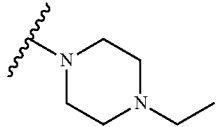
| | | | | | | Target Potency IC50 (μM) | | | | | Antitarget Potency IC50 (μM) | Fold Selectivity |
|---|---|---|---|---|---|---|---|---|---|---|---|---|
| Entry | Previous Entry | * | R1 | R2 | n | TRPM1 | n | SKMEL5 | n | MALME-3M | n | A375 | A375/TRPM1 |
| 3 | — | S | 2,4-diF | 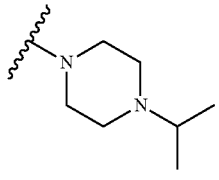 [SMILES: *N1CCN(C(C)C)CC1] | 1 | 7.4 | 1 | 9.0 | 1 | 26.3 | 1 | 70.0 | 9 |
| | | | | Purity (UPLC): 100% | | | | | | | | | |
| 4 | — | S | 2,4-diF | 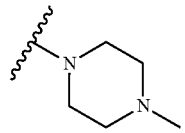 [SMILES: *N1CCN(C)CC1] | 1 | 6.0 | 1 | 8.7 | 1 | 25.4 | 1 | 70.0 | 12 |
| | | | | Purity (UPLC): 100% | | | | | | | | | |
| 5 | — | S | 4-OMe | 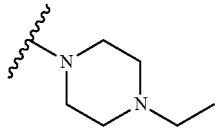 [SMILES: *N1CCN(CC)CC1] | 1 | 24.9 | 1 | 16.4 | 1 | ND | 1 | 70.0 | 3 |
| | | | | Purity (UPLC): 94% | | | | | | | | | |
| 6 | — | S | 4-OMe | 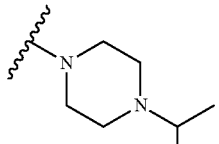 | 1 | 6.9 | 1 | 12.2 | 1 | ND | 1 | 70.0 | 10 |
| | | | | Purity (UPLC): 95% | | | | | | | | | |
| 7 | — | S | 4-OMe | 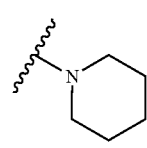 [SMILES: *N1CCCCC1] | 1 | 3.3 | 1 | 16.6 | 1 | ND | 1 | 45.1 | 14 |
| 8 | Table 3/Entry 3 | S | —H |  | 1 | 6.3 | 1 | 17.4 | 1 | 5.8 | 1 | 44.3 | 7 |
| | | | | Purity (UPLC): 92% | | | | | | | | | |

TABLE 9-continued

Round 2 SAR and Anilino- and Nitrogen-heterocycle-substituted Naphthoquinone Compounds Structure

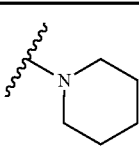

| Entry | Previous Entry | * | R1 | R2 | n | TRPM1 | n | SKMEL5 | n | MALME-3M | n | A375 | A375/TRPM1 |
|---|---|---|---|---|---|---|---|---|---|---|---|---|---|
| | | | | | | Target Potency IC50 (µM) | | | | | | Antitarget Potency IC50 (µM) | Fold Selectivity |
| 9 | — | S | 2,4-diF | 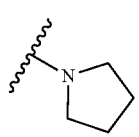 [SMILES: *N1CCCC1] | 1 | 0.9 | 1 | 3.6 | 1 | ND | 1 | 21.8 | 23 |
| | | | | Purity (UPLC): 96% | | | | | | | | | |
| 10 | — | S | 2,4-diF | 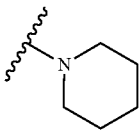 [SMILES: *N1CCCCC1] | 1 | 0.7 | 1 | 2.3 | 1 | ND | 1 | 8.1 | 12 |
| | | | | Purity (UPLC): 95% | | | | | | | | | |
| 11 | — | S | 4-OMe | 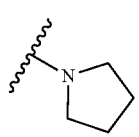 [SMILES: *N1CCCC1] | 1 | 7.2 | 1 | 3.7 | 1 | 11.2 | 1 | 56.2 | 8 |
| | | | | Purity (UPLC): 95% | | | | | | | | | |
| 12 | Table 3/Entry 6 | S | —H | 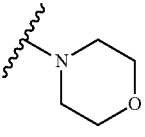 [SMILES: *N1CCOCC1] | 1 | 6.4 | 1 | 37.2 | 1 | 24.9 | 1 | 68.9 | 11 |
| | | | | Purity (UPLC): 96% | | | | | | | | | |
| 13 | Table 3/Entry 7 | S | —H | 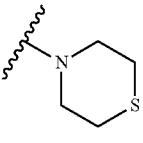 [SMILES: *N1CCSCC1] | 1 | 9.8 | 1 | 62.4 | 1 | 70.0 | 1 | 69.8 | 7 |
| | | | | Purity (UPLC): 93% | | | | | | | | | |
| 14 | Table 3/Entry 9 | S | —H | 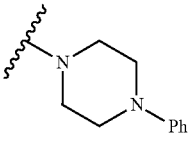 [SMILES: *N1CCN(c2ccccc2)CC1] | 1 | 20.8 | 1 | 70.0 | 1 | 70.0 | 1 | 70.0 | 3 |
| | | | | Purity (UPLC): 95% | | | | | | | | | |

*P = purchased; S = synthesized

TABLE 10

Round 2 SAR and Hydrogen-substituted Naphthoquinone compounds

Structure

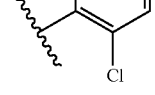

| | | | | | | | | Target Potency IC50 (µM) | | | | | Anti-target Potency IC50 (µM) | Fold Selectivity A375/ |
|---|---|---|---|---|---|---|---|---|---|---|---|---|---|---|
| Entry | Previous Entry | * | R1 | R2 | R3 | X | n | TRPM1 | n | SKMEL5 | n | MALME-3M | n A375 | TRPM1 |
| 1 | Table 3/Entry 13 | S | —H<br>Purity (UPLC): 92% | —H | —H | CH | 1 | 3.2 | 1 | 8.5 | 1 | 7.3 | 1 64.0 | 20 |
| 2 | Table 3/Entry 12 | S | —Me<br>Purity (UPLC): 96% | —H | —H | CH | 1 | 12.6 | 1 | 61.8 | 1 | 44.9 | 1 70.0 | 6 |
| 3 | Table 3/Entry 4 | S | —Ph<br>Purity (UPLC): 99% | —H | —H | CH | 1 | 4.7 | 1 | 2.8 | 1 | 3.4 | 1 59.3 | 13 |
| 4 | — | P | —Ph<br>Purity (UPLC): 100% | —H | —H | N | 1 | 0.4 | 1 | 0.2 | 1 | ND | 1 16.2 | 39 |
| 5 | Table 3/Entry 11 | S | —Ph<br>Purity (UPLC): 94% | —Me | —H | CH | 1 | 16.2 | 1 | 2.3 | 1 | ND | 1 70.0 | 4 |
| 6 | — | S | 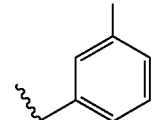<br>Purity (UPLC): 95% | —H | —H | CH | 1 | 5.4 | 1 | 0.2 | 1 | ND | 1 70.0 | 13 |
| 7 | — | S | 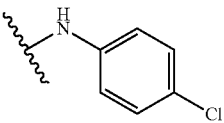 [SMILES: *Nc1ccc(Cl)cc1]<br>Purity (UPLC): 97% | —H | —H | CH | 1 | 23.9 | 1 | 0.7 | 1 | ND | 1 22.3 | 1 |
| 8 | Table 3/Entry 15 | S | 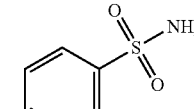<br>Purity (UPLC): 100% | —H | —Me | CH | 1 | 40.7 | | 0.8 | 1 | ND | 1 70.0 | 2 |
| 9 | — | S | <br>Purity (UPLC): 100% | —H | —H | CH | 1 | 1.2 | 1 | 0.1 | 1 | 0.7 | 1 70.0 | 58 |
| 10 | — | S | <br>Purity (UPLC): 98% | —H | —H | CH | 1 | 18.9 | 1 | 0.7 | 1 | ND | 1 70.0 | 4 |

TABLE 10-continued

Round 2 SAR and Hydrogen-substituted Naphthoquinone compounds

Structure:

Naphthoquinone core with $R_1$, $R_2$ on N at one position, $R_3$ at adjacent position, and X in the fused ring.

| Entry | Previous Entry | * | R1 | R2 | R3 | X | n | Target Potency IC50 (μM) TRPM1 | n | SKMEL5 | n | MALME-3M | n | Anti-target Potency IC50 (μM) A375 | Fold Selectivity A375/TRPM1 |
|---|---|---|---|---|---|---|---|---|---|---|---|---|---|---|---|
| 11 | — | S | 4-methylbenzyl (Purity UPLC: 95%) | —H | —H | CH | 1 | 6.6 | 1 | 1.2 | 1 | 13.5 | 1 | 70.0 | 11 |
| 12 | Table 3/Entry 14 | S | NH-CH2-(4-chlorophenyl) (Purity UPLC: 94%) | —H | —H | CH | 1 | 70.0 | 1 | 53.3 | 1 | ND | 1 | 70.0 | 1 |
| 13 | — | S | phenylsulfonyl (Purity UPLC: 99%) | —H | —H | CH | 1 | 7.1 | 1 | 8.9 | 1 | 13.6 | 1 | 70.0 | 10 |
| 14 | Table 6/Entry 6 | S | 2-thienyl (Purity UPLC: 99%) | —H | —H | CH | 1 | 6.5 | 1 | 12.8 | 1 | 27.8 | 1 | 70.0 | 11 |

*P = purchased; S = synthesized

REFERENCES

1. Garraway, L. A., Widlund, H. R., Rubin, M. A., Getz, G., Berger, A. J., Ramaswamy, S., Beroukhim, R., Milner, D. A., Granter, S. R., Du, J., et al. Integrative genomic analyses identify MITF as a lineage survival oncogene amplified in malignant melanoma. Nature 2005 436, 117-122. PMID: 16001072.
2. Goding, C. R. Mitf from neural crest to melanoma: signal transduction and transcription in the melanocyte lineage. Genes Dev. 2000. 14:1712-1728. PMID: 10898786.
3. Weilbaecher, K. N., Motyckova, G., Huber, W. E., Takemoto, C. E., Hemesath, T. J., Xu, Y., Hershey, C. L., Dowland, N. R., Wells, A. G., and Fisher, D. E. Linkage of M-CSF signaling to Mitf, TFE3, and the osteoclast defect in Mitfmi/mi mice. Molecular Cell 2001; 8(4):749-58. PMID: 11684011.
4. Davis, I. J., Kim, J. J., Ozsolak, F., Widlund, H. R., Rozenblatt-Rosen, O., Granter, S. R., Du, J., Fletcher, J. A., Denny, C. T., Lessnick, S. L., Linehan, W. M., Kung, A. L., and Fisher, D. E. Oncogenic MITF dysregulation in clear cell sarcoma: Defining the MiT family of human cancers. Cancer Cell. 2006, 9(6), 473-484. PMID: 16766266.
5. Hemesath, T. J., Steingrimsson, E., McGill, G., Hansen, M. J., Vaught, J., Hodgkinson, C. A., Arnheiter, H., Copeland, N. G., Jenkins, N. A., and Fisher, D. E. microphthalmia, a critical factor in melanocyte development, defines a discrete transcription factor family. Genes & Development 1994 8, 2770-2780. PMID: 7958932.
6. Steingrimsson, E., Copeland, N. G., and Jenkins, N. A. Melanocytes and the microphthalmia transcription factor network. Annu Rev Genet 2004. 38, 365-411. PMID: 15568981.
7. Yasumoto, K., Yokoyama, K., Shibata, K., Tomita, Y., and Shibahara, S. Microphthalmia-associated transcription factor as a regulator for melanocyte-specific transcription of the human tyrosinase gene. Mol Cell Biol 1995 15, 1833. PMID: 7862173.
8. Yasumoto, K., Yokoyama, K., Takahashi, K., Tomita, Y., and Shibahara, S. Functional analysis of microphthalmia-associated transcription factor in pigment cell-specific transcription of the human tyrosinase family genes. J Biol Chem 1997 272, 503-509. PMID: 8995290.
9. Fang, D., Tsuji, Y., and Setaluri, V. Selective downregulation of tyrosinase family gene TYRP1 by inhibition of the activity of melanocyte transcription factor, MITF. Nucleic Acids Res 2002 30, 3096-3106. PMID: 12136092.
10. Turque, N., Denhez, F., Martin, P., Planque, N., Bailly, M., Begue, A., Stehelin, D., and Saule, S. Characterization of a new melanocyte-specific gene (QNR-71) expressed in v-myc-transformed quail neuroretina. EMBO J 1996 15, 3338-3350. PMID: 8670835
11. Du, J., Miller, A. J., Widlund, H. R., Horstmann, M. A., Ramaswamy, S., and Fisher, D. E. MLANA/MART1 and SILV/PMEL17/GP100 are transcriptionally regulated by MITF in melanocytes and melanoma. The American Journal of Pathology 2003 163, 333-343. PMID: 12819038.
12. Du, J., and Fisher, D. E. Identification of Aim-1 as the underwhite mouse mutant and its transcriptional regulation by MITF. J Biol Chem 2002 277, 402-406. PMID: 11700328.
13. Carreira, S., Goodall, J., Aksan, I., La Rocca, S. A., Galibert, M. D., Denat, L., Larue, L., and Goding, C. R. Mitf cooperates with Rb1 and activates p21Cip1 expression to regulate cell cycle progression. Nature 2005 433, 764-769. PMID: 15716956
14. Loercher, A. E., Tank, E. M., Delston, R. B., and Harbour, J. W. MITF links differentiation with cell cycle arrest in melanocytes by transcriptional activation of INK4A. J Cell Biol 2005 168, 35-40. PMID: 15623583
15. McGill, G. G., Horstmann, M., Widlund, H. R., Du, J., Motyckova, G., Nishimura, E. K., Lin, Y. L., Ramaswamy, S., Avery, W., Ding, H. F., Jordan, S. A., Jackson, I. J., Korsmeyer, S. J., Golub, T. R., Fisher, D. E. Bcl2 regulation by the melanocyte master regulator Mitf modulates lineage survival and melanoma cell viability. Cell 2002 109, 707-718. PMID: 12086670
16. Moellering, R. E., Cornejo, M., Davis, T. N., Del Bianco, C., Aster, J. C., Blacklow, S. C., Kung, A. L., Gilliland, D. G., Verdine, G. L., and Bradner, J. E. (2009). Direct inhibition of the NOTCH transcription factor complex. Nature 462, 182-188. PMID: 19907488
17. Miller, A. J., Du, J., Rowan, S., Hershey, C. L., Widlund, H. R., and Fisher, D. E. (2004). Transcriptional regulation of the melanoma prognostic marker melastatin (TRPM1) by MITF in melanocytes and melanoma. Cancer Research 64, 509-516. PMID: 14744763
18. Miyake, M., Yamamoto, S., Sano, O., Fujii, M., Kohno, K., Ushio, S., Iwaki, K., Fukuda, S Inhibitory effects of 2-amino-3H-phenoxazin-3-one on the melanogenesis of murine B16 melanoma cell line. Biosci. Biotechnol. Biochem. 2010. 74(4): 753-758. PMID: 20445320.
19. Um J M, Kim H J, Lee Y, Choi C H, Hoang Nguyen D, Lee H B, Shin J H, Tai No K, Kim E K. A small molecule inhibitor of Mitf-E-box DNA binding and its depigmenting effect in melan-a cells. J Eur Acad Dermatol Venereol. 2012 October; 26(10):1291-7. PMID: 21957942.
20. Yokoyama, S., Feige, E., Poling, L. L., Levy, C., Widlund, H. R., Khaled, M., Kung, A. L., and Fisher, D. E. Pharmacologic suppression of MITF expression via HDAC inhibitors in the melanocyte lineage Pigment Cell Melanoma Res. 2008 August; 21(4):457-63. PMID: 18627530.
21. Villareal, M. O.; Han, J.; Yamada, P.; Shigemori, H.; Isoda, H. Hirseins inhibit melanogenesis by regulating the gene expression of the MITF and melanogenesis enzymes. Exp. Dermatol. 2009, 19, 450-457. PMID: 19765058
22. Villareal, M. O.; Han, J.; Ikuto, K.; Isoda, H. Mechanism of MITF inhibition and morphological differentiation effects of hirsein A on B16 melanoma cells revealed by DNA microarray. J. Dermatol. Sci. 2012, 67, 26-36. PMID: 22564683
23. Li, X.; Guo, Y; Sun, Y.; Zhou, J.; Gu, Y.; Li, Y. Baicalein inhibits melanogenesis through activation of the ERK signaling pathway. Int. J. Mol. Med. 2010, 25, 923-927. PMID: 20428797.
24. Huh, S.; Jung, E.; Lee, J.; Roh, K.; Kim, J.-D.; Lee, J.; Park, D. Mechanism of melanogenesis inhibition by propafenone. Arch. Dermatol. Res. 2010, 302, 561-565. PMID: 20549222.
25. Oh, E. Y.; Jong, J. Y.; Choi, Y. H.; Choi, Y. W.; Choi, B T Inhibitory effects of 1-O-methyl-fructofuranose from Schisandra chinensis fruit on melanogenesis in B16F0 melanoma cells. J. Ethnopharmacol. 2010, 132, 219-224. PMID: 20723590
26. Chou, T.-H.; Ding, H.-Y.; Lin, R.-J.; Ling, J.-Y.; Liang, C.-H Inhibition of melanogenesis and oxidation by protocatechuic acid from *Origanum vulgare* (Oregano). J. Nat. Prod. 2010, 73, 1767-1774. PMID: 20973550.
27. Bolton, T.; Puissant, A.; Cheli, Y.; Tomic, T.; Giuliano, S.; Fajas, L.; Deckert, N.; Ortonne, J.-P.; Bertolotto, C.; Tartare-Deckert, S.; Ballotti, R.; Rocchi, S. Ciglitazone negatively regulates CXCL1 signaling through MITF to suppress melanoma growth. Cell Death and Differentiation. 2011, 18, 109-121. PMID: 20596077.
28. Syed, D. N.; Afaq, F.; Maddodi, N.; Johnson, J. J.; Sarfaraz, S.; Ahmad, A.; Setaluri, V.; Mukhtar, H Inhibition of human melanoma cell growth by the dietary flavonoid fisetin is associated with disruption of Wnt/β-catenin signaling and decreased MITF levels. J. Invest. Dermatol. 2011, 131, 1291-1299. PMID: 21346776.
29. Lee, J.; Cho, B.; Jun, H.-j.; Seo, W.-D.; Kim, D.-W.; Cho, K.-J.; Lee, S.-J., Momilactione B inhibits protein kinase A signaling and reduces tyrosinase-related proteins 1 and 2 expression in melanocytes. Biotechnol. Lett. 2012, 34 (5), 805-812. PMID: 22215377.
30. Kim, E. G. E., Ji Min Microphthalmia transcription factor inhibitor used in skin-whitening cosmetic composition. KR2012016847, 2012.
31. Jin, M. L.; Park, S. Y.; Kim, Y. H.; Park, G.; Son, H.-J.; Lee, S.-J., Suppression of α-MSH and IBMX-induced melanogenesis by cordycepin via inhibition of CREB and MITF, and activation of PI3K/Akt and ERK-dependent mechanisms. Int. J. Mol. Med. 2012, 29 (1), 119-124. PMID: 21972008.
32. Park, S.; Jin, M.; Kim, Y.; Kim, Y.; Lee, S.-J., Aromatic-turmerone inhibits α-MSH and IBMX-induced melanogenesis by inactivating CREB and MITF signaling pathways. Archives of Dermatological Research 2011, 303 (10), 737-744. PMID: 21660443.
33. Kim, D. S.; Lee, H. K.; Park, S. H.; Chae, C. H.; Park, K. C., AVS-1357 inhibits melanogenesis via prolonged ERK activation. Die Pharmazie 2009, 64 (8), 532-7. PMID: 19746843.
34. Kim, J. H.; Baek, S. H.; Kim, D. H.; Choi, T. Y.; Yoon, T. J.; Hwang, J. S.; Kim, M. R.; Kwon, H. J.; Lee, C. H., Downregulation of melanin synthesis by haginin A and its application to in vivo lightening model. J. Invest. Dermatol. 2008, 128 (5), 1227-35. PMID: 18037902.
35. Huang, Y. H.; Lee, T. H.; Chan, K. J.; Hsu, F. L.; Wu, Y. C.; Lee, M. H., Anemonin is a natural bioactive compound that can regulate tyrosinase-related proteins and mRNA in human melanocytes. J. Dermatol Sci. 2008, 49 (2), 115-23. PMID: 17766092.
36. Joung, H. S.; Song, K. H.; Kim, A. K., Antimelanogenic effect of taurine in murine melanoma B16F10 cells. Yakhak Hoechi 2007, 51 (5), 350-354.
37. Lee, H. E.; Kim, E. H.; Choi, H. R.; Sohn, U. D.; Yun, H. Y.; Baek, K. J.; Kwon, N. S.; Park, K. C.; Kim, D. S., Dipeptides Inhibit Melanin Synthesis in Mel-Ab Cells through Down-Regulation of Tyrosinase. The Korean Journal of Physiology & Pharmacology: official journal of the Korean Physiological Society and the Korean Society of Pharmacology 2012, 16 (4), 287-91. PMID: 22915995.
38. Kim, Y. J.; No, J. K.; Lee, J. S.; Kim, M. S.; Chung, H. Y., Antimelanogenic activity of 3,4-dihydroxyacetophenone: inhibition of tyrosinase and MITF. Biosci. Biotechnol. Biochem. 2006, 70 (2), 532-4. PMID: 16495675.
39. Park, S. H.; Kim, D. S.; Kim, W. G.; Ryoo, I. J.; Lee, D. H.; Huh, C. H.; Youn, S. W.; Yoo, I. D.; Park, K. C., Terrein: a new melanogenesis inhibitor and its mechanism. Cell Mol. Life Sci. 2004, 61 (22), 2878-85. PMID: 15558216.
40. Kim, D. S.; Jeong, Y. M.; Park, I. K.; Hahn, H. G.; Lee, H. K.; Kwon, S. B.; Jeong, J. H.; Yang, S. J.; Sohn, U. D.; Park, K. C., A new 2-imino-1,3-thiazoline derivative, KHG22394, inhibits melanin synthesis in mouse B16 melanoma cells. Biol. Pharmaceut. Bull 2007, 30 (1), 180-3. PMID: 17202683
41. Cho, M.; Ryu, M.; Jeong, Y.; Chung, Y. H.; Kim, D. E.; Cho, H. S.; Kang, S.; Han, J. S.; Chang, M. Y.; Lee, C. K.; Jin, M.; Kim, H. J.; Oh, S., Cardamonin suppresses melanogenesis by inhibition of Wnt/beta-catenin signaling. Biochem. Biophys. Res. Comm 2009, 390 (3), 500-5.
42. Kikuchi, T.; Zhang, J.; Huang, Y.; Watanabe, K.; Ishii, K.; Yamamoto, A.; Fukatsu, M.; Tanaka, R.; Akihisa, T., Glycosidic Inhibitors of Melanogenesis from Leaves of *Momordica charantia*. Chem. Biodivers. 2012, 9 (7), 1221-1230. PMID: 22782871
43. Lamb, J., Crawford, E. D., Peck, D., Modell, J. W, Blat, I. C., Wrobel, M. J., Lerner, J., Brunet, J. P., Subramanian, A., Ross, K. N., et al. The Connectivity Map: using gene-expression signatures to connect small molecules, genes, and disease. Science. 2006, 313(5795):1929-35. PMID: 1700852.
44. Feige, E., Yokoyama, S., Levy, C., Khaled, M., Igras, V., Lin, R. J., Lee, S., Widlund, H. R., Granter, S. R., Kung, A. L., Fisher, D. E. Hypoxia-induced transcriptional repression of the melanoma-associated oncogene MITF. Proc Natl Acad Sci USA. 2011, 108(43):E924-33. PMID: 21949374

Example 7

Experiments described in this example were performed using methods as described in Haq et al. (2013). Oncogenic BRAF regulates oxidative metabolism via PGC1α and MITF. Cancer Cell. 2013 Mar. 18; 23(3):302-15.
Effects of ML329 on Cell Viability of Human Melanoma Cell Lines Indicated cell line was treated with varying concentrations of ML329 for 48-72 hours. Viability was measured using the CellTiter-Glo reagent (Promega).

As shown in FIGS. 5-8, ML329 was variably cytotoxic in a large number of melanoma cells (even cell lines that were resistant to the BRAF inhibitor vemurafenib), but was not cytotoxic in non-melanoma cells or melanoma cells lacking MITF. Collectively, the results demonstrate selectivity in the drug's action.

Effects of ML329 on Gene Expression of MITF and MITF Target Genes in Human Melanoma Cell Lines and Primary Melanocytes (qPCR)

Effect of ML329 (24 h at indicated concentration) on MITF mRNA and target gene mRNA expression in melanoma cell lines. mRNA was quantified by qPCR.

Figure 9A:
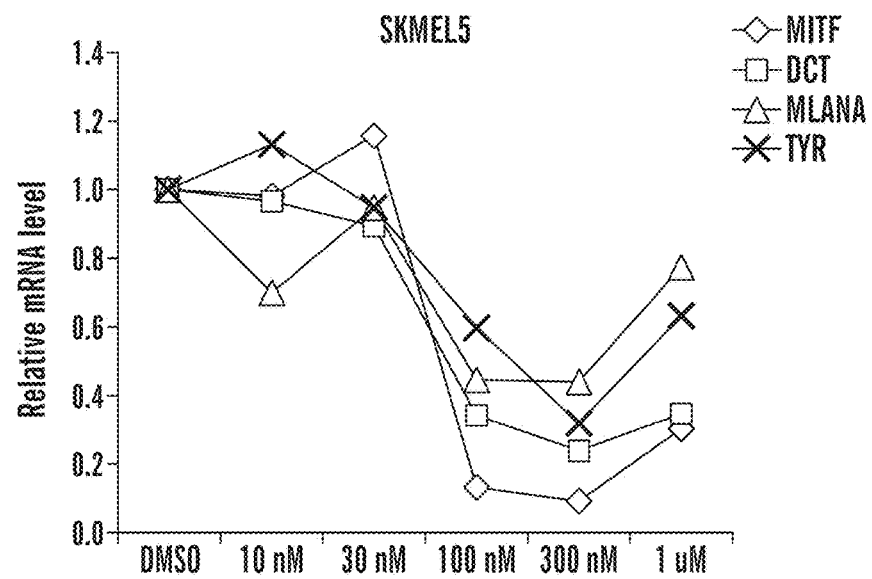
FIGS. 9A and 9B shows the effect of ML329 on MITF and MITF-dependent gene expression in SK-MEL-5 and MALME-3M.
Figure 9B:
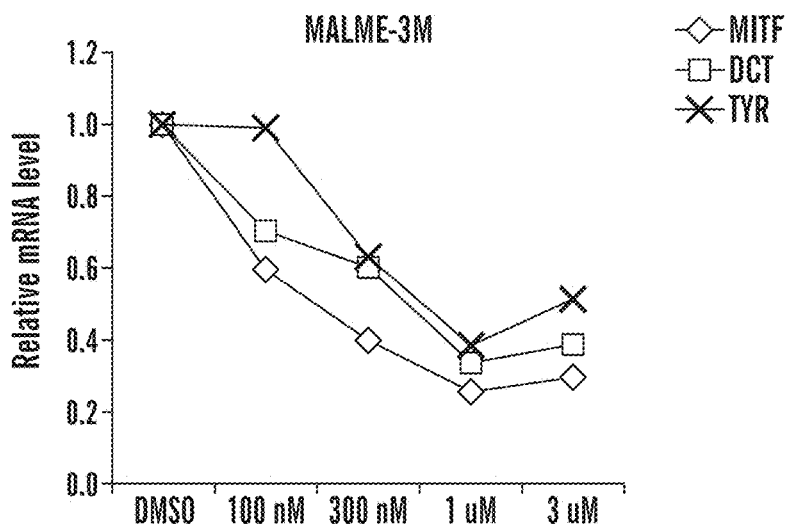
Figure 10A:
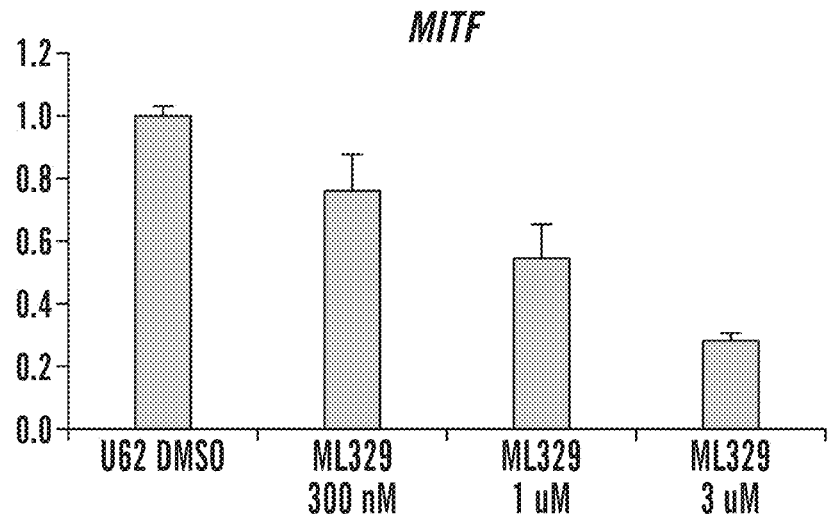
FIGS. 10A-10D shows the effect of ML329 on MITF and MITF-dependent gene expression in UACC62.
Figure 10B:
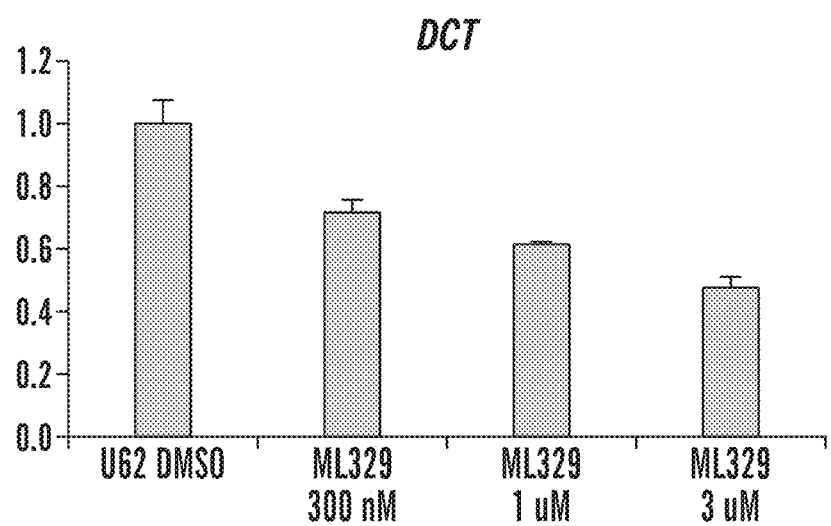
Figure 10C:
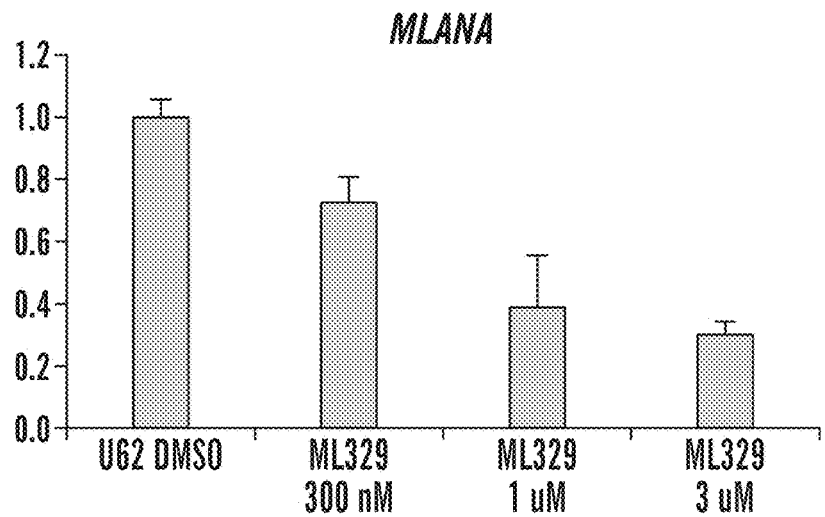
Figure 10D:
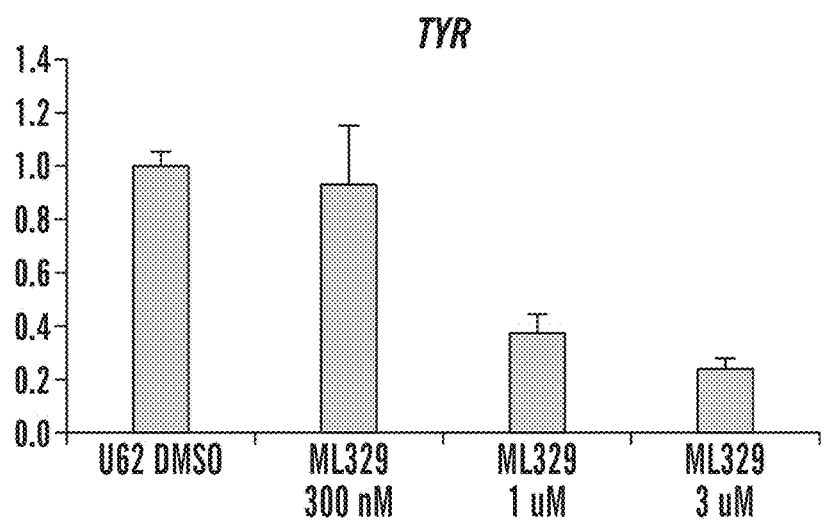
Figure 11A:
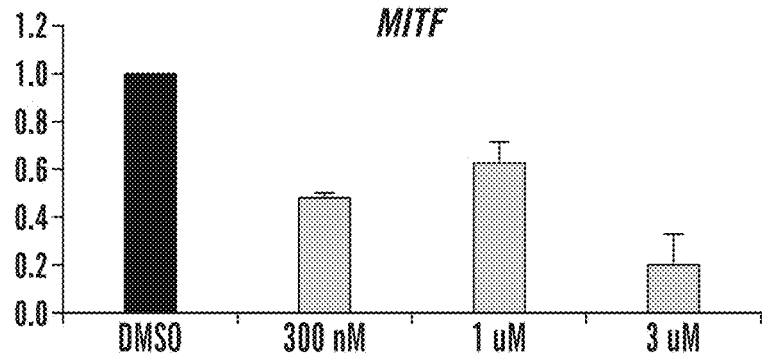
FIGS. 11A-11C shows the effect of ML329 on MITF and MITF-dependent gene expression in primary melanocytes.
Figure 11B:
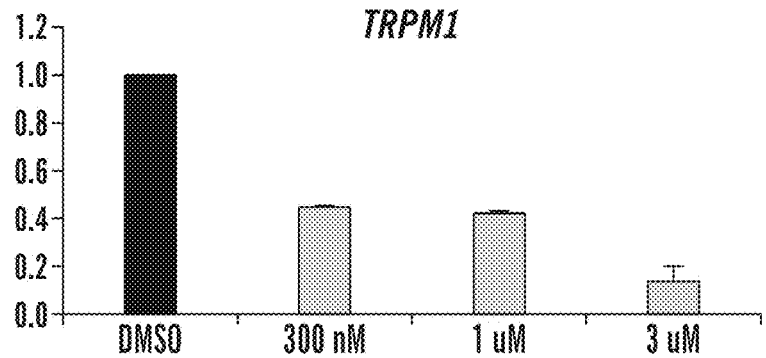
Figure 11C:
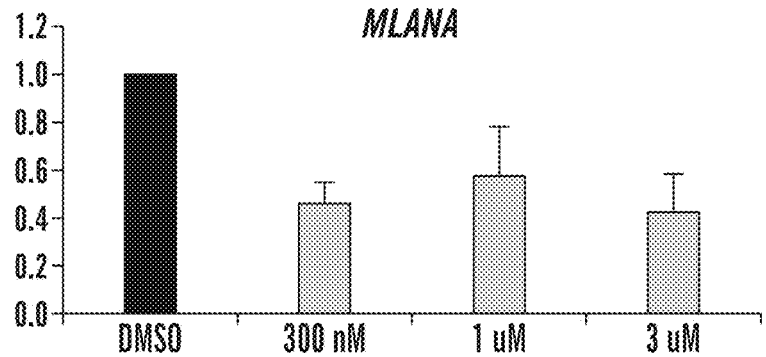

As shown in FIGS. 9-11, the results confirm that ML329 suppresses MITF and its transcriptional activity in multiple cell lines.

Effects of ML329 on MITF Protein

Figures 12A, 12B:
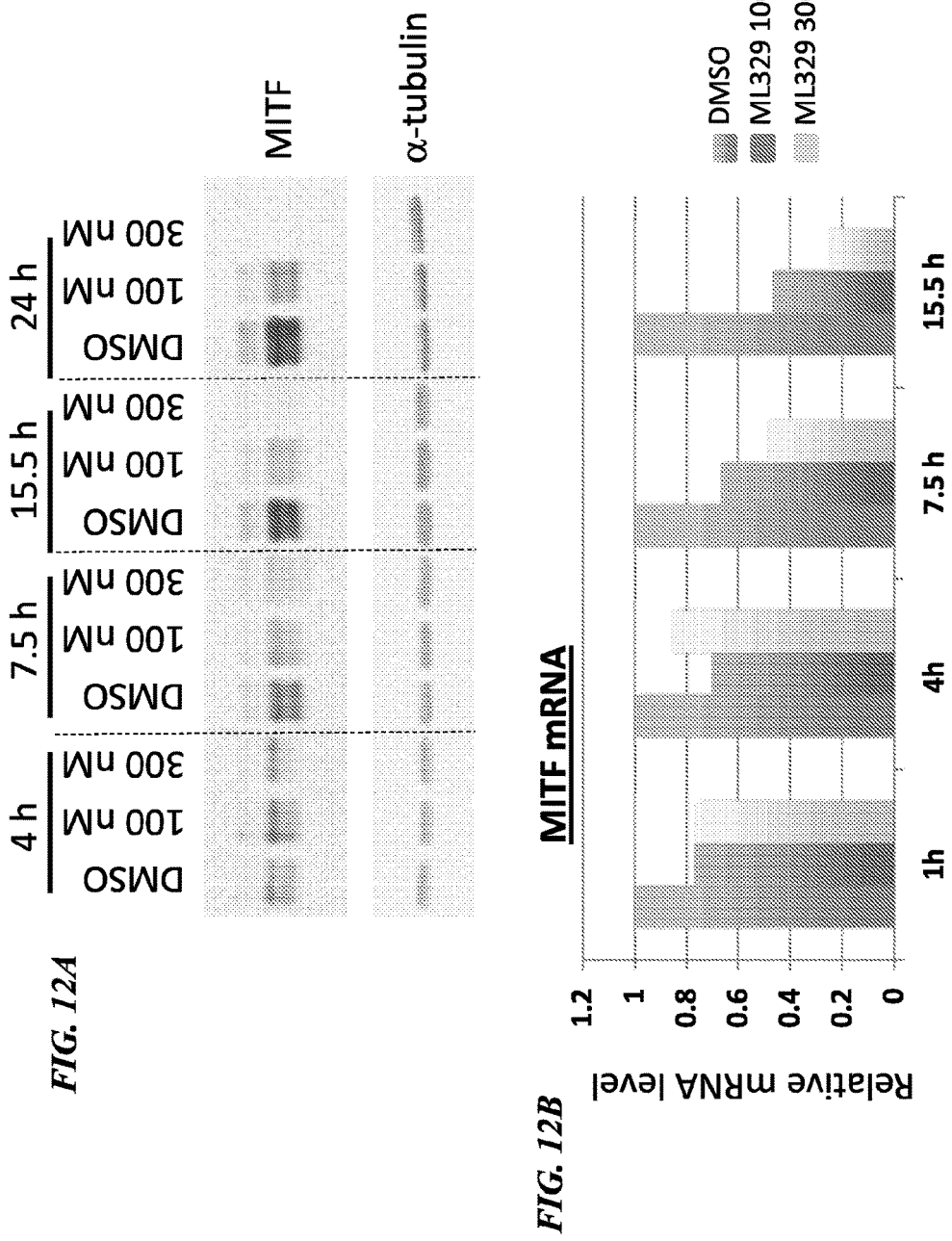
FIGS. 12A and 12B show the effect of ML329 on MITF protein (FIG. 12A) and mRNA (FIG. 12B).
Figure 13A:
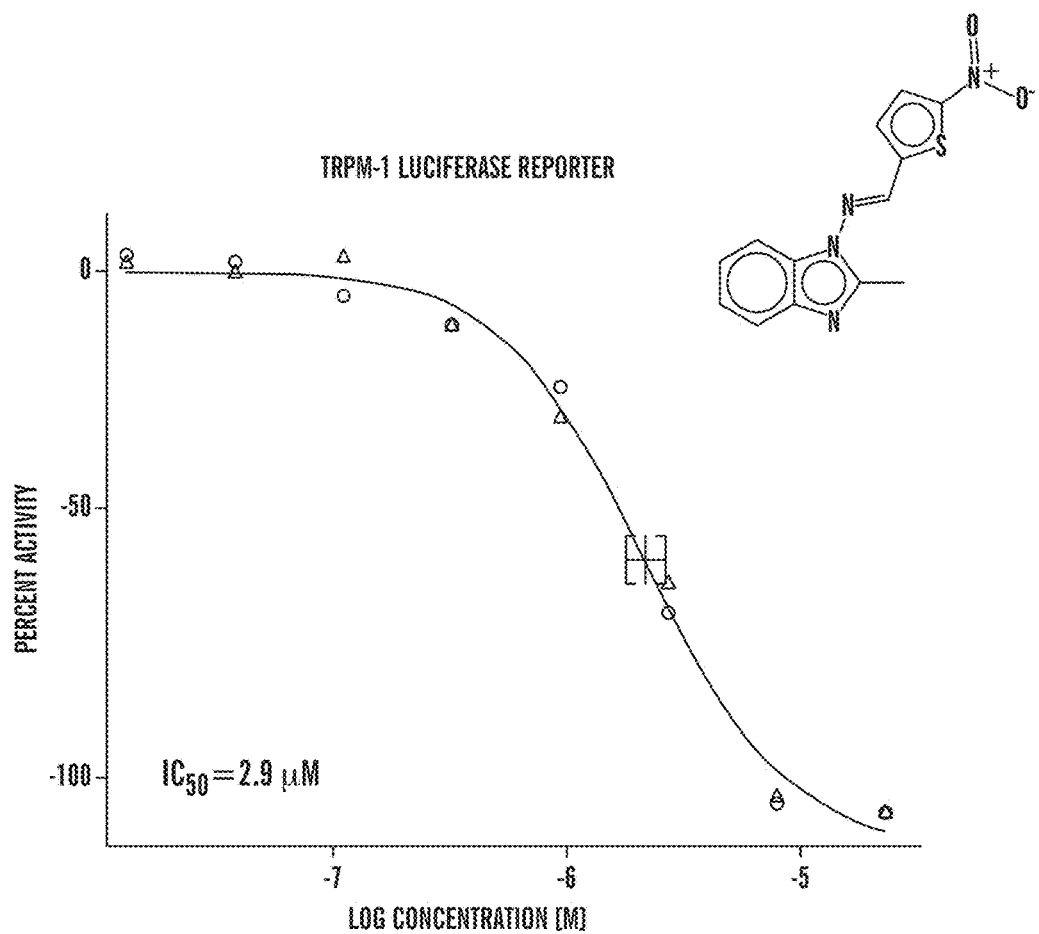
FIG. 13A-13D shows effect of compound of Formula (II) in two MITF-dependent melanoma cell viability assays, SK-MEL-5 and MALME-3M plus an MITF-independent cell line, A-375.
Figure 13B:
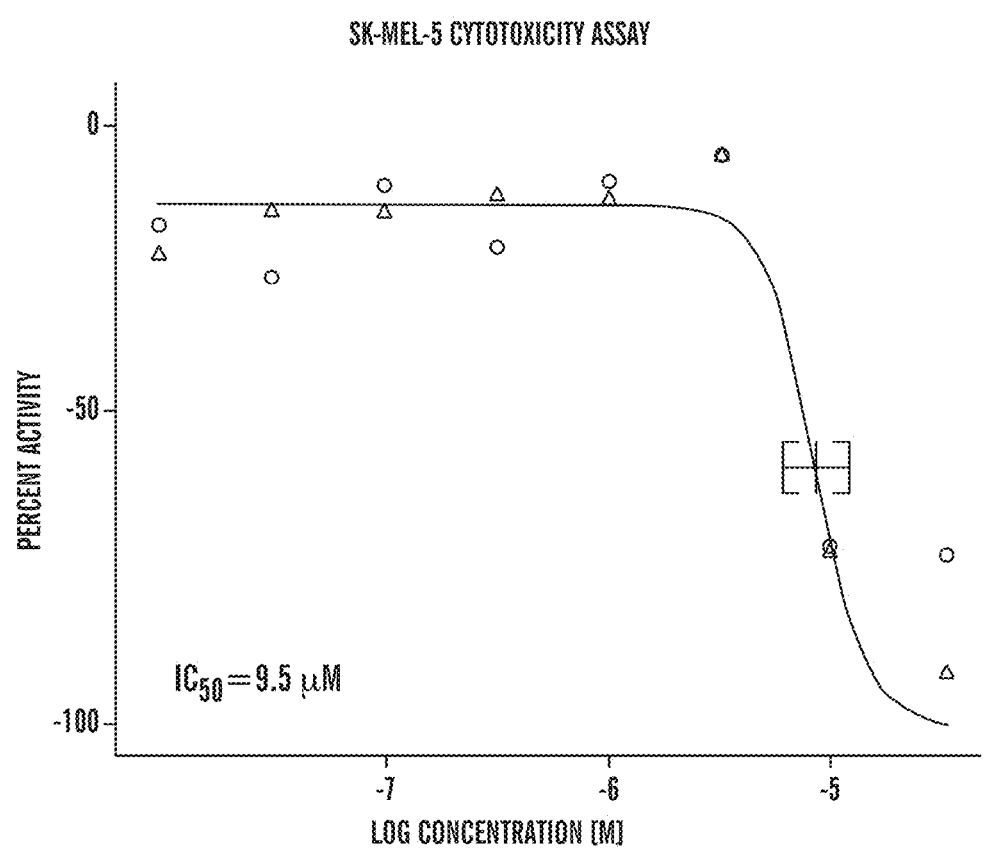
Figure 13C:
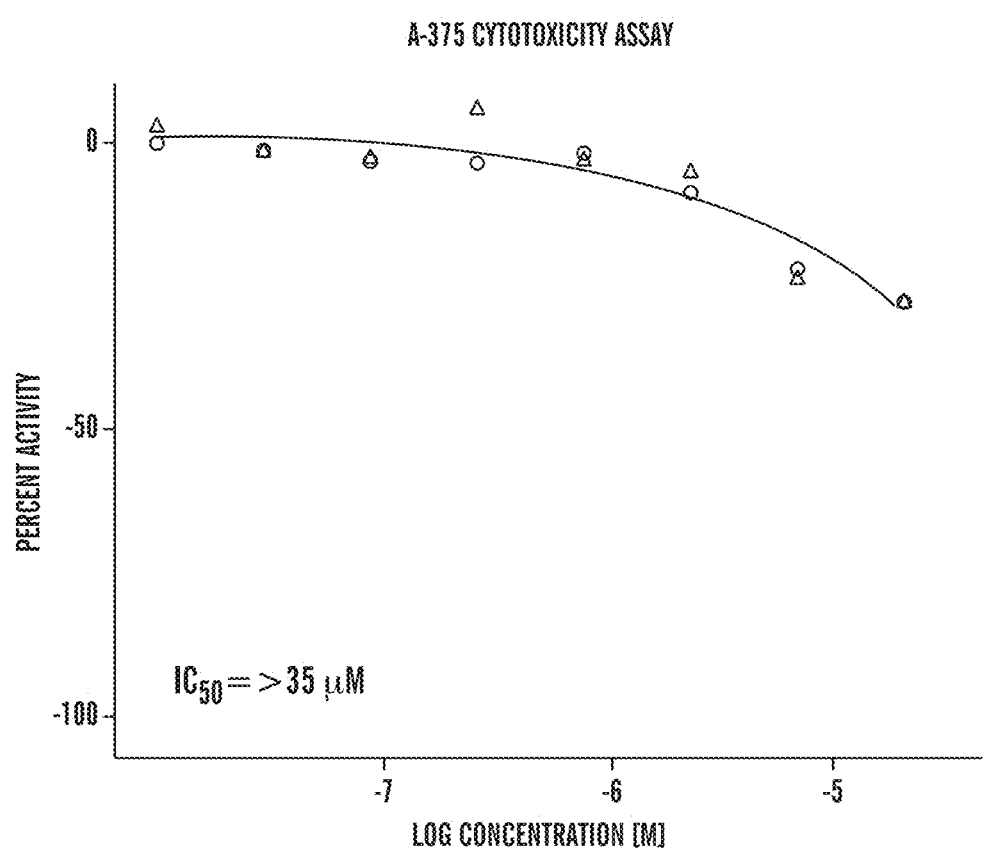
Figure 13D:
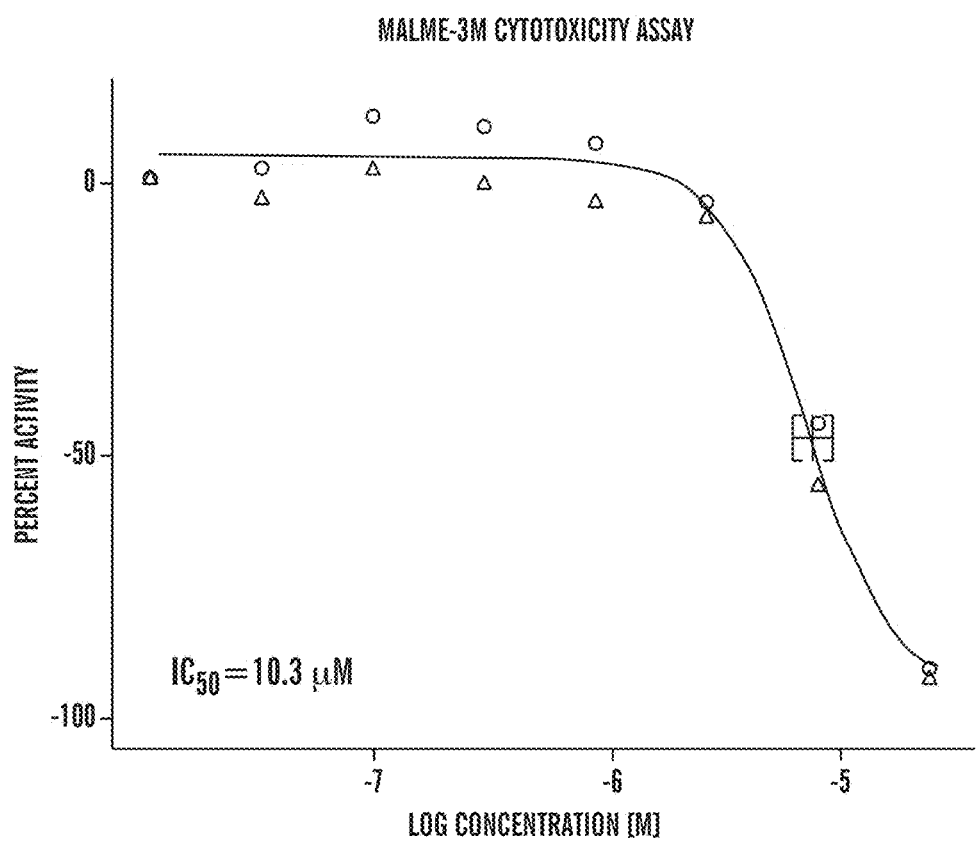

As shown in FIG. 12a, SKMEL-5 cells were treated with ML329 (indicated concentration and time). MITF protein was detected using Western immunoblotting. In parallel, SK-MEL-5 cells treated with ML329 (above) were lysed and MITF mRNA was quantified by qPCR (FIG. 12b). As shown in FIGS. 12a and 12b, ML329 suppresses MITF protein in melanoma cells.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

What is claimed is:
1. A method for treating cancer, comprising administering a therapeutically effective amount of 4-((1,4-dioxo-1,4-dihydronaphthalen-2-yl)amino)benzenesulfonamide to a subject in need thereof, wherein treatment is inhibiting, slowing down or stopping progression of cancer, and wherein the cancer is a MITF-dependent cancer.

* * * * *